United States Patent
Renga et al.

(10) Patent No.: US 10,212,936 B2
(45) Date of Patent: *Feb. 26, 2019

(54) MOLECULES HAVING PESTICIDAL UTILITY, AND INTERMEDIATES, COMPOSITIONS, AND PROCESSES, RELATED THERETO

(71) Applicant: DOW AGROSCIENCES LLC, Indianapolis, IN (US)

(72) Inventors: James M. Renga, Indianapolis, IN (US); Natalie C. Giampietro, Carmel, IN (US); Erich W. Baum, Indianapolis, IN (US); Lindsey G. Fischer, Indianapolis, IN (US); Miriam E. Goldsmith, Indianapolis, IN (US); Gary D. Crouse, Noblesville, IN (US); Thomas C. Sparks, Greenfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/527,578

(22) PCT Filed: Dec. 3, 2015

(86) PCT No.: PCT/US2015/063720
§ 371 (c)(1),
(2) Date: May 17, 2017

(87) PCT Pub. No.: WO2016/099929
PCT Pub. Date: Jun. 23, 2016

(65) Prior Publication Data
US 2017/0360045 A1    Dec. 21, 2017

Related U.S. Application Data

(60) Provisional application No. 62/091,653, filed on Dec. 15, 2014, provisional application No. 62/091,657, filed on Dec. 15, 2014.

(51) Int. Cl.

| | | |
|---|---|---|
| *A01N 47/36* | (2006.01) | |
| *C07D 401/14* | (2006.01) | |
| *C07D 405/12* | (2006.01) | |
| *C07D 409/12* | (2006.01) | |
| *C07D 413/12* | (2006.01) | |
| *C07D 417/12* | (2006.01) | |
| *C07D 403/12* | (2006.01) | |

(52) U.S. Cl.
CPC ........... *A01N 47/36* (2013.01); *C07D 401/14* (2013.01); *C07D 403/12* (2013.01); *C07D 405/12* (2013.01); *C07D 409/12* (2013.01); *C07D 413/12* (2013.01); *C07D 417/12* (2013.01)

(58) Field of Classification Search
None
See application file for complete search history.

(56) References Cited

U.S. PATENT DOCUMENTS

| | | |
|---|---|---|
| 2011/0158907 A1 | 6/2011 | Kung et al. |
| 2013/0019345 A1 | 1/2013 | Crouse et al. |
| 2014/0275563 A1 | 9/2014 | Giampietro et al. |

FOREIGN PATENT DOCUMENTS

| | | |
|---|---|---|
| WO | 2011017513 | 2/2011 |
| WO | 2014011429 A1 | 1/2014 |

*Primary Examiner* — Samantha L Shterengarts
(74) *Attorney, Agent, or Firm* — Barnes & Thornburg LLP

(57) ABSTRACT

This disclosure relates to the field of molecules having pesticidal utility against pests in Phyla Arthropoda, Mollusca, and Nematoda, processes to produce such molecules, intermediates used in such processes, compositions containing such molecules, and processes of using such molecules and compositions against such pests. These molecules and compositions may be used, for example, as acaricides, insecticides, miticides, molluscicides, and nematicides. This document discloses molecules having the following formula ("Formula One").

Formula One

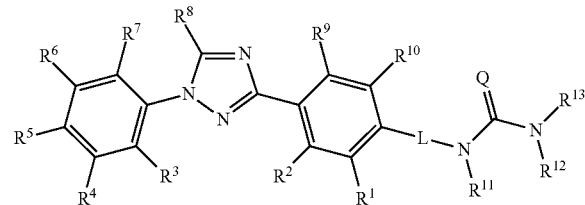

16 Claims, No Drawings

MOLECULES HAVING PESTICIDAL UTILITY, AND INTERMEDIATES, COMPOSITIONS, AND PROCESSES, RELATED THERETO

CROSS REFERENCE TO RELATED APPLICATIONS

The present application is a U.S. National Phase of International Application No. PCT/US2015/063720, filed on 3 Dec. 2015, which claims the benefit of, and priority from, U.S. Provisional Patent Application Ser. No. 62/091,657, filed on 15 Dec. 2014, the entire disclosure of which is hereby expressly incorporated by reference, and U.S. Provisional Patent Application Ser. No. 62/091,653, filed on 15 Dec. 2014, the entire disclosure of which is hereby expressly incorporated by reference.

FIELD OF THIS DISCLOSURE

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides.

BACKGROUND OF THIS DISCLOSURE

"Many of the most dangerous human diseases are transmitted by insect vectors" (Rivero et al.). "Historically, malaria, dengue, yellow fever, plague, filariasis, louse-borne typhus, trypanomiasis, leishmaniasis, and other vector borne diseases were responsible for more human disease and death in the $17^{th}$ through the early $20^{th}$ centuries than all other causes combined" (Gubler). Vector-borne diseases are responsible for about 17% of the global parasitic and infectious diseases. Malaria alone causes over 800,000 deaths a year, 85% of which occur in children under five years of age. Each year there are about 50 to about 100 million cases of dengue fever. A further 250,000 to 500,000 cases of dengue hemorrhagic fever occur each year (Matthews). Vector control plays a critical role in the prevention and control of infectious diseases. However, insecticide resistance, including resistance to multiple insecticides, has arisen in all insect species that are major vectors of human diseases (Rivero et al.). Recently, more than 550 arthropod pest species have developed resistance to at least one pesticide (Whalon et al.).

Each year insects, plant pathogens, and weeds, destroy more than 40% of all food production. This loss occurs despite the application of pesticides and the use of a wide array of non-chemical controls, such as, crop rotations, and biological controls. If just some of this food could be saved, it could be used to feed the more than three billion people in the world who are malnourished (Pimental).

Plant parasitic nematodes are among the most widespread pests, and are frequently one of the most insidious and costly. It has been estimated that losses attributable to nematodes are from about 9% in developed countries to about 15% in undeveloped countries. However, in the United States of America a survey of 35 States on various crops indicated nematode-derived losses of up to 25% (Nicol et al.).

It is noted that gastropods (slugs and snails) are pests of less economic importance than other arthropods or nematodes, but in certain places they may reduce yields substantially, severely affecting the quality of harvested products, as well as, transmitting human, animal, and plant diseases. While only a few dozen species of gastropods are serious regional pests, a handful of species are important pests on a world-wide scale. In particular, gastropods affect a wide variety of agricultural and horticultural crops, such as, arable, pastoral, and fiber crops; vegetables; bush and tree fruits; herbs; and ornamentals (Speiser).

Termites cause damage to all types of private and public structures, as well as, to agricultural and forestry resources. In 2005, it was estimated that termites cause over US$50 billion in damage world-wide each year (Korb).

Consequently, for many reasons, including those mentioned above, there is an on-going need for the costly (estimated to be about US$256 million per pesticide in 2010), time-consuming (on average about 10 years per pesticide), and difficult, development of new pesticides (CropLife America).

CERTAIN REFERENCES CITED IN THIS DISCLOSURE

CropLife America, *The Cost of New Agrochemical Product Discovery, Development & Registration, and Research & Development predictions for the Future*, 2010.

Gubler, D., *Resurgent Vector-Borne Diseases as a Global Health Problem, Emerging Infectious Diseases*, Vol. 4, No. 3, p. 442-450, 1998.

Korb, J., *Termites, Current Biology*, Vol. 17, No. 23, 2007.

Matthews, G., *Integrated Vector Management: Controlling Vectors of Malaria and Other Insect Vector Borne Diseases*, Ch. 1, p. 1-2011.

Nicol, J., Turner S.; Coyne, L.; den Nijs, L., Hocksland, L., Tahna-Maafi, Z., *Current Nematode Threats to World Agriculture, Genomic and Molecular Genetics of Plant—Nematode Interactions*, p. 21-43, 2011).

Pimental, D., *Pest Control in World Agriculture, Agricultural Sciences*—Vol. II, 2009.

Rivero, A., Vezilier, J., Weill, M., Read, A., Gandon, S., *Insect Control of Vector-Borne Diseases: When is Insect Resistance a Problem? Public Library of Science Pathogens*, Vol. 6, No. 8, p. 1-9, 2010.

Speiser, B., *Molluscicides, Encyclopedia of Pest Management*, Ch. 219, p. 506-508, 2002.

Whalon, M., Mota-Sanchez, D., Hollingworth, R., *Analysis of Global Pesticide Resistance in Arthropods, Global Pesticide Resistance in Arthropods*, Ch. 1, p. 5-33, 2008.

Definitions Used in this Disclosure

The examples given in these definitions are generally non-exhaustive and must not be construed as limiting the disclosure. It is understood that a substituent should comply with chemical bonding rules and steric compatibility constraints in relation to the particular molecule to which it is attached. These definitions are only to be used for the purposes of this disclosure.

"active ingredient" means a material having activity useful in controlling pests, and/or that is useful in helping other materials have better activity in controlling pests, examples of such materials include, but are not limited to, acaricides, algicides, avicides, bactericides, fungicides, herbicides, insecticides, molluscicides, nematicides, rodenticides, virucides, antifeedants, bird repellents, chemosterilants, herbicide safeners, insect attractants, insect repellents, mammal repellents, mating disrupters, plant activators, plant growth regulators, and synergists. Specific examples of such materials include, but are not limited to, the materials listed in active ingredient group alpha.

"active ingredient group alpha" (hereafter "AIGA") means collectively the following materials:

(1) (3-ethoxypropyl)mercury bromide, 1,2-dibromoethane, 1,2-dichloroethane, 1,2-dichloropropane, 1,3-dichloropropene, 1-MCP, 1-methylcyclopropene, 1-naphthol, 2-(octylthio)ethanol, 2,3,3-TPA, 2,3,5-tri-iodobenzoic acid, 2,3,6-TBA, 2,4,5-T, 2,4,5-TB, 2,4,5-TP, 2,4-D, 2,4-DB, 2,4-DEB, 2,4-DEP, 2,4-DES, 2,4-DP, 2,4-MCPA, 2,4-MCPB, 2iP, 2-methoxyethylmercury chloride, 2-phenylphenol, 3,4-DA, 3,4-DB, 3,4-DP, 3,6-dichloropicolinic acid, 4-aminopyridine, 4-CPA, 4-CPB, 4-CPP, 4-hydroxyphenethyl alcohol, 8-hydroxyquinoline sulfate, 8-phenylmercurioxyquinoline, abamectin, abamectin-aminomethyl, abscisic acid, ACC, acephate, acequinocyl, acetamiprid, acethion, acetochlor, acetofenate, acetophos, acetoprole, acibenzolar, acifluorfen, aclonifen, ACN, acrep, acrinathrin, acrolein, acrylonitrile, acypetacs, afidopyropen, afoxolaner, alachlor, alanap, alanycarb, albendazole, aldicarb, aldicarb sulfone, aldimorph, aldoxycarb, aldrin, allethrin, allicin, allidochlor, allosamidin, alloxydim, allyl alcohol, allyxycarb, alorac, alpha-cypermethrin, alpha-endosulfan, alphamethrin, altretamine, aluminium phosphide, aluminum phosphide, ametoctradin, ametridione, ametryn, ametryne, amibuzin, amicarbazone, amicarthiazol, amidithion, amidoflumet, amidosulfuron, aminocarb, aminocyclopyrachlor, aminopyralid, aminotriazole, amiprofos-methyl, amiprophos, amiprophos-methyl, amisulbrom, amiton, amitraz, amitrole, ammonium sulfamate, amobam, amorphous silica gel, amorphous silicon dioxide, ampropylfos, AMS, anabasine, ancymidol, anilazine, anilofos, anisuron, anthraquinone, antu, apholate, aramite, arprocarb, arsenous oxide, asomate, aspirin, asulam, athidathion, atraton, atrazine, aureofungin, avermectin B1, AVG, aviglycine, azaconazole, azadirachtin, azafenidin, azamethiphos, azidithion, azimsulfuron, azinphosethyl, azinphos-ethyl, azinphosmethyl, azinphos-methyl, aziprotryn, aziprotryne, azithiram, azobenzene, azocyclotin, azothoate, azoxystrobin, bachmedesh, barban, barbanate, barium hexafluorosilicate, barium polysulfide, barium silicofluoride, barthrin, basic copper carbonate, basic copper chloride, basic copper sulfate, BCPC, beflubutamid, benalaxyl, benalaxyl-M, benazolin, bencarbazone, benclothiaz, bendaqingbingzhi, bendiocarb, bendioxide, benefin, benfluralin, benfuracarb, benfuresate, benmihuangcaoan, benodanil, benomyl, benoxacor, benoxafos, benquinox, bensulfuron, bensulide, bensultap, bentaluron, bentazon, bentazone, benthiavalicarb, benthiazole, benthiocarb, bentranil, benzadox, benzalkonium chloride, benzamacril, benzamizole, benzamorf, benzene hexachloride, benzfendizone, benzimine, benzipram, benzobicyclon, benzoepin, benzofenap, benzofluor, benzohydroxamic acid, benzomate, benzophosphate, benzothiadiazole, benzovindiflupyr, benzoximate, benzoylprop, benzthiazuron, benzuocaotong, benzyl benzoate, benzyladenine, berberine, beta-cyfluthrin, beta-cypermethrin, bethoxazin, BHC, bialaphos, bicyclopyrone, bifenazate, bifenox, bifenthrin, bifujunzhi, bilanafos, binapacryl, bingqingxiao, bioallethrin, bioethanomethrin, biopermethrin, bioresmethrin, biphenyl, bisazir, bismerthiazol, bismerthiazol-copper, bisphenylmercury methylenedi(x-naphthalene-y-sulphonate), bispyribac, bistrifluron, bisultap, bitertanol, bithionol, bixafen, blasticidin-S, borax, Bordeaux mixture, boric acid, boscalid, BPPS, brassinolide, brassinolide-ethyl, brevicomin, brodifacoum, brofenprox, brofenvalerate, broflanilide, brofluthrinate, bromacil, bromadiolone, bromchlorphos, bromethalin, bromethrin, bromfenvinfos, bromoacetamide, bromobonil, bromobutide, bromociclen, bromocyclen, bromo-DDT, bromofenoxim, bromofos, bromomethane, bromophos, bromophos-ethyl, bromopropylate, bromothalonil, bromoxynil, brompyrazon, bromuconazole, bronopol, BRP, BTH, bucarpolate, bufencarb, buminafos, bupirimate, buprofezin, Burgundy mixture, busulfan, busulphan, butacarb, butachlor, butafenacil, butam, butamifos, butane-fipronil, butathiofos, butenachlor, butene-fipronil, butethrin, buthidazole, buthiobate, buthiuron, butifos, butocarboxim, butonate, butopyronoxyl, butoxycarboxim, butralin, butrizol, butroxydim, buturon, butylamine, butylate, butylchlorophos, butylene-fipronil, cacodylic acid, cadusafos, cafenstrole, calciferol, calcium arsenate, calcium chlorate, calcium cyanamide, calcium cyanide, calcium polysulfide, calvinphos, cambendichlor, camphechlor, camphor, captafol, captan, carbam, carbamorph, carbanolate, carbaril, carbaryl, carbasulam, carbathion, carbendazim, carbendazol, carbetamide, carbofenotion, carbofuran, carbon disulfide, carbon tetrachloride, carbonyl sulfide, carbophenothion, carbophos, carbosulfan, carboxazole, carboxide, carboxin, carfentrazone, carpropamid, cartap, carvacrol, carvone, CAVP, CDAA, CDEA, CDEC, cellocidin, CEPC, ceralure, cerenox, cevadilla, Cheshunt mixture, chinalphos, chinalphos-methyl, chinomethionat, chinomethionate, chiralaxyl, chitosan, chlobenthiazone, chlomethoxyfen, chloralose, chloramben, chloramine phosphorus, chloramphenicol, chloraniformethan, chloranil, chloranocryl, chlorantraniliprole, chlorazifop, chlorazine, chlorbenside, chlorbenzuron, chlorbicyclen, chlorbromuron, chlorbufam, chlordane, chlordecone, chlordimeform, chlorempenthrin, chloretazate, chlorethephon, chlorethoxyfos, chloreturon, chlorfenac, chlorfenapyr, chlorfenazole, chlorfenethol, chlorfenidim, chlorfenprop, chlorfenson, chlorfensulphide, chlorfenvinphos, chlorfenvinphos-methyl, chlorfluazuron, chlorflurazole, chlorflurecol, chlorfluren, chlorflurenol, chloridazon, chlorimuron, chlorinate, chlor-IPC, chlormephos, chlormequat, chlormesulone, chlormethoxynil, chlornidine, chlornitrofen, chloroacetic acid, chlorobenzilate, chlorodinitronaphthalenes, chlorofénizon, chloroform, chloromebuform, chloromethiuron, chloroneb, chlorophacinone, chlorophos, chloropicrin, chloropon, chloropropylate, chlorothalonil, chlorotoluron, chloroxifenidim, chloroxuron, chloroxynil, chlorphonium, chlorphoxim, chlorprazophos, chlorprocarb, chlorpropham, chlorpyrifos, chlorpyrifosmethyl, chlorquinox, chlorsulfuron, chlorthal, chlorthiamid, chlorthiophos, chlortoluron, chlozolinate, chltosan, cholecalciferol, choline chloride, chromafenozide, cicloheximide, cimectacarb, cimetacarb, cinerin I, cinerin II, cinerins, cinidon-ethyl, cinmethylin, cinosulfuron, cintofen, ciobutide, cisanilide, cismethrin, clacyfos, clefoxydim, clenpirin, clenpyrin, clethodim, climbazole, cliodinate, clodinafop, cloethocarb, clofencet, clofenotane, clofentezine, clofenvinfos, clofibric acid, clofop, clomazone, clomeprop, clonitralid, cloprop, cloproxydim, clopyralid, cloquintocet, cloransulam, closantel, clothianidin, clotrimazole, cloxyfonac, cloxylacon, clozylacon, CMA, CMMP, CMP, CMU, codlelure, colecalciferol, colophonate, copper 8-quinolinolate, copper acetate, copper acetoarsenite, copper arsenate, copper carbonate, basic, copper hydroxide, copper naphthenate, copper oleate, copper oxychloride, copper silicate, copper sulfate, copper sulfate, basic, copper zinc chromate, coumachlor, coumaféne, coumafos, coumafuryl, coumaphos, coumatetralyl, coumethoxystrobin, coumithoate, coumoxystrobin, CPMC, CPMF, CPPC, credazine, cresol, cresylic acid, crimidine, crotamiton, crotoxyfos, crotoxyphos, crufomate, cryolite, cue-lure, cufraneb, cumyleron, cumyluron, cuprobam, cuprous oxide, curcumenol, CVMP, cyanamide, cyanatryn, cyanazine, cyanofenphos, cyanogen, cyanophos, cyanthoate, cyantraniliprole, cyanuric acid, cyazofamid, cybutryne, cyclafuramid, cyclanilide, cyclaniliprole, cyclethrin, cycloate, cycloheximide, cycloprate, cycloprothrin, cyclopyrimorate, cyclosulfamuron, cycloxydim, cycluron, cyenopyrafen, cyflufenamid, cyflumetofen, cyfluthrin, cyhalofop, cyhalothrin, cyhexatin, cymiazole, cymoxanil, cyometrinil, cypendazole, cypermethrin, cyperquat, cyphenothrin, cyprazine, cyprazole, cyproconazole, cyprodinil, cyprofuram, cypromid, cyprosulfamide, cyromazine, cythioate, cytrex, daimuron, dalapon, daminozide, dayoutong, dazomet, DBCP, d-camphor, DCB, DCIP, DCPA, DCPTA, DCU, DDD, DDPP, DDT, DDVP, debacarb, decafentin, decamethrin, decarbofuran, deet, dehydroacetic acid, deiquat, delachlor, delnav, deltamethrin, demephion, demephion-O, demephion-S, demeton, demeton-methyl, demeton-O, demeton-O-methyl, demeton-S, demeton-S-methyl, demeton-S-methyl sulphone, demeton-S-methylsulphon, DEP, depalléthrine, derris, desmedipham, desmetryn, desmetryne, d-fanshiluquebingjuzhi, diafenthiuron, dialifor, dialifos, diallate, diamidafos, dianat, diatomaceous earth, diatomite, diazinon, dibrom, dibutyl phthalate, dibutyl succinate, dicamba, dicapthon, dichlobenil, dichlofenthion, dichlofluanid, dichlone, dichloralurea, dichlorbenzuron, dichlorfenidim, dichlorflurecol, dichlorflurenol, dichlormate, dichlormid, dichloromethane, dicloromezotiaz, dichlorophen, dichlorprop, dichlorprop-P, dichlorvos, dichlozolin, dichlozoline, diclobutrazol, diclocymet, diclofop, diclomezine, dicloran, diclosulam, dicofol, dicophane, dicoumarol, dicresyl, dicrotophos, dicryl, dicumarol, dicyclanil, dicyclonon, dieldrin, dienochlor, diethamquat, diethatyl, diethion, diéthion, diethofencarb, dietholate, diéthon, diethyl pyrocarbonate, diethyltoluamide, difenacoum, difenoconazole, difenopenten, difenoxuron, difenzoquat, difethialone, diflovidazin, diflubenzuron, diflufenican, diflufenicanil, diflufenzopyr, diflumetorim, dikegulac, dilor, dimatif, dimefluthrin, dimefox, dimefuron, dimehypo, dimepiperate, dimetachlone, dimetan, dimethacarb, dimethachlone, dimethachlor, dimethametryn, dimethenamid, dimethenamid-P, dimethipin, dimethirimol, dimethoate, dimethomorph, dimethrin, dimethyl carbate, dimethyl disulfide, dimethyl phthalate, dimethylvinphos, dimetilan, dimexano, dimidazon, dimoxystrobin, dimpylate, dimuron, dinex, dingjunezuo, diniconazole, diniconazole-M, dinitramine, dinitrophenols, dinobuton, dinocap, dinocap-4, dinocap-6, dinocton, dinofenate, dinopenton, dinoprop, dinosam, dinoseb, dinosulfon, dinotefuran, dinoterb, dinoterbon, diofenolan, dioxabenzofos, dioxacarb, dioxathion, dioxation, diphacin, diphacinone, diphenadione, diphenamid, diphenamide, diphenyl sulfone, diphenylamine, diphenylsulphide, diprogulic acid, dipropalin, dipropetryn, dipterex, dipymetitrone, dipyrithione, diquat, disodium tetraborate, disosultap, disparlure, disugran, disul, disulfiram, disulfoton, ditalimfos, dithianon, dithicrofos, dithioether, dithiométon, dithiopyr, diuron, dixanthogen, d-limonene, DMDS, DMPA, DNOC, dodemorph, dodicin, dodine, dofenapyn, doguadine, dominicalure, doramectin, DPC, drazoxolon, DSMA, d-trans-allethrin, d-trans-resmethrin, dufulin, dymron, EBEP, EBP, ebufos, ecdysterone, echlomezol, EDB, EDC, EDDP, edifenphos, eglinazine, emamectin, EMPC, empenthrin, enadenine, endosulfan, endothal, endothall, endothion, endrin, enestroburin, enilconazole, enoxastrobin, ephirsulfonate, EPN, epocholeone, epofenonane, epoxiconazole, eprinomectin, epronaz, EPTC, erbon, ergocalciferol, erlujixiancaoan, esdépalléthrine, esfenvalerate, ESP, esprocarb, etacelasil, etaconazole, etaphos, etem, ethaboxam, ethachlor, ethalfluralin, ethametsulfuron, ethaprochlor, ethephon, ethidimuron, ethiofencarb, ethiolate, ethion, ethiozin, ethiprole, ethirimol, ethoate-methyl, ethobenzanid, ethofumesate, ethohexadiol, ethoprop, ethoprophos, ethoxyfen, ethoxyquin, ethoxysulfuron, ethychlozate, ethyl formate, ethyl pyrophosphate, ethylan, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, ETM, etnipromid, etobenzanid, etofenprox, etoxazole, etridiazole, etrimfos, étrimphos, eugenol, EXD, famoxadone, famphur, fenac, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorphos, fenclofos, fenclorim, fenethacarb, fenfluthrin, fenfuram, fenhexamid, fenidin, fenitropan, fenitrothion, fénizon, fenjuntong, fenobucarb, fenolovo, fenoprop, fenothiocarb, fenoxacrim, fenoxanil, fenoxaprop, fenoxaprop-P, fenoxasulfone, fenoxycarb, fenpiclonil, fenpirithrin, fenpropathrin, fenpropidin, fenpropimorph, fenpyrazamine, fenpyroximate, fenquinotrione, fenridazon, fenson, fensulfothion, fenteracol, fenthiaprop, fenthion, fenthion-ethyl, fentiaprop, fentin, fentrazamide, fentrifanil, fenuron, fenuron-TCA, fenvalerate, ferbam, ferimzone, ferric phosphate, ferrous sulfate, fipronil, flamprop, flamprop-M, flazasulfuron, flocoumafen, flometoquin, flonicamid, florasulam, fluacrypyrim, fluazifop, fluazifop-P, fluazinam, fluazolate, fluazuron, flubendiamide, flubenzimine, flubrocythrinate, flucarbazone, flucetosulfuron, fluchloralin, flucofuron, flucycloxuron, flucythrinate, fludioxonil, fluénéthyl, fluenetil, fluensulfone, flufenacet, flufenerim, flufenican, flufenoxuron, flufenoxystrobin, flufenprox, flufenpyr, flufenzine, flufiprole, fluhexafon, flumethrin, flumetover, flumetralin, flumetsulam, flumezin, flumiclorac, flumioxazin, flumipropyn, flumorph, fluometuron, fluopicolide, fluopyram, fluorbenside, fluoridamid, fluoroacetamide, fluoroacetic acid, fluorochloridone, fluorodifen, fluoroglycofen, fluoroimide, fluoromide, fluoromidine, fluoronitrofen, fluoroxypyr, fluothiuron, fluotrimazole, fluoxastrobin, flupoxam, flupropacil, flupropadine, flupropanate, flupyradifurone, flupyrsulfuron, fluquinconazole, fluralaner, flurazole, flurecol, flurenol, fluridone, flurochloridone, fluromidine, fluroxypyr, flurprimidol, flursulamid, flurtamone, flusilazole, flusulfamide, flutenzine, fluthiacet, fluthiamide, flutianil, flutolanil, flutriafol, fluvalinate, fluxapyroxad, fluxofenim, folpel, folpet, fomesafen, fonofos, foramsulfuron, forchlorfenuron, formaldehyde, formetanate, formothion, formparanate, fosamine, fosetyl, fosmethilan, fospirate, fosthiazate, fosthietan, frontalin, fthalide, fuberidazole, fucaojing, fucaomi, fujunmanzhi, fulumi, fumarin, funaihecaoling, fuphenthiourea, furalane, furalaxyl, furamethrin, furametpyr, furan tebufenozide, furathiocarb, furcarbanil, furconazole, furconazole-cis, furethrin, furfural, furilazole, furmecyclox, furophanate, furyloxyfen, gamma-BHC, gamma-cyhalothrin, gamma-HCH, genit, gibberellic acid, gibberellin A3, gibberellins, gliftor, glitor, glucochloralose, glufosinate, glufosinate-P, glyodin, glyoxime, glyphosate, glyphosine, gossyplure, grandlure, griseofulvin, guanoctine, guazatine, halacrinate, halauxifen, halfenprox, halofenozide, halosafen, halosulfuron, haloxydine, haloxyfop, haloxyfop-P, haloxyfop-R, HCA, HCB, HCH, hemel, hempa, HEOD, heptachlor, heptafluthrin, heptenophos, heptopargil, herbimycin, herbimycin A, heterophos, hexachlor, hexachloran, hexachloroacetone, hexachlorobenzene, hexachlorobutadiene, hexachlorophene, hexaconazole, hexaflumuron, hexafluoramin, hexaflurate, hexalure, hexamide, hexazinone, hexylthiofos, hexythiazox, HHDN, holosulf, homobrassinolide, huancaiwo, huanchongjing, huangcaoling, huanjunzuo, hydramethylnon, hydrargaphen, hydrated lime, hydrogen cyanamide, hydrogen cyanide, hydroprene, hydroxyisoxazole, hymexazol, hyquincarb, IAA, IBA, IBP, icaridin, imazalil, imazamethabenz, imazamox, imazapic, imazapyr, imazaquin, imazethapyr, imazosulfuron, imibenconazole, imicyafos, imidacloprid, imidaclothiz, iminoctadine, imiprothrin, inabenfide, indanofan, indaziflam, indoxacarb, inezin, infusorial earth, iodobonil, iodocarb, iodofenphos, iodomethane, iodosulfuron, iofensulfuron, ioxynil, ipazine, IPC, ipconazole, ipfencarbazone, iprobenfos, iprodione, iprovalicarb, iprymidam, ipsdienol, ipsenol, IPSP, IPX, isamidofos, isazofos, isobenzan, isocarbamid, isocarbamide, isocarbophos, isocil, isodrin, isofenphos, isofenphos-methyl, isofetamid, isolan, isomethiozin, isonoruron, isopamphos, isopolinate, isoprocarb, isoprocil, isopropalin, isopropazol, isoprothiolane, isoproturon, isopyrazam, isopyrimol, isothioate, isotianil, isouron, isovaledione, isoxaben, isoxachlortole, isoxadifen, isoxaflutole, isoxapyrifop, isoxathion, isuron, ivermectin, ixoxaben, izopamfos, izopamphos, japonilure, japothrins, jasmolin I, jasmolin II, jasmonic acid, jiahuangchongzong, jiajizengxiaolin, jiaxiangjunzhi, jiecaowan, jiecaoxi, Jinganmycin A, jodfenphos, juvenile hormone I, juvenile hormone II, juvenile hormone III, kadethrin, kappa-bifenthrin, kappa-tefluthrin, karbutilate, karetazan, kasugamycin, kejunlin, kelevan, ketospiradox, kieselguhr, kinetin, kinoprene, kiralaxyl, kresoxim-methyl, kuicaoxi, lactofen, lambda-cyhalothrin, latilure, lead arsenate, lenacil, lepimectin, leptophos, lianbenjingzhi, lime sulfur, lindane, lineatin, linuron, lirimfos, litlure, looplure, lufenuron, lüxiancaolin, lvdingjunzhi, lvfumijvzhi, lvxiancaolin, lythidathion, M-74, M-81, MAA, magnesium phosphide, malathion, maldison, maleic hydrazide, malonoben, maltodextrin, MAMA, mancopper, mancozeb, mandestrobin, mandipropamid, maneb, matrine, mazidox, MCC, MCP, MCPA, MCPA-thioethyl, MCPB, MCPP, mebenil, mecarbam, mecarbinzid, mecarphon, mecoprop, mecoprop-P, medimeform, medinoterb, medlure, mefenacet, mefenoxam, mefenpyr, mefluidide, megatomoic acid, melissyl alcohol, melitoxin, MEMC, menazon, MEP, mepanipyrim, meperfluthrin, mephenate, mephosfolan, mepiquat, mepronil, meptyldinocap, mercaptodimethur, mercaptophos, mercaptophos thiol, mercaptothion, mercuric chloride, mercuric oxide, mercurous chloride, merphos, merphos oxide, mesoprazine, mesosulfuron, mesotrione, mesulfen, mesulfenfos, mesulphen, metacresol, metaflumizone, metalaxyl, metalaxyl-M, metaldehyde, metam, metamifop, metamitron, metaphos, metaxon, metazachlor, metazosulfuron, metazoxolon, metconazole, metepa, metflurazon, methabenzthiazuron, methacrifos, methalpropalin, metham, methamidophos, methasulfocarb, methazole, methfuroxam, methibenzuron, methidathion, methiobencarb, methiocarb, methiopyrisulfuron, methiotepa, methiozolin, methiuron, methocrotophos, métholcarb, methometon, methomyl, methoprene, methoprotryn, methoprotryne, methoquin-butyl, methothrin, methoxychlor, methoxyfenozide, methoxyphenone, methyl apholate, methyl bromide, methyl eugenol, methyl iodide, methyl isothiocyanate, methyl parathion, methylacetophos, methylchloroform, methyldithiocarbamic acid, methyldymron, methylene chloride, methyl-isofenphos, methylmercaptophos, methylmercaptophos oxide, methylmercaptophos thiol, methylmercury benzoate, methylmercury dicyandiamide, methylmercury pentachlorophenoxide, methylneodecanamide, methylnitrophos, methyltriazothion, metiozolin, metiram, metiram-zinc, metobenzuron, metobromuron, metofluthrin, metolachlor, metolcarb, metometuron, metominostrobin, metosulam, metoxadiazone, metoxuron, metrafenone, metriam, metribuzin, metrifonate, metriphonate, metsulfovax, metsulfuron, mevinphos, mexacarbate, miechuwei, mieshuan, miewenjuzhi, milbemectin, milbemycin oxime, milneb, mima2nan, mipafox, MIPC, mirex, MNAF, moguchun, molinate, molosultap, momfluorothrin, monalide, monisuron, monoamitraz, monochloroacetic acid, monocrotophos, monolinuron, monomehypo, monosulfiram, monosulfuron, monosultap, monuron, monuron-TCA, morfamquat, moroxydine, morphothion, morzid, moxidectin, MPMC, MSMA, MTMC, muscalure, myclobutanil, myclozolin, myricyl alcohol, N-(ethylmercury)-p-toluenesulphonanilide, NAA, NAAm, nabam, naftalofos, naled, naphthalene, naphthalic anhydride, naphthalophos, naphthoxyacetic acids, naphthylacetic acids, naphthylindane-1,3-diones, naphthyloxyacetic acids, naproanilide, napropamide, napropamide-M, naptalam, natamycin, NBPOS, neburea, neburon, nendrin, neonicotine, nichlorfos, niclofen, niclosamide, nicobifen, nicosulfuron, nicotine, nicotine sulfate, nifluridide, nikkomycins, NIP, nipyraclofen, nipyralofen, nitenpyram, nithiazine, nitralin, nitrapyrin, nitrilacarb, nitrofen, nitrofluorfen, nitrostyrene, nitrothal-isopropyl, nobormide, nonanol, norbormide, norea, norflurazon, nornicotine, noruron, novaluron, noviflumuron, NPA, nuarimol, nuranone, OCH, octachlorodipropyl ether, octhilinone, o-dichlorobenzene, ofurace, omethoate, o-phenylphenol, orbencarb, orfralure, orthobencarb, ortho-dichlorobenzene, orthosulfamuron, oryctalure, orysastrobin, oryzalin, osthol, osthole, ostramone, ovatron, ovex, oxabetrinil, oxadiargyl, oxadiazon, oxadixyl, oxamate, oxamyl, oxapyrazon, oxapyrazone, oxasulfuron, oxathiapiprolin, oxaziclomefone, oxine-copper, oxine-Cu, oxolinic acid, oxpoconazole, oxycarboxin, oxydemeton-methyl, oxydeprofos, oxydisulfoton, oxyenadenine, oxyfluorfen, oxymatrine, oxytetracycline, oxythioquinox, PAC, paclobutrazol, paichongding, palléthrine, PAP, para-dichlorobenzene, parafluron, paraquat, parathion, parathion-methyl, parinol, Paris green, PCNB, PCP, PCP-Na, p-dichlorobenzene, PDJ, pebulate, pédinex, pefurazoate, pelargonic acid, penconazole, pencycuron, pendimethalin, penfenate, penflufen, penfluron, penoxalin, penoxsulam, pentachlorophenol, pentachlorophenyl laurate, pentanochlor, penthiopyrad, pentmethrin, pentoxazone, perchlordecone, perfluidone, permethrin, pethoxamid, PHC, phenamacril, phenamacril-ethyl, phénaminosulf, phenazine oxide, phénétacarbe, phenisopham, phenkapton, phenmedipham, phenmedipham-ethyl, phenobenzuron, phenothiol, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosametine, phosazetim, phosazetin, phoscyclotin, phosdiphen, phosethyl, phosfolan, phosfolan-methyl, phosglycin, phosmet, phosnichlor, phosphamide, phosphamidon, phosphine, phosphinothricin, phosphocarb, phosphorus, phostin, phoxim, phoxim-methyl, phthalide, phthalophos, phthalthrin, picarbutrazox, picaridin, picloram, picolinafen, picoxystrobin, pimaricin, pindone, pinoxaden, piperalin, piperazine, piperonyl butoxide, piperonyl cyclonene, piperophos, piproctanly, piproctanyl, piprotal, pirimetaphos, pirimicarb, piriminil, pirimioxyphos, pirimiphos-ethyl, pirimiphos-methyl, pival, pivaldione, plifenate, PMA, PMP, polybutenes, polycarbamate, polychlorcamphene, polyethoxyquinoline, polyoxin D, polyoxins, polyoxorim, polythialan, potassium arsenite, potassium azide, potassium cyanate, potassium ethylxanthate, potassium naphthenate, potassium polysulfide, potassium thiocyanate, pp'-DDT, prallethrin, precocene I, precocene II, precocene III, pretilachlor, primidophos, primisulfuron, probenazole, prochloraz, proclonol, procyazine, procymidone, prodiamine, profenofos, profluazol, profluralin, profluthrin, profoxydim, profurite-aminium, proglinazine, prohexadione, prohydrojasmon, promacyl, promecarb, prometon, prometryn, prometryne, promurit, pronamide, propachlor, propafos, propamidine, propamocarb, propanil, propaphos, propaquizafop, propargite, proparthrin, propazine, propetamphos, propham, propiconazole, propidine, propineb, propisochlor, propoxur, propoxycarbazone, propyl isome, propyrisulfuron, propyzamide, proquinazid, prosuler, prosulfalin, prosulfocarb, prosulfuron, prothidathion, prothiocarb, prothioconazole, prothiofos, prothoate, protrifenbute, proxan, prymidophos, prynachlor, psoralen, psoralene, pydanon, pyflubumide, pymetrozine, pyracarbolid, pyraclofos, pyraclonil, pyraclostrobin, pyraflufen, pyrafluprole, pyramat, pyrametostrobin, pyraoxystrobin, pyrasulfotole, pyraziflumid, pyrazolate, pyrazolynate, pyrazon, pyrazophos, pyrazosulfuron, pyrazothion, pyrazoxyfen, pyresmethrin, pyrethrin I, pyrethrin II, pyrethrins, pyribambenz-isopropyl, pyribambenz-propyl, pyribencarb, pyridalyl, pyributicarb, pyriclor, pyridaben, pyridafol, pyridalyl, pyridaphenthion, pyridaphenthione, pyridate, pyridinitril, pyrifenox, pyrifluquinazon, pyriftalid, pyrimétaphos, pyrimethanil, pyrimicarbe, pyrimidifen, pyriminobac, pyriminostrobin, pyrimiphos-ethyl, pyrimiphos-méthyl pyrimisulfan, pyrimitate, pyrinuron, pyriofenone, pyriprole, pyripropanol, pyriproxyfen, pyrisoxazole, pyrithiobac, pyrolan, pyroquilon, pyroxasulfone, pyroxsulam, pyroxychlor, pyroxyfur, qincaosuan, qingkuling, quassia, quinacetol, quinalphos, quinalphos-methyl, quinazamid, quinclorac, quinconazole, quinmerac, quinoclamine, quinomethionate, quinonamid, quinothion, quinoxyfen, quintiofos, quintozene, quizalofop, quizalofop-P, quwenzhi, quyingding, rabenzazole, rafoxanide, R-diniconazole, rebemide, reglone, renriduron, rescalure, resmethrin, rhodethanil, rhodojaponin-III, ribavirin, rimsulfuron, rizazole, R-metalaxyl, rodéthanil, ronnel, rotenone, ryania, sabadilla, saflufenacil, saijunmao, saisentong, salicylanilide, salifluofen, sanguinarine, santonin, S-bioallethrin, schradan, scilliroside, sebuthylazine, secbumeton, sedaxane, selamectin, semiamitraz, sesamex, sesamolin, sesone, sethoxydim, sevin, shuangjiaancaolin, shuangjianancaolin, S-hydroprene, siduron, sifumijvzhi, siglure, silafluofen, silatrane, silica aerogel, silica gel, silthiofam, silthiopham, silthiophan, silvex, simazine, simeconazole, simeton, simetryn, simetryne, sintofen, S-kinoprene, slaked lime, SMA, S-methoprene, S-metolachlor, sodium arsenite, sodium azide, sodium chlorate, sodium cyanide, sodium fluoride, sodium fluoroacetate, sodium hexafluorosilicate, sodium naphthenate, sodium o-phenylphenoxide, sodium orthophenylphenoxide, sodium pentachlorophenate, sodium pentachlorophenoxide, sodium polysulfide, sodium silicofluoride, sodium tetrathiocarbonate, sodium thiocyanate, solan, sophamide, spinetoram, spinosad, spirodiclofen, spiromesifen, spirotetramat, spiroxamine, stirofos, streptomycin, strychnine, sulcatol, sulcofuron, sulcotrione, sulfallate, sulfentrazone, sulfiram, sulfluramid, sulfodiazole, sulfometuron, sulfosate, sulfosulfuron, sulfotep, sulfotepp, sulfoxaflor, sulfoxide, sulfoxime, sulfur, sulfuric acid, sulfuryl fluoride, sulglycapin, sulphosate, sulprofos, sultropen, swep, tau-fluvalinate, tavron, tazimcarb, TBTO, TBZ, TCA, TCBA, TCMTB, TCNB, TDE, tebuconazole, tebufenozide, tebufenpyrad, tebufloquin, tebupirimfos, tebutam, tebuthiuron, tecloftalam, tecnazene, tecoram, tedion, teflubenzuron, tefluthrin, tefuryltrione, tembotrione, temefos, temephos, tepa, TEPP, tepraloxydim, teproloxydim, terallethrin, terbacil, terbucarb, terbuchlor, terbufos, terbumeton, terbuthylazine, terbutol, terbutryn, terbutryne, terraclor, terramicin, terramycin, tetcyclacis, tetrachloroethane, tetrachlorvinphos, tetraconazole, tetradifon, tetradisul, tetrafluron, tetramethrin, tetramethylfluthrin, tetramine, tetranactin, tetraniliprole, tetrapion, tetrasul, thallium sulfate, thallous sulfate, thenylchlor, theta-cypermethrin, thiabendazole, thiacloprid, thiadiazine, thiadifluor, thiamethoxam, thiameturon, thiapronil, thiazafluron, thiazfluron, thiazone, thiazopyr, thicrofos, thicyofen, thidiazimin, thidiazuron, thiencarbazone, thifensulfuron, thifluzamide, thimerosal, thimet, thiobencarb, thiocarboxime, thiochlorfenphim, thiochlorphenphime, thiocyanatodinitrobenzenes, thiocyclam, thiodan, thiodiazole-copper, thiodicarb, thiofanocarb, thiofanox, thiofluoximate, thiohempa, thiomersal, thiometon, thionazin, thiophanate, thiophanate-ethyl, thiophanate-methyl, thiophos, thioquinox, thiosemicarbazide, thiosultap, thiotepa, thioxamyl, thiram, thiuram, thuringiensin, tiabendazole, tiadinil, tiafenacil, tiaojiean, TIBA, tifatol, tiocarbazil, tioclorim, tioxazafen, tioxymid, tirpate, TMTD, tolclofos-methyl, tolfenpyrad, tolprocarb, tolpyralate, tolyfluanid, tolylfluanid, tolylmercury acetate, tomarin, topramezone, toxaphene, TPN, tralkoxydim, tralocythrin, tralomethrin, tralopyril, transfluthrin, transpermethrin, tretamine, triacontanol, triadimefon, triadimenol, triafamone, triallate, triallate, triamiphos, triapenthenol, triarathene, triarimol, triasulfuron, triazamate, triazbutil, triaziflam, triazophos, triazothion, triazoxide, tribasic copper chloride, tribasic copper sulfate, tribenuron, tribufos, tributyltin oxide, tricamba, trichlamide, trichlopyr, trichlorfon, trichlormetaphos-3, trichloronat, trichloronate, trichlorotrinitrobenzenes, trichlorphon, triclopyr, triclopyricarb, tricresol, tricyclazole, tricyclohexyltin hydroxide, tridemorph, tridiphane, trietazine, trifenmorph, trifenofos, trifloxystrobin, trifloxysulfuron, trifludimoxazin, triflumezopyrim, triflumizole, triflumuron, trifluralin, triflusulfuron, trifop, trifopsime, triforine, trihydroxytriazine, trimedlure, trimethacarb, trimeturon, trinexapac, triphenyltin, triprene, tripropindan, triptolide, tritac, trithialan, triticonazole, tritosulfuron, trunc-call, tuoyelin, uniconazole, uniconazole-P, urbacide, uredepa, valerate, validamycin, validamycin A, valifenalate, valone, vamidothion, vangard, vaniliprole, vernolate, vinclozolin, vitamin D3, warfarin, xiaochongliulin, xinjunan, xiwojunan, xiwojunzhi, XMC, xylachlor, xylenols, xylylcarb, xymiazole, yishijing, zarilamid, zeatin, zengxiaoan, zengxiaolin, zeta-cypermethrin, zinc naphthenate, zinc phosphide, zinc thiazole, zinc thiozole, zinc trichlorophenate, zinc trichlorophenoxide, zineb, ziram, zolaprofos, zoocoumarin, zoxamide, zuoanjunzhi, zuocaoan, zuojunzhi, zuomihuanglong, α-chlorohydrin, α-ecdysone, α-multistriatin, α-naphthaleneacetic acids, and β-ecdysone;

(2) the following molecule

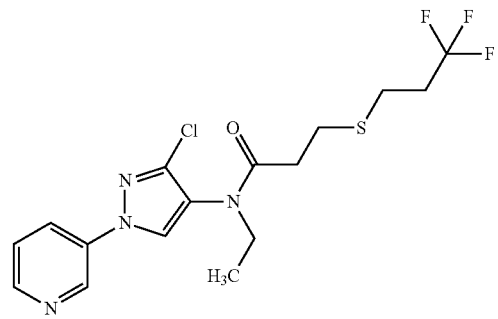 [SMILES: CCN(C(=O)CCSCCC(F)(F)F)c1cn(-c2cccnc2)nc1Cl]

N-(3-chloro-1-(pyridin-3-yl)-1H-pyrazol-4-yl)-N-ethyl-3-((3,3,3-trifluoropropyl)thio)propanamide In this document, this molecule, for ease of use, is named as "AI-1;"

(3) a molecule known as lotilaner which has the following structure

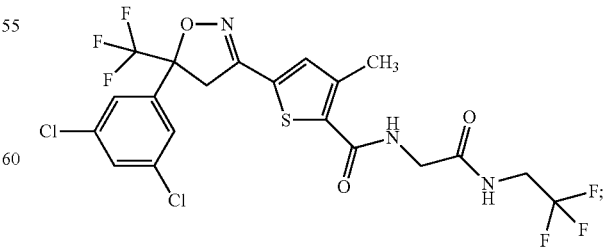

and (4) the following molecules in Table A

TABLE A
Structure of M - active ingredients
| Name | Structure |
|---|---|
| M1 | 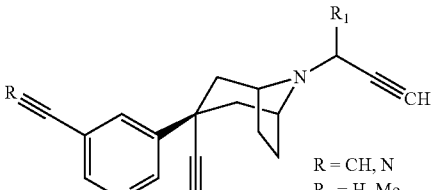 R = CH, N; R₁ = H, Me |
| M2 | 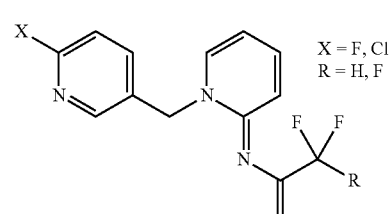 X = F, Cl; R = H, F |
| M3 | 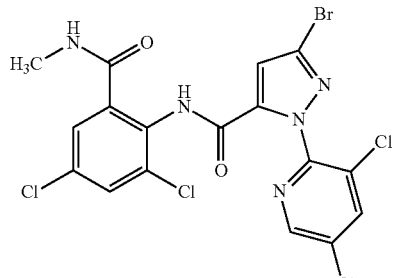 |
| M4 | 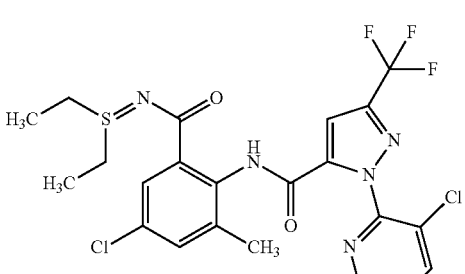 |
| M5 | 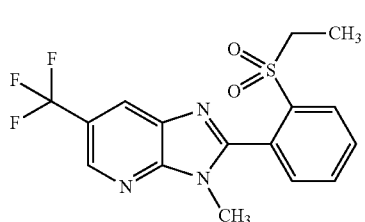 |
| M6 | 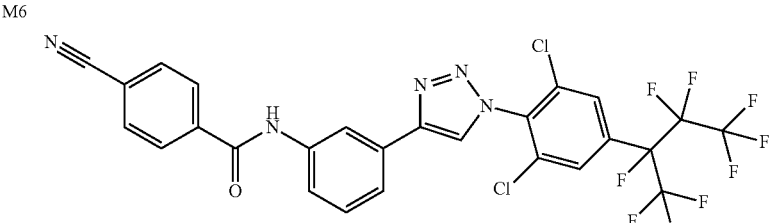 |

As used in this disclosure, each of the above is an active ingredient, and two or more are active ingredients. For more information consult the "COMPENDIUM OF PESTICIDE COMMON NAMES" located at Alanwood.net and various editions, including the on-line edition, of "THE PESTICIDE MANUAL" located at bcpcdata.com.

"alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"alkenyloxy" means an alkenyl further consisting of a carbon-oxygen single bond, for example, allyloxy, butenyloxy, pentenyloxy, hexenyloxy.

"alkoxy" means an alkyl further consisting of a carbon-oxygen single bond, for example, methoxy, ethoxy, propoxy, isopropoxy, butoxy, isobutoxy, and tert-butoxy.

"alkyl" means an acyclic, saturated, branched or unbranched, substituent consisting of carbon and hydrogen, for example, methyl, ethyl, propyl, isopropyl, butyl, and tert-butyl.

"alkynyl" means an acyclic, unsaturated (at least one carbon-carbon triple bond), branched or unbranched, substituent consisting of carbon and hydrogen, for example, ethynyl, propargyl, butynyl, and pentynyl.

"alkynyloxy" means an alkynyl further consisting of a carbon-oxygen single bond, for example, pentynyloxy, hexynyloxy, heptynyloxy, and octynyloxy.

"aryl" means a cyclic, aromatic substituent consisting of hydrogen and carbon, for example, phenyl, naphthyl, and biphenyl.

"biopesticide" means a microbial biological pest control agent which, in general, is applied in a similar manner to chemical pesticides. Commonly they are bacterial, but there are also examples of fungal control agents, including *Trichoderma* spp. and *Ampelomyces quisqualis*. One well-known biopesticide example is *Bacillus thuringiensis*, a bacterial disease of Lepidoptera, Coleoptera, and Diptera. Biopesticides include products based on:
(1) entomopathogenic fungi (e.g. *Metarhizium anisopliae*);
(2) entomopathogenic nematodes (e.g. *Steinemema feltiae*); and
(3) entomopathogenic viruses (e.g. *Cydia pomonella* granulovirus).

Other examples of entomopathogenic organisms include, but are not limited to, baculoviruses, protozoa, and Microsproridia. For the avoidance of doubt biopesticides are consider to be active ingredients.

"cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"halo" means fluoro, chloro, bromo, and iodo.

"haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"heterocyclyl" means a cyclic substituent that may be aromatic, fully saturated, or partially or fully unsaturated, where the cyclic structure contains at least one carbon and at least one heteroatom, where said heteroatom is nitrogen, sulfur, or oxygen. Examples are:
(1) aromatic heterocyclyl substituents include, but are not limited to, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl;
(2) fully saturated heterocyclyl substituents include, but are not limited to, piperazinyl, piperidinyl, morpholinyl, pyrrolidinyl, tetrahydrofuranyl, and tetrahydropyranyl;
(3) partially or fully unsaturated heterocyclyl substituents include, but are not limited to, 1,2,3,4-tetrahydro-quinolinyl, 4,5-dihydro-oxazolyl, 4,5-dihydro-1H-pyrazolyl, 4,5-dihydro-isoxazolyl, and 2,3-dihydro-[1,3,4]-oxadiazolyl; and
(4) Additional examples of heterocyclyls include the following:

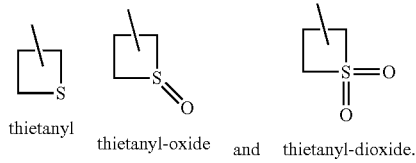

thietanyl    thietanyl-oxide   and   thietanyl-dioxide.

"locus" means a habitat, breeding ground, plant, seed, soil, material, or environment, in which a pest is growing, may grow, or may traverse, for example, a locus may be: where crops, trees, fruits, cereals, fodder species, vines, turf, and/or ornamental plants, are growing; where domesticated animals are residing; the interior or exterior surfaces of buildings (such as places where grains are stored); the materials of construction used in buildings (such as impregnated wood); and the soil around buildings.

"MoA Material" means a material having a mode of action ("MoA") as indicated in IRAC MoA Classification v. 7.3, located at irac-online.org., which describes:
(1) Acetylcholinesterase (AChE) inhibitors;
(2) GABA-gated chloride channel antagonists;
(3) Sodium channel modulators;
(4) Nicotinic acetylcholine receptor (nAChR) agonists;
(5) Nicotinic acetylcholine receptor (nAChR) allosteric activators;
(6) Chloride channel activators;
(7) Juvenile hormone mimics;
(8) Miscellaneous nonspecific (multi-site) inhibitors;
(9) Modulators of Chordotonal Organs;
(10) Mite growth inhibitors;
(11) Microbial disruptors of insect midgut membranes;
(12) Inhibitors of mitochondrial ATP synthase;
(13) Uncouplers of oxidative phosphorylation via disruption of the proton gradient;
(14) Nicotinic acetylcholine receptor (nAChR) channel blockers;
(15) Inhibitors of chitin biosynthesis, type 0;

(16) Inhibitors of chitin biosynthesis, type 1;
(17) Moulting disruptor, Dipteran;
(18) Ecdysone receptor agonists;
(19) Octopamine receptor agonists;
(20) Mitochondrial complex III electron transport inhibitors;
(22) Mitochondrial complex I electron transport inhibitors;
(23) Voltage-dependent sodium channel blockers;
(24) Inhibitors of acetyl CoA carboxylase;
(25) Mitochondrial complex IV electron transport inhibitors;
(26) Mitochondrial complex II electron transport inhibitors; and
(27) Ryanodine receptor modulators.

"MoA material group alpha" (hereafter "MoAMGA") means collectively the following materials, abamectin, acephate, acequinocyl, acetamiprid, acrinathrin, alanycarb, aldicarb, allethrin, alpha-Cypermethrin, aluminium phosphide, amitraz, azamethiphos, azinphos-ethyl, azinphos-methyl, azocyclotin, bendiocarb, benfuracarb, bensultap, beta-cyfluthrin, beta-cypermethrin, bifenthrin, bioallethrin, bioallethrin S-cyclopentenyl isomer, bioresmethrin, bistrifluron, borax, buprofezin, butocarboxim, butoxycarboxim, cadusafos, calcium phosphide, carbaryl, carbofuran, carbosulfan, cartap hydrochloride, chlorantraniliprole, chlordane, chlorethoxyfos, chlorfenapyr, chlorfenvinphos, chlorfluazuron, chlormephos, chloropicrin, chlorpyrifos, chlorpyrifos-methyl, chromafenozide, clofentezine, clothianidin, coumaphos, cyanide, cyanophos, cyantraniliprole, cyclprothrin, cyenopyrafen, cyflumetofen, cyfluthrin, cyhalothrin, cyhexatin, cypermethrin, cyphenothrin, cyromazine, d-cis-trans allethrin, DDT, deltamethrin, demeton-S-methyl, diafenthiuron, diazinon, dichlorvos/DDVP, dicrotophos, diflovidazin, diflubenzuron, dimethoate, dimethylvinphos, dinotefuran, disulfoton, DNOC, d-trans allethrin, emamectin benzoate, empenthrin, endosulfan, EPN, esfenvalerate, ethiofencarb, ethion, ethoprophos, etofenprox, etoxazole, famphur, fenamiphos, fenazaquin, fenbutatin oxide, fenitrothion, fenobucarb, fenoxycarb, fenpropathrin, fenpyroximate, fenthion, fenvalerate, flonicamid, fluacrypyrim, flubendiamide, flucycloxuron, flucythrinate, flufenoxuron, flumethrin, flupyradifurone, formetanate, fosthiazate, furathiocarb, gamma-cyhalothrin, halfenprox, halofenozide, heptenophos, hexaflumuron, hexythiazox, hydramethylnon, hydroprene, imicyafos, imidacloprid, imiprothrin, indoxacarb, isofenphos, isoprocarb, isoxathion, kadethrin, kinoprene, lambda-cyhalothrin, lepimectin, lufenuron, malathion, mecarbam, metaflumizone, methamidophos, methidathion, methiocarb, methomyl, methoprene, (methoxyaminothio-phosphoryl) salicylate, methoxychlor, methoxyfenozide, methyl bromide, metolcarb, mevinphos, milbemectin, monocrotophos, naled, nicotine, nitenpyram, novaluron, noviflumuron, oxamyl, oxydemeton-methyl, parathion, parathion-methyl, permethrin, phenothrin, phenthoate, phorate, phosalone, phosmet, phosphamidon, phosphine, phoxim, pirimicarb, pirimiphos-methyl, prallethrin, profenofos, propargite, propetamphos, propoxur, prothiofos, pymetrozine, pyraclofos, pyrethrin, pyridaben, pyridaphenthion, pyrimidifen, pyriproxyfen, quinalphos, resmethrin, rotenone, silafluofen, spinetoram, spinosad, spirodiclofen, spiromesifen, spirotetramat, sulfluramid, sulfotep, sulfoxaflor, sulfuryl fluoride, tartar emetic, tau-fluvalinate, tebufenozide, tebufenpyrad, tebupirimfos, teflubenzuron, tefluthrin, temephos, terbufos, tetrachlorvinphos, tetradifon, tetramethrin, tetramethrin, theta-cypermethrin, thiacloprid, thiamethoxam, thiocyclam, thiodicarb, thiofanox, thiometon, thiosultap-sodium, tolfenpyrad, tralomethrin, transfluthrin, triazamate, triazophos, trichlorfon, triflumuron, trimethacarb, vamidothion, XMC, xylylcarb, zeta-cypermethrin, and zinc phosphide. For the avoidance of doubt, each of the foregoing materials is an active ingredient.

"pest" means an organism that is detrimental to humans, or human concerns (such as, crops, food, livestock, etc.), where said organism is from Phyla Arthropoda, Mollusca, or Nematoda, particular examples are ants, aphids, beetles, bristletails, cockroaches, crickets, earwigs, fleas, flies, grasshoppers, leafhoppers, lice, locusts, mites, moths, nematodes, scales, symphylans, termites, thrips, ticks, wasps, and whiteflies, additional examples are pests in:

(1) Subphyla Chelicerata, Myriapoda, and Hexapoda;
(2) Classes of Arachnida, Symphyla, and Insecta;
(3) Order Anoplura,
a non-exhaustive list of particular genera includes, but is not limited to, *Haematopinus* spp., *Hoplopleura* spp., *Linognathus* spp., *Pediculus* spp., and *Polyplax* spp.,
a non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*;

(4) Order Coleoptera,
a non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp.,
a non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcate, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile*, and *Zabrus tenebrioides*;

(5) Order Dermaptera;
(6) Order Blattaria,
a non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis*, and *Supella longipalpa*;

(7) Order Diptera,
a non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp., a non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana,* and *Stomoxys calcitrans;*

(8) Order Hemiptera, a non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp., a non-exhaustive list of particular species includes, but is not limited to, *Acrostemum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicomis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris califomicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana;*

(9) Order Hymenoptera, a non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp., a non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni,* and *Tapinoma sessile;*

(10) Order Isoptera, a non-exhaustive list of particular genera includes, but is not limited to, *Coptotermes* spp., *Comitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp., a non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus;*

(11) Order Lepidoptera, a non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Collas* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp., a non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transverse, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarps, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae,* and *Zeuzera pyrina;*

(12) Order Mallophaga, a non-exhaustive list of particular genera includes, but is not limited to, *Anaticola* spp., *Bovicola* spp., *Chelopistes* spp., *Goniodes* spp., *Menacanthus* spp., and *Trichodectes* spp., a non-exhaustive list of particular species includes, but is not limited to, *Bovicola bovis, Bovicola caprae, Bovicola*

*ovis, Chelopistes meleagridis, Goniodes dissimilis, Goniodes gigas, Menacanthus stramineus, Menopon gallinae,* and *Trichodectes canis;*

(13) Order Orthoptera, a non-exhaustive list of particular genera includes, but is not limited to, *Melanoplus* spp., and *Pterophylla* spp., a non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata;*

(14) Order Siphonaptera, a non-exhaustive list of particular species includes, but is not limited to, *Ceratophyllus gallinae, Ceratophyllus niger, Ctenocephalides canis, Ctenocephalides fells,* and *Pulex irritans;*

(15) Order Thysanoptera, a non-exhaustive list of particular genera includes, but is not limited to, *Caliothrips* spp., *Frankliniella* spp., *Scirtothrips* spp., and *Thrips* spp., a non-exhaustive list of particular species includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis, Taeniothrips rhopalantennalis, Thrips hawaiiensis, Thrips nigropilosus, Thrips orientalis,* and *Thrips tabaci;*

(16) Order Thysanura, a non-exhaustive list of particular genera includes, but is not limited to, *Lepisma* spp. and *Thermobia* spp.;

(17) Order Acarina, a non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp., a non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae,* and *Varroa destructor;*

(18) Order Symphyla, a non-exhaustive list of particular species includes, but is not limited to, *Scutigerella immaculata;*

(19) Phylum Nematoda, a non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp., a non-exhaustive list of particular sp. includes, but is not limited to, *Dirofilaria immitis, Heterodera zeae, Meloidogyne incognita, Meloidogyne javanica, Onchocerca volvulus, Radopholus similis,* and *Rotylenchulus reniformis.*

"pesticidally effective amount" means the amount of a pesticide needed to achieve an observable effect on a pest, for example, the effects of necrosis, death, retardation, prevention, removal, destruction, or otherwise diminishing the occurrence and/or activity of a pest in a locus, this effect may come about when, pest populations are repulsed from a locus, pests are incapacitated in, or around, a locus, and/or pests are exterminated in, or around, a locus. Of course, a combination of these effects can occur. Generally, pest populations, activity, or both are desirably reduced more than fifty percent, preferably more than 90 percent, and most preferably more than 99 percent. In general a pesticidally effective amount, for agricultural purposes, is from about 0.0001 grams per hectare to about 5000 grams per hectare, preferably from about 0.0001 grams per hectare to about 500 grams per hectare, and it is even more preferably from about 0.0001 grams per hectare to about 50 grams per hectare.

DETAILED DESCRIPTION OF THE DISCLOSURE

This document discloses molecules of Formula One

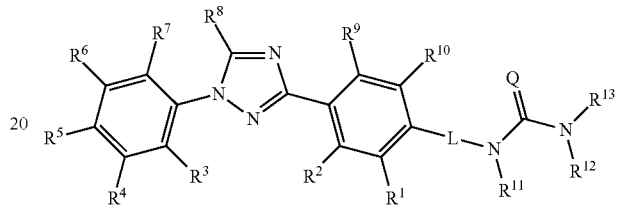

Formula One wherein:

(A) $R^1$, $R^2$, $R^3$, $R^4$, $R^5$, $R^6$, $R^7$, $R^9$, and $R^{10}$ are each independently selected from the group consisting of H, F, Cl, Br, I, CN, $NO_2$, OH, $(C_1-C_4)$alkyl, $(C_2-C_4)$alkenyl, $(C_1-C_4)$haloalkyl, $(C_1-C_4)$alkoxy, $(C_1-C_4)$haloalkoxy, and $(C_3-C_6)$cycloalkyl, wherein each alkyl, alkenyl, haloalkyl, alkoxy, haloalkoxy, and cycloalkyl, are optionally substituted with one or more substituents independently selected from F, Cl, Br, I, CN, $NO_2$, OH, $(C_1-C_4)$alkyl, $(C_2-C_4)$alkenyl, $(C_1-C_4)$haloalkyl, $(C_1-C_4)$alkoxy, $(C_1-C_4)$haloalkoxy, and $(C_3-C_6)$cycloalkyl;

(B) $R^8$ is H;

(C) L is selected from the group consisting of (1) a bond connecting nitrogen to carbon in the ring, and (2) a $(C_1-C_4)$alkyl wherein said alkyl is optionally substituted with one or more substituents independently selected from the group consisting of F, Cl, CN, OH, and oxo;

(D) $R^{11}$ and $R^{12}$ are each independently selected from the group consisting of H, $(C_1-C_4)$alkyl, $(C_2-C_4)$alkenyl, $(C_2-C_4)$alkenyloxy, $(C_2-C_4)$alkynyl, $(C_2-C_4)$alkynyloxy, $(C_1-C_4)$haloalkyl, $(C_1-C_4)$alkoxy, $(C_1-C_4)$haloalkoxy, $(C_3-C_6)$cycloalkyl, $(C_3-C_6)$cycloalkoxy, $(C_3-C_6)$cycloalkenyl, $(C_3-C_6)$cycloalkenyloxy, $((C_1-C_4)$alkyl$)((C_3-C_6)$cycloalkyl$)$, $C(O)((C_1-C_4)$alkyl$)$, $((C_1-C_4)$alkyl$)C(O)((C_1-C_4)$alkyl$)$, and $((C_1-C_4)$alkyl$)C(O)O((C_1-C_4)$alkyl$)$, wherein each alkyl, alkenyl, alkenyloxy, alkynyl, alkynyloxy, haloalkyl, alkoxy, haloalkoxy, cycloalkyl, cycloalkoxy, cycloalkenyl, and cycloalkenyloxy, are optionally substituted with one or more substituents independently selected from the group consisting of F, Cl, Br, I, CN, $NO_2$, OH, and oxo;

(E) $R^{13}$ is heterocyclyl, wherein said heterocyclyl is selected from the group consisting of dihydrofuranyl, furanyl, indazolyl, indolyl, imidazolyl, isoindolyl, isothiazolyl, isoxazolyl, oxadiazolyl, oxazolyl, pyrazolinyl, pyrazolyl, pyrrolyl, tetrazolyl, thiazolyl, thienyl, triazinyl, and triazolyl, wherein each heterocyclyl is optionally substituted with one or more substituents independently selected from the group consisting of oxo, $(C_1-C_8)$alkyl, $C(O)O(C_1-C_4)$alkyl, phenyl, and pyridyl, wherein each phenyl is optionally substituted with one or more substituents R, independently selected from the group consisting of F, Cl, Br, I, $(C_1-C_4)$alkyl, $(C_1-C_4)$alkoxy, and $(C_1-C_4)$haloalkoxy;

(F) Q is selected from the group consisting of O and S; and agriculturally acceptable acid addition salts, salt derivatives, solvates, ester derivatives, crystal polymorphs, isotopes, resolved stereoisomers, and tautomers, of the molecules of Formula One.

In another embodiment $R^1$, $R^2$, $R^3$, $R^4$, $R^6$, $R^7$, $R^8$, $R^9$, $R^{10}$, $R^{11}$, and $R^{12}$ are H. This embodiment may be used in combination with the other embodiments of $R^5$, $R^{13}$, L, and Q.

In another embodiment $R^5$ is $(C_1-C_4)$haloalkoxy. This embodiment may be used in combination with the other embodiments of $R^1$, $R^2$, $R^3$, $R^4$, $R^6$, $R^7$, $R^8$, $R^9$, $R^{10}$, $R^{11}$, $R^{12}$, $R^{13}$, L, and Q.

In another embodiment $R^5$ is $OCF_3$ or $OCF_2CF_3$. This embodiment may be used in combination with the other embodiments of $R^1$, $R^2$, $R^3$, $R^4$, $R^6$, $R^7$, $R^8$, $R^9$, $R^{10}$, $R^{11}$, $R^{12}$, $R^{13}$, L, and Q.

In another embodiment L is a bond. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, and Q.

In another embodiment L is —$CH_2CH_2$—. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, and Q.

In another embodiment Q is O. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, and Q.

In another embodiment Q is S. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, and Q.

In another embodiment $R^{13}$ is a heterocyclyl selected from the group consisting of dihydrofuranyl, imidazolyl, isoxazolyl, oxadiazolyl, oxazolyl, pyrazolyl, thienyl, or thiazolyl, that is optionally substituted with one or more substituents selected from the group consisting of oxo, $CH_3$, $CH(CH_3)CH_2CH(CH_3)_2$, $C(O)OCH_2CH_3$, phenyl, and pyridyl that is optionally substituted with one or more substituents R, selected from the group consisting of F, Cl, $CH_3$, $CH_2CH_3$, $CH(CH_3)_2$, $OCH_3$, and $OCF_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, L, and Q.

In another embodiment $R^{13}$ is heterocyclyl, wherein said heterocyclyl is selected from the group consisting of imidazolyl, isoxazolyl, oxadiazolyl, oxazolyl, pyrazolyl, thiazolyl, and thienyl, wherein each heterocyclyl is optionally substituted with one or more substituents independently selected from the group consisting of oxo, $(C_1-C_8)$alkyl, $C(O)O(C_1-C_4)$alkyl, phenyl, and pyridyl, wherein each phenyl is optionally substituted with one or more substituents R, independently selected from the group consisting of F, Cl, Br, I, $(C_1-C_4)$alkyl, $(C_1-C_4)$alkoxy, and $(C_1-C_4)$haloalkoxy. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, L, and Q.

In another embodiment:
(A) $R^1$, $R^2$, $R^3$, $R^4$, $R^5$, $R^6$, $R^7$, $R^9$, and $R^{10}$ and H;
(B) $R^8$ is H;
(C) L is selected from the group consisting of
 (1) a bond connecting nitrogen to carbon in the ring, and
 (2) a $(C_1-C_4)$alkyl;
(D) $R^{11}$ and $R^{12}$ are H;
(E) $R^{13}$ is heterocyclyl, wherein said heterocyclyl is selected from the group consisting of dihydrofuranyl, imidazolyl, isoxazolyl, oxadiazolyl, oxazolyl, pyrazolyl, thiazolyl, and thienyl, wherein each heterocyclyl is optionally substituted with one or more substituents independently selected from the group consisting of oxo, $(C_1-C_8)$alkyl, $C(O)O(C_1-C_4)$alkyl, phenyl, and pyridyl, wherein each phenyl is optionally substituted with one or more substituents R, independently selected from the group consisting of F, Cl, $(C_1-C_4)$alkyl, $(C_1-C_4)$alkoxy, and $(C_1-C_4)$haloalkoxy; and (F) Q is selected from the group consisting of O and S.

Preparation of Ureas and Thioureas

Ureas disclosed herein may be prepared from the corresponding isocyanates 1-2, wherein $R^1$, $R^2$, $R^3$, $R^4$, $R^5$, $R^6$, $R^7$, $R^8$, $R^9$, $R^{10}$, and L are as previously disclosed. In certain instances, isocyanates 1-2 are not isolated, but may be instead generated in situ from a suitable precursor and used directly in the preparation of a urea. Suitable precursors are amines 1-1, wherein $R^1$, $R^2$, $R^3$, $R^4$, $R^5$, $R^6$, $R^7$, $R^8$, $R^9$, $R^{10}$, and L are as previously disclosed, which may be converted into an isocyanate by using one of several common reagents such as phosgene, diphosgene, triphosgene, or oxalyl chloride (Scheme 1, step a), in a mixed solvent system comprising a polar aprotic solvent preferably dichloromethane or diethyl ether and a polar protic solvent preferably water, in the presence of a base such as sodium bicarbonate or triethylamine, at temperatures from about −10° C. to about 50° C.

Scheme 1

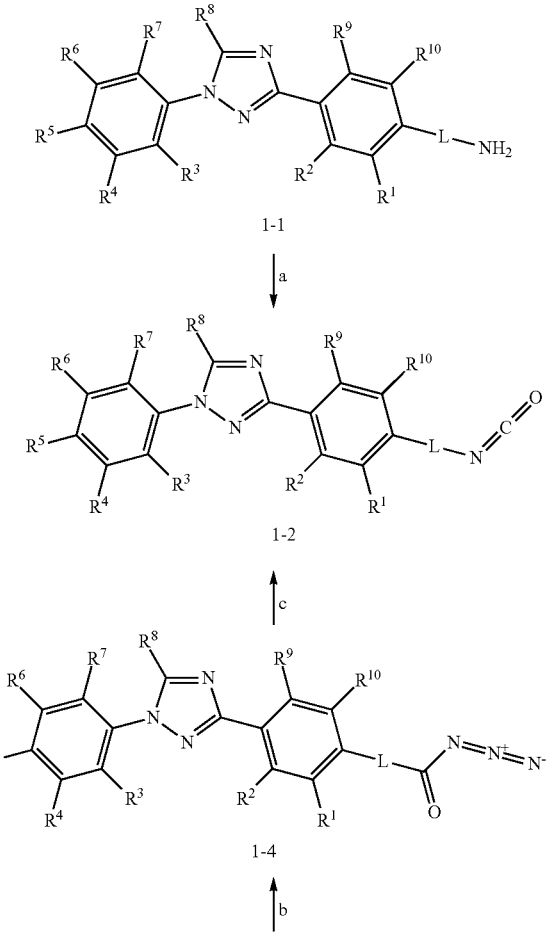

-continued

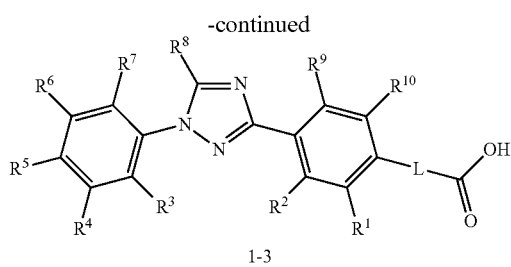

1-3

Alternatively, isocyanates 1-2 may be generated via a Curtius rearrangement of acyl azides 1-4, wherein $R^1$, $R^2$, $R^3$, $R^4$, $R^5$, $R^6$, $R^7$, $R^8$, $R^9$, $R^{10}$, and L are as previously disclosed, which, in turn, may be prepared from corresponding carboxylic acids 1-3, wherein $R^1$, $R^2$, $R^3$, $R^4$, $R^5$, $R^6$, $R^7$, $R^8$, $R^9$, $R^{10}$, and L are as previously disclosed. Formation of acyl azides 1-4 (Scheme 1, step b) may occur either by treatment of the carboxylic acid with ethyl chloroformate and sodium azide in the presence of an amine base such as triethylamine, or with diphenylphosphoryl azide in the presence of an amine base such as triethylamine. Acyl azides 1-4 may then undergo a Curtius rearrangement (Scheme 1, step c), leading to corresponding isocyanates 1-2. Depending on the nature of the particular acyl azide, this rearrangement may occur spontaneously at about room temperature (about 22° C.), or it may require heating from about 40° C. to about 100° C. in a polar aprotic solvent preferably toluene, acetonitrile, or an ethereal solvent preferably dioxane or tetrahydrofuran. Due to their reactivity, acyl azides are not often isolated as pure materials. Accordingly, acyl azides are not always fully characterized, but may simply be heated directly without characterization, to generate isocyanates 1-2.

Scheme 2

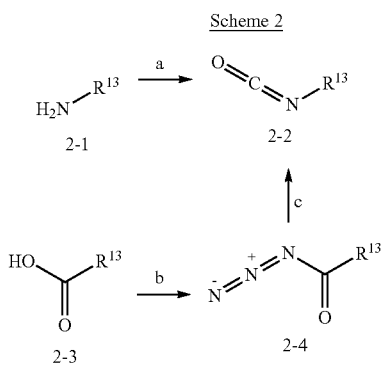

Ureas disclosed herein may also be prepared from the corresponding isocyanates 2-2, wherein $R^{13}$ is as previously disclosed. In certain instances, isocyanates 2-2 are not isolated, but may be instead generated in situ from a suitable precursor and used directly in the preparation of a urea. Suitable precursors are amines 2-1, wherein $R^{13}$ is as previously disclosed, which may be converted into an isocyanate by using one of several common reagents such as phosgene, diphosgene, triphosgene, or oxalyl chloride (Scheme 2, step a), in a mixed solvent system comprising a polar aprotic solvent preferably dichloromethane or diethyl ether and a polar protic solvent preferably water, in the presence of a base such as sodium bicarbonate or triethylamine, at temperatures from about −10° C. to about 50° C.

Alternatively, isocyanates 2-2 may also be generated via a Curtius rearrangement of acyl azides 2-4, wherein $R^{13}$ is as previously disclosed, which, in turn, may be prepared from corresponding carboxylic acids 2-3, wherein $R^{13}$ is as previously disclosed. Formation of acyl azides 2-4 (Scheme 2, step b) may occur either by treatment of the carboxylic acid with ethyl chloroformate and sodium azide in the presence of an amine base such as triethylamine, or with diphenylphosphoryl azide in the presence of an amine base such as triethylamine. Acyl azides 2-4 may then undergo a Curtius rearrangement (Scheme 2, step c), leading to corresponding isocyanates 2-2. Depending on the nature of the particular acyl azide, this rearrangement may occur spontaneously at about room temperature, or it may require heating from about 40° C. to about 100° C. in a polar aprotic solvent preferably toluene, acetonitrile, or an ethereal solvent preferably dioxane or tetrahydrofuran.

Isocyanates 1-2 may be treated directly with heterocyclyl amines 3-1, wherein $R^{12}$ and $R^{13}$ are as previously disclosed, either in the absence of base or in the presence of about 0.1 equivalents to about 2 equivalents of an inorganic base such as cesium carbonate or sodium hydride, or in the presence of an amine base such as triethylamine or diisopropylethylamine, or in the presence of an organometallic base such as n-butyllithium, resulting in the formation of ureas 3-2, wherein $R^{11}$ is H and $R^1$, $R^2$, $R^3$, $R^4$, $R^5$, $R^6$, $R^7$, $R^8$, $R^9$, $R^{10}$, $R^{12}$, $R^{13}$, and L are as previously disclosed (Scheme 3, step a). The reaction may be performed at temperatures from about 0° C. to about 100° C., preferably from about 20° C. to about 80° C., in a polar aprotic solvent such as acetonitrile, acetone, toluene, tetrahydrofuran, 1,2-dichloroethane, or dichloromethane. Alternatively, amines 3-3, wherein $R^1$, $R^2$, $R^3$, $R^4$, $R^5$, $R^6$, $R^7$, $R^8$, $R^9$, $R^{10}$, $R^{11}$ and L are as previously disclosed, may be treated with isocyanates 2-4 under similar conditions to provide ureas 3-2, wherein $R^{12}$ is H and $R^1$, $R^2$, $R^3$, $R^4$, $R^5$, $R^6$, $R^7$, $R^8$, $R^9$, $R^{10}$, $R^{11}$, $R^{13}$, and L are as previously disclosed (Scheme 3, step b).

Scheme 3

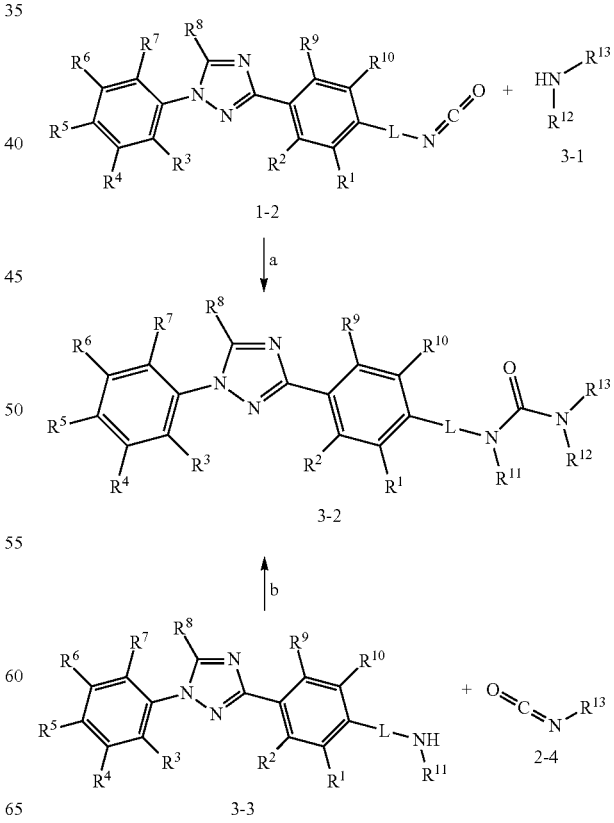

Alternatively, ureas 3-2 may be prepared by first preparing O-aryl carbamates of amines 3-3 using phenyl chloroformate or para-nitrophenyl chloroformates, followed by treatment with heterocyclyl amines 2-1 using conditions described above.

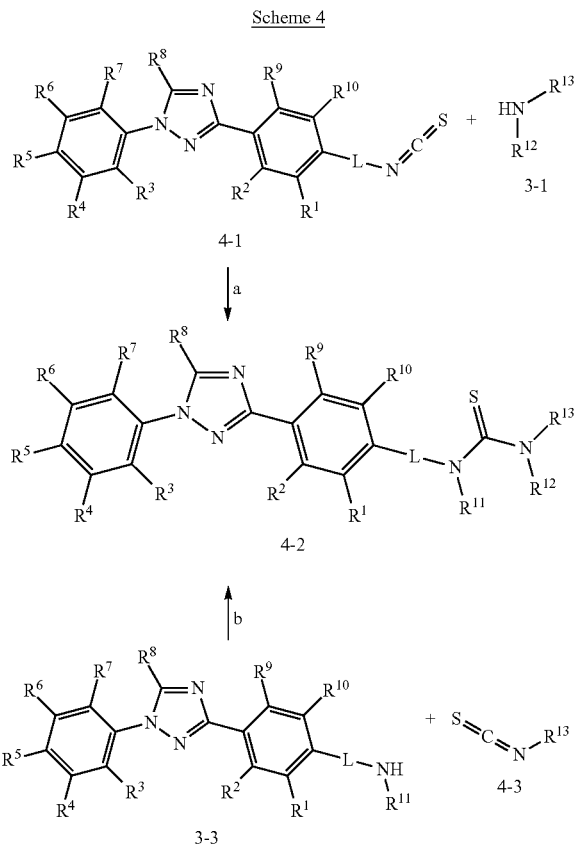

Thioureas 4-2, wherein $R^{11}$ is H and $R^1$, $R^2$, $R^3$, $R^4$, $R^5$, $R^6$, $R^7$, $R^8$, $R^9$, $R^{10}$, L, $R^{12}$ and $R^{13}$ are as previously disclosed, may be prepared from the corresponding aryl amines 3-1 by treatment with aryl isothiocyanates 4-1, wherein $R^1$, $R^2$, $R^3$, $R^4$, $R^5$, $R^6$, $R^7$, $R^8$, $R^9$, $R^{10}$, and L are as previously disclosed (Scheme 4, step a), under a variety of conditions. For example, heating the two intermediates in a polar aprotic solvent preferably tetrahydrofuran or dichloromethane or in a polar protic solvent preferably isopropyl alcohol, either without base or in the presence of an inorganic base such as cesium carbonate or potassium carbonate, or in the presence of an amine base such as triethylamine, at a temperature of from about 20° C. to about 65° C. for about 1 hour to about 24 hours. Alternatively, amines 3-3 may be combined with aryl isothiocyanates 4-3, wherein $R^{13}$ is as previously disclosed, under conditions similar to those described above, to produce a thioureas 4-2 (Scheme 4, step b).

Alternatively, thioureas 4-2 may be prepared by first preparing O-aryl thiocarbamates of amines 4-3 using phenyl chlorothionoformate, followed by treatment with aryl amines 4-1 using conditions described above.

Preparation of Tricyclic Intermediates

Molecules of Formula One may be prepared by making tricyclic intermediates and then linking them to appropriate intermediates to form desired molecules. A wide variety of tricyclic intermediates may be used to prepare molecules of Formula One, provided that such tricyclic intermediates contain a suitable functional group to which desired functional groups may be attached, functional groups such as amino, isocyanate, carboxyl, or halogen (preferably bromo or iodo). These tricyclic intermediates may be prepared by methods previously described in the chemical literature, including WO 2009/102736.

Tricyclic acids 1-3, wherein L is a bond, used as precursors in the preparation of the molecules of Formula One may be prepared according to procedures described in US 2012/0202688. Some of the procedures described above require use of tricyclic intermediates 5-4, wherein $R^1$, $R^2$, $R^3$, $R^4$, $R^5$, $R^6$, $R^7$, $R^8$, $R^9$, and $R^{10}$ are as previously disclosed. Triazoles 5-2, wherein $R^1$, $R^2$, $R^8$, $R^9$, and $R^{10}$ are as previously disclosed. (Scheme 5, step a) may be prepared in two steps from benzamides 5-1, wherein $R^1$, $R^2$, $R^8$, $R^9$, and $R^{10}$ are as previously disclosed, under reported conditions (WO 2009/102736). Triazoles 5-2 may then be coupled to aryl halides 5-3, wherein $R^3$, $R^4$, $R^5$, $R^6$, and $R^7$ are as previously disclosed, such as 4-trifluoromethoxyphenyl iodobenzene, in the presence of cesium carbonate or potassium phosphate, in a polar aprotic solvent such as N,N-dimethylformamide. This reaction may be catalyzed by a copper salt such as copper(I) iodide in the presence of a chelator such as 8-hydroxyquinoline, both present in about 0.05 equivalents to about 0.25 equivalents, at a temperature ranging between about 80° C. and about 140° C., to form tricyclic intermediates 5-4 (Scheme 5, step b).

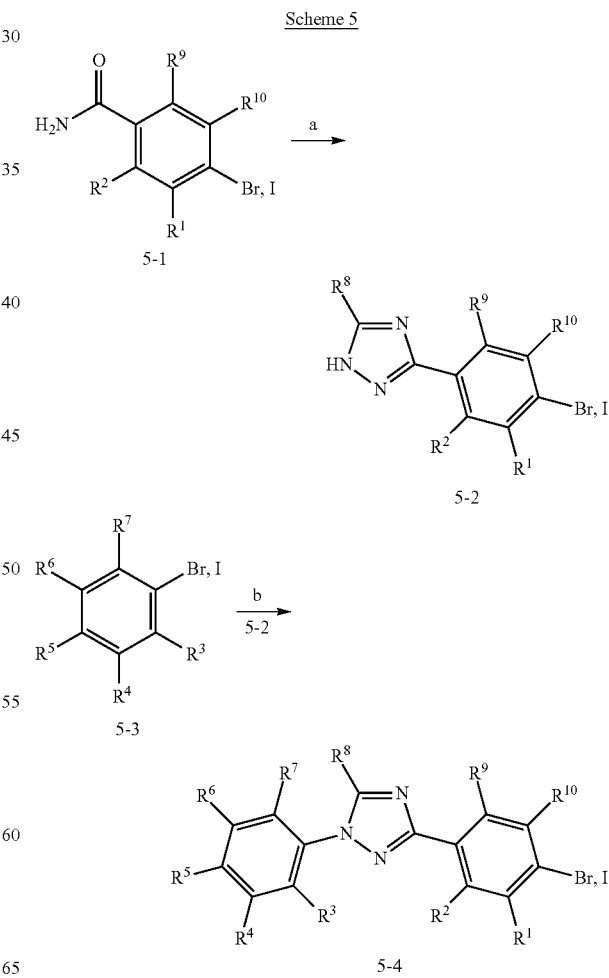

Preparation of Tricyclic Acid Intermediates

Condensation of tricyclic aldehydes 6-1, wherein $R^1$, $R^2$, $R^3$, $R^4$, $R^5$, $R^6$, $R^7$, $R^8$, $R^9$, and $R^{10}$ are as previously disclosed (US 2012/0202688), with reagents such as ethyl diethylphosphonoacetate or a Wittig reagent such as ethyl 2-(triphenylphosphoranylidene) propanoate) in the presence of a suitable base such as sodium hydride or n-butyl lithium in a polar aprotic solvent preferably tetrahydrofuran or diethyl ether at temperatures from about −78° C. to about 20° C. may be used to prepare acrylic esters 6-2, wherein $R^1$, $R^2$, $R^3$, $R^4$, $R^5$, $R^6$, $R^7$, $R^8$, $R^9$, and $R^{10}$ are as previously disclosed (Scheme 6, step a). Acrylic ester 6-2 may be reduced to the parent alkane esters 6-3, wherein $R^1$, $R^2$, $R^3$, $R^4$, $R^5$, $R^6$, $R^7$, $R^8$, $R^9$, and $R^{10}$ are as previously disclosed, using hydrogen gas and a palladium catalyst (step 6b). Saponification of the parent alkane esters 6-3 may be achieved by using a base such as sodium hydroxide in methanol or ethanol with or without tetrahydrofuran/water to furnish tricyclic acids 6-4, wherein $R^1$, $R^2$, $R^3$, $R^4$, $R^5$, $R^6$, $R^7$, $R^8$, $R^9$, and $R^{10}$ are as previously disclosed (Scheme 6, step c).

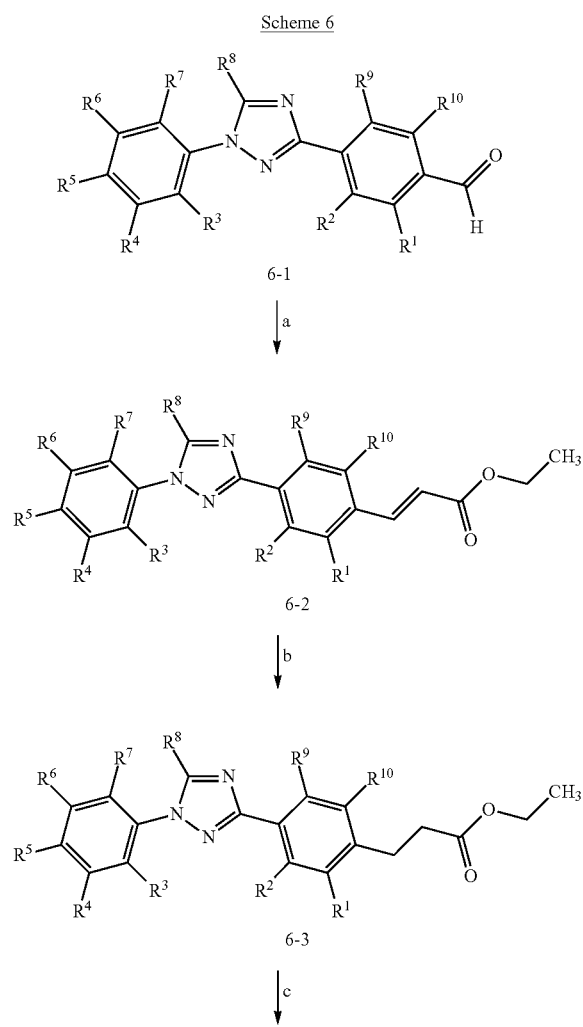

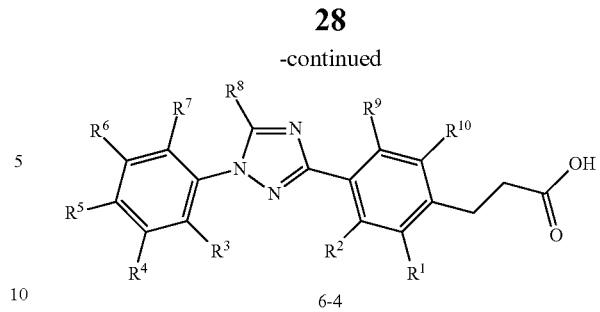

Preparation of Tricyclic Amine Intermediates

Treatment of tricyclic intermediates 5-4 with potassium (2-((tert-butoxycarbonyl)amino)ethyl)trifluoroborate in the presence of a palladium catalyst such as palladium(II) acetate, and a base such as cesium carbonate, at temperatures from about 80° C. to about 120° C., resulting in the formation of the corresponding 2-(tert-butoxycarbonyl) amino)ethyl derivatives 7-1, wherein $R^1$, $R^2$, $R^3$, $R^4$, $R^5$, $R^6$, $R^7$, $R^8$, $R^9$, and $R^{10}$ are as previously disclosed (Scheme 7, step a). Subsequent treatment of 7-1 with about 1 equivalents to about 5 equivalents of an acid such as trifluoroacetic acid or hydrogen chloride, in a polar aprotic solvent preferably dichloromethane or dioxane at temperatures from about 0° C. to about 50° C., resulting in the cleavage of the tert-butoxycarbonyl group and the formation of tricyclic amine salts 7-2, wherein $R^1$, $R^2$, $R^3$, $R^4$, $R^5$, $R^6$, $R^7$, $R^8$, $R^9$, and $R^{10}$ are as previously disclosed and X is trifluoroacetate or chloride (step 7b). Treatment of tricyclic amine salts 7-2 with a base such as sodium bicarbonate or sodium hydroxide resulting in the formation of free tricyclic amines 7-3, wherein $R^1$, $R^2$, $R^3$, $R^4$, $R^5$, $R^6$, $R^7$, $R^8$, $R^9$, and $R^{10}$ are as previously disclosed (Scheme 7, step c).

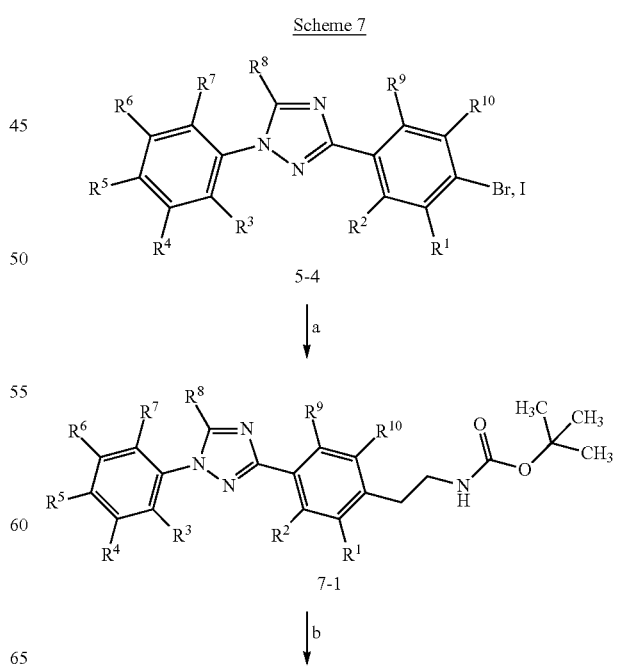

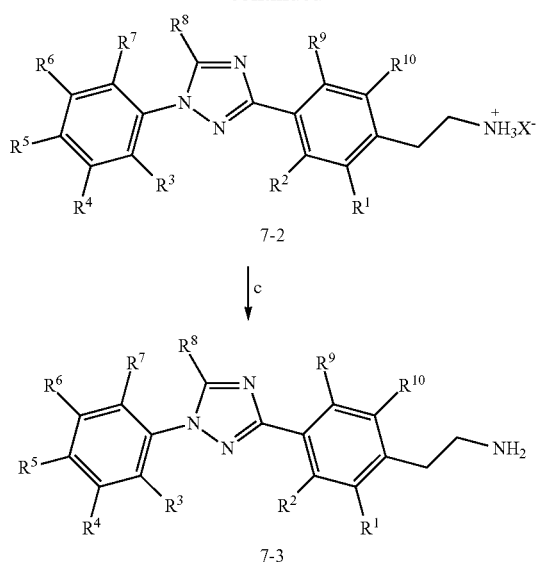

Preparation of Heterocyclyl Amine Intermediates

Heterocyclyl amines 3-1 used as precursors in the preparation of the molecules of Formula One may be prepared according to procedures described in schemes 8, 9, 10, 11, 12, 13, and 14. Treatment of substituted phenyl hydrazine hydrochlorides 8-1, wherein R is F, Cl, Br, I, ($C_1$-$C_4$)alkyl, ($C_1$-$C_4$)alkoxy, or ($C_1$-$C_4$)haloalkoxy, with (Z)-ethyl 2-cyano-3-ethoxyacrylate 8-2 in polar aprotic solvents such as ethanol at temperatures from about 60° C. to about 100° C. result in the formation of pyrazole amines 8-3, wherein R is F, Cl, Br, I, ($C_1$-$C_4$)alkyl, ($C_1$-$C_4$)alkoxy, or ($C_1$-$C_4$) haloalkoxy (Scheme 8, step a). Decarboxylation of 8-3 may be effected by treatment with concentrated hydrochloric acid at temperatures from about 90° C. to about 110° C. resulting in the formation of pyrazole amines 8-4, wherein R is F, Cl, Br, I, ($C_1$-$C_4$)alkyl, ($C_1$-$C_4$)alkoxy, or ($C_1$-$C_4$)haloalkoxy (Scheme 8, step b).

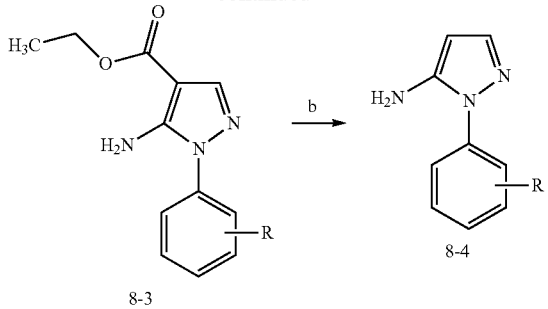

Treatment of substituted benzaldehydes 9-1, wherein R is F, Cl, Br, I, ($C_1$-$C_4$)alkyl, ($C_1$-$C_4$)alkoxy, or ($C_1$-$C_4$)haloalkoxy, with hydroxylamine hydrochloride in the presence of a base such as sodium bicarbonate in a polar aprotic solvent such as methanol at temperatures from about 60° C. to about 100° C. results in the formation of benzaldehyde oximes 9-2, wherein R is F, Cl, Br, I, ($C_1$-$C_4$)alkyl, ($C_1$-$C_4$) alkoxy, or ($C_1$-$C_4$)haloalkoxy (Scheme 9, step a). Chlorination of benzaldehyde oximes 9-2 with chlorinating agents such as N-chlorosuccinimide and catalytic amounts of N,N-dimethylformamide in polar solvent such as 1,2-dichloroethane at temperatures from about 0° C. to about 50° C. results in the formation of benzimidoyl chlorides 9-3, wherein R is F, Cl, Br, I, ($C_1$-$C_4$)alkyl, ($C_1$-$C_4$)alkoxy, or ($C_1$-$C_4$)haloalkoxy (Scheme 9, step b). Treatment of benzimidoyl chlorides 9-3 with potassium cyanide (Scheme 9, step c) followed by treatment with hydroxylamine hydrochloride in the presence of a base such as sodium carbonate (Scheme 9, step d) results in the formation of hydroxyiminoacetimidamides 9-5, wherein R is F, Cl, Br, I, ($C_1$-$C_4$)alkyl, ($C_1$-$C_4$) alkoxy, or ($C_1$-$C_4$)haloalkoxy. Cyclization of 9-5 may be effected by treatment with a base such as sodium hydroxide at temperatures from about 90° C. to about 110° C. resulting in the formation of 1,2,5-oxadiazolyl amines 9-6, wherein R is F, Cl, Br, I, ($C_1$-$C_4$)alkyl, ($C_1$-$C_4$)alkoxy, or ($C_1$-$C_4$) haloalkoxy (Scheme 9, step e).

Scheme 8

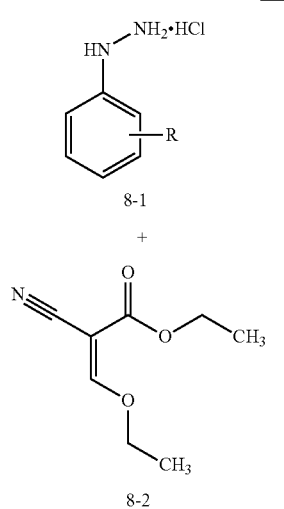

Scheme 9

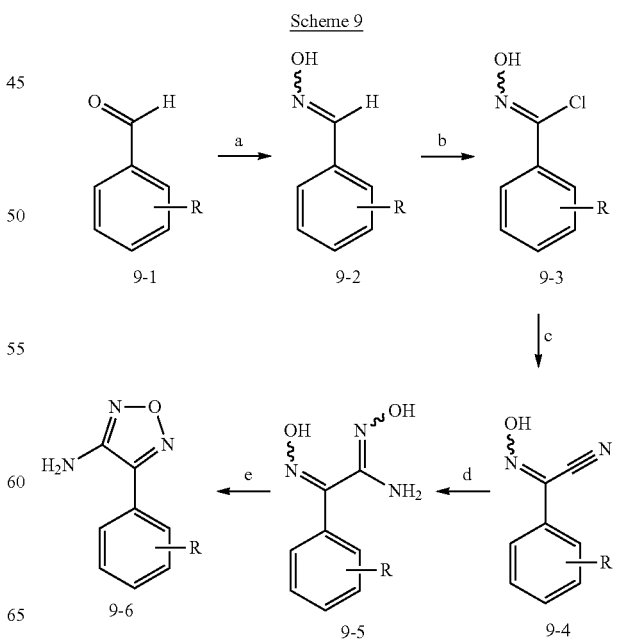

Treatment of substituted anilines 10-1, wherein R is F, Cl, Br, I, $(C_1-C_4)$alkyl, $(C_1-C_4)$alkoxy, or $(C_1-C_4)$haloalkoxy, with cyanamide in the presence of an acid such as nitric acid in a polar aprotic solvent such as ethanol at temperatures from about 80° C. to about 110° C. results in the formation of guanidine nitrates 10-2, wherein R is F, Cl, Br, I, $(C_1-C_4)$alkyl, $(C_1-C_4)$alkoxy, or $(C_1-C_4)$haloalkoxy (Scheme 10, step a). Cyclization of guanidine nitrates 10-2 with chloroacetaldehyde in the presence of a base such as sodium bicarbonate in a polar aprotic solvent such as ethanol at temperatures from about 60° C. to about 110° C. results in the formation of imidazoyl amines 10-3, wherein R is F, Cl, Br, I, $(C_1-C_4)$alkyl, $(C_1-C_4)$alkoxy, or $(C_1-C_4)$haloalkoxy (Scheme 10, step b).

12-3 such as methyl 2-methoxyacetate in the presence of a base such as sodium ethoxide in a polar protic solvent such as ethanol at temperatures from about 60° C. to about 110° C. results in the formation of acylated benzylnitriles 12-4, wherein R is F, Cl, Br, I, $(C_1-C_4)$alkyl, $(C_1-C_4)$alkoxy, or $(C_1-C_4)$haloalkoxy (Scheme 12, step b). Cyclization of acylated benzylnitriles 12-4 may be effected by treatment with an acid such as sulfuric acid in an acidic solvent such as acetic acid at temperatures from about 60° C. to about 120° C. resulting in the formation of amino furanones 12-5, wherein R is F, Cl, Br, I, $(C_1-C_4)$alkyl, $(C_1-C_4)$alkoxy, or $(C_1-C_4)$haloalkoxy (Scheme 12, step c).

Scheme 10

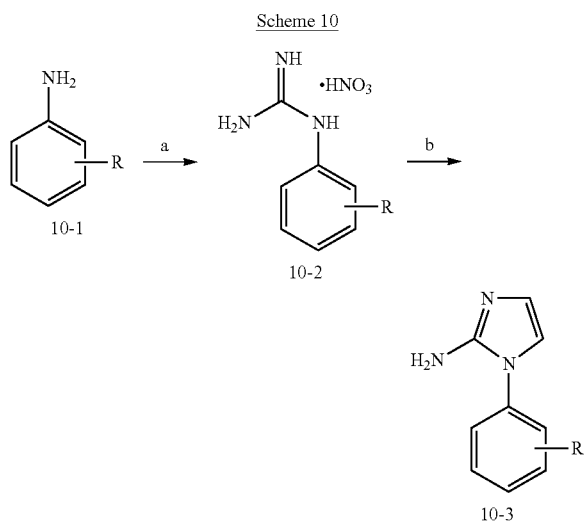

Imidazoyl amines 11-3 may be prepared by treating iodopyridines 11-1 with 2-amino imidazoles 11-2 in the presence of a copper(I) source such as copper(I) iodide, an amine ligand such as 8-hydroxy quinoline, and a base such as cesium carbonate in a polar solvent such as tert-butanol at temperatures from about 80° C. to about 110° C. (Scheme 11, step a).

Scheme 11

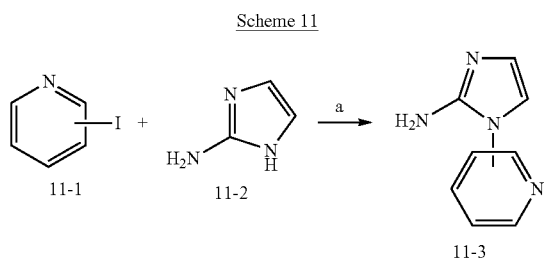

Treatment of substituted benzyl halides 12-1, wherein R is F, Cl, Br, I, $(C_1-C_4)$alkyl, $(C_1-C_4)$alkoxy, or $(C_1-C_4)$haloalkoxy, with potassium cyanide in a polar aprotic solvent such as dimethylformamide at temperatures from about 60° C. to about 90° C. results in the formation of benzylnitriles 12-2, wherein R is F, Cl, Br, I, $(C_1-C_4)$alkyl, $(C_1-C_4)$alkoxy, or $(C_1-C_4)$haloalkoxy (Scheme 12, step a). Acylation of benzylnitriles 12-2 with alkyl 2-alkoxyacetates Scheme 12

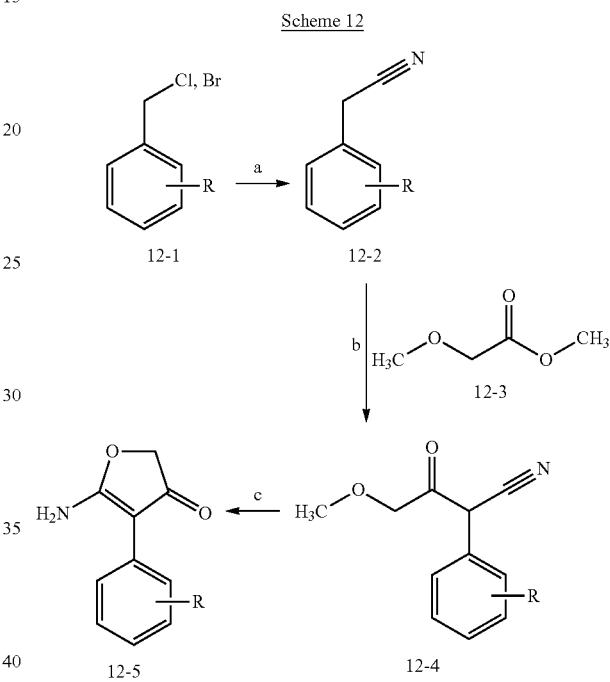

Scheme 13

-continued

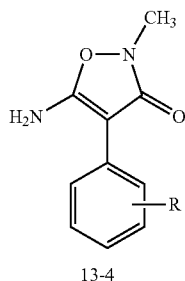

13-4

Treatment of substituted aryl halides 13-1, wherein R is F, Cl, Br, I, ($C_1$-$C_4$)alkyl, ($C_1$-$C_4$)alkoxy, or ($C_1$-$C_4$)haloalkoxy, with alkyl cyanoacetates 13-2 in the presence of a base such as sodium phosphate, a palladium catalyst such as bis(dibenzylideneacetone)palladium(0), and a phosphine ligand such as tri-tert-butylphosphine in a solvent such as toluene at temperatures from about 80° C. to about 110° C. results in the formation of aryl substituted alkyl cyanoacetates 13-3, wherein R is F, Cl, Br, I, ($C_1$-$C_4$)alkyl, ($C_1$-$C_4$)alkoxy, or ($C_1$-$C_4$)haloalkoxy (Scheme 13, step a). Cyclization of aryl substituted alkyl cyanoacetates 13-3 with N-methyl hydroxylamine hydrochloride in the presence of a base such as sodium ethoxide in a polar protic solvent such as ethanol at temperatures from about 60° C. to about 120° C. results in the formation of amino methylisoxazolones 13-4, wherein R is F, Cl, Br, I, ($C_1$-$C_4$)alkyl, ($C_1$-$C_4$)alkoxy, or ($C_1$-$C_4$)haloalkoxy (Scheme 13, step b).

Treatment of benzylnitriles 12-2 with tert-butoxy bis(dimethylamino)methane 14-1 in a polar aprotic solvent such as dimethylformamide at temperatures from about 80° C. to about 110° C. results in the formation of acrylonitriles 14-2, wherein R is F, Cl, Br, I, ($C_1$-$C_4$)alkyl, ($C_1$-$C_4$)alkoxy, or ($C_1$-$C_4$)haloalkoxy (Scheme 14, step a). Cyclization of acrylonitriles 14-2 with hydroxylamine hydrochloride in a polar protic solvent such as ethanol at temperatures from about 60° C. to about 120° C. results in the formation of isoxazolyl amines 14-3, wherein R is F, Cl, Br, I, ($C_1$-$C_4$)alkyl, ($C_1$-$C_4$)alkoxy, or ($C_1$-$C_4$)haloalkoxy (Scheme 14, step b).

Preparation of Heterocyclyl Acid Intermediates

Treatment of substituted benzoylchlorides 15-1, wherein R is F, Cl, Br, I, ($C_1$-$C_4$)alkyl, ($C_1$-$C_4$)alkoxy, or ($C_1$-$C_4$) haloalkoxy, with alkyl hydrogen malonates such as ethyl hydrogen malonate in the presence of a base such as n-butyllithium in a polar aprotic solvent such as tetrahydrofuran at temperatures from about −78° C. to about 20° C. results in the formation of alkyl aryl malonates 15-2, wherein R is F, Cl, Br, I, ($C_1$-$C_4$)alkyl, ($C_1$-$C_4$)alkoxy, or ($C_1$-$C_4$)haloalkoxy (Scheme 15, step a). Bromination of alkyl aryl malonates 15-2 with bromine in a polar aprotic solvent such as dioxane at temperatures from about 0° C. to about 50° C. results in the formation of brominated alkyl aryl malonates 15-3, wherein R is F, Cl, Br, I, ($C_1$-$C_4$)alkyl, ($C_1$-$C_4$)alkoxy, or ($C_1$-$C_4$)haloalkoxy (Scheme 15, step b). Cyclization of brominated alkyl aryl malonates 15-3 with thiourea in a polar protic solvent such as ethanol at temperatures from about 60° C. to about 90° C. results in the formation of amino alkyl thiazolyl carboxylates 15-4, wherein R is F, Cl, Br, I, ($C_1$-$C_4$)alkyl, ($C_1$-$C_4$)alkoxy, or ($C_1$-$C_4$)haloalkoxy (Scheme 15, step c). Treatment of amino alkyl thiazolyl carboxylates 15-4 with sodium nitrite in the presence of an acid such as hypophosphorus acid in a polar aprotic solvent such as diethyl ether followed by an aqueous quench results in the formation of alkyl thiazolyl carboxylates 15-5, wherein R is F, Cl, Br, I, ($C_1$-$C_4$)alkyl, ($C_1$-$C_4$) alkoxy, or ($C_1$-$C_4$)haloalkoxy (Scheme 15, step d). Saponification of alkyl thiazolyl carboxylates 15-5 may be effected by treatment with a base such as lithium hydroxide in mixed solvent system comprising a polar aprotic solvent preferably tetrahydrofuran and a polar protic solvent preferably water at temperatures from about 0° C. to about 30° C. resulting in the formation of thiazolyl acids 15-6, wherein R is F, Cl, Br, I, ($C_1$-$C_4$)alkyl, ($C_1$-$C_4$)alkoxy, or ($C_1$-$C_4$)haloalkoxy (Scheme 15, step e).

Scheme 14

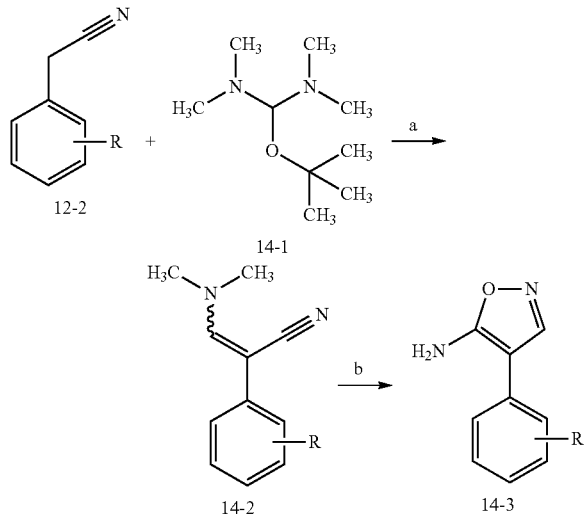

Scheme 15

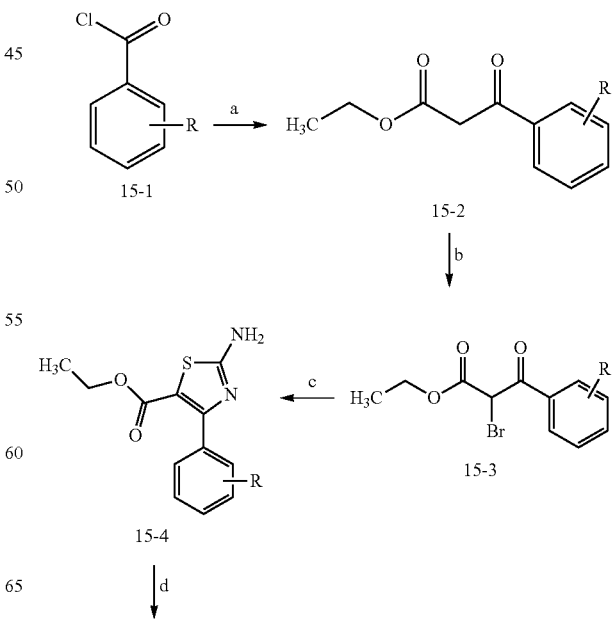

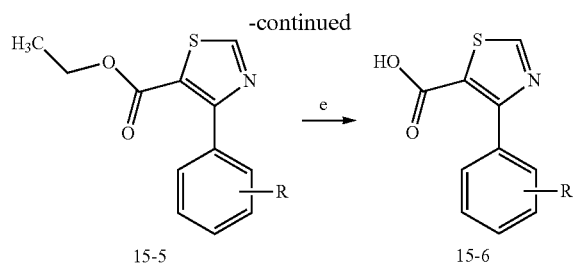

EXAMPLES

These examples are for illustration purposes and are not to be construed as limiting this disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw, or ACD Name Pro. If such programs are unable to name a molecule, such molecule is named using conventional naming rules. $^1$H NMR spectral data are in ppm ($\delta$) and were recorded at 300, 400, 500, or 600 MHz; $^{13}$C NMR spectral data are in ppm ($\delta$) and were recorded at 75, 100, or 150 MHz, and $^{19}$F NMR spectral data are in ppm ($\delta$) and were recorded at 376 MHz, unless otherwise stated.

Example 1: Preparation of ethyl 4-methyl-2-(3-(4-(1-(4-(trifluoromethoxy)phenyl)-1H-1,2,4-triazol-3-yl)phenyl)ureido)thiophene-3-carboxylate (F1)

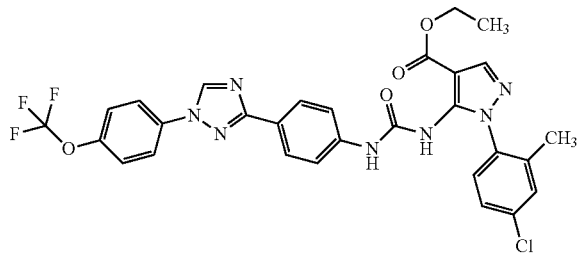 [SMILES: CCOC(=O)c1cnn(-c2ccc(Cl)cc2C)c1NC(=O)Nc1ccc(-c2ncn(-c3ccc(OC(F)(F)F)cc3)n2)cc1]

To 4-(1-(4-(trifluoromethoxy)phenyl)-1H-1,2,4-triazol-3-yl)benzoyl azide (0.50 g, 1.3 mmol) in a 25 mL vial equipped with a stir bar and vigreux column was added 1,2-dichloroethane (6.7 mL). The reaction was heated to 85° C. After several hours the reaction was cooled to room temperature. Ethyl 2-amino-4-methylthiophene-3-carboxylate (0.25 g, 1.3 mmol) was added in one portion. The reaction was heated to reflux overnight. The reaction was cooled to room temperature. The reaction mixture was diluted with ethyl acetate and washed with water. The water layer was extracted with ethyl acetate. The combined organic layer was washed with water (3×). The organic layers were poured through a phase separator and dry packed onto Celite®. Purification by flash column chromatography using 5-50% ethyl acetate/(1:1 dichloromethane/hexanes) provided a white solid which was triturated with diethyl ether and hexanes. The solid was dried overnight at 50° C. at 25 in. Hg providing the title molecule as a white solid (0.45 g, 64%).

The following molecules were prepared according to the procedures disclosed in Example 1:

Ethyl 1-(4-chloro-2-methylphenyl)-5-(3-(4-(1-(4-(trifluoromethoxy)phenyl)-1H-1,2,4-triazol-3-yl)phenyl)ureido)-1H-pyrazole-4-carboxylate (F2)

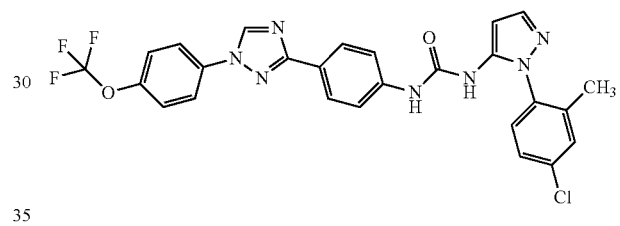

Isolated as a white solid (0.12 g, 21%).

1-(1-(4-Chloro-2-methylphenyl)-1H-pyrazol-5-yl)-3-(4-(1-(4-(trifluoromethoxy)phenyl)-1H-1,2,4-triazol-3-yl)phenyl)urea (F3)

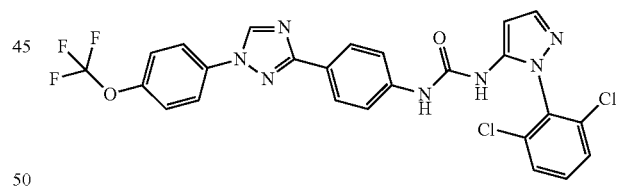

Isolated as a white solid (0.38 g, 54%).

1-(1-(2,6-Dichlorophenyl)-1H-pyrazol-5-yl)-3-(4-(1-(4-(trifluoromethoxy)phenyl)-1H-1,2,4-triazol-3-yl)phenyl)urea (F4)

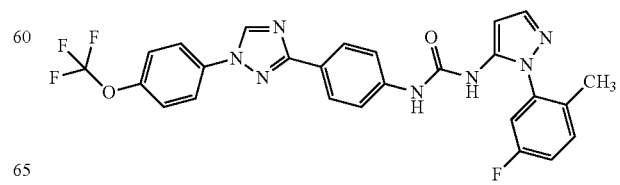

Isolated as a white solid (0.12 g, 53%).

1-(1-(5-Fluoro-2-methylphenyl)-1H-pyrazol-5-yl)-3-(4-(1-(4-(trifluoromethoxy)phenyl)-1H-1,2,4-triazol-3-yl)phenyl)urea (F5)

Isolated as a white solid (0.13 g, 60%).

1-(1-(2-Ethylphenyl)-1H-pyrazol-5-yl)-3-(4-(1-(4-(trifluoromethoxy)phenyl)-1H-1,2,4-triazol-3-yl)phenyl)urea (F6)

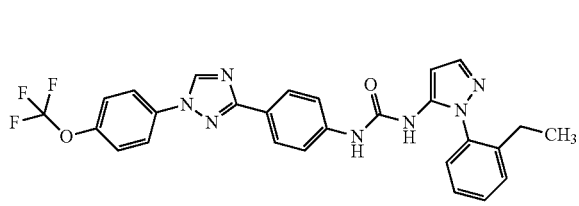 [SMILES: CCc1ccccc1-n1nccc1NC(=O)Nc1ccc(-c2ncn(-c3ccc(OC(F)(F)F)cc3)n2)cc1]

Isolated as a white solid (0.060 g, 28%).

1-(1-(2,5-Dimethylphenyl)-1H-pyrazol-5-yl)-3-(4-(1-(4-(trifluoromethoxy)phenyl)-1H-1,2,4-triazol-3-yl)phenyl)urea (F7)

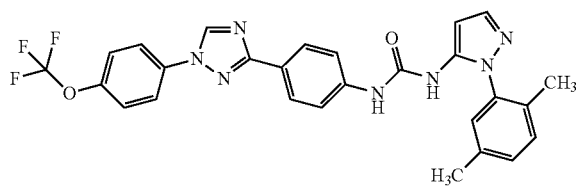 [SMILES: Cc1ccc(C)c(-n2nccc2NC(=O)Nc2ccc(-c3ncn(-c4ccc(OC(F)(F)F)cc4)n3)cc2)c1]

Isolated as a white solid (0.133 g, 62%).

1-(2-(4-Methylpentan-2-yl)thiophen-3-yl)-3-(4-(1-(4-(trifluoromethoxy)phenyl)-1H-1,2,4-triazol-3-yl)phenyl)urea (F8)

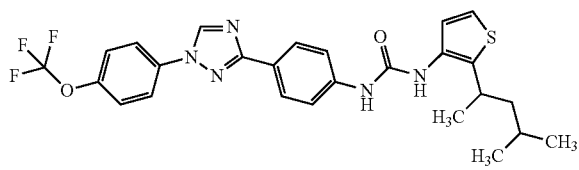 [SMILES: CC(C)CC(C)c1sccc1NC(=O)Nc1ccc(-c2ncn(-c3ccc(OC(F)(F)F)cc3)n2)cc1]

Isolated as a white solid (0.151 g, 71%).

1-(1-(2,4-Dimethylphenyl)-1H-pyrazol-5-yl)-3-(4-(1-(4-(trifluoromethoxy)phenyl)-1H-1,2,4-triazol-3-yl)phenyl)urea (F9)

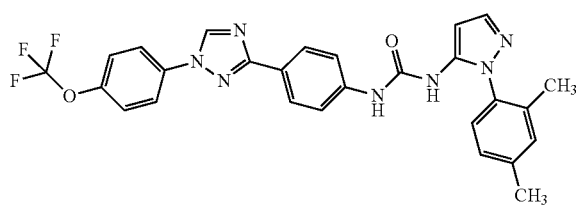 [SMILES: Cc1ccc(-n2nccc2NC(=O)Nc2ccc(-c3ncn(-c4ccc(OC(F)(F)F)cc4)n3)cc2)c(C)c1]

Isolated as a white solid (0.089 g, 41%).

1-(1-Phenyl-1H-pyrazol-5-yl)-3-(4-(1-(4-(trifluoromethoxy)phenyl)-1H-1,2,4-triazol-3-yl)phenyl)urea (F10)

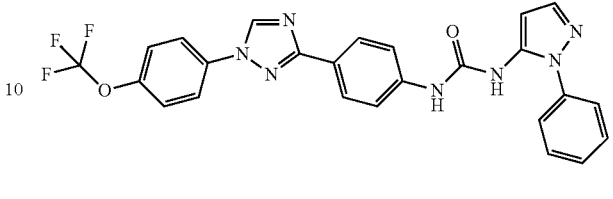

Isolated as a white solid (0.089 g, 41%).

1-(1-Mesityl-1H-pyrazol-5-yl)-3-(4-(1-(4-(trifluoromethoxy)phenyl)-1H-1,2,4-triazol-3-yl)phenyl)urea (F11)

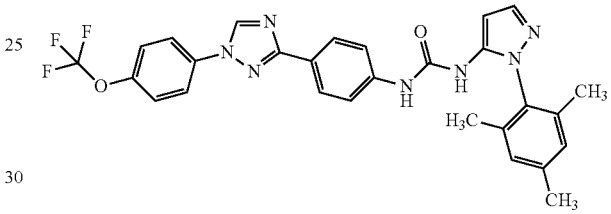

Isolated as a white solid (0.15 g, 69%).

1-(1-(2,5-Dichlorophenyl)-1H-pyrazol-5-yl)-3-(4-(1-(4-(trifluoromethoxy)phenyl)-1H-1,2,4-triazol-3-yl)phenyl)urea (F12)

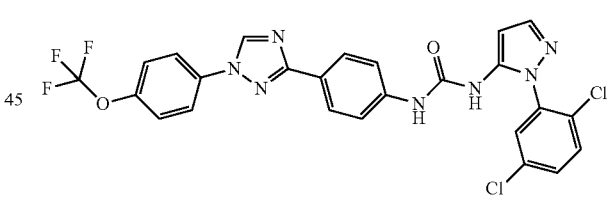

Isolated as a white solid (0.126 g, 55%).

1-(1-(2-Methoxyphenyl)-1H-pyrazol-5-yl)-3-(4-(1-(4-(trifluoromethoxy)phenyl)-1H-1,2,4-triazol-3-yl)phenyl)urea (F13)

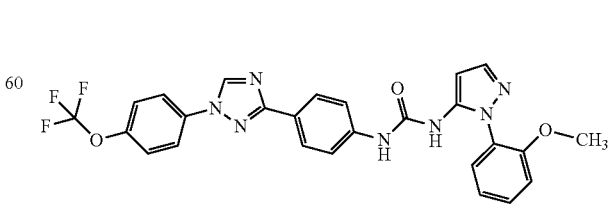

Isolated as a white solid (0.080 g, 37%).

1-(1-(2,6-Dichlorophenyl)-1H-pyrazol-5-yl)-3-(4-(1-(4-(perfluoroethoxy)phenyl)-1H-1,2,4-triazol-3-yl)phenyl)urea (F14)

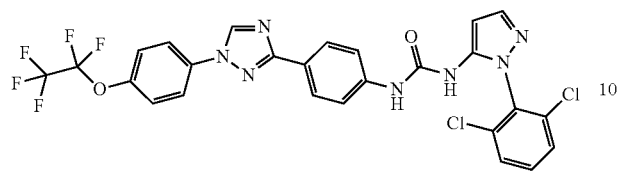

Isolated as a white solid (0.13 g, 60%).

1-(1-(2,4-Dimethylphenyl)-1H-pyrazol-5-yl)-3-(4-(1-(4-(perfluoroethoxy)phenyl)-1H-1,2,4-triazol-3-yl)phenyl)urea (F15)

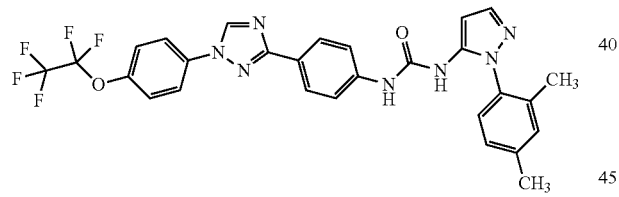

Isolated as a white solid (0.13 g, 62%).

1-(1-(5-Fluoro-2-methylphenyl)-1H-pyrazol-5-yl)-3-(4-(1-(4-(perfluoroethoxy)phenyl)-1H-1,2,4-triazol-3-yl)phenyl)urea (F16)

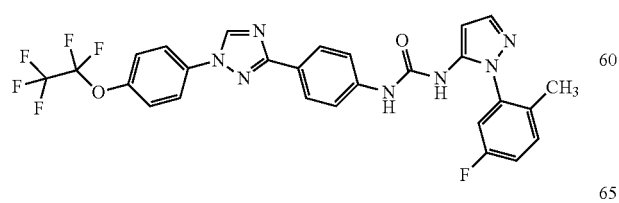

Isolated as a white solid (0.14 g, 66%).

1-(1-(2,5-Dimethylphenyl)-1H-pyrazol-5-yl)-3-(4-(1-(4-(perfluoroethoxy)phenyl)-1H-1,2,4-triazol-3-yl)phenyl)urea (F17)

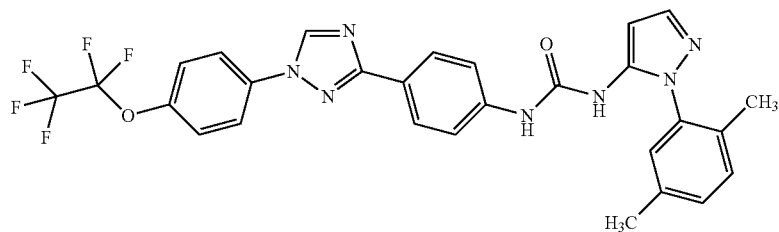 [SMILES: Cc1ccc(C)c(-n2nccc2NC(=O)Nc2ccc(-c3ncn(-c4ccc(OC(F)(F)C(F)(F)F)cc4)n3)cc2)c1]

Isolated as a white solid (0.13 g, 64%).

1-(1-Mesityl-1H-pyrazol-5-yl)-3-(4-(1-(4-(perfluoroethoxy)phenyl)-1H-1,2,4-triazol-3-yl)phenyl)urea (F18)

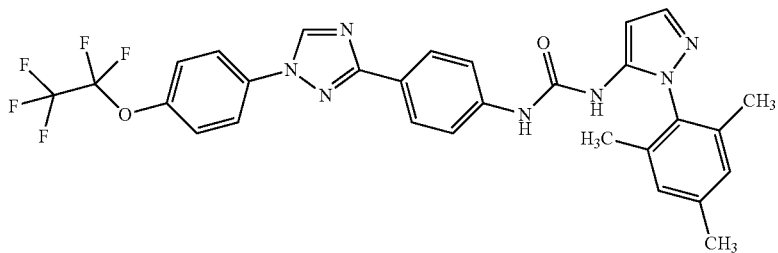 [SMILES: Cc1cc(C)c(-n2nccc2NC(=O)Nc2ccc(-c3ncn(-c4ccc(OC(F)(F)C(F)(F)F)cc4)n3)cc2)c(C)c1]

Isolated as a pink solid (0.097 g, 46%).

1-(1-(2-Methoxyphenyl)-1H-pyrazol-5-yl)-3-(4-(1-(4-(perfluoroethoxy)phenyl)-1H-1,2,4-triazol-3-yl)phenyl)urea (F19)

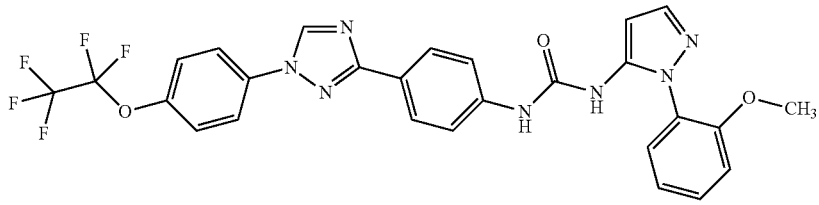 [SMILES: COc1ccccc1-n1nccc1NC(=O)Nc1ccc(-c2ncn(-c3ccc(OC(F)(F)C(F)(F)F)cc3)n2)cc1]

Isolated as a tan solid (0.18 g, 86%).

1-(4-(2,4-Dimethylphenyl)-1,2,5-oxadiazol-3-yl)-3-(4-(1-(4-(trifluoromethoxy)phenyl)-1H-1,2,4-triazol-3-yl)phenyl)urea (F36)

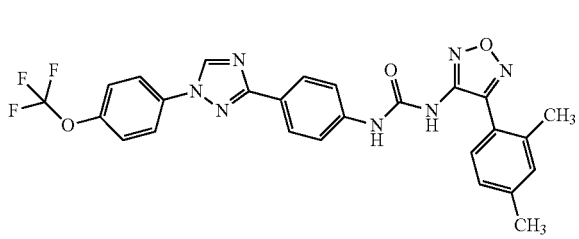 [SMILES: Cc1ccc(-c2nonc2NC(=O)Nc2ccc(-c3ncn(-c4ccc(OC(F)(F)F)cc4)n3)cc2)c(C)c1]

Isolated as an off-white solid (0.085 g, 24%).

1-(4-Phenyl-1,2,5-oxadiazol-3-yl)-3-(4-(1-(4-(trifluoromethoxy)phenyl)-1H-1,2,4-triazol-3-yl)phenyl)urea (F37)

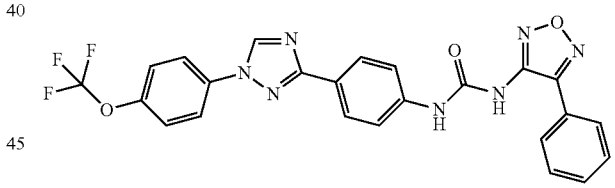

Isolated as an off-white solid (0.075 g, 21%).

1-(4-(2-Methoxyphenyl)-1,2,5-oxadiazol-3-yl)-3-(4-(1-(4-(trifluoromethoxy)phenyl)-1H-1,2,4-triazol-3-yl)phenyl)urea (F38)

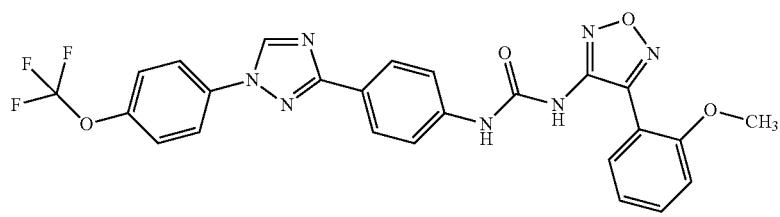

Isolated as an off-white solid (0.085 g, 24%).

1-(4-(4-Methoxyphenyl)-1,2,5-oxadiazol-3-yl)-3-(4-(1-(4-(trifluoromethoxy)phenyl)-1H-1,2,4-triazol-3-yl)phenyl)urea (F39)

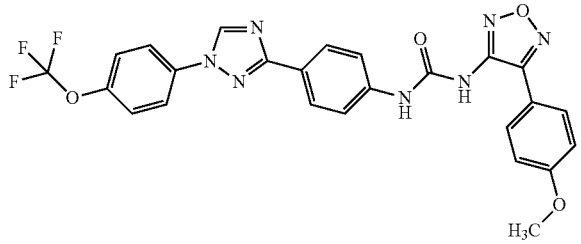 [SMILES: COc1ccc(-c2nonc2NC(=O)Nc2ccc(-c3ncn(-c4ccc(OC(F)(F)F)cc4)n3)cc2)cc1]

Isolated as an off-white solid (0.085 g, 24%).

1-(4-Mesityl-1,2,5-oxadiazol-3-yl)-3-(4-(1-(4-(trifluoromethoxy)phenyl)-1H-1,2,4-triazol-3-yl)phenyl)urea (F40)

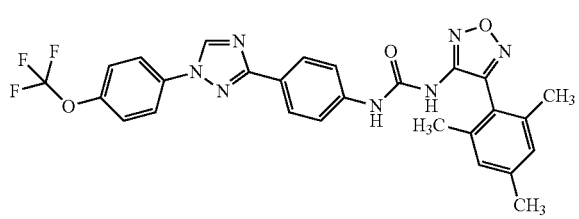 [SMILES: Cc1cc(C)c(-c2nonc2NC(=O)Nc2ccc(-c3ncn(-c4ccc(OC(F)(F)F)cc4)n3)cc2)c(C)c1]

Isolated as an off-white solid (0.070 g, 19%).

1-(4-(3-Methoxyphenyl)-1,2,5-oxadiazol-3-yl)-3-(4-(1-(4-(trifluoromethoxy)phenyl)-1H-1,2,4-triazol-3-yl)phenyl)urea (F41)

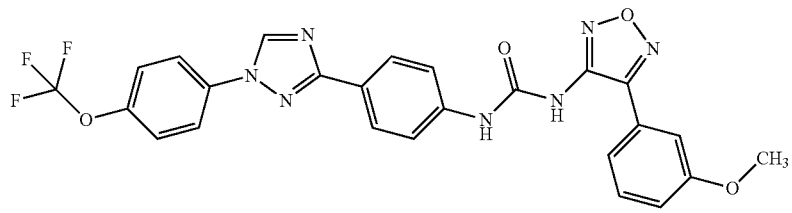 [SMILES: COc1cccc(-c2nonc2NC(=O)Nc2ccc(-c3ncn(-c4ccc(OC(F)(F)F)cc4)n3)cc2)c1]

Isolated as an off-white solid (0.055 g, 15%).

1-(4-(2,6-Dichlorophenyl)-1,2,5-oxadiazol-3-yl)-3-(4-(1-(4-(trifluoromethoxy)phenyl)-1H-1,2,4-triazol-3-yl)phenyl)urea (F42)

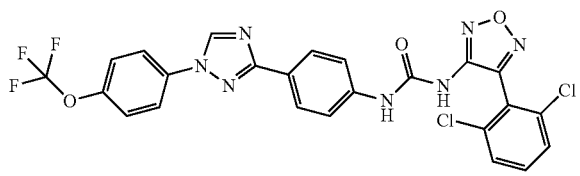 [SMILES: O=C(Nc1ccc(-c2ncn(-c3ccc(OC(F)(F)F)cc3)n2)cc1)Nc1nonc1-c1c(Cl)cccc1Cl]

Isolated as an off-white solid (0.115 g, 29%).

1-(4-(4-Chloro-2-methylphenyl)-1,2,5-oxadiazol-3-yl)-3-(4-(1-(4-(trifluoromethoxy)phenyl)-1H-1,2,4-triazol-3-yl)phenyl)urea (F43)

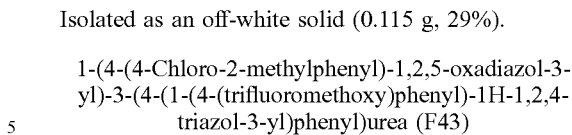

Isolated as an off-white solid (0.065 g, 20%).

1-(4-(2-Ethylphenyl)-1,2,5-oxadiazol-3-yl)-3-(4-(1-(4-(trifluoromethoxy)phenyl)-1H-1,2,4-triazol-3-yl)phenyl)urea (F44)

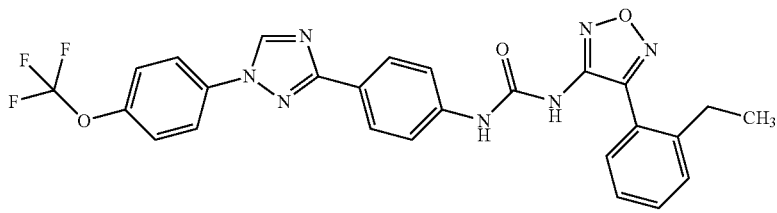

Isolated as a white solid (0.075 g, 19%).

1-(4-(2-(Trifluoromethoxy)phenyl)-1,2,5-oxadiazol-3-yl)-3-(4-(1-(4-(trifluoromethoxy)phenyl)-1H-1,2,4-triazol-3-yl)phenyl)urea (F45)

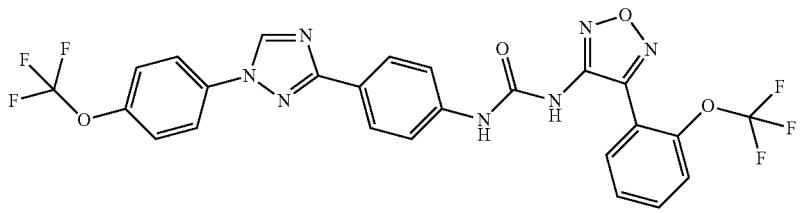 [SMILES: O=C(Nc1ccc(-c2ncn(-c3ccc(OC(F)(F)F)cc3)n2)cc1)Nc1nonc1-c1ccccc1OC(F)(F)F]

Isolated as an off-white solid (0.05 g, 14%).

Example 2: Preparation of ethyl 5-amino-1-(4-chloro-2-methylphenyl)-1H-pyrazole-4-carboxylate (C1)

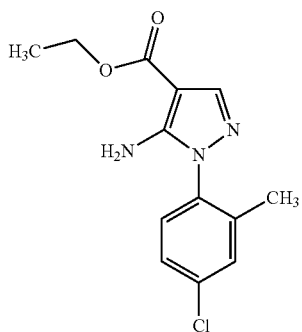 [SMILES: CCOC(=O)c1cnn(-c2ccc(Cl)cc2C)c1N]

To (4-chloro-2-methylphenyl)hydrazine hydrochloride (1.00 g, 5.18 mmol) and (Z)-ethyl 2-cyano-3-ethoxyacrylate (0.964 g, 5.70 mmol) in a 25 mL vial equipped with a stir bar and a vigreux column was added ethanol (6.47 mL) followed by triethylamine (0.794 mL, 5.70 mmol). The reaction was heated to reflux overnight. The reaction was cooled. The solution was diluted with ethyl acetate and washed with water. The aqueous layer was extracted with ethyl acetate. The combined organic layers were dried over magnesium sulfate, filtered, and concentrated. Purification by flash column chromatography using 0-20% ethyl acetate/hexanes as eluent provided the title molecule as a tan solid (1.08 g, 75%): mp 82-84° C.; $^1$H NMR (400 MHz, CDCl$_3$) δ 7.79 (s, 1H), 7.37 (d, J=2.3 Hz, 1H), 7.34-7.29 (m, 1H), 7.26-7.24 (m, 1H), 4.99 (s, 2H), 4.31 (q, J=7.1 Hz, 2H), 2.15 (s, 3H), 1.37 (t, J=7.1 Hz, 3H); ESIMS m/z 280 ([M+H]$^+$).

The following molecules were prepared according to the procedures disclosed in Example 2:

Ethyl 5-amino-1-(2,6-dichlorophenyl)-1H-pyrazole-4-carboxylate (C2)

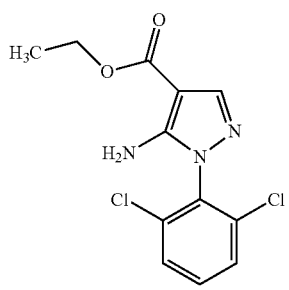 [SMILES: CCOC(=O)c1cnn(-c2c(Cl)cccc2Cl)c1N]

Isolated as a light yellow solid (1.21 g, 86%): mp 130-131° C.; $^1$H NMR (400 MHz, CDCl$_3$) δ 7.89 (s, 1H), 7.52 (d, J=1.3 Hz, 1H), 7.50 (d, J=0.6 Hz, 1H), 7.42 (dd, J=9.0, 7.2 Hz, 1H), 5.03 (s, 2H), 4.32 (q, J=7.1 Hz, 2H), 1.37 (t, J=7.1 Hz, 3H); ESIMS m/z 301 ([M+H]$^+$).

Ethyl 5-amino-1-(5-fluoro-2-methylphenyl)-1H-pyrazole-4-carboxylate (C3)

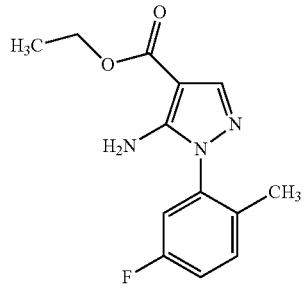 [SMILES: CCOC(=O)c1cnn(-c2cc(F)ccc2C)c1N]

Isolated as an amber oil (1.18 g, 79%): ¹H NMR (400 MHz, CDCl₃) δ 7.79 (s, 1H), 7.37-7.30 (m, 1H), 7.12 (td, J=8.3, 2.7 Hz, 1H), 7.07 (dd, J=8.6, 2.7 Hz, 1H), 5.04 (s, 2H), 4.31 (q, J=7.1 Hz, 2H), 2.13 (s, 3H), 1.37 (t, J=7.1 Hz, 3H); ¹³C NMR (101 MHz, CDCl₃) δ 163.37 (d, $J_{CF}$=230.8 Hz), 159.77, 149.59, 140.68, 136.18 (d, $J_{CF}$=9.6 Hz), 132.65 (d, $J_{CF}$=8.6 Hz), 132.33 (d, $J_{CF}$=3.7 Hz), 117.03 (d, JCF=20.6 Hz), 114.93 (d, $J_{CF}$=22.8 Hz), 95.36, 59.72, 16.87, 14.55; ESIMS m/z 264 ([M+H]⁺).

Ethyl 5-amino-1-(2-ethylphenyl)-1H-pyrazole-4-carboxylate (C4)

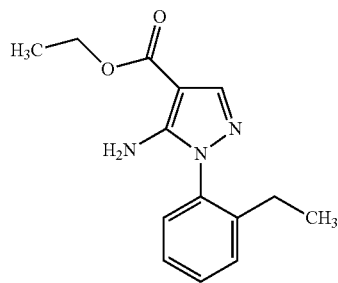 [SMILES: CCOC(=O)c1cnn(-c2ccccc2CC)c1N]

Isolated as an amber solid (1.06 g, 79%): ¹H NMR (400 MHz, CDCl₃) δ 7.80 (s, 1H), 7.49-7.39 (m, 2H), 7.33 (ddd, J=8.7, 6.8, 2.0 Hz, 1H), 7.30-7.27 (m, 1H), 4.97 (s, 2H), 4.31 (q, J=7.1 Hz, 2H), 2.50 (q, J=7.5 Hz, 2H), 1.37 (t, J=7.1 Hz, 3H), 1.11 (t, J=7.6 Hz, 3H); ¹³C NMR (101 MHz, CDCl₃) δ 164.63, 149.77, 142.75, 140.22, 134.91, 130.24, 130.04, 127.87, 127.10, 95.11, 59.62, 24.13, 14.57, 14.46; ESIMS m/z 260 ([M+H]⁺).

Ethyl 5-amino-1-(2,5-dimethylphenyl)-1H-pyrazole-4-carboxylate (C5)

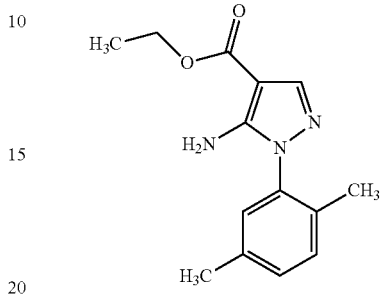

Isolated as an amber oil (1.37 g, 91%): ¹H NMR (400 MHz, CDCl₃) δ 7.78 (s, 1H), 7.24 (d, J=7.8 Hz, 1H), 7.19 (ddd, J=7.9, 1.8, 0.8 Hz, 1H), 7.13-7.08 (m, 1H), 4.99 (s, 2H), 4.30 (q, J=7.1 Hz, 2H), 2.42-2.29 (m, 3H), 2.10 (s, 3H), 1.37 (t, J=7.1 Hz, 3H); ¹³C NMR (101 MHz, CDCl₃) δ 164.63, 149.56, 140.26, 137.09, 135.24, 133.21, 131.33, 130.69, 128.12, 95.15, 59.59, 20.71, 16.94, 14.56; ESIMS m/z 260 ([M+H]⁺).

Ethyl 5-amino-1-(2,4-dimethylphenyl)-1H-pyrazole-4-carboxylate (C6)

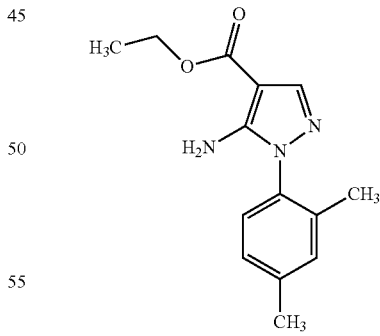

Isolated as a white solid (1.38 g, 92%): ¹H NMR (400 MHz, CDCl₃) δ 7.78 (s, 1H), 7.20-7.15 (m, 2H), 7.14-7.08 (m, 1H), 4.95 (s, 2H), 4.30 (q, J=7.1 Hz, 2H), 2.38 (s, 3H), 2.11 (s, 3H), 1.37 (t, J=7.1 Hz, 3H); ¹³C NMR (101 MHz, CDCl₃) δ 164.64, 149.67, 140.22, 140.03, 136.31, 132.88, 132.19, 127.74, 127.43, 95.14, 59.58, 21.20, 17.32, 14.57; ESIMS m/z 260 ([M+H]⁺).

Ethyl 5-amino-1-mesityl-1H-pyrazole-4-carboxylate (C7)

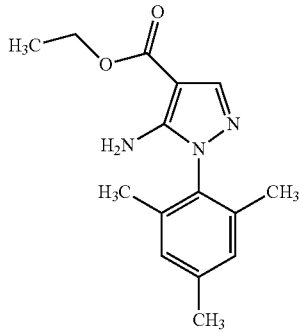 [SMILES: CCOC(=O)c1cnn(-c2c(C)cc(C)cc2C)c1N]

Isolated as a white solid (1.18 g, 81%): mp 169-170° C.; $^1$H NMR (400 MHz, CDCl$_3$) δ 7.81 (s, 1H), 6.98 (dd, J=1.3, 0.7 Hz, 2H), 4.87 (s, 2H), 4.31 (q, J=7.1 Hz, 2H), 2.33 (s, 3H), 2.02 (s, 6H), 1.37 (t, J=7.1 Hz, 3H); ESIMS m/z 274 ([M+H]$^+$).

Ethyl 5-amino-1-(2,5-dichlorophenyl)-1H-pyrazole-4-carboxylate (C8)

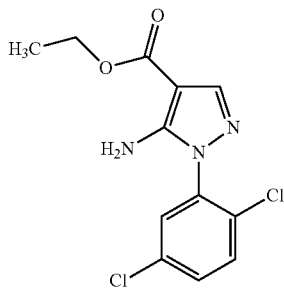 [SMILES: CCOC(=O)c1cnn(-c2cc(Cl)ccc2Cl)c1N]

Isolated as an amber oil (0.77 g, 55%): $^1$H NMR (400 MHz, CDCl$_3$) δ 7.83 (s, 1H), 7.54-7.47 (m, 2H), 7.44 (dd, J=8.6, 2.5 Hz, 1H), 5.15 (s, 2H), 4.31 (q, J=7.1 Hz, 2H), 1.37 (t, J=7.1 Hz, 3H); $^{13}$C NMR (101 MHz, CDCl$_3$) δ 164.41, 150.24, 141.49, 135.54, 133.71, 131.56, 131.17, 130.40, 130.07, 95.71, 59.81, 14.53; ESIMS m/z 301 ([M+H]$^+$).

Ethyl 5-amino-1-(2-methoxyphenyl)-1H-pyrazole-4-carboxylate (C9)

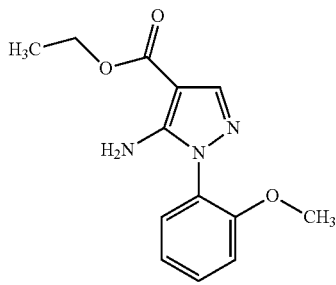 [SMILES: CCOC(=O)c1cnn(-c2ccccc2OC)c1N]

Isolated as an amber oil (1.37 g, 92%): $^1$H NMR (400 MHz, CDCl$_3$) δ 7.82 (s, 1H), 7.47-7.39 (m, 2H), 7.13-7.04 (m, 2H), 5.23 (s, 2H), 4.30 (q, J=7.1 Hz, 2H), 3.88 (s, 3H), 1.36 (t, J=7.1 Hz, 3H); $^{13}$C NMR (101 MHz, CDCl$_3$) δ 164.72, 153.43, 150.69, 140.98, 130.41, 128.80, 126.40, 121.68, 112.57, 95.85, 59.56, 56.27, 14.58; ESIMS m/z 262 ([M+H]$^+$).

Example 3: Preparation of 1-(4-chloro-2-methylphenyl)-1H-pyrazol-5-amine (C10)

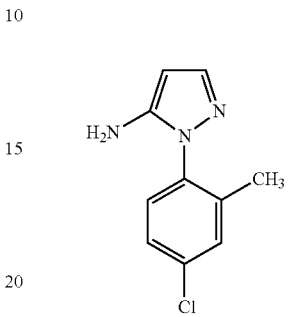

To ethyl 5-amino-1-(4-chloro-2-methylphenyl)-1H-pyrazole-4-carboxylate (C1) (0.750 g, 2.68 mmol) in a 25 mL vial equipped with a stir bar, vigreux column and tube to vent hydrochloric acid gas into a sodium hydroxide (1N) trap was added concentrated hydrochloric acid (8.04 mL, 97.0 mmol). The reaction was heated to reflux. Upon completion, the reaction was cooled and the mixture was transferred to a beaker and diluted with water (100 mL). The solution was treated with solid sodium bicarbonate until the acid was neutralized. The aqueous layer was extracted with dichloromethane (2×). The organic layers were poured through a phase separator and concentrated. The resultant oil was dried under house vacuum overnight providing the title molecule as an amber oil (0.532 g, 96%): $^1$H NMR (400 MHz, CDCl$_3$) δ 7.44 (d, J=1.9 Hz, 1H), 7.34 (dt, J=1.6, 0.7 Hz, 1H), 7.31-7.23 (m, 2H), 5.60 (d, J=1.9 Hz, 1H), 3.55 (s, 2H), 2.14 (s, 3H); $^{13}$C NMR (101 MHz, CDCl$_3$) δ 145.35, 140.39, 138.82, 135.30, 135.00, 131.22, 129.17, 126.98, 89.28, 17.43; ESIMS m/z 208 ([M+H]$^+$).

The following molecules were prepared according to the procedures disclosed in Example 3:

1-(2,6-Dichlorophenyl)-1H-pyrazol-5-amine (C11)

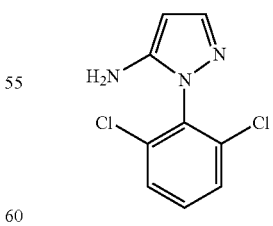

Isolated as a white solid (0.85 g, 97%): $^1$H NMR (400 MHz, CDCl$_3$) δ 7.59-7.53 (m, 1H), 7.49 (dd, J=8.1, 0.8 Hz, 2H), 7.38 (dd, J=8.9, 7.3 Hz, 1H), 5.69 (dd, J=1.9, 0.5 Hz, 1H), 3.56 (s, 2H); $^{13}$C NMR (101 MHz, CDCl$_3$) δ 145.83, 141.60, 135.83, 133.69, 131.16, 128.87, 90.28; ESIMS m/z 229 ([M+H]$^+$).

1-(5-Fluoro-2-methylphenyl)-1H-pyrazol-5-amine (C12)

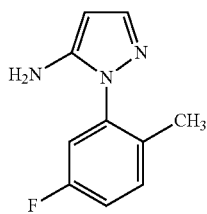

Isolated as an amber oil (0.73 g, 89%): $^1$H NMR (400 MHz, CDCl$_3$) δ 7.43 (d, J=1.9 Hz, 1H), 7.34-7.27 (m, 1H), 7.12-7.04 (m, 2H), 5.60 (d, J=1.9 Hz, 1H), 3.61 (s, 2H); $^{13}$C NMR (101 MHz, CDCl$_3$) δ 160.91 (d, J$_{CF}$=246.6 Hz), 145.30, 140.43, 137.47 (d, J$_{CF}$=9.6 Hz), 132.48 (d, J$_{CF}$=3.6 Hz), 132.25 (d, J$_{CF}$=8.4 Hz), 116.38 (d, J$_{CF}$=20.6 Hz), 115.14 (d, J$_{CF}$=22.5 Hz), 89.28, 16.83; ESIMS m/z 192 ([M+H]$^+$).

1-(2-Ethylphenyl)-1H-pyrazol-5-amine (C13)

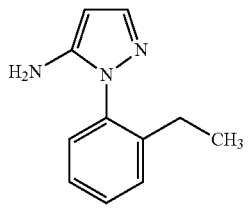

Isolated as an amber oil (0.69 g, 95%): $^1$H NMR (400 MHz, CDCl$_3$) δ 7.46-7.35 (m, 3H), 7.34-7.27 (m, 2H), 5.59 (d, J=1.9 Hz, 1H), 3.57 (s, 2H), 2.49 (q, J=7.6 Hz, 2H), 1.11 (t, J=7.6 Hz, 3H); $^{13}$C NMR (101 MHz, CDCl$_3$) δ 145.41, 142.84, 139.87, 136.14, 129.69, 129.64, 128.10, 126.78, 88.87, 24.09, 14.37; ESIMS m/z 188 ([M+H]$^+$).

1-(2,5-Dimethylphenyl)-1H-pyrazol-5-amine (C14)

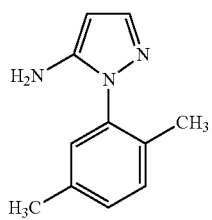

Isolated as an amber oil (0.84 g, 88%): $^1$H NMR (400 MHz, CDCl$_3$) δ 7.42 (d, J=1.9 Hz, 1H), 7.21 (d, J=7.8 Hz, 1H), 7.19-7.10 (m, 2H), 5.59 (d, J=1.9 Hz, 1H), 3.57 (s, 2H), 2.34 (d, J=0.9 Hz, 3H), 2.09 (s, 3H); $^{13}$C NMR (101 MHz, CDCl$_3$) δ 145.24, 139.92, 136.70, 136.44, 133.37, 131.02, 130.12, 128.43, 88.94, 20.70, 16.90; ESIMS m/z 188 ([M+H]$^+$).

1-(2,4-Dimethylphenyl)-1H-pyrazol-5-amine (C15)

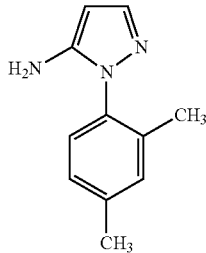

Isolated as an amber oil (1.04 g, 104%): $^1$H NMR (400 MHz, CDCl$_3$) δ 7.42 (d, J=1.9 Hz, 1H), 7.18 (d, J=7.9 Hz, 1H), 7.16-7.12 (m, 1H), 7.11-7.06 (m, 1H), 5.58 (d, J=1.9 Hz, 1H), 3.56 (s, 2H), 2.37 (s, 3H), 2.09 (s, 3H); $^{13}$C NMR (101 MHz, CDCl$_3$) δ 145.35, 139.85, 139.32, 136.46, 134.10, 131.89, 127.66, 127.43, 88.88, 21.17, 17.27; ESIMS m/z 188 ([M+H]$^+$).

1-Mesityl-1H-pyrazol-5-amine (C16)

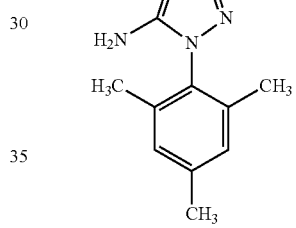

Isolated as an amber oil (0.89 g, 103%): $^1$H NMR (400 MHz, CDCl$_3$) δ 7.45 (d, J=1.9 Hz, 1H), 6.99-6.92 (m, 2H), 5.60 (d, J=1.9 Hz, 1H), 3.48 (s, 2H), 2.32 (s, 3H), 2.00 (s, 6H); $^{13}$C NMR (101 MHz, CDCl$_3$) δ 145.09, 140.02, 139.22, 137.22, 132.91, 129.05, 88.49, 21.12, 17.25; ESIMS m/z 202 ([M+H]$^+$).

1-(2,5-Dichlorophenyl)-1H-pyrazol-5-amine (C17)

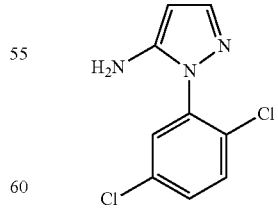

Isolated as an amber oil (0.47 g, 81%): $^1$H NMR (400 MHz, CDCl$_3$) δ 7.54-7.45 (m, 3H), 7.39 (dd, J=8.7, 2.5 Hz, 1H), 5.65 (d, J=1.9 Hz, 1H), 3.67 (s, 2H); $^{13}$C NMR (101 MHz, CDCl$_3$) δ 145.92, 141.45, 136.85, 133.45, 131.21, 130.52, 130.39, 130.27, 90.60; ESIMS m/z 229 ([M+H]$^+$).

1-(2-Methoxyphenyl)-1H-pyrazol-5-amine (C18)

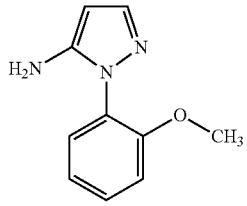

Isolated as an amber oil (0.93 g, 94%): $^1$H NMR (400 MHz, CDCl$_3$) δ 7.47 (d, J=1.9 Hz, 1H), 7.44 (dd, J=7.7, 1.7 Hz, 1H), 7.39 (ddd, J=8.3, 7.5, 1.7 Hz, 1H), 7.09 (dd, J=7.6, 1.3 Hz, 1H), 7.05 (dd, J=8.5, 1.2 Hz, 1H), 5.62 (d, J=1.9 Hz, 1H), 3.86 (s, 3H), 3.85-3.78 (m, 2H); $^{13}$C NMR (101 MHz, CDCl$_3$) δ 153.49, 146.30, 140.72, 129.77, 128.99, 127.64, 121.60, 112.43, 90.39, 56.27; ESIMS m/z 190 ([M+H]$^+$).

Example 4: Preparation of
4-chloro-2-methylbenzaldehyde oxime (C19)

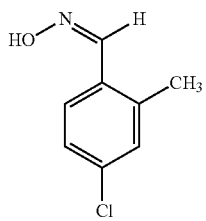

To a solution of 4-chloro-2-methylbenzaldehyde (1.0 g, 6.5 mmol) in methanol (10 mL) was added hydroxylamine hydrochloride (0.68 g, 9.7 mmol) and sodium bicarbonate (0.82 g, 9.7 mmol) and the reaction mixture was stirred at 70° C. overnight. The solvent was concentrated and the crude product obtained was purified by flash column chromatography to give the title product as an off-white solid (0.90 g, 90%): $^1$H NMR (300 MHz, DMSO-d$_6$) δ 11.38 (s, 1H), 8.29 (s, 1H), 7.63 (d, J=8.4 Hz, 1H), 7.33 (d, J=1.8 Hz 1H), 7.27 (dd, J=8.4, 2.1 Hz, 1H), 2.37 (s, 3H).

The following molecules were prepared according to the procedures disclosed in Example 4:

2-Ethylbenzaldehyde oxime (C20)

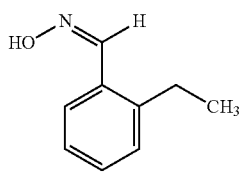

Isolated as an off-white solid (3.8 g, 86%): $^1$H NMR (300 MHz, DMSO-d$_6$) δ 11.24 (s, 1H), 8.33 (s, 1H), 7.6 (d, J=8.1 Hz, 1H), 7.30-7.21 (m, 3H), 7.60 (d, J=8.1 Hz, 1H), 2.74 (q, J=7.2 Hz, 2H), 1.12 (t, J=7.5 Hz, 3H).

Example 5: Preparation of
4-chloro-N-hydroxy-2-methylbenzimidoyl chloride
(C21)

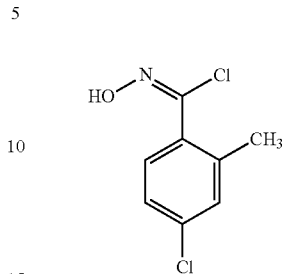

To a solution of 4-chloro-2-methylbenzaldehyde oxime (C19) (0.90 g, 5.3 mmol) in 1,2-dichloroethane (10 mL) was added N-chlorosuccinimide (0.78 g, 5.9 mmol) and a catalytic amount of N,N-dimethylformamide (0.5 mL). The reaction mixture was stirred at room temperature for 3 hours. The reaction mixture was diluted with ethyl acetate, and washed with water and a saturated sodium chloride solution. The organic phase was dried over sodium sulfate, filtered, and concentrated. Purification by flash column chromatography provided the title molecule as an off-white solid (0.70 g, 70%): $^1$H NMR (400 MHz, CDCl$_3$) δ 10.10 (br s, 1H), 7.73 (d, J=8.4 Hz, 1H), 7.33 (d, J=8.0 Hz, 1H), 7.27-7.25 (m, 1H), 2.65 (s, 3H).

The following molecules were prepared according to the procedures disclosed in Example 5:

2-Ethyl-N-hydroxybenzimidoyl chloride (C22)

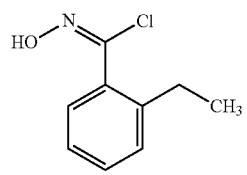

Isolated as an off-white solid (4.0 g, 82%): $^1$H NMR (300 MHz, CDCl$_3$) δ 7.8 (brs, 1H), 7.43-7.35 (m, 2H), 7.29-7.21 (m, 2H), 2.77 (q, J=7.8 Hz 2H), 1.25 (t, J=7.5 Hz, 3H).

Example 6: Preparation of 4-(4-chloro-2-methylphenyl)-1,2,5-oxadiazol-3-amine (C23)

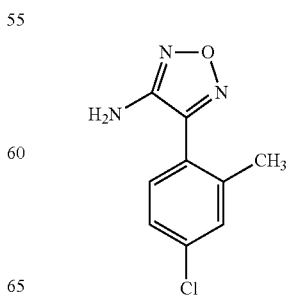

Step 1. 4-chloro-N-hydroxy-2-methylbenzimidoyl cyanide

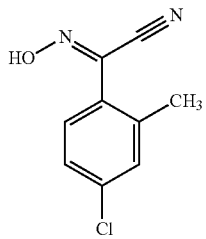

To a solution of 4-chloro-N-hydroxy-2-methylbenzimidoyl chloride (C21) (3.00 g, 14.7 mmol) in diethyl ether (30 mL) was added potassium cyanide (1.40 g, 22.1 mmol). The reaction mixture was stirred at room temperature overnight. The reaction mixture was diluted with diethyl ether and filtered. The filtrate was evaporated to give 4-chloro-N-hydroxy-2-methylbenzimidoyl cyanide as brown liquid (2.5 g) which was used for the next step without purification.

Step 2. 2-(4-chloro-2-methylphenyl)-N'-hydroxy-2-(hydroxyimino)acetimidamide

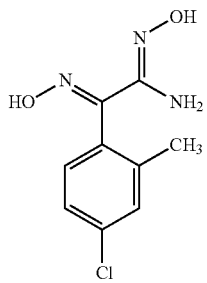

To a solution of 4-chloro-N-hydroxy-2-methylbenzimidoyl cyanide (2.50 g, 12.9 mmol) in methanol (20 mL) was added hydroxylamine hydrochloride (1.35 g, 19.3 mmol) and sodium carbonate (1.62 g, 19.3 mmol). The reaction mixture was stirred at room temperature overnight. The solvent was concentrated to obtain 2-(4-chloro-2-methylphenyl)-N'-hydroxy-2-(hydroxyimino)acetimidamide as thick gummy material (2.0 g) which was used for the next step without any further purification: ESIMS m/z 229 ([M+H]$^+$).

Step 3. 4-(4-chloro-2-methylphenyl)-1,2,5-oxadiazol-3-amine (C23)

A solution of 2-(4-chloro-2-methylphenyl)-N'-hydroxy-2-(hydroxyimino)acetimidamide (2.0 g, 8.8 mmol) in sodium hydroxide (2 N, 10 mL) was heated to reflux for 12 hours. The reaction mixture was cooled to room temperature and diluted with water. The reaction mixture was extracted with ethyl acetate. The organic layer was washed with water and brine, dried over sodium sulfate, filtered, and concentrated. The crude product obtained was purified by flash column chromatography to provide the title molecule as pale-yellow liquid (0.80 g, 44%): $^1$H NMR (300 MHz, DMSO-d$_6$) δ 7.52 (s, 1H), 7.41 (d, J=1.2 Hz, 2H), 6.11 (br s, 2H), 2.34 (s, 3H).

The following molecules were prepared according to the procedures disclosed in Example 6:

4-(2-Ethylphenyl)-1,2,5-oxadiazol-3-amine (C24)

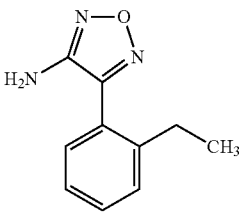

Isolated as a pale yellow liquid (0.8 g, 44%): $^1$H NMR (300 MHz, DMSO-d$_6$) δ 7.49-7.42 (m, 2H), 7.35 (d, J=3.3 Hz, 2H), 6.03 (br s, 2H), 2.54 (q, J=7.8 Hz, 2H), 1.06 (t, J=7.5 Hz, 3H).

4-(2,4-Dimethylphenyl)-1,2,5-oxadiazol-3-amine (C25)

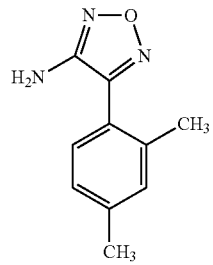

Isolated as a pale yellow liquid (2.0 g, 72%): $^1$H NMR (300 MHz, DMSO-d$_6$) δ 7.27 (d, J=8.1 Hz, 1H), 7.22 (s, 1H), 7.14 (d, J=8.1 Hz, 1H), 6.01 (br s, 2H), 2.34 (s, 3H), 2.21 (s, 3H).

4-Mesityl-1,2,5-oxadiazol-3-amine (C26)

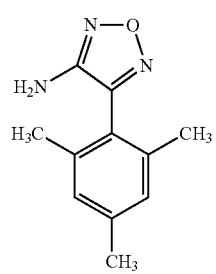

Isolated as a pale yellow liquid (0.065 g, 35%): $^1$H NMR (300 MHz, DMSO-d$_6$) δ 7.02 (s, 2H), 5.95 (br s, 2H), 2.30 (s, 3H), 2.01 (s, 6H).

4-(3-Methoxyphenyl)-1,2,5-oxadiazol-3-amine (C27)

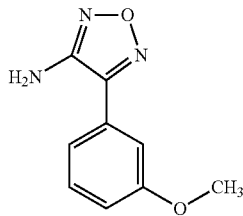

Isolated as a pale yellow liquid (0.12 g, 10%): $^1$H NMR (300 MHz, DMSO-$d_6$) δ 7.47 (t, J=7.5 Hz, 1H), 7.32 (d, J=7.8 Hz, 1H), 7.27-7.25 (m, 1H), 7.12 (dd, J=9.0, 2.4 Hz, 1H), 6.20 (br s, 2H).

4-(2,6-Dichlorophenyl)-1,2,5-oxadiazol-3-amine (C28)

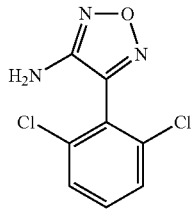 [SMILES: Nc1nonc1-c1c(Cl)cccc1Cl]

Isolated as a pale yellow liquid (0.2 g, 22%): $^1$H NMR (300 MHz, DMSO-$d_6$) δ 7.70-7.58 (m, 3H), 6.27 (bs, 2H).

4-(2-(Trifluoromethoxy)phenyl)-1,2,5-oxadiazol-3-amine (C29)

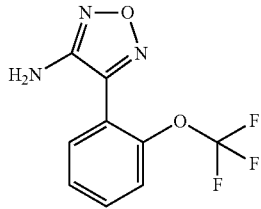 [SMILES: Nc1nonc1-c1ccccc1OC(F)(F)F]

Isolated as an off-white solid (0.25 g, 28%): $^1$H NMR (300 MHz, DMSO-$d_6$) δ 7.76-7.68 (m, 2H), 7.68-7.55 (m, 2H), 6.18 (br s, 2H).

Example 7: Preparation of 1-(thiazol-2-yl)-3-(4-(1-(4-(trifluoromethoxy)phenyl)-1H-1,2,4-triazol-3-yl)phenethyl)urea (F50)

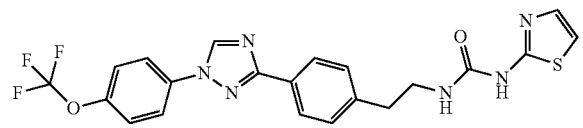 [SMILES: O=C(NCCc1ccc(-c2ncn(-c3ccc(OC(F)(F)F)cc3)n2)cc1)Nc1nccs1]

4-Nitrophenyl 4-(1-(4-(trifluoromethoxy)phenyl)-1H-1,2,4-triazol-3-yl)phenethylcarbamate (C33) (0.137 g, 0.270 mmol), pyridine (2 mL), and 2-aminothiazole (0.0400 g, 0.400 mmol) were capped in a 25-mL vial and heated at 140° C. for 30 minutes in a Biotage Initiator® microwave reactor with an external IR-sensor temperature monitoring from the side of the vessel. The solution was diluted with ethyl acetate (5 mL) and adsorbed onto Celite®. Purification by flash column chromatography using 0-100% ethyl acetate/(1:1 hexanes/dichloromethane) as eluent provided the title molecule as a white solid (0.0650 g, 48%).

Example 8: Preparation of 1-(1-phenyl-1H-pyrazol-5-yl)-3-(4-(1-(4-(trifluoromethoxy)phenyl)-1H-1,2,4-triazol-3-yl)phenethyl)urea (F51)

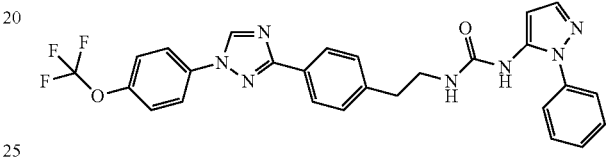

To a solution of 4-nitrophenyl 4-(1-(4-(trifluoromethoxy)phenyl)-1H-1,2,4-triazol-3-yl)phenethylcarbamate (C33) (0.151 g, 0.300 mmol) in pyridine (3 mL) was added 1-phenyl-1H-pyrazol-5-amine (0.0860 g, 0.540 mmol). The mixture was refluxed for 20 hours. The solution was cooled to room temperature, diluted with ethyl acetate (5 mL), and adsorbed onto Celite®. Purification by flash column chromatography using 0-100% ethyl acetate/(1:1 hexanes/dichloromethane) as eluent provided the title molecule as a white solid (0.0240 g, 13%).

Example 9: Preparation of 1-(5-phenyloxazol-2-yl)-3-(4-(1-(4-(trifluoromethoxy)phenyl)-1H-1,2,4-triazol-3-yl)phenethyl)urea (F52)

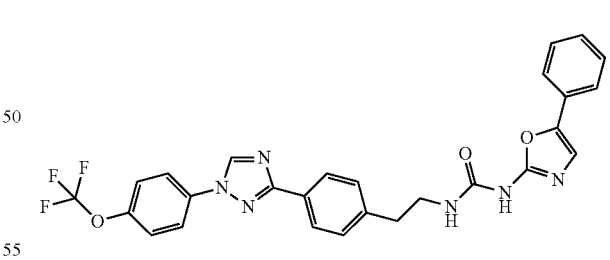

To a solution of 4-nitrophenyl 4-(1-(4-(trifluoromethoxy)phenyl)-1H-1,2,4-triazol-3-yl)phenethylcarbamate (C33) (0.174 g, 0.340 mmol) in tetrahydrofuran (3.4 mL) was added 5-phenyloxazol-2-amine (0.0570 g, 0.360 mmole) and diisopropylethylamine (0.120 mL, 0.689 mmol). The mixture was refluxed for 5 hours. After cooling, the solution was diluted with methanol (5 mL) and adsorbed onto Celite®. Purification by flash column chromatography using 0-100% ethyl acetate/(1:1 hexanes/dichloromethane) as eluent provided the title molecule as a white solid (0.0310 g, 18%).

Example 10: Preparation of 3-(4-bromophenyl)-1-(4-(trifluoromethoxy)phenyl)-1H-1,2,4-triazole (C30)

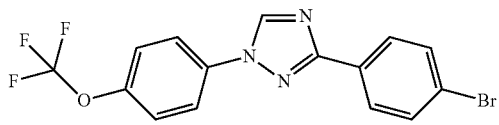 [SMILES: FC(F)(F)Oc1ccc(-n2cnc(-c3ccc(Br)cc3)n2)cc1]

A solution of 3-(4-bromophenyl)-1H-1,2,4-triazole (10.9 g, 48.5 mmol), 1-iodo-4-(trifluoromethoxy)benzene (13.2 g, 45.8 mmol), copper(I) iodide (2.38 g, 12.5 mmol), and cesium carbonate (30.3 g, 93.0 mmol) in dimethylsulfoxide (85 mL) was degassed with nitrogen for 5 minutes. The mixture was heated at 100° C. for 60 hours. After cooling, ethyl acetate (200 mL) was added and the mixture was filtered through Celite®. The filtrate was added to a solution of saturated ammonium chloride (200 mL) and stirred for one and a half hours. The layers were separated and the aqueous layer was extracted with ethyl acetate (3×100 mL). The combined organic extracts were dried over anhydrous magnesium sulfate, filtered, and adsorbed onto Celite®. Purification by flash column chromatography using 0-40% ethyl acetate/hexanes as eluent provided the title molecule as an off-white solid (9.65 g, 52%): mp 109-112° C.; $^1$H NMR (400 MHz, CDCl$_3$) δ 8.56 (s, 1H), 8.10-8.03 (m, 2H), 7.83-7.75 (m, 2H), 7.64-7.57 (m, 2H), 7.42-7.35 (m, 2H); ESIMS m/z 384 ([M+H]$^+$).

Example 11: Preparation of tert-butyl 4-(1-(4-(trifluoromethoxy)phenyl)-1H-1,2,4-triazol-3-yl)phenethylcarbamate (C31)

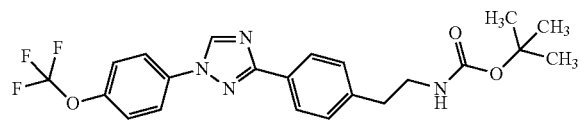 [SMILES: CC(C)(C)OC(=O)NCCc1ccc(-c2ncn(-c3ccc(OC(F)(F)F)cc3)n2)cc1]

3-(4-Bromophenyl)-1-(4-(trifluoromethoxy)phenyl)-1H-1,2,4-triazole (C30) (7.21 g, 18.8 mmol), potassium (2-((tert-butoxycarbonyl)amino)ethyl)trifluoroborate (5.21 g, 20.8 mmol), 1,1'-bis(diphenylphosphino)ferrocene]dichloropalladium(II), complex with dichloromethane (0.770 g, 0.940 mmole), cesium carbonate (19.1 g, 58.6 mmol), and toluene (100 mL) and water (21 mL) were heated at 95° C. for 20 hours. Upon cooling to room temperature, the reaction mixture was diluted with ethyl acetate (100 mL) and filtered through Celite®. The filter cake was washed with ethyl acetate (60 mL). The layers were separated and the aqueous layer was extracted with ethyl acetate (2×20 mL). The combined organic layers were washed with saturated sodium chloride, dried over anhydrous magnesium sulfate, filtered, and adsorbed onto Celite®. Purification by flash column chromatography using 0-50% ethyl acetate/hexanes as eluent provided the title molecule as a white solid (2.48 g, 28%): $^1$H NMR (400 MHz, CDCl$_3$) δ 8.55 (s, 1H), 8.15-8.10 (m, 2H), 7.82-7.76 (m, 2H), 7.41-7.35 (m, 2H), 7.31 (d, J=8.2 Hz, 2H), 4.56 (s, 1H), 3.42 (d, J=6.4 Hz, 2H), 2.86 (t, J=7.0 Hz, 2H), 1.44 (s, 9H); ESIMS m/z 449 ([M+H]$^+$).

Example 12: Preparation of 2-(4-(1-(4-(trifluoromethoxy)phenyl)-1H-1,2,4-triazol-3-yl)phenyl)ethanamine 2,2,2-trifluoroacetate (C32)

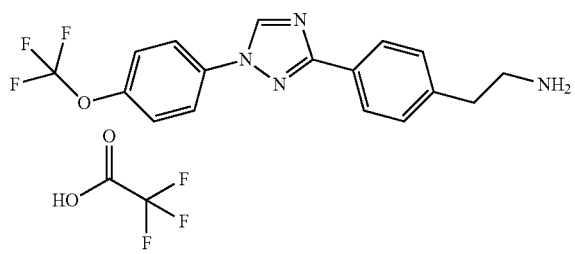

To a cooled solution of tert-butyl 4-(1-(4-(trifluoromethoxy)phenyl)-1H-1,2,4-triazol-3-yl)phenethylcarbamate (2.46 g, 8.01 mmol) in dichloromethane (20 mL) was added trifluoroacetic acid (0.840 mL, 78.0 mmol). After allowing the reaction to warm to room temperature over 20 hours, added additional trifluoroacetic acid (0.420 mL, 39.0 mmol) and water (2 drops). After 20 hours, added additional trifluoroacetic acid (0.420 mL, 39.0 mmol) and stirred at room temperature for 20 hours. The solution was concentrated to dryness to give a the title molecule as a sticky white solid (3.55 g, 133%) used without further purification: $^1$H NMR (400 MHz, DMSO-d$_6$) δ 9.39 (s, 1H), 8.36 (s, 1H), 8.12-8.03 (m, 4H), 7.89 (s, 2H), 7.62 (d, J=8.3 Hz, 2H), 7.43 (d, J=8.3 Hz, 2H), 3.11 (dq, J=11.2, 6.1, 5.5 Hz, 2H), 3.00-2.91 (m, 2H); ESIMS m/z 349 ([M+H]$^+$).

Example 13: Preparation of 4-nitrophenyl 4-(1-(4-(trifluoromethoxy)phenyl)-1H-1,2,4-triazol-3-yl) phenethylcarbamate (C33)

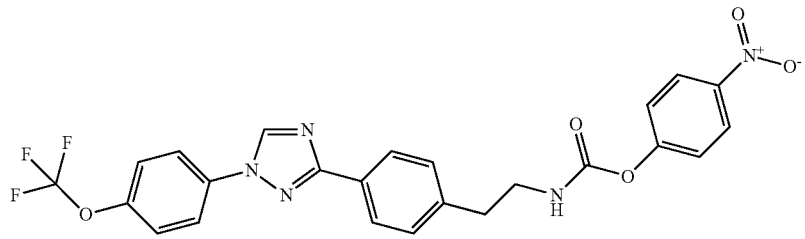 [SMILES: O=C(NCCc1ccc(-c2ncn(-c3ccc(OC(F)(F)F)cc3)n2)cc1)Oc1ccc([N+](=O)[O-])cc1]

To a solution of 2-(4-(1-(4-(trifluoromethoxy)phenyl)-1H-1,2,4-triazol-3-yl)phenyl)ethanamine 2,2,2-trifluoroacetate (C32) (2.05 g, 4.44 mmol) in tetrahydrofuran (30 mL) was added 4-nitrophenyl carbonochloridate (0.960 g, 4.75 mmol) and diisopropylethylamine (4.6 mL). The reaction mixture was stirred under nitrogen for 60 hours. The solution was diluted with ethyl acetate (50 mL) and washed successively with water (30 mL), saturated sodium bicarbonate (2×30 mL), and saturated sodium chloride (30 mL). The organic layer was dried over anhydrous magnesium sulfate, filtered, and adsorbed onto Celite®. Purification by flash column chromatography using 0-100% ethyl acetate/(1:1 hexanes/dichloromethane) as eluent provided the title molecule as an off-white solid (0.640 g, 28%): $^1$H NMR (400 MHz, CDCl$_3$) δ 8.57 (s, 1H), 8.26-8.20 (m, 2H), 8.17 (d, J=8.3 Hz, 2H), 7.83-7.77 (m, 2H), 7.42-7.33 (m, 4H), 7.31-7.25 (m, 2H), 5.21 (t, J=5.8 Hz, 1H), 3.61 (q, J=6.8 Hz, 2H), 2.98 (t, J=6.9 Hz, 2H); ESIMS m/z 514 ([M+H]$^+$).

Example 14: Preparation of 1-(1-(2-isopropylphenyl)-1H-imidazol-2-yl)-3-(4-(1-(4-(perfluoroethoxy)phenyl)-1H-1,2,4-triazol-3-yl)phenyl)urea (F34)

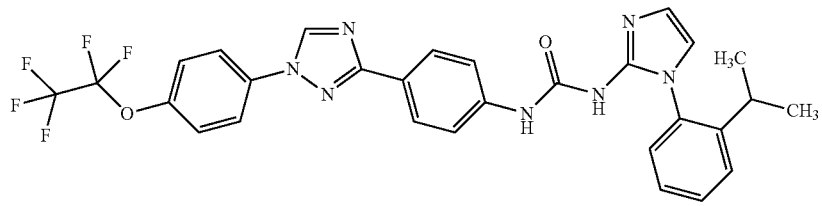 [SMILES: CC(C)c1ccccc1-n1ccnc1NC(=O)Nc1ccc(-c2ncn(-c3ccc(OC(F)(F)C(F)(F)F)cc3)n2)cc1]

To 3-(4-isocyanatophenyl)-1-(4-(perfluoroethoxy)phenyl)-1H-1,2,4-triazole (C34) (0.100 g, 0.252 mmol) in tetrahydrofuran (0.841 mL) was added 1-(2-isopropylphenyl)-1H-imidazol-2-amine (C36) (0.0508 g, 0.252 mmol). The reaction mixture was heated to 40° C. for 1 hour. The reaction mixture was cooled to room temperature. The reaction mixture was diluted with dichloromethane and concentrated. Purification by flash column chromatography using ethyl acetate/hexanes) as eluent to provide the title molecule as an off-white solid (0.0890 g, 58%).

The following molecule was prepared according to the procedures disclosed in Example 14:

1-(1-(3-Chlorophenyl)-1H-imidazol-2-yl)-3-(4-(1-(4-(perfluoroethoxy)phenyl)-1H-1,2,4-triazol-3-yl)phenyl)urea (F35)

Isolated as an off-white solid (0.087 g, 58%).

Example 15: General Procedure for the Preparation of 1-(1-(phenyl, Substituted phenyl, or pyridyl)-1H-imidazol-2-yl)-3-(4-(1-(4-(trifluoromethoxy)phenyl)-1H-1,2,4-triazol-3-yl)phenyl)ureas

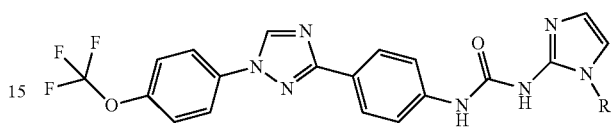

To a stirred solution of 4-nitrophenyl (4-(1-(4-(trifluoromethoxy)phenyl)-1H-1,2,4-triazol-3-yl)phenyl)carbamate (1.0 equivalent) in acetonitrile (1 mL/mmol) was added a 1-(phenyl, substituted phenyl, or heterocyclyl)-1H-imidazol-2-amine (1.0 equivalent) and potassium phosphate (2.0 equivalents) and the reaction mixture was cooled to 0° C. Diisopropylethylamine (2.0 equivalents) was added and the reaction mixture was stirred at room temperature for 18 hours. The reaction mixture was diluted with ethyl acetate. The organic layer was washed with water. The aqueous layer was separated and extracted with ethyl acetate (3×). The combined organic extracts were washed with water (3×), a saturated brine solution, dried over sodium sulfate, and concentrated. Purification by preparative HPLC provided the title molecule.

The following molecules were prepared according to the procedures disclosed in Example 15:

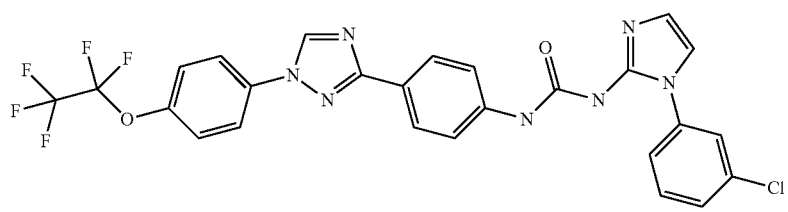 [SMILES: O=C(Nc1ccc(-c2ncn(-c3ccc(OC(F)(F)C(F)(F)F)cc3)n2)cc1)Nc1nccn1-c1cccc(Cl)c1]

1-(1-Phenyl-1H-imidazol-2-yl)-3-(4-(1-(4-(trifluoromethoxy)phenyl)-1H-1,2,4-triazol-3-yl)phenyl)urea (F20)

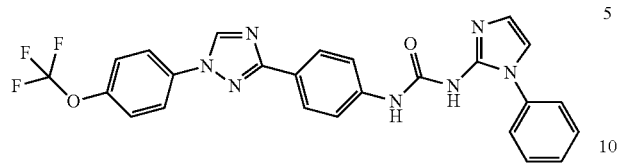

1-(1-(o-Tolyl)-1H-imidazol-2-yl)-3-(4-(1-(4-(trifluoromethoxy)phenyl)-1H-1,2,4-triazol-3-yl)phenyl)urea (F21)

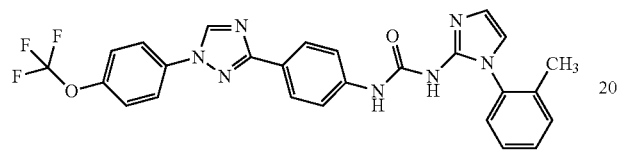

1-(1-(2-Isopropylphenyl)-1H-imidazol-2-yl)-3-(4-(1-(4-(trifluoromethoxy)phenyl)-1H-1,2,4-triazol-3-yl)phenyl)urea (F22)

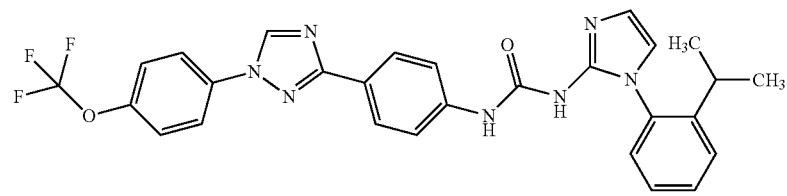

1-(1-(3-Methoxyphenyl)-1H-imidazol-2-yl)-3-(4-(1-(4-(trifluoromethoxy)phenyl)-1H-1,2,4-triazol-3-yl)phenyl)urea (F23)

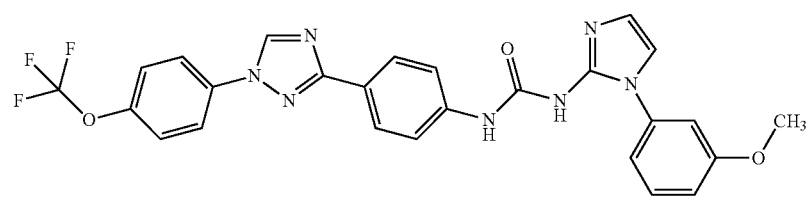

1-(1-(m-Tolyl)-1H-imidazol-2-yl)-3-(4-(1-(4-(trifluoromethoxy)phenyl)-1H-1,2,4-triazol-3-yl)phenyl)urea (F24)

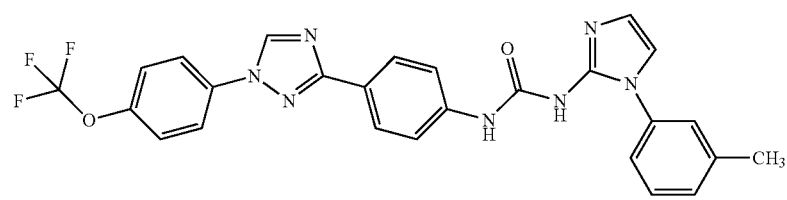 [SMILES: Cc1cccc(-n2ccnc2NC(=O)Nc2ccc(-c3ncn(-c4ccc(OC(F)(F)F)cc4)n3)cc2)c1]

1-(1-(3-Isopropylphenyl)-1H-imidazol-2-yl)-3-(4-(1-(4-(trifluoromethoxy)phenyl)-1H-1,2,4-triazol-3-yl)phenyl)urea (F25)

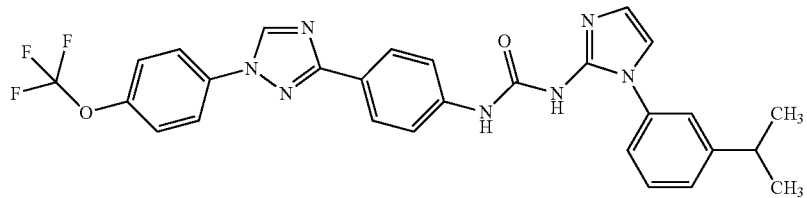

1-(1-(3-Ethylphenyl)-1H-imidazol-2-yl)-3-(4-(1-(4-(trifluoromethoxy)phenyl)-1H-1,2,4-triazol-3-yl)phenyl)urea (F26)

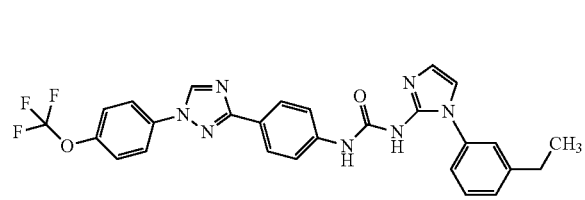 [SMILES: CCc1cccc(-n2ccnc2NC(=O)Nc2ccc(-c3ncn(-c4ccc(OC(F)(F)F)cc4)n3)cc2)c1]

1-(1-(3-Chlorophenyl)-1H-imidazol-2-yl)-3-(4-(1-(4-(trifluoromethoxy)phenyl)-1H-1,2,4-triazol-3-yl)phenyl)urea (F27)

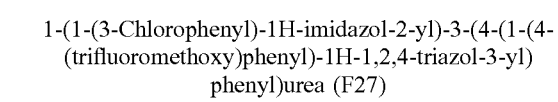

1-(1-(3,5-Dichlorophenyl)-1H-imidazol-2-yl)-3-(4-(1-(4-(trifluoromethoxy)phenyl)-1H-1,2,4-triazol-3-yl)phenyl)urea (F28)

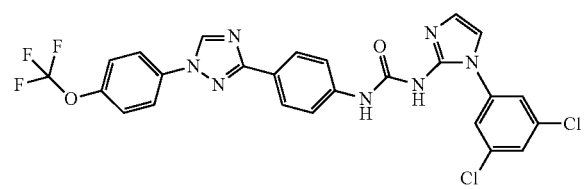

1-(1-(p-Tolyl)-1H-imidazol-2-yl)-3-(4-(1-(4-(trifluoromethoxy)phenyl)-1H-1,2,4-triazol-3-yl)phenyl)urea (F29)

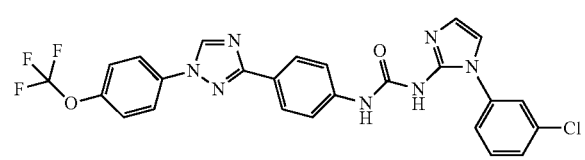 [SMILES: O=C(Nc1ccc(-c2ncn(-c3ccc(OC(F)(F)F)cc3)n2)cc1)Nc1nccn1-c1cccc(Cl)c1]

1-(1-(4-Methoxyphenyl)-1H-imidazol-2-yl)-3-(4-(1-(4-(trifluoromethoxy)phenyl)-1H-1,2,4-triazol-3-yl)phenyl)urea (F30)

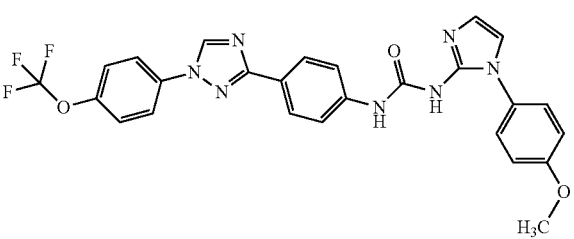 [SMILES: COc1ccc(-n2ccnc2NC(=O)Nc2ccc(-c3ncn(-c4ccc(OC(F)(F)F)cc4)n3)cc2)cc1]

1-(1-(Pyridin-2-yl)-1H-imidazol-2-yl)-3-(4-(1-(4-(trifluoromethoxy)phenyl)-1H-1,2,4-triazol-3-yl)phenyl)urea (F31)

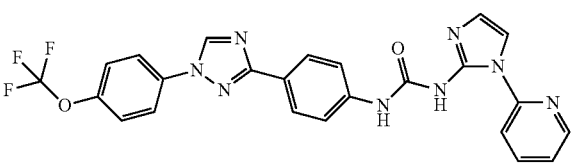 [SMILES: O=C(Nc1ccc(-c2ncn(-c3ccc(OC(F)(F)F)cc3)n2)cc1)Nc1nccn1-c1ccccn1]

1-(1-(Pyridin-3-yl)-1H-imidazol-2-yl)-3-(4-(1-(4-(trifluoromethoxy)phenyl)-1H-1,2,4-triazol-3-yl)phenyl)urea (F32)

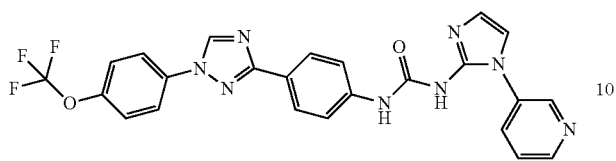

1-(1-(Pyridin-4-yl)-1H-imidazol-2-yl)-3-(4-(1-(4-(trifluoromethoxy)phenyl)-1H-1,2,4-triazol-3-yl)phenyl)urea (F33)

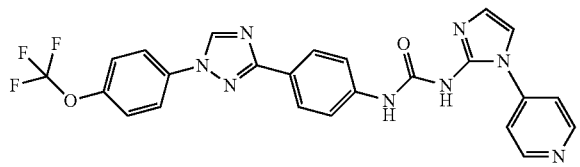 [SMILES: O=C(Nc1ccc(-c2ncn(-c3ccc(OC(F)(F)F)cc3)n2)cc1)Nc1nccn1-c1ccncc1]

Example 16: Preparation of 3-(4-isocyanatophenyl)-1-(4-(perfluoroethoxy)phenyl)-1H-1,2,4-triazole (C34)

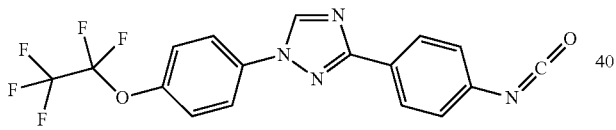

A 250 mL, 3-neck flask, fitted with magnetic stirring, air condenser, temperature probe, and nitrogen inlet, was charged with 4-(1-(4-(perfluoroethoxy)phenyl)-1H-1,2,4-triazol-3-yl)benzoyl azide (5.00 g, 11.2 mmol) and toluene (100 mL). The brown solution was heated to 100° C. slowly and allowed to stir for 1 hour. The reaction was cooled to room temperature and concentrated. The solid was dissolved in dichloromethane, filtered, and concentrated. The solid was dissolved in methyl tert-butylether (30 mL), heated to effect a slightly turbid solution, and filtered hot. The filtrate was reheated to effect a solution again and heptane (~10-15 mL) was slowly added. The solution was placed on a rotovap and the methyl tert-butylether was slowly removed under reduced pressure. When the first sign of solid was noted, the vacuum was broken and the mixture was allowed to slowly rotate at 40° C. to effect precipitation of solid. The solid was filtered, rinsed with heptane, and vacuum dried (3 crops) to provide the title molecule as a light-tan solid (3.40 g, 77%): $^1$H NMR (600 MHz, DMSO-$d_6$) δ 9.41 (s, 1H), 8.13-8.04 (m, 4H), 7.60 (d, J=8.6 Hz, 2H), 7.38 (dd, J=8.5, 1.6 Hz, 2H); $^{19}$F NMR (376 MHz, CDCl$_3$) δ −80.54 (d, J=3.3 Hz), −82.25; ESIMS m/z 429 ([M+H]$^+$) methyl carbamate.

Example 17: General Procedure for the Preparation of 1-(phenyl or Substituted phenyl)-1H-imidazol-2-amines

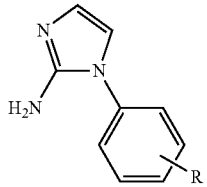

Step 1. 1-(phenyl, substituted phenyl, or heterocyclyl)guanidine nitrates

To a stirred solution of aniline (1.0 equivalent) and cyanamide (1.5 equivalents) in ethanol (20 volumes) was added concentrated nitric acid (1.0 equivalent). The reaction mixture was heated at 100° C. for 18 hours. The reaction mixture was cooled to room temperature, concentrated, and directly taken to the next step.

Step 2. 1-(phenyl, substituted phenyl, or heterocyclyl)-1H-imidazol-2-amines To a stirred solution of 1-(phenyl, substituted phenyl, or heterocyclyl)guanidine nitrate (1.0 equivalent) in ethanol (6 volumes) was added sodium bicarbonate (2.5 equivalents) followed by chloroacetaldehyde (1.2 equivalents). The reaction mixture was heated at 80° C. for 18 hours. The reaction mixture was cooled to room temperature and concentrated. The residue was diluted with ethyl acetate and washed with water and a saturated brine solution, dried over anhydrous sodium sulfate, and concentrated. Purification by preparative HPLC provided the title molecules.

The following molecules were prepared according to the procedures disclosed in Example 17:

1-(o-Tolyl)-1H-imidazol-2-amine (C35)

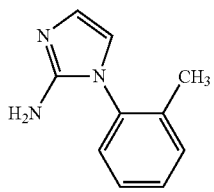

$^1$H NMR (300 MHz, DMSO-$d_6$) δ 12.70 (s, 1H), 7.64 (s, 2H), 7.44 (d, J=23.5 Hz, 3H), 7.26-6.94 (m, 2H), 2.09 (s, 3H); ESIMS m/z 175 ([M+H]$^+$); IR (thin film) 3123, 2361, 1667 cm$^{-1}$.

1-(2-Isopropylphenyl)-1H-imidazol-2-amine (C36)

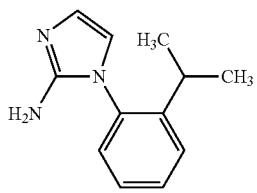

¹H NMR (300 MHz, DMSO-d₆) δ 12.94 (s, 2H), 7.69 (s, 2H), 7.58 (dd, J=4.1, 1.5 Hz, 1H), 7.50-7.29 (m, 2H), 7.13 (s, 1H), 2.67-2.52 (m, 1H), 1.40-0.75 (m, 6H); ESIMS m/z 202 ([M+H]⁺); IR (thin film) 3138, 2690, 1659 cm⁻¹.

1-(3-Methoxyphenyl)-1H-imidazol-2-amine (C37)

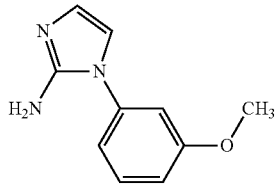

¹H NMR (300 MHz, DMSO-d₆) δ 12.95 (s, 1H), 7.82 (s, 2H), 7.62-7.35 (m, 1H), 7.20 (d, J=2.5 Hz, 1H), 7.13-7.04 (m, 3H), 3.81 (s, 3H); ESIMS m/z 190 ([M+H]⁺); IR (thin film) 3134, 2696, 1655 cm⁻¹.

1-(m-Tolyl)-1H-imidazol-2-amine (C38)

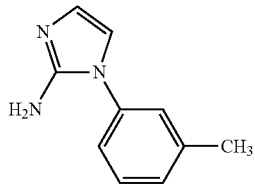

¹H NMR (400 MHz, DMSO-d₆) δ 12.59 (s, 1H), 7.74 (s, 1H), 7.50 (t, J=7.7 Hz, 1H), 7.40-7.30 (m, 3H), 7.21 (d, J=2.4 Hz, 1H), 7.13 (d, J=2.5 Hz, 1H), 2.40 (s, 3H); ESIMS m/z 175 ([M+H]⁺); IR (thin film) 3117, 2735, 1660 cm⁻¹.

1-(3-Isopropylphenyl)-1H-imidazol-2-amine (C39)

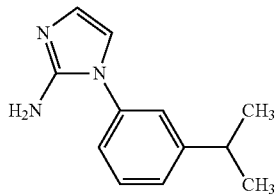

¹H NMR (400 MHz, DMSO-d₆) δ 12.84 (s, 1H), 7.76 (s, 2H), 7.52 (t, J=7.8 Hz, 1H), 7.47-7.41 (m, 1H), 7.38 (t, J=2.0 Hz, 1H), 7.33 (ddd, J=7.8, 2.3, 1.1 Hz, 1H), 7.21 (d, J=2.5 Hz, 1H), 2.98 (p, J=6.9 Hz, 1H), 1.24 (d, J=6.9 Hz, 6H); ESIMS m/z 202 ([M+H]⁺); IR (thin film) 3146, 2965, 1667 cm⁻¹.

1-(3-Ethylphenyl)-1H-imidazol-2-amine (C40)

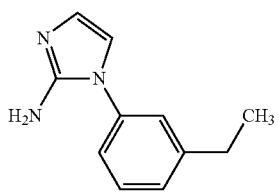

¹H NMR (400 MHz, DMSO-d₆) δ 12.84 (s, 1H), 7.77 (s, 1H), 7.51 (t, J=7.7 Hz, 1H), 7.44-7.26 (m, 3H), 7.26-7.16 (m, 1H), 7.13 (d, J=2.5 Hz, 1H), 2.69 (q, J=7.6 Hz, 2H), 1.22 (t, J=7.6 Hz, 3H); ESIMS m/z 188 ([M+H]⁺); IR (thin film) 3154, 2972, 1664 cm⁻¹.

1-(3-Chlorophenyl)-1H-imidazol-2-amine (C41)

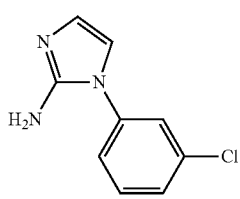 [SMILES: Nc1nccn1-c1cccc(Cl)c1]

¹H NMR (400 MHz, DMSO-d₆) δ 12.86 (s, 1H), 7.90 (s, 2H), 7.73 (d, J=2.1 Hz, 1H), 7.64 (d, J=5.7 Hz, 1H), 7.54 (dt, J=5.3, 2.7 Hz, 1H), 7.25 (d, J=2.5 Hz, 1H), 7.15 (d, J=2.6 Hz, 1H); ESIMS m/z 194 ([M+H]⁺); IR (thin film) 3096, 2698, 1650 cm⁻¹.

1-(3,5-Dichlorophenyl)-1H-imidazol-2-amine (C42)

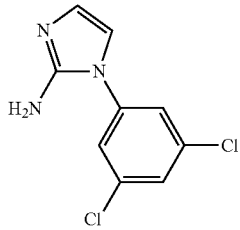 [SMILES: Nc1nccn1-c1cc(Cl)cc(Cl)c1]

¹H NMR (400 MHz, DMSO-d₆) δ 12.97 (s, 1H), 8.00 (s, 1H), 7.86 (t, J=1.9 Hz, 1H), 7.75 (d, J=1.9 Hz, 2H), 7.26 (d, J=2.5 Hz, 1H), 7.15 (d, J=2.5 Hz, 1H); ESIMS m/z 230 ([M+H]⁺); IR (thin film) 3148, 2361, 1672 cm⁻¹.

1-(p-Tolyl)-1H-imidazol-2-amine (C43)

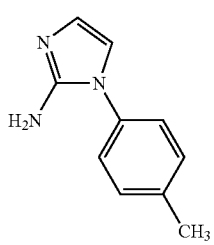

¹H NMR (400 MHz, DMSO-d₆) δ 12.85 (s, 1H), 7.76 (s, 1H), 7.42 (s, 4H), 7.15 (dd, J=19.1, 2.5 Hz, 2H), 2.40 (s, 3H); ESIMS m/z 175 ([M+H]⁺); IR (thin film) 3149, 1657 cm⁻¹.

1-(4-Methoxyphenyl)-1H-imidazol-2-amine (C44)

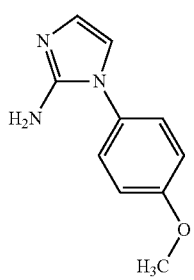

¹H NMR (400 MHz, DMSO-d₆) δ 12.54 (s, 1H), 7.65 (s, 1H), 7.51-7.40 (m, 2H), 7.23-7.02 (m, 4H), 3.83 (s, 3H); ESIMS m/z 191 ([M+H]⁺); IR (thin film) 3129, 2717, 1662 cm⁻¹.

Example 18: General Procedure for the Preparation of 1-(pyridyl)-1H-imidazol-2-amines

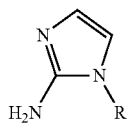

To a stirred solution of iodopyridine (1.0 equivalent) and 2-amino imidazole (1.1 equivalents) in tert-butanol (15 volumes) was added cesium carbonate (1.5 equivalents). The reaction mixture was degassed by purging with nitrogen continuously for 15 minutes. 8-Hydroxyquinoline (0.15 equivalents) and copper(I) iodide (0.1 equivalents) were added, and the reaction mixture was heated to 90° C. for 18 hours. The reaction mixture was cooled to room temperature and quenched with water and extracted with ethyl acetate (3×). The combined organic extracts were washed with water and a saturated brine solution, dried over sodium sulfate, and concentrated. Purification by preparative HPLC provided the title molecule.

The following molecules were prepared according to the procedures disclosed in Example 18:

1-(Pyridin-2-yl)-1H-imidazol-2-amine (C45)

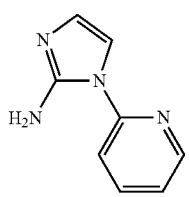

¹H NMR (400 MHz, DMSO-d₆) δ 12.79 (br s, 1H), 8.77 (s, 1H), 8.57-8.56 (m, 1H), 8.12-8.11 (m, 1H), 7.85 (d, J=8.36 Hz, 1H), 7.77 (d, J=1.84 Hz, 1H), 7.49-7.22 (m, 1H), 7.21 (s, 1H); ESIMS m/z 161 ([M+H]⁺).

1-(Pyridin-3-yl)-1H-imidazol-2-amine (C46)

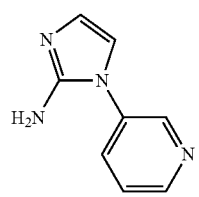 [SMILES: Nc1nccn1-c1cccnc1]

¹H NMR (400 MHz, DMSO-d₆) δ 12.97 (s, 1H), 8.89-8.72 (m, 2H), 8.06 (ddd, J=8.2, 2.6, 1.3 Hz, 1H), 7.97 (s, 1H), 7.68 (dd, J=8.2, 4.7 Hz, 1H), 7.28 (d, J=2.5 Hz, 1H), 7.18 (d, J=2.5 Hz, 1H); ESIMS m/z 161 ([M+H]⁺).

1-(Pyridin-4-yl)-1H-imidazol-2-amine (C47)

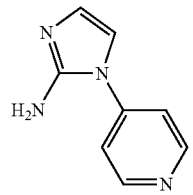 [SMILES: Nc1nccn1-c1ccncc1]

¹H NMR (400 MHz, DMSO-d₆) δ 12.93 (s, 1H), 8.88 (s, 1H), 8.10 (s, 2H), 7.69 (d, J=4.5 Hz, 2H), 7.36 (d, J=2.6 Hz, 1H), 7.22 (d, J=2.6 Hz, 1H); ESIMS m/z 161 ([M+H]⁺).

Example 19: Preparation of 1-(4-(2-ethylphenyl)thiazol-5-yl)-3-(4-(1-(4-(trifluoromethoxy)phenyl)-1H-1,2,4-triazol-3-yl)phenyl)urea (F49)

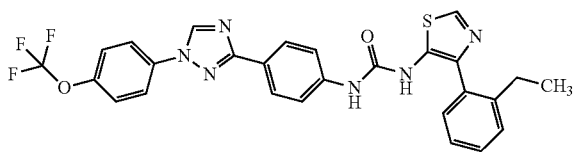 [SMILES: CCc1ccccc1-c1ncsc1NC(=O)Nc1ccc(-c2ncn(-c3ccc(OC(F)(F)F)cc3)n2)cc1]

4-(2-Ethylphenyl)thiazole-5-carbonyl azide (C68) (0.077 g, 0.30 mmol) in acetonitrile (1.3 mL) was heated at 80° C. for 2 hours. The reaction was cooled and 4-(1-(4-(trifluoromethoxy)phenyl)-1H-1,2,4-triazol-3-yl)aniline (0.080 g, 0.25 mmol) was added. After 3 hours a catalytic amount of cesium carbonate was added and the reaction was stirred overnight. Purification by flash column chromatography using 0-100% ethyl acetate/(1:1 hexanes/dichloromethane) as eluent followed by reverse-phase flash column chromatography using 0-100% acetonitrile/water as eluent provided the title molecule as a pink oil (0.0080 mg, 6%).

The following molecules were prepared according to the procedures disclosed in Example 19:

73

1-(4-(4-Methoxy-2-methylphenyl)thiazol-5-yl)-3-(4-(1-(4-(trifluoromethoxy)phenyl)-1H-1,2,4-triazol-3-yl)phenyl)urea (F46)

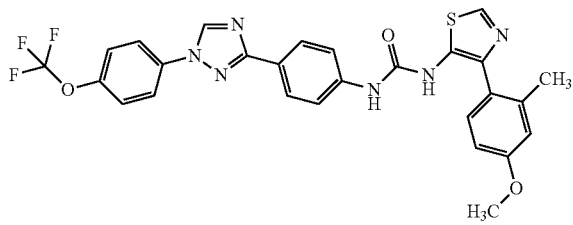 [SMILES: COc1ccc(-c2ncsc2NC(=O)Nc2ccc(-c3ncn(-c4ccc(OC(F)(F)F)cc4)n3)cc2)c(C)c1]

Isolated as a brown solid (0.088 g, 59%).

1-(4-(2,5-Dimethylphenyl)thiazol-5-yl)-3-(4-(1-(4-(trifluoromethoxy)phenyl)-1H-1,2,4-triazol-3-yl)phenyl)urea (F47)

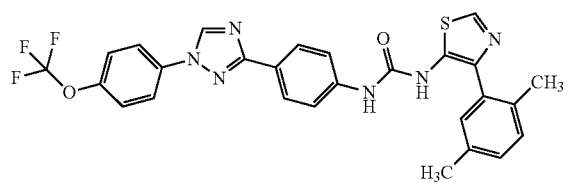

74

Isolated as a brown solid (0.045 g, 31%).

1-(4-(2,6-Dichlorophenyl)thiazol-5-yl)-3-(4-(1-(4-(trifluoromethoxy)phenyl)-1H-1,2,4-triazol-3-yl)phenyl)urea (F48)

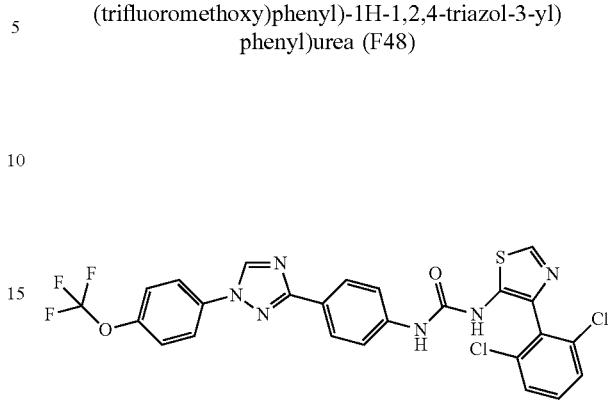

Isolated as an off-white solid (0.061 g, 39%).

Example 20: Preparation of 1-(4-(2-ethylphenyl)thiazol-5-yl)-3-(4-(1-(4-(trifluoromethoxy)phenyl)-1H-1,2,4-triazol-3-yl)phenethyl)urea (F61)

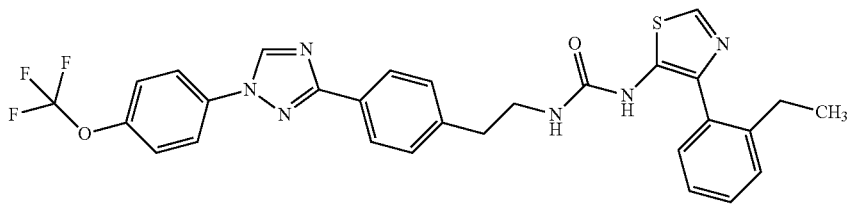 [SMILES: CCc1ccccc1-c1ncsc1NC(=O)NCCc1ccc(-c2ncn(-c3ccc(OC(F)(F)F)cc3)n2)cc1]

4-(2-Ethylphenyl)thiazole-5-carbonyl azide (C68) (0.090 g, 0.35 mmol) in acetonitrile (1.4 mL) was heated at 80° C. for 2 hours. The reaction was cooled and 2-(4-(1-(4-(trifluoromethoxy)phenyl)-1H-1,2,4-triazol-3-yl)phenyl)ethanamine (C72) (0.10 g, 0.29 mmol) was added. The reaction was stirred at room temperature for 2 hours. Purification by flash column chromatography using 0-100% ethyl acetate/(1:1 hexanes/dichloromethane) as eluent provided the title molecule as an off-white oil (0.10 g, 61%).

The following molecules were prepared according to the procedures disclosed in Example 20:

1-(4-(2,5-Dimethylphenyl)thiazol-5-yl)-3-(4-(1-(4-(trifluoromethoxy)phenyl)-1H-1,2,4-triazol-3-yl)phenethyl)urea (F62)

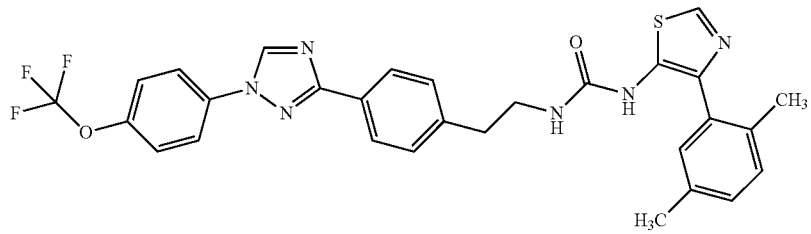 [SMILES: Cc1ccc(C)c(-c2ncsc2NC(=O)NCCc2ccc(-c3ncn(-c4ccc(OC(F)(F)F)cc4)n3)cc2)c1]

Isolated as a tan foam (0.061 g, 48%).

1-(4-(4-Methoxy-2-methylphenyl)thiazol-5-yl)-3-(4-(1-(4-(trifluoromethoxy)phenyl)-1H-1,2,4-triazol-3-yl)phenethyl)urea (F63)

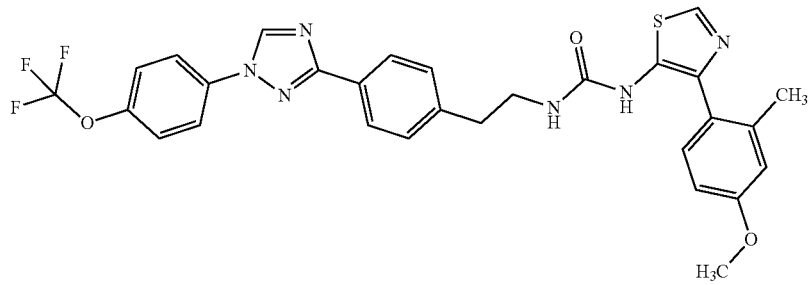 [SMILES: COc1ccc(-c2ncsc2NC(=O)NCCc2ccc(-c3ncn(-c4ccc(OC(F)(F)F)cc4)n3)cc2)c(C)c1]

Isolated as a tan foam (0.072 g, 64%).

1-(4-(2,6-Dichlorophenyl)thiazol-5-yl)-3-(4-(1-(4-(trifluoromethoxy)phenyl)-1H-1,2,4-triazol-3-yl)phenethyl)urea (F64)

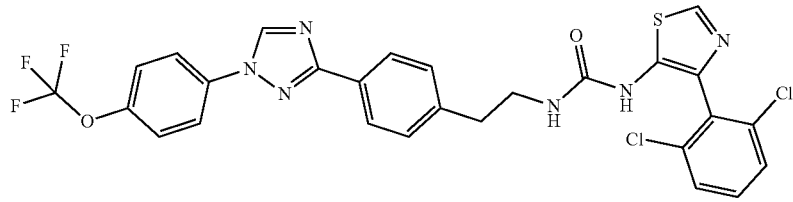 [SMILES: O=C(NCCc1ccc(-c2ncn(-c3ccc(OC(F)(F)F)cc3)n2)cc1)Nc1scnc1-c1c(Cl)cccc1Cl]

Isolated as a tan solid (0.059 g, 49%).

Example 21: Preparation of ethyl 3-(4-methoxy-2-methylphenyl)-3-oxopropanoate (C48)

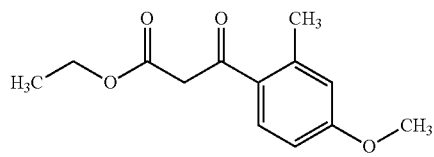 [SMILES: CCOC(=O)CC(=O)c1ccc(OC)cc1C]

A stirred solution of ethyl hydrogen malonate (8.20 mL, 75.0 mmol) in tetrahydrofuran (450 mL), under an inert atmosphere was cooled to −78° C., and n-butyllithium (1.6 M in hexanes, 93.4 mL, 149 mmol) was added drop wise over 45 minutes at −78° C. The reaction mixture was warmed to −5° C., stirred for 20 minutes, then re-cooled to −78° C., and a solution of 4-methoxy-2-methylbenzoyl chloride (12.5 g, 67.9 mmol) in tetrahydrofuran (50 mL) was added dropwise to the reaction mixture. On completion of addition, the solution was warmed to room temperature and stirred for 1 hour. The reaction was quenched with hydrochloric acid (1N, 50 mL) at 0° C. The organic and aqueous layers were separated and the aqueous layer was extracted with diethyl ether (3×30 mL). The combined organic layer was washed with a saturated sodium bicarbonate solution and brine, dried over sodium sulfate, and concentrated. Purification by flash column chromatography provided the title product as a pale-yellow liquid (9.20 g, 57%): ESIMS m/z 236 ([M+H]$^+$).

The following molecules were prepared according to the procedures disclosed in Example 21:

Ethyl 3-(2,5-dimethylphenyl)-3-oxopropanoate (C49)

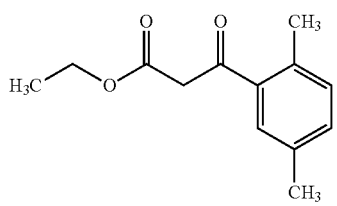 [SMILES: CCOC(=O)CC(=O)c1cc(C)ccc1C]

Isolated as a pale-yellow liquid (20 g, 61%): ESIMS m/z 221 ([M+H]$^+$).

Ethyl 3-(2,6-dichlorophenyl)-3-oxopropanoate (C50)

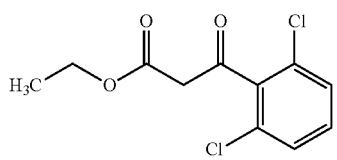 [SMILES: CCOC(=O)CC(=O)c1c(Cl)cccc1Cl]

Isolated as a pale-yellow liquid (10 g, 50%): ESIMS m/z 261 ([M+H]$^+$).

Ethyl 3-(2-ethylphenyl)-3-oxopropanoate (C51)

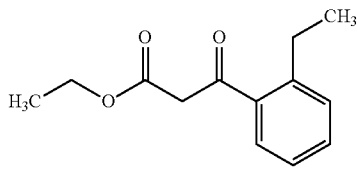 [SMILES: CCOC(=O)CC(=O)c1ccccc1CC]

Isolated as a pale-yellow liquid (16 g, 49%): ESIMS m/z 221 ([M+H]⁺).

Example 22: Preparation of ethyl 2-bromo-3-(4-methoxy-2-methylphenyl)-3-oxopropanoate (C52)

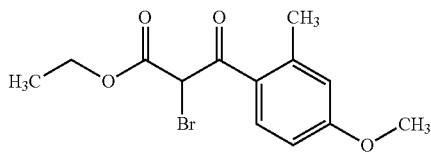 [SMILES: CCOC(=O)C(Br)C(=O)c1ccc(OC)cc1C]

To a solution of ethyl 3-(4-methoxy-2-methylphenyl)-3-oxopropanoate (C48) (9.00 g, 38.1 mmol) in dioxane was added bromine (2.30 mL, 45.7 mmol) dropwise at room temperature. The reaction mixture was stirred for 60 minutes at room temperature. The reaction was diluted with diethyl ether (120 mL) and the organic layer was washed with water (3×100 mL), a saturated sodium carbonate (50 mL) solution, and a brine solution. The organic layers were dried over sodium sulfate, filtered, and concentrated. Purification by flash column chromatography provided the title molecule as a light brown liquid (9.50 g, 79%): ¹H NMR (300 MHz, CDCl₃) δ 7.72 (d, J=8.1 Hz, 1H), 6.79 (s, 1H), 6.76 (d, J=2.4 Hz, 1H), 5.63 (s, 1H), 4.26 (q, J=6.9 Hz, 2H), 3.86 (s, 3H), 2.55 (s, 3H), 1.25 (t, J=7.5 Hz, 3H); ESIMS m/z 315 ([M+H]⁺).

The following molecules were prepared according to the procedures disclosed in Example 22:

Ethyl 2-bromo-3-(2,5-dimethylphenyl)-3-oxopropanoate (C53)

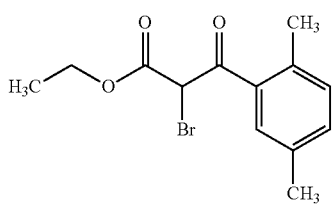

Isolated as a light brown liquid (20.2 g, 74%): ESIMS m/z 299 ([M+H]⁺).

Ethyl 2-bromo-3-(2,6-dichlorophenyl)-3-oxopropanoate (C54)

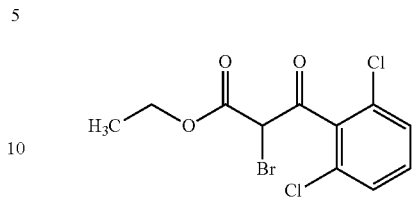

Isolated as a light brown liquid (2.1 g, 80%): ESIMS m/z 337 [(M−H)⁻].

Ethyl 2-bromo-3(2-ethylphenyl)-3-oxopropanoate (C55)

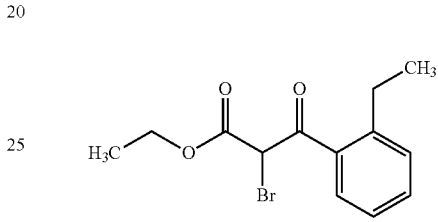

Isolated as a light brown liquid (12.1 g, 74%): ESIMS m/z 299 ([M+H]⁺).

Example 23: Preparation of ethyl 2-amino-4-(4-methoxy-2-methylphenyl)thiazole-5-carboxylate (C56)

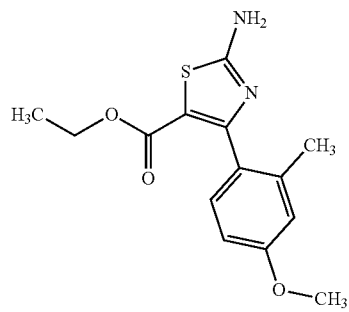 [SMILES: CCOC(=O)c1sc(N)nc1-c1ccc(OC)cc1C]

To a solution of ethyl 2-bromo-3-(4-methoxy-2-methylphenyl)-3-oxopropanoate (C52) (8.50 g, 27.1 mmol) in ethanol (110 mL) under nitrogen, thiourea (4.10 g, 54.1 mmol) was added and the reaction was heated to reflux for 16 hours. The reaction mixture was concentrated to half its volume, diluted with ethyl acetate (150 mL), and washed with water (3×20 mL) and brine (20 mL). The organic layer was dried over sodium sulfate, filtered, and concentrated. Purification by flash column chromatography provided the title molecule as a pale-yellow solid (4.80 g, 61%): ¹H NMR (400 MHz, DMSO-d₆) δ 7.76 (s, 2H), 7.08 (d, J=8.8 Hz, 1H), 6.78 (d, J=2.4 Hz, 1H), 6.72 (dd, J=2.4, 8.4 Hz, 1H), 3.98 (q, J=7.2 Hz, 2H), 3.75 (s, 3H), 2.12 (s, 3H), 1.05 (t, J=7.2 Hz, 3H); ESIMS m/z 293 ([M+H]⁺).

The following molecules were prepared according to the procedures disclosed in Example 23:

Ethyl 2-amino-4-(2,5-dimethylphenyl)thiazole-5-carboxylate (C57)

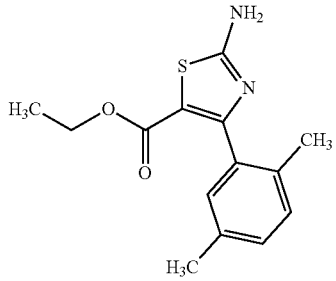 [SMILES: CCOC(=O)c1sc(N)nc1-c1cc(C)ccc1C]

Isolated as a brown solid (7.2 g, 52%): $^1$H NMR (300 MHz, DMSO-d$_6$) δ 7.78 (s, 2H), 7.10-7.03 (m, 2H), 6.96 (s, 1H), 3.97 (q, J=6.9 Hz, 2H), 2.25 (s, 3H), 2.07 (s, 3H), 1.02 (t, J=6.9 Hz, 3H).

Ethyl 2-amino-4-(2,6-dichlorophenyl)thiazole-5-carboxylate (C58)

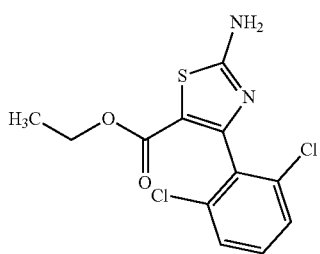 [SMILES: CCOC(=O)c1sc(N)nc1-c1c(Cl)cccc1Cl]

Isolated as a thick brown solid (4.0 g, 21%): $^1$H NMR (400 MHz, DMSO-d$_6$) δ 7.94 (s, 2H), 7.51 (d, J=8.8 Hz, 2H), 7.44-7.40 (m, $^1$H), 3.94 (q, J=6.8 Hz, 2H), 0.97 (t, J=6.8 Hz, 3H); ESIMS m/z 315 ([M−H]$^−$).

Ethyl 2-amino-4-(2-ethylphenyl)thiazole-5-carboxylate (C59)

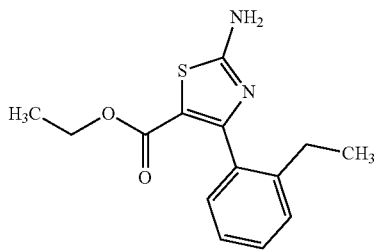 [SMILES: CCOC(=O)c1sc(N)nc1-c1ccccc1CC]

Isolated as a brown solid (4.2 g, 37%): $^1$H NMR (300 MHz, DMSO-d$_6$) δ 7.79 (s, 2H), 7.33-7.22 (m, 2H), 7.19-7.09 (m, 2H), 3.94 (q, J=6.9 Hz, 1H), 2.49 (q, J=7.8 2H), 1.01 (t, J=7.5 Hz, 3H), 0.97 (t, J=6.9 Hz, 3H).

Example 24: Preparation of ethyl 4-(4-methoxy-2-methylphenyl)thiazole-5-carboxylate (C60)

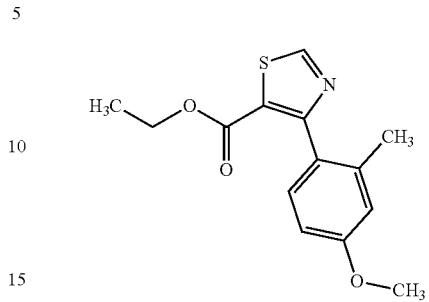

To a solution of ethyl 2-amino-4-(4-methoxy-2-methylphenyl) thiazole-5-carboxylate (C56) (9.00 g, 30.8 mmol) in diethyl ether (30 mL) and hypophosporus acid (180 mL) was added sodium nitrite (4.25 g, 61.6 mmol) and the reaction mixture was stirred at 0° C. for 1 hour. The reaction mixture was poured into a saturated sodium bicarbonate solution until pH 8. The solution was extracted with diethyl ether (3×50 mL) and the combined organic layer was washed with brine, dried over sodium sulfate, filtered, and, concentrated. Purification by flash column chromatography provided the title molecule as a black solid (5.00 g, 59%): $^1$H NMR (300 MHz, CDCl$_3$) δ 8.90 (s, 1H), 7.22 (d, J=8.4 Hz, 1H), 6.81-6.76 (m, 2H), 4.43 (q, J=6.9 Hz, 2H), 3.83 (s, 3H), 2.17 (s, 3H), 1.22 (t, J=6.9 Hz, 3H); ESIMS m/z 278 ([M+H]$^+$).

The following molecules were prepared according to the procedures disclosed in Example 24:

Ethyl 4-(2,5-dimethylphenyl)thiazole-5-carboxylate (C61)

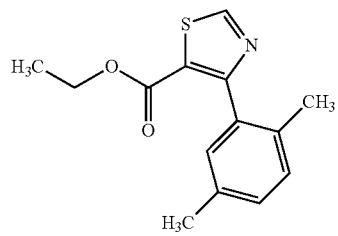 [SMILES: CCOC(=O)c1scnc1-c1cc(C)ccc1C]

Isolated as a thick brown solid (4.2 g, 63%): $^1$H NMR (400 MHz, CDCl$_3$) δ 8.91 (s, 1H), 7.16-7.13 (m, 2H), 7.08 (s, 1H), 4.20 (q, J=7.2 Hz, 2H), 2.33 (s, 3H), 2.12 (s, 3H), 1.18 (t, J=7.2 Hz, 3H); ESIMS m/z 262 ([M+H]$^+$).

Ethyl 4-(2,6-dichlorophenyl)thiazole-5-carboxylate (C62)

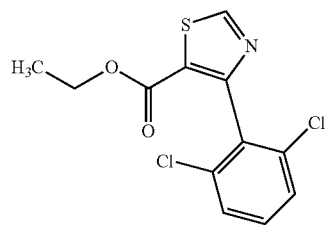 [SMILES: CCOC(=O)c1scnc1-c1c(Cl)cccc1Cl]

Isolated as an off-white solid (2.2 g, 57%): ¹H NMR (400 MHz, DMSO-d₆) δ 7.52 (d, J=1.2 Hz, 2H), 7.50 (s, 1H), 7.44 (t, J=6.8 Hz, 1H), 3.98 (q, J=6.8 Hz, 2H), 0.98 (t, J=6.8 Hz, 3H).

Ethyl 4-(2-ethylphenyl)thiazole-5-carboxylate (C63)

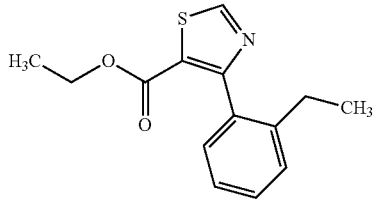 [SMILES: CCOC(=O)c1scnc1-c1ccccc1CC]

Isolated as a thick brown solid (5.1 g, 60%): ¹H NMR (400 MHz, CDCl₃) δ 8.92 (s, 1H), 7.39-7.34 (m, 1H), 7.31 (d, J=7.2 Hz, 1H), 7.24-7.20 (m, 2H), 4.17 (q, J=7.2 Hz, 2H), 2.49 (q, J=7.2 Hz, 2H), 1.13 (t, J=7.2 Hz, 3H), 1.06 (t, J=7.2 Hz, 3H); ESIMS m/z 262 ([M+H]⁺).

Example 25: Preparation of 4-(4-methoxy-2-methylphenyl)thiazole-5-carboxylic acid (C64)

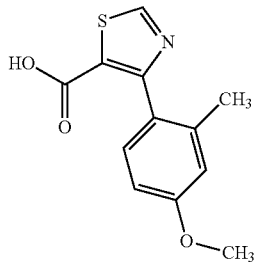

To a solution of ethyl 4-(4-methoxy-2-methylphenyl) thiazole-5-carboxylate (C60) (5.0 g, 18 mmol) in tetrahydrofuran (25 mL) and water (5 mL) was added lithium hydroxide (1.5 g, 36 mmol) and the solution was stirred at room temperature for 16 hours. The reaction was acidified with hydrochloric acid (1N) to pH 2 and the aqueous layer extracted with ethyl acetate (3×25 mL). The organic layer was washed with brine, dried over sodium sulfate, filtered, and concentrated. Purification by flash column chromatography provided the title molecule as a pale-yellow solid (3.3 g, 72%): mp 165-167° C.; ¹H NMR (300 MHz, DMSO-d₆) δ 13.12 (s, 1H), 9.27 (s, 1H), 7.17 (d, J=8.4 Hz, 1H), 6.84 (s, 1H), 6.78 (dd, J=2.1, 8.4 Hz, 1H), 3.78 (s, 3H), 2.09 (s, 3H); ESIMS m/z 250 ([M+H]⁺).

The following molecules were prepared according to the procedures disclosed in Example 25:

4-(2,5-Dimethylphenyl)thiazole-5-carboxylic acid (C65)

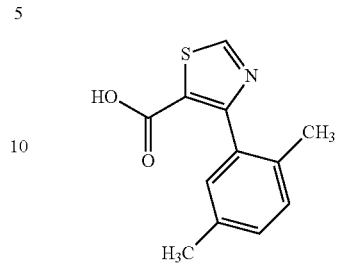

Isolated as a pale-yellow solid (3.5 g, 90%): mp 178-180° C.; ¹H NMR (300 MHz, CDCl₃) δ 10.05 (s, 1H), 9.00 (s, 1H), 7.13 (s, 2H), 7.06 (s, 1H), 2.31 (s, 3H), 2.09 (s, 3H); ESIMS m/z 234 ([M+H]⁺).

4-(2,6-Dichlorophenyl)thiazole-5-carboxylic acid (C66)

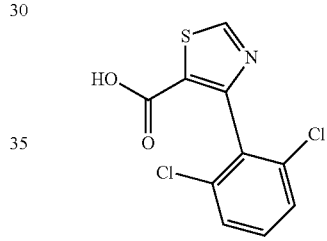

Isolated as an off-white solid (1.71 g, 90%): mp 182-184° C.; ¹H NMR (400 MHz, CDCl₃) δ 9.07 (s, 1H), 7.39-7.26 (m, 3H), 7.00 (s, 2H); ESIMS m/z 274 ([M+H]⁺).

4-(2-Ethylphenyl)thiazole-5-carboxylic acid (C67)

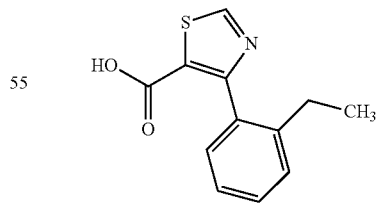

Isolated as an off-white solid (4.0 g, 90%): mp 155-157° C.; ¹H NMR (400 MHz, DMSO-d₆) δ 8.98 (s, 1H), 7.42-7.36 (d, J=4.8 Hz, ¹H), 7.32 (d, J=7.2 Hz, 1H), 7.25-7.22 (m, 2H), 2.50 (q, J=7.2 Hz, 2H), 1.06 (t, J=7.2 Hz, 3H); ESIMS m/z 234 ([M+H]⁺).

Example 26: Preparation of 4-(2-ethylphenyl)thiazole-5-carbonyl azide (C68)

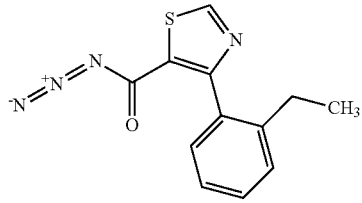

To 4-(2-ethylphenyl)thiazole-5-carboxylic acid (C67) (0.535 g, 2.30 mmol) in anhydrous toluene (9 mL) at 0° C. was added triethylamine (0.380 mL, 2.80 mmol) and diphenylphosphoryl azide (0.540 mL, 2.50 mmol) slowly. The reaction was warmed to room temperature over 3 hours and then directly purified by flash column chromatography 0-40% ethyl acetate/hexanes providing the title molecule as an orange oil (0.652 g, 99%): $^1$H NMR (400 MHz, CDCl$_3$) δ 8.96 (s, 1H), 7.41-7.23 (m, 4H), 2.50 (q, J=7.6 Hz, 2H), 1.08 (t, J=7.6 Hz, 3H); ESIMS m/z 231 ([M+H]$^+$) (isocyanate).

The following molecules were prepared according to the procedures disclosed in Example 26:

4-(2,5-Dimethylphenyl)thiazole-5-carbonyl azide (C69)

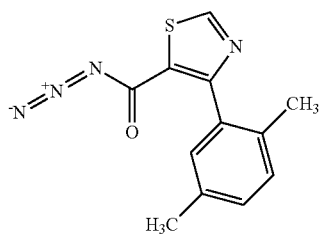

Isolated as a brown oily solid (0.768 g, 116%): $^1$H NMR (400 MHz, CDCl$_3$) δ 8.96 (s, 1H), 7.40-7.36 (m, 1H), 7.19-7.15 (m, 2H), 7.08 (s, 1H), 2.37-2.31 (m, 3H), 2.13 (s, 3H); ESIMS m/z 231 ([M+H]$^+$) (isocyanate).

4-(2,6-Dichlorophenyl)thiazole-5-carbonyl azide (C70)

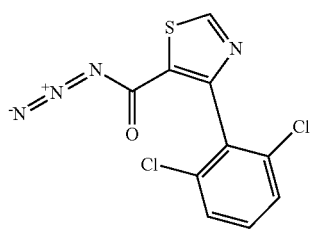

Isolated as a yellow oily solid (0.597 g, 94%): $^1$H NMR (400 MHz, CDCl$_3$) δ 9.06 (s, 1H), 7.45-7.32 (m, 3H); ESIMS m/z 271 ([M+H]$^+$) (isocyanate).

4-(4-Methoxy-2-methylphenyl)thiazole-5-carbonyl azide (C71)

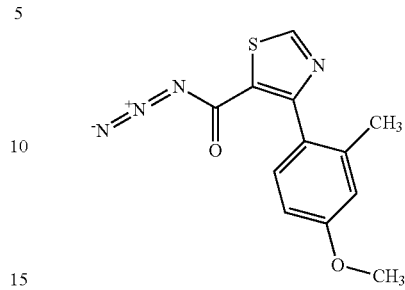

Isolated as a brown oil (0.624 g, 94%): $^1$H NMR (400 MHz, CDCl$_3$) δ 8.94 (s, 1H), 7.22 (d, J=8.4 Hz, 1H), 6.86-6.77 (m, 2H), 3.85 (s, 3H), 2.19 (s, 3H); ESIMS m/z 246 ([M+H]$^+$) (isocyanate).

Example 27: Preparation of 2-(4-(1-(4-(trifluoromethoxy)phenyl)-1H-1,2,4-triazol-3-yl)phenyl)ethanamine (C72)

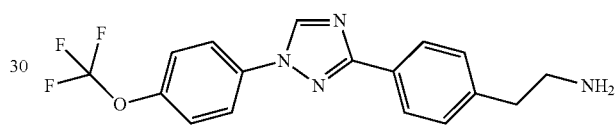

To 2-(4-(1-(4-(trifluoromethoxy)phenyl)-1H-1,2,4-triazol-3-yl)phenyl)ethanamine 2,2,2-trifluoroacetate (C32) (0.404 g, 0.870 mmol) in dichloromethane (10 mL) was added sodium hydroxide (1N, 10 mL). The solution was extracted with dichloromethane (3×). The organic layers were filtered through a phase separator and concentrated providing the title molecule as a pale-yellow waxy solid (0.314 g, 100%): $^1$H NMR (400 MHz, CDCl$_3$) δ 8.56 (s, 1H), 8.16-8.11 (m, 2H), 7.83-7.77 (m, 2H), 7.39 (dq, J=8.9, 0.9 Hz, 2H), 7.35-7.29 (m, 2H), 3.02 (t, J=6.8 Hz, 2H), 2.82 (t, J=6.8 Hz, 2H), 1.09 (s, 2H); $^{19}$F NMR (376 MHz, CDCl$_3$) δ −58.03; ESIMS m/z 349 ([M+H]$^+$).

Example 28: Preparation of 1-(3-mesityl-4-oxo-4,5-dihydrofuran-2-yl)-3-(4-(1-(4-(trifluoromethoxy)phenyl)-1H-1,2,4-triazol-3-yl)phenethyl)urea (F53)

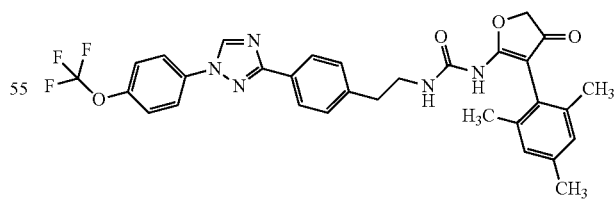

3-(4-(2-Isocyanatoethyl)phenyl)-1-(4-(trifluoromethoxy)phenyl)-1H-1,2,4-triazole (C90) (0.078 g, 0.21 mmol), 5-amino-4-mesitylfuran-3(2H)-one (C79) (0.060 g, 0.28 mmol), and cesium carbonate (0.070 g, 0.22 mmol) in acetonitrile (1 mL) were stirred at room temperature for 4 hours. The reaction was quenched with water and extracted with dichloromethane. The organic layers were filtered through a phase separator and concentrated under a stream of nitrogen. Purification by flash column chromatography 0-100% ethyl acetate/(1:1 dichloromethane/hexanes) as eluent provided the title molecule as a white solid (0.078 g, 63%).

The following molecules were prepared according to the procedures disclosed in Example 28:

1-(3-(2,6-Dichlorophenyl)-4-oxo-4,5-dihydrofuran-2-yl)-3-(4-(1-(4-(trifluoromethoxy)phenyl)-1H-1,2,4-triazol-3-yl)phenethyl)urea (F54)

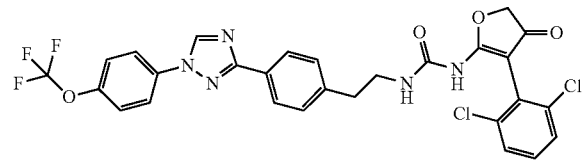 [SMILES: O=C(NCCc1ccc(-c2ncn(-c3ccc(OC(F)(F)F)cc3)n2)cc1)NC1=C(c2c(Cl)cccc2Cl)C(=O)CO1]

Isolated as a white solid (0.102 g, 61%).

1-(3-(2,6-Dimethylphenyl)-4-oxo-4,5-dihydrofuran-2-yl)-3-(4-(1-(4-(trifluoromethoxy)phenyl)-1H-1,2,4-triazol-3-yl)phenethyl)urea (F55)

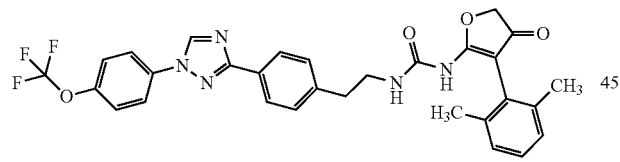

Isolated as a white solid (0.111 g, 71%).

1-(3-(2,5-Dimethylphenyl)-4-oxo-4,5-dihydrofuran-2-yl)-3-(4-(1-(4-(trifluoromethoxy)phenyl)-1H-1,2,4-triazol-3-yl)phenethyl)urea (F56)

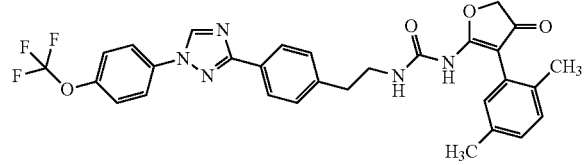 [SMILES: Cc1ccc(C)c(C2=C(NC(=O)NCCc3ccc(-c4ncn(-c5ccc(OC(F)(F)F)cc5)n4)cc3)OCC2=O)c1]

Isolated as a white solid (0.091 g, 59%).

1-(4-(2,5-Dimethylphenyl)-2-methyl-3-oxo-2,3-dihydroisoxazol-5-yl)-3-(4-(1-(4-(trifluoromethoxy)phenyl)-1H-1,2,4-triazol-3-yl)phenethyl)urea (F57)

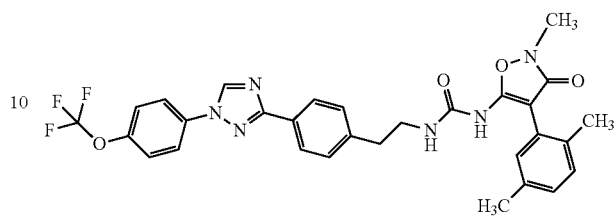

Isolated as a white solid (0.120 g, 75%).

1-(4-(2-Isopropylphenyl)-2-methyl-3-oxo-2,3-dihydroisoxazol-5-yl)-3-(4-(1-(4-(trifluoromethoxy)phenyl)-1H-1,2,4-triazol-3-yl)phenethyl)urea (F58)

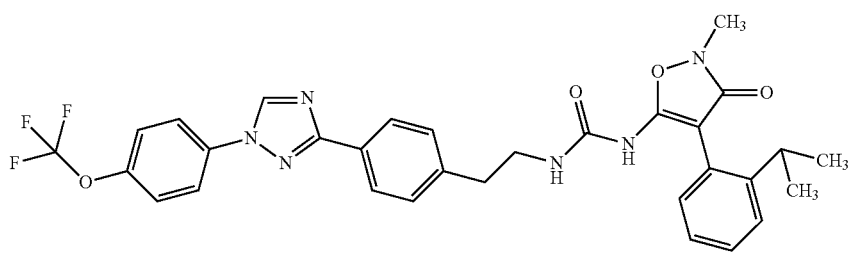 [SMILES: CC(C)c1ccccc1-c1c(NC(=O)NCCc2ccc(-c3ncn(-c4ccc(OC(F)(F)F)cc4)n3)cc2)on(C)c1=O]

Isolated as a white solid (0.083 g, 51%).

1-(4-Mesityl-2-methyl-3-oxo-2,3-dihydroisoxazol-5-yl)-3-(4-(1-(4-(trifluoromethoxy)phenyl)-1H-1,2,4-triazol-3-yl)phenethyl)urea (F59)

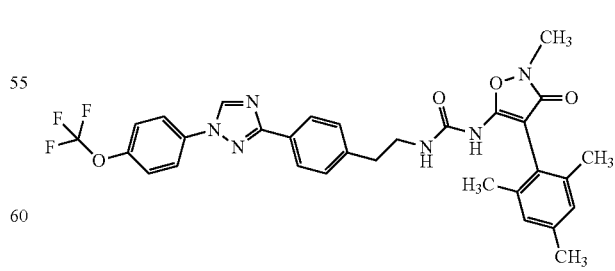

Isolated as a white solid (0.058 g, 36%).

1-(4-(2,6-Dichlorophenyl)-2-methyl-3-oxo-2,3-dihydroisoxazol-5-yl)-3-(4-(1-(4-(trifluoromethoxy)phenyl)-1H-1,2,4-triazol-3-yl)phenethyl)urea (F60)

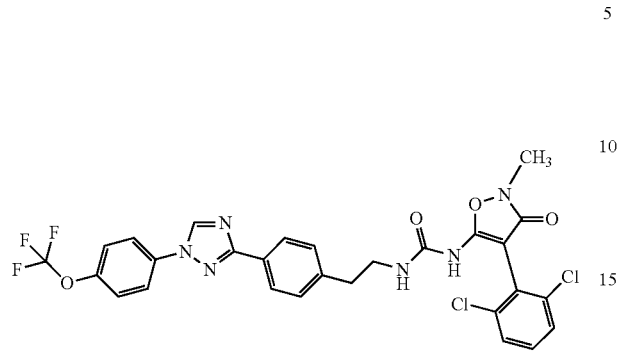

Isolated as a white solid (0.047 g, 29%).

1-(3-(2,5-Dimethylphenyl)-4-oxo-4,5-dihydrofuran-2-yl)-3-(4-(1-(4-(trifluoromethoxy)phenyl)-1H-1,2,4-triazol-3-yl)phenyl)urea (P3)

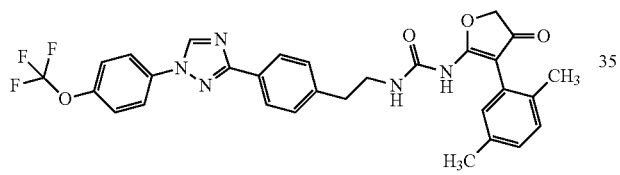

Isolated as an off-white oily solid (0.015 g, 9%).

1-(4-(2-Isopropylphenyl)-2-methyl-3-oxo-2,3-dihydroisoxazol-5-yl)-3-(4-(1-(4-(trifluoromethoxy)phenyl)-1H-1,2,4-triazol-3-yl)phenyl)urea (P6)

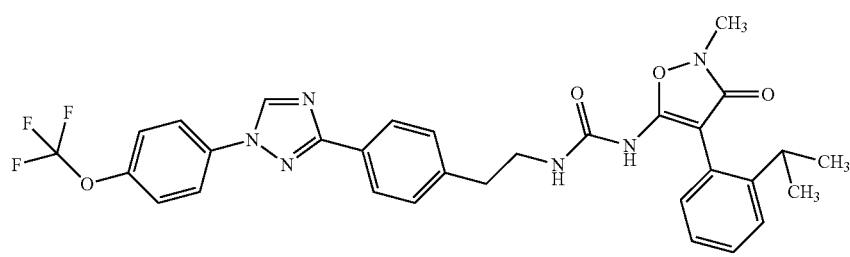 [SMILES: CC(C)c1ccccc1-c1c(NC(=O)NCCc2ccc(-c3ncn(-c4ccc(OC(F)(F)F)cc4)n3)cc2)on(C)c1=O]

Isolated as an oily solid, without base and with heating to reflux (0.010 g, 13%).

Example 29: Preparation of 2-(2,5-dimethylphenyl)-4-methoxy-3-oxobutanenitrile (C73)

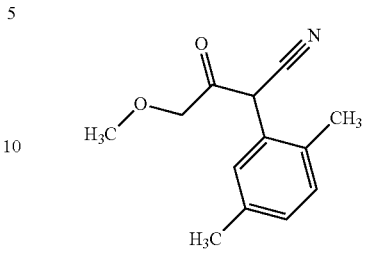

To a stirred solution of sodium ethoxide (21% in ethanol, 5.34 mL, 68.9 mmol) was added methyl 2-methoxyacetate (5.34 mL, 51.7 mmol) and 2-(2,5-dimethylphenyl)acetonitrile (5.00 g, 34.5 mmol). The resulting reaction mixture was heated to reflux for 14 hours. The reaction was cooled, concentrated, diluted with ethyl acetate (80 mL), and washed with hydrochloric acid (2N). The combined organic layer was dried over sodium sulfate, filtered, and concentrated. Purification by flash column chromatography provided the title molecule as a pale yellow oil (4.00 g, 53%): ESIMS m/z 218 ([M+H]$^+$).

The following molecules were prepared according to the procedures disclosed in Example 29:

2-Mesityl-4-methoxy-3-oxobutanenitrile (C74)

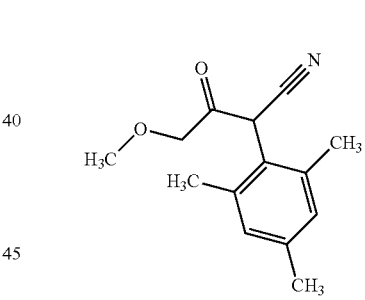

Isolated as a yellow liquid (4.0 g, 52%): ESIMS m/z 232 ([M+H]$^+$).

2-(2,6-Dichlorophenyl)-4-methoxy-3-oxobutanenitrile (C75)

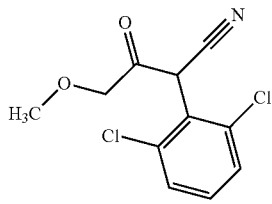

Isolated as a yellow liquid (3.5 g, 50%): ESIMS m/z 258 ([M+H]$^+$).

2-(2,6-Dimethylphenyl)-4-methoxy-3-oxobutanenitrile (C76)

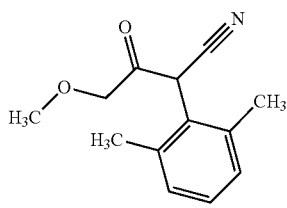

Isolated as a yellow liquid (4.0 g, 53%): $^1$H NMR (400 MHz, CDCl$_3$) δ 7.19 (t, J=7.6 Hz, 1H), 7.10 (d, J=7.2 Hz, 2H), 4.50 (s, 2H), 4.07 (s, 1H), 3.55 (s, 3H), 2.30 (s, 6H); ESIMS m/z 218 ([M+H]$^+$).

Example 30: Preparation of 2-(2,6-dimethylphenyl)acetonitrile (C77)

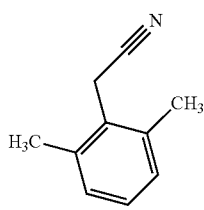

To a stirred solution of 2-(chloromethyl)-1,3-dimethylbenzene (4.0 g, 26 mmol) in Br$_2$ (50 mL) was added sodium cyanide (1.7 g, 29 mmol), the resulting reaction mixture was heated to 80° C. and stirred for 3 hours. The reaction mixture was cooled to room temperature and poured in to ice-cold water and extracted with diethyl ether (3×100 mL). The combined organic layers were dried over sodium sulfate, filtered, and concentrated. Purification by flash column chromatography provided the title molecule as a pale yellow oil (3.0 g, 79%): $^1$H NMR (400 MHz, CDCl$_3$) δ 7.14 (dd, J=6.8, 8.0 Hz, 1H), 7.07 (d, J=7.2 Hz, 2H), 3.64 (s, 2H), 2.40 (s, 6H); EIMS m/z 145 ([M]$^+$).

Example 31: Preparation of 5-amino-4-(2,5-dimethylphenyl)furan-3(2H)-one (C78)

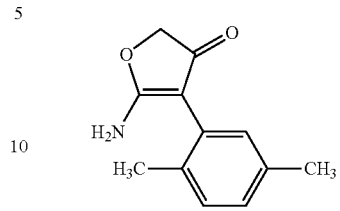

To a stirred solution of 2-(2,5-dimethylphenyl)-4-methoxy-3-oxobutanenitrile (C73) (3.00 g, 13.8 mmol) in acetic acid (15 mL) was added sulfuric acid (1.50 mL, 27.6 mmol). The reaction mixture was heated to reflux for 30 minutes. The acetic acid was concentrated, diluted with ethyl acetate (60 mL), washed with a sodium bicarbonate solution, dried over sodium sulfate, filtered, and concentrated. Purification by flash column chromatography provided the title molecule as a pale yellow solid (2.00 g, 71%): mp 172-174° C.; $^1$H NMR (300 MHz, DMSO-d$_6$) δ 7.62 (bs, 2H), 7.09 (d, J=7.5 Hz, 1H), 6.96 (d, J=7.5 Hz, 1H), 6.87 (s, 1H), 4.51 (s, 2H), 2.24 (s, 3H), 2.11 (s, 3H); ESIMS m/z 204 ([M+H]$^+$).

The following molecules were prepared according to the procedures disclosed in Example 31:

5-Amino-4-mesitylfuran-3(2H)-one (C79)

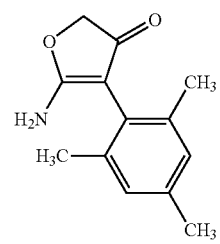

Isolated as a pale brown solid (3.61 g, 78%): mp 205-208° C.; $^1$H NMR (300 MHz, DMSO-d$_6$) δ 7.47 (bs, 2H), 6.85 (s, 2H), 4.52 (s, 2H), 2.22 (s, 3H), 2.06 (s, 6H); ESIMS m/z 218 ([M+H]$^+$).

5-Amino-4-(2,6-dichlorophenyl)furan-3(2H)-one (C80)

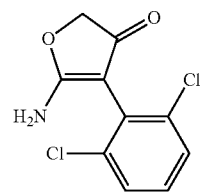

Isolated as a brown solid (3.09 g, 69%): mp 235-237° C.; $^1$H NMR (400 MHz, DMSO-d$_6$) δ 7.84 (bs, 2H), 7.47 (d, J=8.0 Hz, 2H), 7.33 (dd, J=7.6, 8.4 Hz, 1H), 4.58 (s, 2H); ESIMS m/z 244 ([M+H]$^+$).

5-Amino-4-(2,6-dimethylphenyl)furan-3(2H)-one (C81)

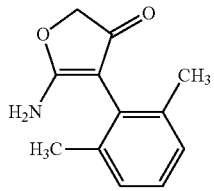

Isolated as a pale-yellow solid (1.51 g, 58%): mp 201-205° C.; $^1$H NMR (400 MHz, DMSO-d$_6$) δ 7.52 (bs, 2H), 7.15-7.04 (m, 3H), 4.54 (s, 2H), 2.10 (s, 6H); ESIMS m/z 204 ([M+H]$^+$).

Example 32: Preparation of ethyl 2-cyano-2-(2-isopropylphenyl)acetate (C82)

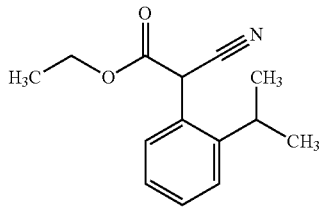 [SMILES: CCOC(=O)C(C#N)c1ccccc1C(C)C]

1-Bromo-2-Isopropylbenzene (6.0 g, 30 mmol) was dissolved in dry toluene (70 mL), and ethyl cyanoacetate (6.8 g, 60 mmol) and sodium phosphate (15 g, 90 mmol) were added. The reaction mixture was degassed by bubbling with argon gas. Bis(dibenzylideneacetone) palladium(0) (0.35 g, 0.60 mmol) and tri-tert-butylphosphine (0.25 g, 1.2 mmol) were added. The reaction mixture was charged in a 500 mL sealed tube and heated to 90° C. for 20 hours. The reaction was cooled to room temperature and filtered through a Celite® pad. The filtrate was concentrated and the residue was dissolved in ethyl acetate (120 mL) followed by a washing with water (2×100 mL). The organic layer was dried over anhydrous sodium sulfate, filtered, and concentrated. Purification by flash column chromatography provided the title molecule as a colorless liquid (4.4 g, 63%): $^1$H NMR (400 MHz, CDCl$_3$) δ 7.44 (d, J=7.6 Hz, 1H), 7.38-7.36 (m, 2H), 7.24-7.22 (m, 1H), 4.97 (s, 1H), 4.30-4.21 (m, 2H), 3.14 (hep, J=5.2 Hz, 1H), 1.30-1.23 (m, 9H); EIMS m/z 216 ([M−CH$_3$]$^+$).

The following molecules were prepared according to the procedures disclosed in Example 32:

Ethyl 2-cyano-2-mesitylacetate (C83)

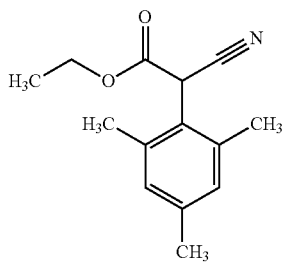

Isolated as a colorless liquid (1.6 g, 17%): $^1$H NMR (300 MHz, CDCl$_3$) δ 6.90 (s, 2H), 5.10 (s, 1H), 4.30-4.22 (m, 2H), 2.37 (s, 6H), 2.29 (s, 3H), 1.32 (t, J=9 Hz, 3H); EIMS m/z 231 ([M]$^+$).

Ethyl 2-cyano-2-(2,5-dimethylphenyl)acetate (C84)

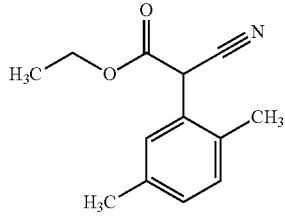

Isolated as a colorless liquid (2.7 g, 38%): $^1$H NMR (300 MHz, CDCl$_3$) δ 7.25 (s, 1H), 7.10 (s, 2H), 4.81 (s, 1H), 4.29-4.21 (m, 2H), 2.35 (d, J=3.9 Hz, 6H), 1.28 (t, J=7.5 Hz, 3H); EIMS m/z 217 ([M]$^+$).

Example 33: Preparation of 5-amino-4-(2-isopropylphenyl)-2-methylisoxazol-3(2H)-one (C85)

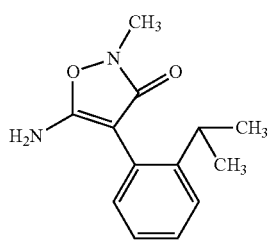 [SMILES: CC(C)c1ccccc1-c1c(N)on(C)c1=O]

Ethyl 2-cyano-2-(2-isopropylphenyl)acetate (C82) (4.30 g, 18.6 mmol), ethanol (40 mL), N-methyl hydroxylamine hydrochloride (3.10 g, 37.2 mmol), and sodium ethoxide (21% in ethanol, 10.5 mL, 37.2 mmol) were combined in a 250 mL sealed tube. The reaction mixture was heated to 90° C. for 16 hours. The reaction mixture was cooled to room temperature and quenched with cold water. The ethanol was concentrated, and the residue was dissolved in ethyl acetate (100 mL) and washed with water (2×100 mL). The organic layer was dried over anhydrous sodium sulfate, filtered, and concentrated. Purification by flash column chromatography provided the title molecule as an off-white solid (1.1 g, 25%): mp 147-150° C.; $^1$H NMR (400 MHz, DMSO-d$_6$) δ 7.38-7.28 (m, 2H), 7.18 (dt, J=1.6, 7.6 Hz, 1H), 7.07 (d, J=6.4 Hz, 1H), 6.88 (s, 2H), 3.17 (s, 3H), 3.03-2.93 (m, 1H), 1.18-1.08 (m, 6H); ESIMS m/z 233 ([M+H]$^+$).

The following molecules were prepared according to the procedures disclosed in Example 33:

5-Amino-4-mesityl-2-methylisoxazol-3(2H)-one (C86)

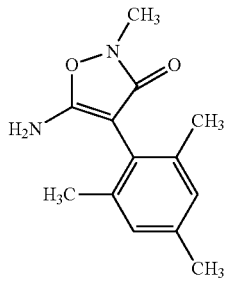 [SMILES: Cc1cc(C)c(-c2c(N)on(C)c2=O)c(C)c1]

Isolated as an off-white solid (6%): $^1$H NMR (400 MHz, DMSO-d$_6$) δ 6.88 (s, 2H), 6.81 (s, 2H), 3.15 (s, 3H), 2.23 (s, 3H), 2.09 (s, 6H); ESIMS m/z 233 ([M+H]$^+$).

5-Amino-4-(2,5-dimethylphenyl)-2-methylisoxazol-3(2H)-one (C87)

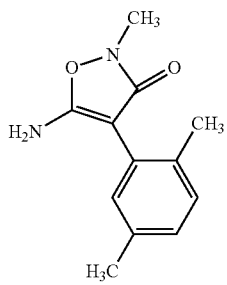 [SMILES: Cc1ccc(C)c(-c2c(N)on(C)c2=O)c1]

Isolated as an off-white solid (12%): $^1$H NMR (300 MHz, DMSO-d$_6$) δ 7.11 (d, J=7.8 Hz, 1H), 7.00 (d, J=7.8 Hz, 1H), 6.98-6.88 (m, 3H), 3.17 (s, 3H); ESIMS m/z 219 ([M+H]$^+$).

Example 34: Preparation of (E/Z)-2-(2,6-dichlorophenyl)-3-(dimethylamino)acrylonitrile (C88)

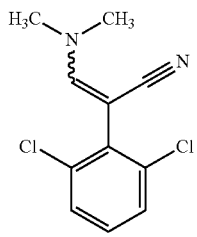

2-(2,6-Dichlorophenyl)acetonitrile (4.00 g, 21.5 mmol) and tert-butoxy bis(dimethyl amino)methane (5.62 g, 32.3 mmol) were dissolved in dimethylformamide (40 mL) and the solution was sealed in a 100 mL tube and stirred at 90° C. for 3 hours. The cooled reaction mixture was added to cold water and extracted with ethyl acetate (2×). The combined organic layer was washed with cold water (3×), dried over anhydrous sodium sulfate, filtered, and concentrated. Purification by flash column chromatography provided the title molecule as a colorless liquid (2.70 g, 52%): ESIMS m/z 241 ([M+H]$^+$).

Example 35: Preparation of 4-(2,6-dichlorophenyl)isoxazol-5-amine (C89)

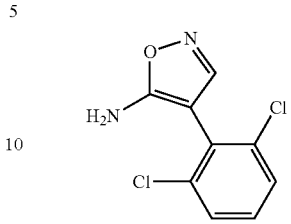

To a stirred solution of 2-(2,6-dichlorophenyl)-3-(dimethylamino)acrylonitrile (C88) (3.80 g, 15.8 mmol) in ethanol (40 mL) was added hydroxylamine hydrochloride (2.52 g, 31.7 mmol) and the mixture was stirred at 90° C. for 16 hours. The solvent was concentrated, and the residue was dissolved in ethyl acetate (100 mL) and washed with water (2×100 mL). The organic layer was dried over anhydrous sodium sulfate, filtered, and concentrated. Purification by flash column chromatography provided the title molecule as a white solid (1.20 g, 33%): mp 89-92° C.; $^1$H NMR (400 MHz, DMSO-d$_6$) δ 8.16 (s, 1H), 7.52 (d, J=8.0 Hz, 2H), 7.36 (t, J=7.6 Hz, 1H), 6.86 (s, 2H); ESIMS m/z 229 ([M+H]$^+$).

Example 36: Preparation of 3-(4-(2-isocyanatoethyl)phenyl)-1-(4-(trifluoromethoxy)phenyl)-1H-1,2,4-triazole (C90)

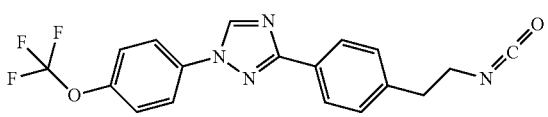 [SMILES: O=C=NCCc1ccc(-c2ncn(-c3ccc(OC(F)(F)F)cc3)n2)cc1]

A 1 L three-neck round bottomed flask was equipped with mechanical stirrer, thermocouple, and condenser. Tetrahydrofuran (120 mL) was added. After it was cooled to −3° C., ethyl carbonochloridate (3.16 mL, 33.2 mmol) and triethylamine (4.64 mL, 33.2 mmol) were added. 3-(4-(1-(4-(Trifluoromethoxy)phenyl)-1H-1,2,4-triazol-3-yl)phenyl)propanoic acid (C91) (11.4 g, 30.2 mmol) was added in portions, keeping the reaction temperature below 0° C. The reaction mixture turned into white suspension quickly. A solution of sodium azide (2.16 g, 33.2 mmol) in water (44 mL) was added slowly, keeping the reaction temperature below −2° C. The reaction mixture was stirred at −2° C. for 2 hours. Cold water (200 mL) was added to the reaction mixture very slowly while stirring at 0° C. It was stirred at 0° C. for 30 minutes after the addition. The white solid that formed was filtered while it was cold. The solid was dried in vacuum under a stream of nitrogen at room temperature for 48 hours to afford the isocyanate as a tan solid (10.5 g, 86%): $^1$H NMR (400 MHz, CDCl$_3$) δ 8.56 (s, 1H), 8.20-8.11 (m, 2H), 7.85-7.76 (m, 2H), 7.47-7.30 (m, 4H), 3.59 (t, J=6.9 Hz, 2H), 2.97 (t, J=6.9 Hz, 2H); $^{19}$F NMR (376 MHz, CDCl$_3$) δ −58.02; ESIMS m/z 375 ([M+H]$^+$).

Example 37: Preparation of 3-(4-(1-(4-(trifluoromethoxy)phenyl)-1H-1,2,4-triazol-3-yl)phenyl)propanoic acid (C91)

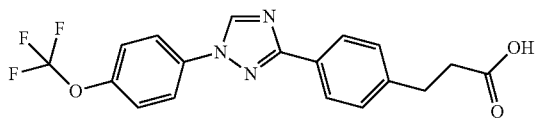 [SMILES: O=C(O)CCc1ccc(-c2ncn(-c3ccc(OC(F)(F)F)cc3)n2)cc1]

To ethyl 3-(4-(1-(4-(trifluoromethoxy)phenyl)-1H-1,2,4-triazol-3-yl)phenyl)propanoate (C92) (0.975 g, 2.41 mmol) in methanol (60 mL) was added sodium hydroxide (2 N, 12.0 mL, 24.1 mmol) and the solution was stirred at room temperature overnight. The methanol was concentrated under vacuum, and the residue was acidified with hydrogen chloride (2 N). The white precipitate was vacuum filtered and dried to afford the title molecule as a white solid (0.945 g, 99%): mp 145° C. (dec.); $^1$H NMR (400 MHz, DMSO-$d_6$) δ 9.39 (s, 1H), 8.04 (dd, J=21.4, 8.7 Hz, 4H), 7.62 (d, J=8.3 Hz, 2H), 7.38 (d, J=8.4 Hz, 2H), 2.89 (t, J=7.6 Hz, 2H), 2.59 (t, J=7.6 Hz, 2H); $^{19}$F NMR (376 MHz, DMSO-$d_6$) δ −56.98; ESIMS m/z 378 ([M+H]$^+$).

Example 38: Preparation of ethyl 3-(4-(1-(4-(trifluoromethoxy)phenyl)-1H-1,2,4-triazol-3-yl)phenyl)propanoate (C92)

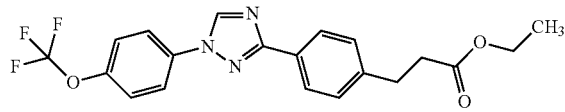 [SMILES: CCOC(=O)CCc1ccc(-c2ncn(-c3ccc(OC(F)(F)F)cc3)n2)cc1]

A mixture of (E)-ethyl 3-(4-(1-(4-(trifluoromethoxy)phenyl)-1H-1,2,4-triazol-3-yl)phenyl)acrylate (C93) (1.08 g, 2.68 mmol) and palladium on carbon (10%, 0.285 g, 0.270 mmol) in ethyl acetate (10.7 mL) was stirred at room temperature. The reaction flask was evacuated under vacuum, backfilled with nitrogen, evacuated under vacuum again, and then backfilled with hydrogen by balloon (~1 atm). The reaction was stirred at room temperature overnight and then filtered through a pad of Celite® and concentrated to afford the title molecule as a gray oil that solidified to a wax upon standing at room temperature (0.999 g, 87%): $^1$H NMR (400 MHz, CDCl$_3$) δ 8.56 (s, 1H), 8.14-8.07 (m, 2H), 7.80 (d, J=9.1 Hz, 2H), 7.42-7.36 (m, 2H), 7.32 (d, J=8.4 Hz, 2H), 4.14 (q, J=7.1 Hz, 2H), 3.02 (t, J=7.8 Hz, 2H), 2.67 (t, J=7.8 Hz, 2H), 1.24 (t, J=7.1 Hz, 3H); $^{19}$F NMR (376 MHz, CDCl$_3$) δ −58.03; ESIMS m/z 406 ([M+H]$^+$).

Example 39: Preparation of (E)-ethyl 3-(4-(1-(4-(trifluoromethoxy)phenyl)-1H-1,2,4-triazol-3-yl)phenyl)acrylate (C93)

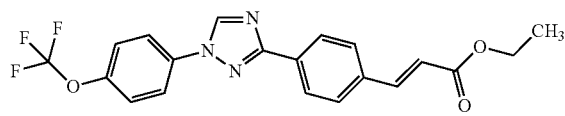 [SMILES: CCOC(=O)/C=C/c1ccc(-c2ncn(-c3ccc(OC(F)(F)F)cc3)n2)cc1]

To an oven-dried 2 L three-necked round bottomed flask equipped with a stirring bar was added sodium hydride (60% oil immersion, 7.20 g, 180 mmol) as a solid that was pre-weighed into a 25-mL vial. This was diluted with anhydrous tetrahydrofuran (1 L) under nitrogen, and the solution was stirred in an ice bath. Ethyl 2-(diethoxyphosphoryl)acetate (30.0 mL, 151 mmol) was added dropwise in portions over 20 minutes, and the reaction was stirred at 0° C. for an additional 2 hours. 4-(1-(4-(Trifluoromethoxy)phenyl)-1H-1,2,4-triazol-3-yl)benzaldehyde (50.0. g, 150 mmol) was added in solid portions over 20 minutes, and the reaction turned orange. After stirring for 30 minutes, the ice bath was removed and the reaction was warmed to room temperature over 1 hour. The reaction was quenched with slow addition of saturated aqueous ammonium chloride (500 mL) and allowed to stand at room temperature overnight. The biphasic reaction mixture was diluted with water and extracted with 1:1 ethyl acetate/hexanes (3×). The combined organic layers were dried over anhydrous sodium sulfate, filtered, and concentrated to afford the title molecule as an orange solid (61.4 g, 100%): mp 135-137° C.; $^1$H NMR (400 MHz, CDCl$_3$) δ 8.59 (s, 1H), 8.22 (d, J=8.4 Hz, 2H), 7.85-7.77 (m, 2H), 7.73 (d, J=16.0 Hz, 1H), 7.64 (d, J=8.3 Hz, 2H), 7.40 (d, J=8.3 Hz, 2H), 6.51 (d, J=16.0 Hz, 1H), 4.29 (q, J=7.1 Hz, 2H), 1.35 (t, J=7.1 Hz, 3H); $^{19}$F NMR (376 MHz, CDCl$_3$) δ −58.02; ESIMS m/z 404 ([M+H]$^+$).

Example 40: Preparation of 3-(4-(2-isothiocyanatoethyl)phenyl)-1-(4-(trifluoromethoxy)phenyl)-1H-1,2,4-triazole (C94)

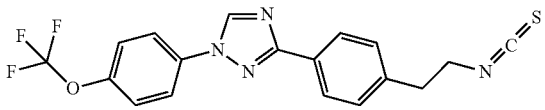

To 2-(4-(1-(4-(trifluoromethoxy)phenyl)-1H-1,2,4-triazol-3-yl)phenyl)ethanamine 2,2,2-trifluoroacetate (C32) (2.10 g, 4.55 mmol) in tetrahydrofuran (11.5 mL) under nitrogen was stirred at room temperature was added triethylamine (3.00 mL, 21.5 mmol). Carbon disulfide (0.290 mL, 4.82 mmol) was then added in portions via syringe over 12 minutes. The reaction mixture was allowed to stir for 3.5 hrs, then it was cooled to 0° C. and para-toluenesulfonyl chloride (0.970 g, 5.09 mmol) was added. After 30 minutes the solution was allowed to warm to room temperature and stirring was continued overnight. The solution was poured onto hydrochloric acid (1 N) and the product was extracted with diethyl ether (3×). The combined organic layer was washed with a saturated sodium bicarbonate solution, dried, filtered, and concentrated to provide the title molecule as an off-white solid (1.58 g, 85%): mp 110-115° C.; $^1$H NMR (400 MHz, CDCl$_3$) δ 8.57 (s, 1H), 8.20-8.14 (m, 2H), 7.82-7.77 (m, 2H), 7.42-7.36 (m, 2H), 7.34 (d, J=8.4 Hz, 2H), 3.78 (t, J=6.9 Hz, 2H), 3.06 (t, J=6.9 Hz, 2H).

Example 41: Preparation of 1-(1-phenyl-1H-pyrazol-5-yl)-3-(4-(1-(4-(trifluoromethoxy)phenyl)-1H-1,2,4-triazol-3-yl)phenethyl)thiourea (F65)

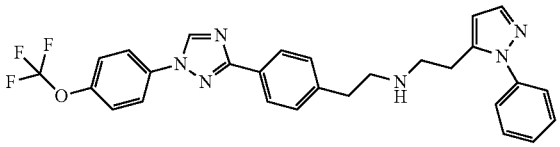 [SMILES: FC(F)(F)Oc1ccc(-n2cnc(-c3ccc(CCNCCc4ccnn4-c4ccccc4)cc3)n2)cc1]

To 3-(4-(2-isothiocyanatoethyl)phenyl)-1-(4-(trifluoromethoxy)phenyl)-1H-1,2,4-triazole (C94) (0.129 g, 0.330 mmol) in tetrahydrofuran (4 mL) was added 1-phenyl-1H-pyrazole-5-amine (0.130 g, 0.817 mmol). The solution was heated at 55° C. for 18 hours. An additional amount of 1-phenyl-1H-pyrazole-5-amine (0.0600 g, 0.565 mmol) was added and the solution was heated at reflux for 24 hours. The cooled solution was then adsorbed onto Celite®. Purification by flash column chromatography using 0-100% ethyl acetate/(1:1 hexanes:dichloromethane) as eluent provided the title molecule as a white solid (0.102 g, 53%).

The following molecules in Table 1 may be prepared according to the procedures disclosed in Example PE1: P1, P2, P3, P4, P5, P6, P7, and P8

TABLE 1

Structure and Preparation Method for Prophetic Molecules

| No. | Structure | May be Prepared according to Example: |
|---|---|---|
| P1 | 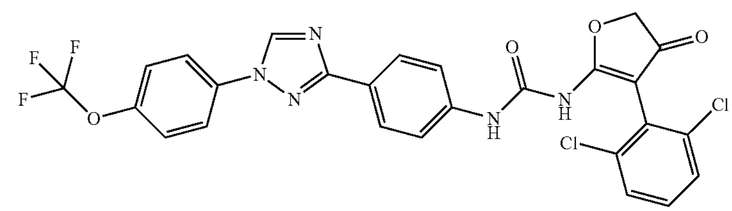 [SMILES: O=C(NC1=C(c2c(Cl)cccc2Cl)C(=O)CO1)Nc1ccc(-c2ncn(-c3ccc(OC(F)(F)F)cc3)n2)cc1] | 28 |
| P2 | 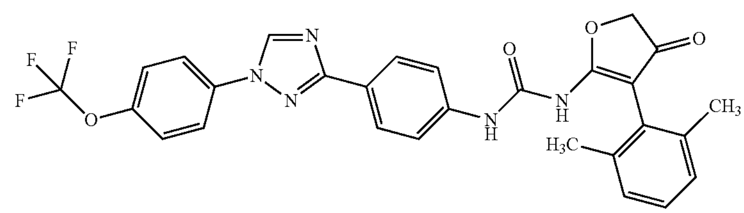 [SMILES: Cc1cccc(C)c1C1=C(NC(=O)Nc2ccc(-c3ncn(-c4ccc(OC(F)(F)F)cc4)n3)cc2)OCC1=O] | 28 |
| P3 | 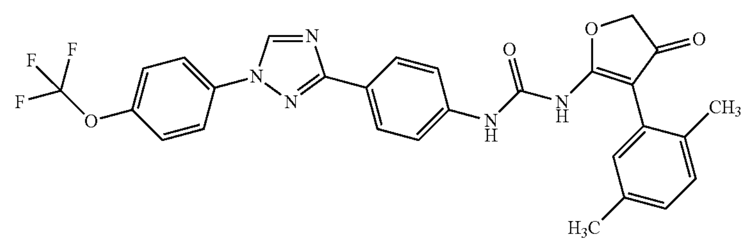 [SMILES: Cc1ccc(C)c(C2=C(NC(=O)Nc3ccc(-c4ncn(-c5ccc(OC(F)(F)F)cc5)n4)cc3)OCC2=O)c1] | 28 |
| P4 | 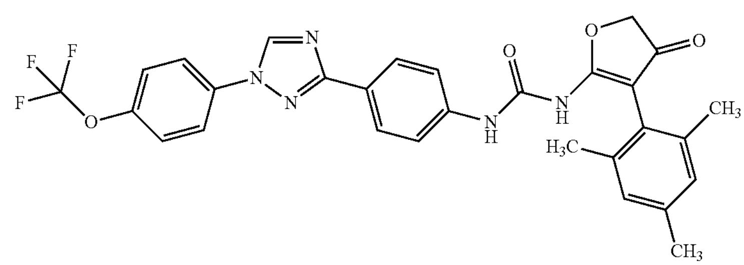 [SMILES: Cc1cc(C)c(C2=C(NC(=O)Nc3ccc(-c4ncn(-c5ccc(OC(F)(F)F)cc5)n4)cc3)OCC2=O)c(C)c1] | 28 |
| P5 | 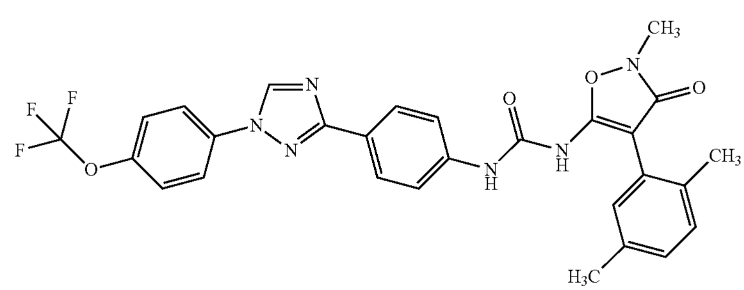 [SMILES: Cc1ccc(C)c(-c2c(NC(=O)Nc3ccc(-c4ncn(-c5ccc(OC(F)(F)F)cc5)n4)cc3)on(C)c2=O)c1] | 28 |

TABLE 1-continued

Structure and Preparation Method for Prophetic Molecules

| No. | Structure | May be Prepared according to Example: |
|---|---|---|
| P6 | 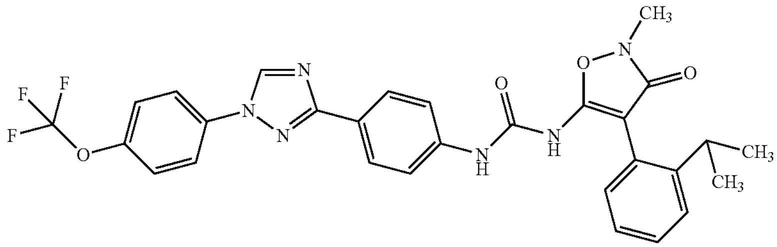 [SMILES: CC(C)c1ccccc1-c1c(NC(=O)Nc2ccc(-c3ncn(-c4ccc(OC(F)(F)F)cc4)n3)cc2)on(C)c1=O] | 28 |
| P7 | 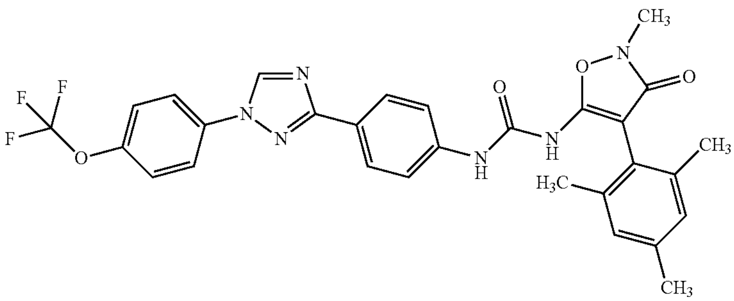 [SMILES: Cc1cc(C)c(-c2c(NC(=O)Nc3ccc(-c4ncn(-c5ccc(OC(F)(F)F)cc5)n4)cc3)on(C)c2=O)c(C)c1] | 28 |
| P8 | 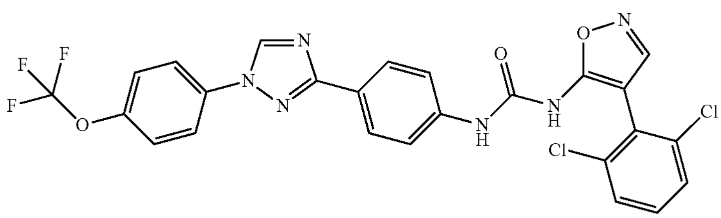 [SMILES: O=C(Nc1ccc(-c2ncn(-c3ccc(OC(F)(F)F)cc3)n2)cc1)Nc1oncc1-c1c(Cl)cccc1Cl] | 28 |

Biological Assays

The following bioassays against Beet Armyworm (*Spodoptera exigua*), Cabbage Looper (*Trichoplusia ni*), Corn Earworm (*Helicoverpa zea*), Green Peach Aphid (*Myzus persicae*), and Yellow Fever Mosquito (*Aedes aegypti*), are included herein due to the damage they inflict. Furthermore, the Beet Armyworm, Corn Earworm, and Cabbage Looper are three good indicator species for a broad range of chewing pests. Additionally, the Green Peach Aphid is a good indicator species for a broad range of sap-feeding pests. The results with these four indicator species along with the Yellow Fever Mosquito show the broad usefulness of the molecules of Formula One in controlling pests in Phyla Arthropoda, Mollusca, and Nematoda (For further information see Methods for the Design and Optimization of New Active Ingredients, *Modern Methods in Crop Protection Research*, Edited by Jeschke, P., Kramer, W., Schirmer, U., and Matthias W., p. 1-20, 2012).

Example A: Bioassays on Beet Armyworm (*Spodoptera exigua*, LAPHEG) ("BAW"), Corn Earworm (*Helicoverpa zea*, HELIZE) ("CEW"), and Cabbage Looper (*Trichoplusia ni*, TRIPNI) ("CL")

Beet army worm is a serious pest of economic concern for alfalfa, asparagus, beets, citrus, corn, cotton, onions, peas, peppers, potatoes, soybeans, sugar beets, sunflowers, tobacco, tomatoes, among other crops. It is native to Southeast Asia but is now found in Africa, Australia, Japan, North America, and Southern Europe. The larvae may feed in large swarms causing devastating crop losses. It is known to be resistant to several pesticides.

Cabbage Looper is a serious pest found throughout the world. It attacks alfalfa, beans, beets, broccoli, Brussel sprouts, cabbage, cantaloupe, cauliflower, celery, collards, cotton, cucumbers, eggplant, kale, lettuce, melons, mustard, parsley, peas, peppers, potatoes, soybeans, spinach, squash, tomatoes, turnips, and watermelons, among other crops. This species is very destructive to plants due to its voracious appetite. The larvae consume three times their weight in food daily. The feeding sites are marked by large accumulations of sticky, wet, fecal material. It is known to be resistant to several pesticides.

Corn earworm is considered by some to be the most costly crop pest in North America. It often attacks valuable crops, and the harvested portion of the crop. This pest damages alfalfa, artichoke, asparagus, cabbage, cantaloupe, collard, corn, cotton, cowpea, cucumber, eggplant, lettuce, lima bean, melon, okra, pea, pepper, potato, pumpkin, snap bean, soybean, spinach, squash, sugarcane, sweet potato, tomato, and watermelon, among other crops. Furthermore, this pest is also known to be resistant to certain insecticides.

Consequently, because of the above factors control of these pests is important. Furthermore, molecules that control these pests (BAW, CEW, and CL), which are known as chewing pests, are useful in controlling other pests that chew on plants.

Certain molecules disclosed in this document were tested against BAW, CEW, and CL using procedures described in the following examples. In the reporting of the results, the "BAW, CEW, & CL Rating Table" was used (See Table Section).

Bioassays on BAW

Bioassays on BAW were conducted using a 128-well diet tray assay. one to five second instar BAW larvae were placed in each well (3 mL) of the diet tray that had been previously filled with 1 mL of artificial diet to which 50 μg/cm$^2$ of the test molecule (dissolved in 50 μL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Bioassays on CEW

Bioassays on CEW were conducted using a 128-well diet tray assay. one to five second instar CEW larvae were placed in each well (3 mL) of the diet tray that had been previously filled with 1 mL of artificial diet to which 50 μg/cm$^2$ of the test molecule (dissolved in 50 μL of 90:10 acetone-water mixture) had been applied (to each of eight wells) and then allowed to dry. Trays were covered with a clear self-adhesive cover, and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Bioassays on CL

Bioassays on CL were conducted using a 128-well diet tray assay. one to five second instar CL larvae were placed in each well (3 mL) of the diet tray that had been previously filled with 1 mL of artificial diet to which 50 μg/cm$^2$ of the test molecule (dissolved in 50 μL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Example B: Bioassays on Green Peach Aphid (*Myzus persicae*, MYZUPE) ("GPA")

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other crops. GPA also attacks many ornamental crops such as carnation, chrysanthemum, flowering white cabbage, poinsettia, and roses. GPA has developed resistance to many pesticides. Consequently, because of the above factors control of this pest is important. Furthermore, molecules that control this pest (GPA), which is known as a sap-feeding pest, are useful in controlling other pests that feed on the sap from plants.

Certain molecules disclosed in this document were tested against GPA using procedures described in the following example. In the reporting of the results, the "GPA Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test molecules (2 mg) were dissolved in 2 mL of acetone/methanol (1:1) solvent, forming stock solutions of 1000 ppm test molecule. The stock solutions were diluted 5× with 0.025% Tween 20 in water to obtain the solution at 200 ppm test molecule. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

$$\text{Corrected \% Control} = 100*(X-Y)/X$$

where
X=No. of live aphids on solvent check plants and
Y=No. of live aphids on treated plants The results are indicated in the table entitled "Table ABC: Biological Results" (See Table Section).

Example C: Bioassays on Yellow Fever Mosquito (*Aedes aegypti*, AEDSAE) ("YFM")

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths, worldwide each year. Dengue fever is a nasty, viral disease; it is sometimes called "breakbone fever" or "breakheart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "YFM Rating Table" was used (See Table Section).

Master plates containing 400 μg of a molecule dissolved in 100 μL of dimethyl sulfoxide (DMSO) (equivalent to a 4000 ppm solution) are used. A master plate of assembled molecules contains 15 μL per well. To this plate, 135 μL of a 90:10 water:acetone mixture is added to each well. A robot (Biomek® NXP Laboratory Automation Workstation) is programmed to dispense 15 μL aspirations from the master plate into an empty 96-well shallow plate ("daughter" plate). There are 6 reps ("daughter" plates) created per master. The created daughter plates are then immediately infested with YFM larvae.

The day before plates are to be treated, mosquito eggs are placed in Millipore water containing liver powder to begin hatching (4 g. into 400 mL). After the daughter plates are created using the robot, they are infested with 220 μL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality. The results are indicated in the table entitled "Table ABC: Biological Results" (See Table Section).

Agriculturally Acceptable Acid Addition Salts, Salt Derivatives, Solvates, Ester Derivatives, Polymorphs, Isotopes, and Radionuclides Molecules of Formula One may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative may be prepared by contacting a free base with a sufficient amount of the desired acid to produce a salt. A free base may be regenerated by treating the salt with a suitable dilute aqueous base solution such as dilute aqueous sodium hydroxide, potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the molecules disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) or $^3H$ (also known as tritium) in place of 1H. Molecules of Formula One may be made with different radionuclides. Of particular importance are molecules having $^{14}C$. Molecules of Formula One having deuterium, tritium, or $^{14}C$ may be used in biological studies allowing tracing in chemical and physiological processes and half-life studies, as well as, MoA studies.

Stereoisomers

Molecules of Formula One may exist as one or more stereoisomers. Thus, certain molecules may be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

In another embodiment of this invention, molecules of Formula One may be used in combination (such as, in a compositional mixture, or a simultaneous or sequential application) with one or more active ingredients.

In another embodiment of this invention, molecules of Formula One may be used in combination (such as, in a compositional mixture, or a simultaneous or sequential application) with one or more active ingredients each having a MoA that is the same as, similar to, but more likely— different from, the MoA of the molecules of Formula One.

In another embodiment, molecules of Formula One may be used in combination (such as, in a compositional mixture, or a simultaneous or sequential application) with one or more molecules having acaricidal, algicidal, avicidal, bactericidal, fungicidal, herbicidal, insecticidal, molluscicidal, nematicidal, rodenticidal, and/or virucidal properties.

In another embodiment, the molecules of Formula One may be used in combination (such as, in a compositional mixture, or a simultaneous or sequential application) with one or more molecules that are antifeedants, bird repellents, chemosterilants, herbicide safeners, insect attractants, insect repellents, mammal repellents, mating disrupters, plant activators, plant growth regulators, and/or synergists.

In another embodiment, molecules of Formula One may also be used in combination (such as in a compositional mixture, or a simultaneous or sequential application) with one or more biopesticides.

In another embodiment, in a pesticidal composition combinations of a molecule of Formula One and an active ingredient may be used in a wide variety of weight ratios. For example, in a two component mixture, the weight ratio of a molecule of Formula One to an active ingredient, may be from about 100:1 to about 1:100; in another example the weight ratio may be about 50:1 to about 1:50; in another example the weight ratio may be about 20:1 to about 1 to 20; in another example the weight ratio may be about 10:1 to about 1:10; in another example the weight ratio may be about 5:1 to 1:5; in another example the weight ratio may be about 3:1 to about 1:3; in another example the weight ratio may be about 2:1 to about 1:2; and in a final example the weight ratio may be about 1:1 (See Table B). However, in general, weight ratios less than about 10:1 to about 1:10 are preferred. It is also preferred sometimes to use a three or four component mixture comprising a molecule of Formula One and one or more active ingredients.

TABLE B

| Weight Ratios Molecule of the Formula One:active ingredient |
|---|
| 100:1 to 1:100 |
| 50:1 to 1:50 |
| 20:1 to 1:20 |
| 10:1 to 1:10 |
| 5:1 to 1:5 |
| 3:1 to 1:3 |

TABLE B-continued

Weight Ratios
Molecule of the Formula One:active ingredient

2:1 to 1:2
1:1

Weight ratios of a molecule of Formula One to an active ingredient may also be depicted as X:Y; wherein X is the parts by weight of a molecule of Formula One and Y is the parts by weight of active ingredient. The numerical range of the parts by weight for X is $0<X\leq100$ and the parts by weight for Y is $0<Y\leq100$ and is shown graphically in TABLE C. By way of non-limiting example, the weight ratio of a molecule of Formula One to an active ingredient may be 20:1.

TABLE C

| active ingredient (Y) Parts by weight | 100 | X, Y |      | X, Y |      |      | X, Y |      |      |      |
|---|---|---|---|---|---|---|---|---|---|---|
|   | 50  | X, Y | X, Y | X, Y |      |      | X, Y | X, Y |      |      |
|   | 20  | X, Y |      | X, Y | X, Y |      | X, Y |      | X, Y |      |
|   | 15  | X, Y | X, Y |      |      |      |      | X, Y | X, Y | X, Y |
|   | 10  | X, Y |      | X, Y |      |      |      |      |      |      |
|   | 5   | X, Y | X, Y | X, Y |      | X, Y |      | X, Y | X, Y | X, Y |
|   | 3   | X, Y | X, Y |      | X, Y | X, Y |      | X, Y | X, Y | X, Y |
|   | 2   | X, Y |      | X, Y | X, Y |      | X, Y |      | X, Y |      |
|   | 1   | X, Y | X, Y | X, Y | X, Y | X, Y | X, Y | X, Y | X, Y | X, Y |
|   |     | 1    | 2    | 3    | 5    | 10   | 15   | 20   | 50   | 100  | molecule of Formula One
(X) Parts by weight

Ranges of weight ratios of a molecule of Formula One to an active ingredient may be depicted as $X_1{:}Y_1$ to $X_2{:}Y_2$, wherein X and Y are defined as above.

In one embodiment, the range of weight ratios may be $X_1{:}Y_1$ to $X_2{:}Y_2$, wherein $X_1>Y_1$ and $X_2<Y_2$. By way of non-limiting example, the range of a weight ratio of a molecule of Formula One to an active ingredient may be between 3:1 and 1:3, inclusive of the endpoints.

In another embodiment, the range of weight ratios may be $X_1{:}Y_1$ to $X_2{:}Y_2$, wherein $X_1>Y_1$ and $X_2>Y_2$. By way of non-limiting example, the range of weight ratio of a molecule of Formula One to an active ingredient may be between 15:1 and 3:1, inclusive of the endpoints.

In another embodiment, the range of weight ratios may be $X_1{:}Y_1$ to $X_2{:}Y_2$, wherein $X_1<Y_1$ and $X_2<Y_2$. By way of non-limiting example, the range of weight ratios of a molecule of Formula One to an active ingredient may be between about 1:3 and about 1:20, inclusive of the endpoints.

It is envisioned that certain weight ratios of a molecule of Formula One to an active ingredient, as presented in Table B and C, will be synergistic.

Formulations

A pesticide is rarely suitable for application in its pure form. It is usually necessary to add other substances so that the pesticide may be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions.

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and molecule and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. Dusts may be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. Baits may be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides may be microencapsulated by suspending the pesticide particles or droplets in plastic polymers of various types. By altering the chemistry of the polymer or by changing factors in the processing, microcapsules may be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one molecule which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra-low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

Applications

Molecules of Formula One may be applied to any locus. Particular crop loci to apply such molecules include loci where alfalfa, almonds, apples, barley, beans, canola, corn, cotton, crucifers, lettuce, oats, oranges, pears, peppers, potatoes, rice, sorghum, soybeans, strawberries, sugarcane, sugar beets, sunflowers, tobacco, tomatoes, wheat, and other valuable crops are growing or the seeds thereof are going to be planted.

Molecules of Formula One may also be applied where plants, such as crops, are growing and where there are low levels (even no actual presence) of pests that can commercially damage such plants. Applying such molecules in such locus is to benefit the plants being grown in such locus. Such benefits, may include, but are not limited to: helping the plant grow a better root system; helping the plant better withstand stressful growing conditions; improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

Molecules of Formula One may be applied with ammonium sulfate when growing various plants as this may provide additional benefits.

Molecules of Formula One may be applied on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

Molecule of Formula One may be applied to the foliar and/or fruiting portions of plants to control pests. Such molecules will either come in direct contact with the pest, or the pest will consume such molecules when eating the plant or while extracting sap from the plant.

Molecule of Formula One may also be applied to the soil, and when applied in this manner, root and stem feeding pests may be controlled. The roots may absorb such molecules thereby taking it up into the foliar portions of the plant to control above ground chewing and sap feeding pests.

Systemic movement of pesticides in plants may be utilized to control pests on one portion of the plant by applying (for example by spraying a locus) a molecule of Formula One to a different portion of the plant. For example, control of foliar-feeding insects may be achieved by drip irrigation or furrow application, by treating the soil with for example pre- or post-planting soil drench, or by treating the seeds of a plant before planting.

Molecules of Formula One may be used with baits. Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait.

Molecules of Formula One may be encapsulated inside, or placed on the surface of a capsule. The size of the capsules can range from nanometer size (about 100-900 nanometers in diameter) to micrometer size (about 10-900 microns in diameter).

Molecules of Formula One may be applied to eggs of pests. Because of the unique ability of the eggs of some pests to resist certain pesticides, repeated applications of such molecules may be desirable to control newly emerged larvae.

Molecules of Formula One may be applied as seed treatments. Seed treatment may be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with molecules of Formula One may further enhance the ability of a plant to better withstand stressful growing conditions. This results in a healthier, more vigorous plant, which can lead to higher yields at harvest time. Generally, about 1 gram of such molecules to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

Molecules of Formula One may be applied with one or more active ingredients in a soil amendment.

Molecules of Formula One may be used for controlling endoparasites and ectoparasites in the veterinary medicine sector or in the field of non-human-animal keeping. Such molecules may be applied by oral administration in the form of, for example, tablets, capsules, drinks, granules, by dermal application in the form of, for example, dipping, spraying, pouring on, spotting on, and dusting, and by parenteral administration in the form of, for example, an injection.

Molecules of Formula One may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

Molecules of Formula One may also be used for controlling parasitic worms, especially of the intestine, in the animals listed above.

Molecules of Formula One may also be employed in therapeutic methods for human health care. Such methods include, but are limited to, oral administration in the form of, for example, tablets, capsules, drinks, granules, and by dermal application.

Molecules of Formula One may also be applied to invasive pests. Pests around the world have been migrating to new environments (for such pest) and thereafter becoming a new invasive species in such new environment. Such molecules may also be used on such new invasive species to control them in such new environments.

Consequently, in light of the above and the Tables in the Table Section, the following items are provided.

1. A molecule having the following formula

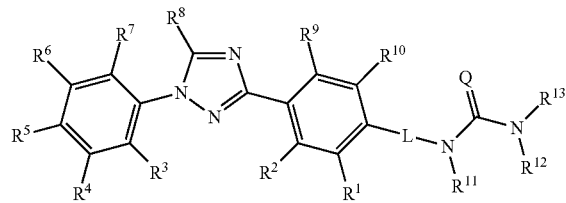

Formula One wherein:

(A) $R^1$, $R^2$, $R^3$, $R^4$, $R^5$, $R^6$, $R^7$, $R^9$, and $R^{10}$ are each independently selected from the group consisting of H, F, Cl, Br, I, CN, $NO_2$, OH, $(C_1$-$C_4)$alkyl, $(C_2$-$C_4)$alkenyl, $(C_1$-$C_4)$ haloalkyl, $(C_1$-$C_4)$alkoxy, $(C_1$-$C_4)$haloalkoxy, and $(C_3$-$C_6)$ cycloalkyl, wherein each alkyl, alkenyl, haloalkyl, alkoxy, haloalkoxy, and cycloalkyl, are optionally substituted with one or more substituents independently selected from the group consisting of F, Cl, Br, I, CN, $NO_2$, OH, $(C_1$-$C_4)$alkyl, $(C_2$-$C_4)$alkenyl, $(C_1$-$C_4)$haloalkyl, $(C_1$-$C_4)$alkoxy, $(C_1$-$C_4)$haloalkoxy, and $(C_3$-$C_6)$cycloalkyl preferably, $R^1$, $R^2$, $R^3$, $R^4$, $R^5$, $R^6$, $R^7$, $R^8$, $R^9$, $R^{10}$, $R^{11}$, and $R^{12}$ are H, and $R^5$ is $(C_1$-$C_4)$haloalkoxy, even more preferably $R^5$ is $OCF_3$ or $OCF_2CF_3$;

(B) $R^8$ is H;

(C) L is selected from the group consisting of
(1) a bond connecting nitrogen to carbon in the ring, and
(2) a $(C_1$-$C_4)$alkyl wherein said alkyl is optionally substituted with one or more substituents independently selected from the group consisting of F, Cl, CN, OH, and oxo
preferably L is a bond or L is —$CH_2CH_2$—;

(D) $R^{11}$ and $R^{12}$ are each independently selected from the group consisting of H, $(C_1$-$C_4)$alkyl, $(C_2$-$C_4)$alkenyl, $(C_2$-$C_4)$alkenyloxy, $(C_2$-$C_4)$alkynyl, $(C_2$-$C_4)$alkynyloxy, $(C_1$-$C_4)$ haloalkyl, $(C_1$-$C_4)$alkoxy, $(C_1$-$C_4)$haloalkoxy, $(C_3$-$C_6)$cycloalkyl, $(C_3$-$C_6)$cycloalkoxy, $(C_3$-$C_6)$cycloalkenyl, $(C_3$-$C_6)$ cycloalkenyloxy, $((C_1$-$C_4)$alkyl)$((C_3$-$C_6)$cycloalkyl), $C(O)$ $((C_1$-$C_4)$alkyl), $((C_1$-$C_4)$alkyl)$C(O)((C_1$-$C_4)$alkyl), and $((C_1$-$C_4)$alkyl)$C(O)O((C_1$-$C_4)$alkyl), wherein each alkyl, alkenyl, alkenyloxy, alkynyl, alkynyloxy, haloalkyl, alkoxy, haloalkoxy, cycloalkyl, cycloalkoxy, cycloalkenyl, and cycloalkenyloxy, are optionally substituted with one or more substituents independently selected from the group consisting of F, Cl, Br, I, CN, $NO_2$, OH, and oxo;

(E) $R^{13}$ is heterocyclyl, wherein said heterocyclyl is selected from the group consisting of dihydrofuranyl, furanyl, indazolyl, indolyl, imidazolyl, isoindolyl, isothiazolyl, isoxazolyl, oxadiazolyl, oxazolyl, pyrazolinyl, pyrazolyl, pyrrolyl, tetrazolyl, thiazolyl, thienyl, triazinyl, and triazolyl, wherein each heterocyclyl is optionally substituted with one or more substituents independently selected from the group consisting of oxo, $(C_1$-$C_8)$alkyl, $C(O)O(C_1$-$C_4)$alkyl, phenyl, and pyridyl, wherein each phenyl is optionally substituted with one or more substituents R, independently selected from the group consisting of F, Cl, Br, I, $(C_1$-$C_4)$alkyl, $(C_1$-$C_4)$ alkoxy, and $(C_1$-$C_4)$haloalkoxy preferably, $R^{13}$ is dihydrofuranyl, imidazolyl, isoxazolyl, oxadiazolyl, oxazolyl, pyrazolyl, thienyl, or thiazolyl that is substituted with one or more substituents selected from the group consisting of oxo, $CH_3$, $CH(CH_3)CH_2CH(CH_3)_2$, $C(O)OCH_2CH_3$, phenyl, and pyridyl that is further substituted with one or more substituents R, selected from the group consisting of F, Cl, $CH_3$, $CH_2CH_3$, $CH(CH_3)_2$, $OCH_3$, and $OCF_3$;

(F) Q is selected from the group consisting of O and S; and agriculturally acceptable acid addition salts, salt derivatives, solvates, ester derivatives, crystal polymorphs, isotopes, resolved stereoisomers, and tautomers, of the molecules of Formula One.

2. A molecule according to 1 wherein
(A) $R^1$, $R^2$, $R^3$, $R^4$, $R^5$, $R^6$, $R^7$, $R^9$, and $R^{10}$ are H;
(B) $R^8$ is H;
(C) L is selected from the group consisting of
(1) a bond connecting nitrogen to carbon in the ring, and
(2) a $(C_1$-$C_4)$alkyl;

(D) R$^{11}$ and R$^{12}$ are H;

(E) R$^{13}$ is heterocyclyl, wherein said heterocyclyl is selected from the group consisting of dihydrofuranyl, imidazolyl, isoxazolyl, oxadiazolyl, oxazolyl, pyrazolyl, thiazolyl, and thienyl,
  wherein each heterocyclyl is optionally substituted with one or more substituents independently selected from the group consisting of oxo, (C$_1$-C$_8$)alkyl, C(O)O(C$_1$-C$_4$)alkyl, phenyl, and pyridyl, wherein each phenyl is optionally substituted with one or more substituents R, independently selected from the group consisting of F, Cl, (C$_1$-C$_4$)alkyl, (C$_1$-C$_4$)alkoxy, and (C$_1$-C$_4$)haloalkoxy; and (F) Q is selected from the group consisting of O and S.

3. A molecule according to 1 wherein said molecule is selected from one of the following molecules

| No. | Structure |
|---|---|
| F3 | 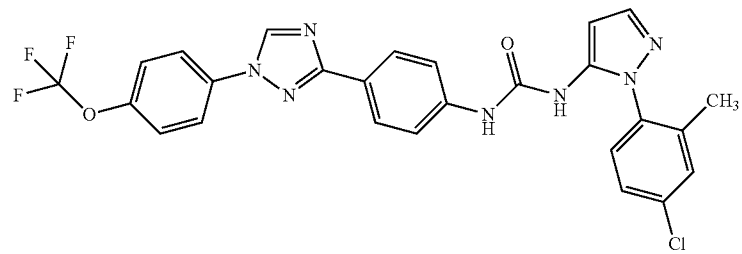 [SMILES: Cc1cc(Cl)ccc1-n1nccc1NC(=O)Nc1ccc(-c2ncn(-c3ccc(OC(F)(F)F)cc3)n2)cc1] |
| F4 | 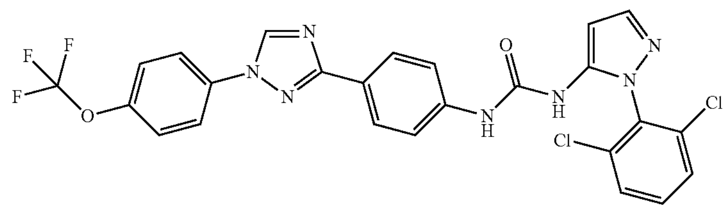 [SMILES: O=C(Nc1ccc(-c2ncn(-c3ccc(OC(F)(F)F)cc3)n2)cc1)Nc1ccnn1-c1c(Cl)cccc1Cl] |
| F5 | 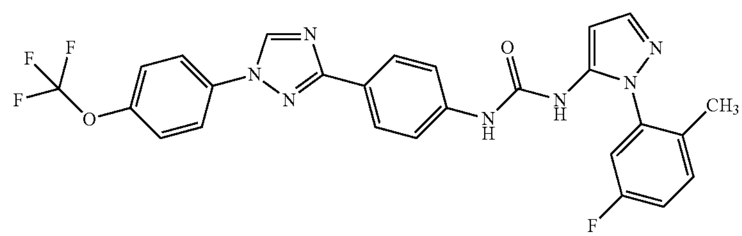 [SMILES: Cc1ccc(F)cc1-n1nccc1NC(=O)Nc1ccc(-c2ncn(-c3ccc(OC(F)(F)F)cc3)n2)cc1] |
| F6 | 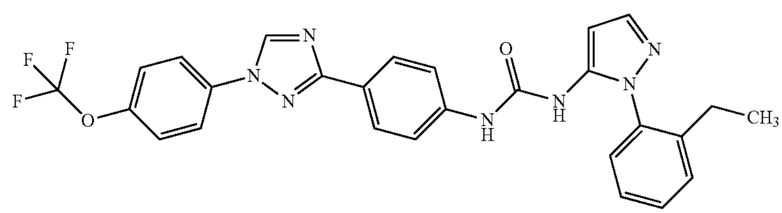 [SMILES: CCc1ccccc1-n1nccc1NC(=O)Nc1ccc(-c2ncn(-c3ccc(OC(F)(F)F)cc3)n2)cc1] |
| F7 | 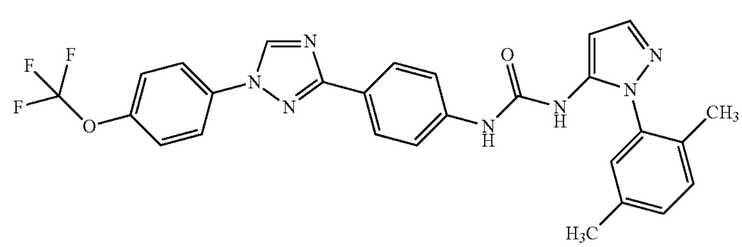 |
| F8 | 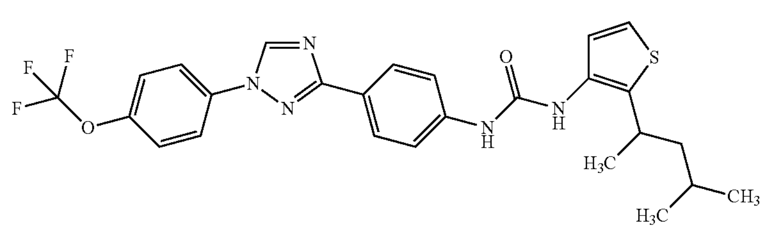 [SMILES: CC(C)CC(C)c1sccc1NC(=O)Nc1ccc(-c2ncn(-c3ccc(OC(F)(F)F)cc3)n2)cc1] |

-continued
| No. | Structure |
|---|---|
| F9 | 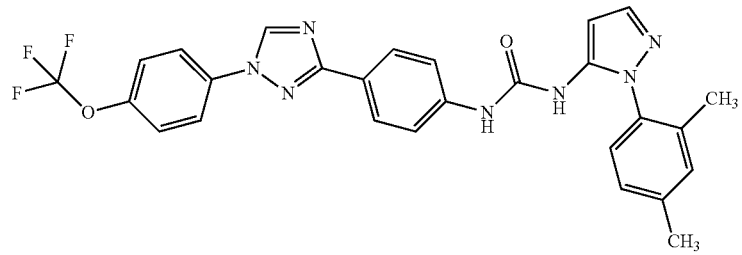 [SMILES: Cc1ccc(-n2nccc2NC(=O)Nc2ccc(-c3ncn(-c4ccc(OC(F)(F)F)cc4)n3)cc2)c(C)c1] |
| F10 | 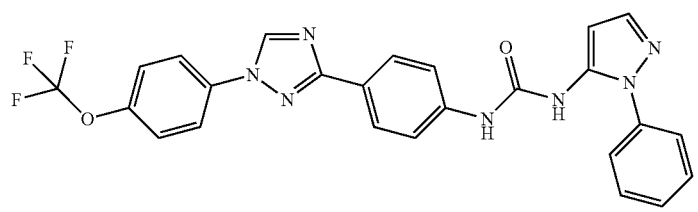 [SMILES: O=C(Nc1ccc(-c2ncn(-c3ccc(OC(F)(F)F)cc3)n2)cc1)Nc1ccnn1-c1ccccc1] |
| F11 | 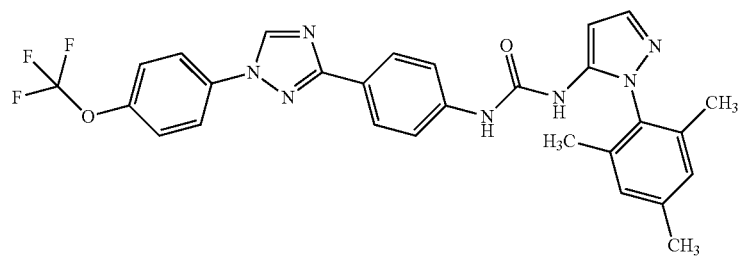 [SMILES: Cc1cc(C)c(-n2nccc2NC(=O)Nc2ccc(-c3ncn(-c4ccc(OC(F)(F)F)cc4)n3)cc2)c(C)c1] |
| F12 | 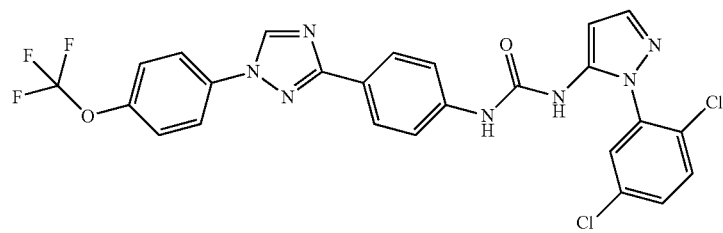 [SMILES: O=C(Nc1ccc(-c2ncn(-c3ccc(OC(F)(F)F)cc3)n2)cc1)Nc1ccnn1-c1cc(Cl)ccc1Cl] |
| F13 | 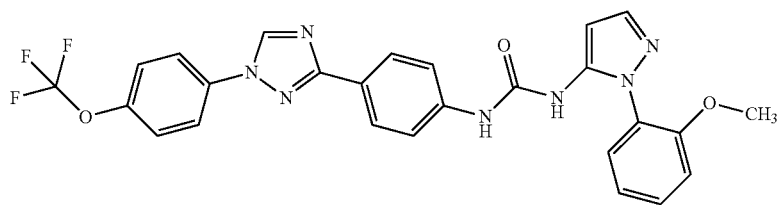 [SMILES: COc1ccccc1-n1nccc1NC(=O)Nc1ccc(-c2ncn(-c3ccc(OC(F)(F)F)cc3)n2)cc1] |
| F14 | 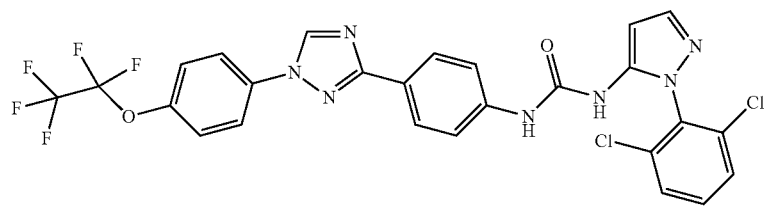 [SMILES: O=C(Nc1ccc(-c2ncn(-c3ccc(OC(F)(F)C(F)(F)F)cc3)n2)cc1)Nc1ccnn1-c1c(Cl)cccc1Cl] |

-continued
| No. | Structure |
|---|---|
| F15 | 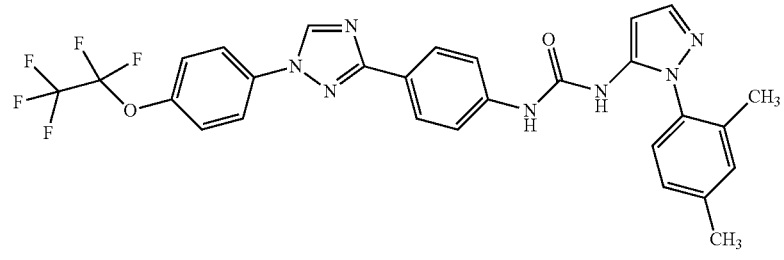 [SMILES: Cc1ccc(-n2nccc2NC(=O)Nc2ccc(-c3ncn(-c4ccc(OC(F)(F)C(F)(F)F)cc4)n3)cc2)c(C)c1] |
| F16 | 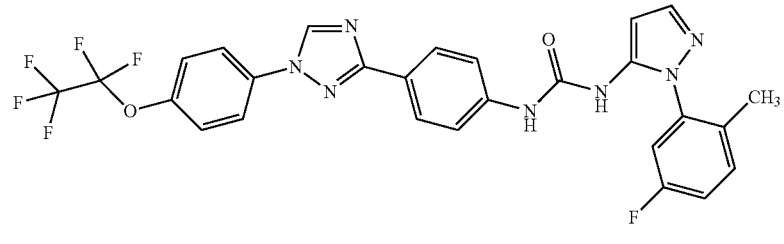 [SMILES: Cc1ccc(F)cc1-n1nccc1NC(=O)Nc1ccc(-c2ncn(-c3ccc(OC(F)(F)C(F)(F)F)cc3)n2)cc1] |
| F17 | 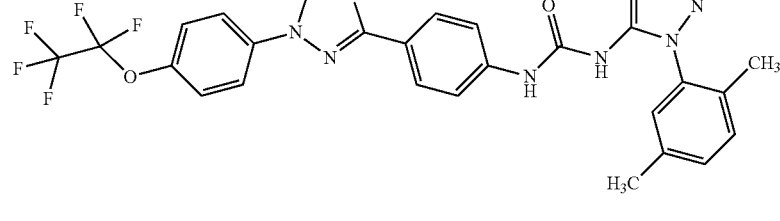 |
| F18 | 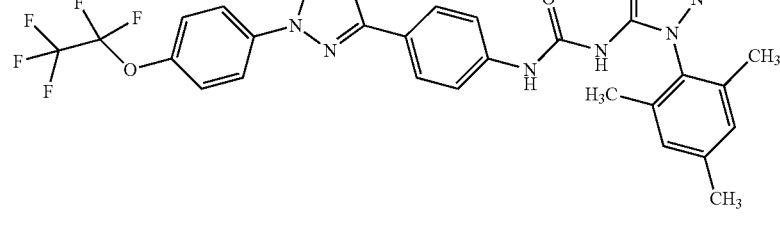 |
| F19 | 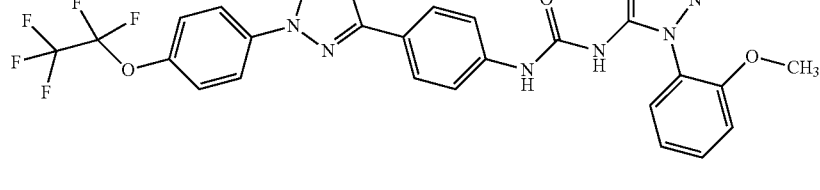 |
| F20 | 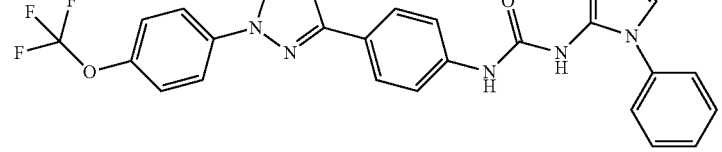 |

| No. | Structure |
|---|---|
| F21 | 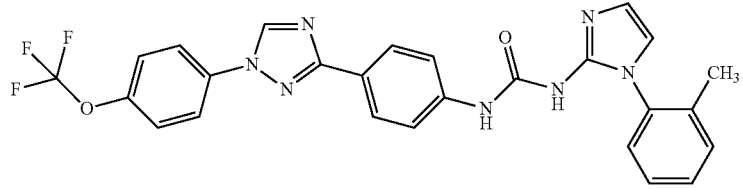 |
| F22 | 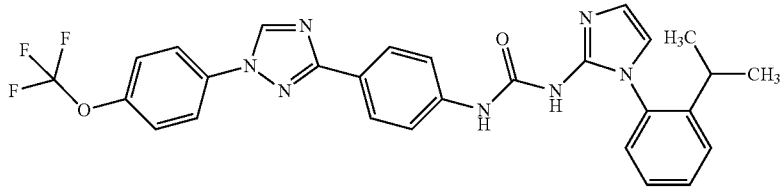 [SMILES: CC(C)c1ccccc1-n1ccnc1NC(=O)Nc1ccc(-c2ncn(-c3ccc(OC(F)(F)F)cc3)n2)cc1] |
| F23 | 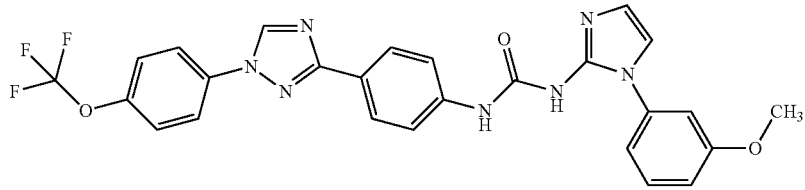 |
| F24 | 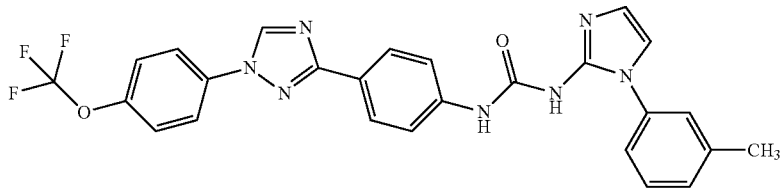 [SMILES: Cc1cccc(-n2ccnc2NC(=O)Nc2ccc(-c3ncn(-c4ccc(OC(F)(F)F)cc4)n3)cc2)c1] |
| F25 | 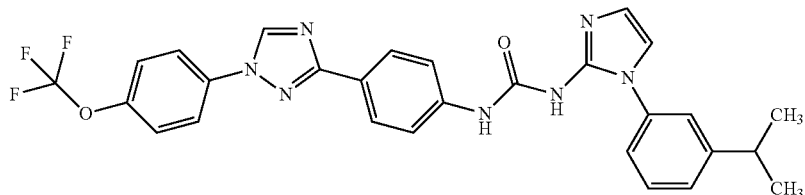 |
| F26 | 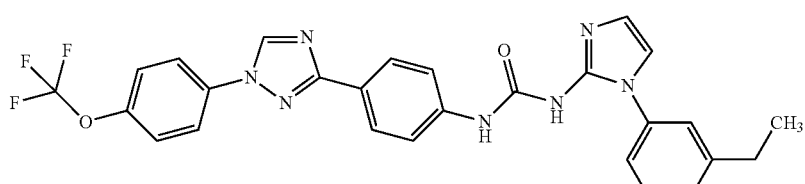 |
| F27 | 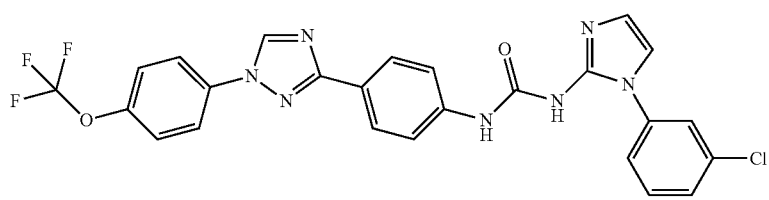 [SMILES: O=C(Nc1ccc(-c2ncn(-c3ccc(OC(F)(F)F)cc3)n2)cc1)Nc1nccn1-c1cccc(Cl)c1] |

-continued
| No. | Structure |
|---|---|
| F28 | 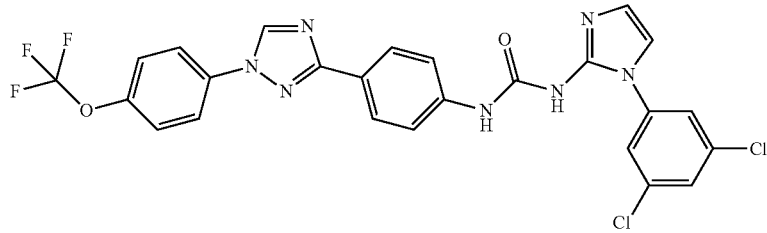 [SMILES: O=C(Nc1ccc(-c2ncn(-c3ccc(OC(F)(F)F)cc3)n2)cc1)Nc1nccn1-c1cc(Cl)cc(Cl)c1] |
| F29 | 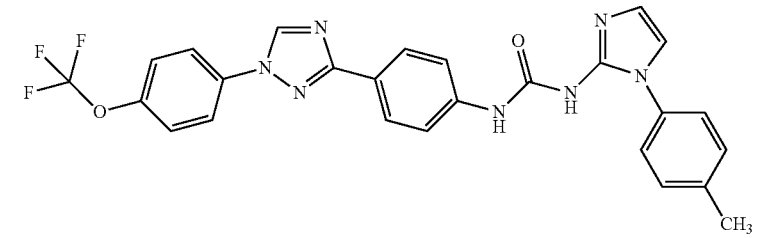 [SMILES: Cc1ccc(-n2ccnc2NC(=O)Nc2ccc(-c3ncn(-c4ccc(OC(F)(F)F)cc4)n3)cc2)cc1] |
| F30 | 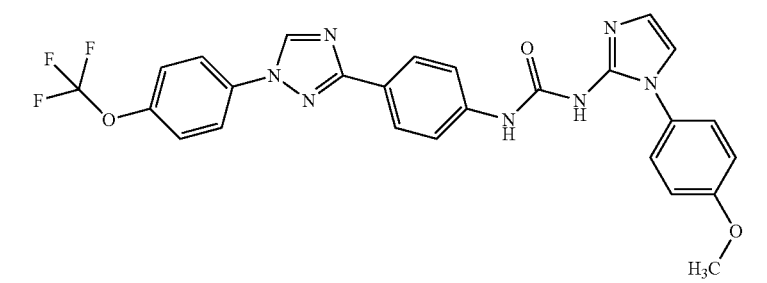 [SMILES: COc1ccc(-n2ccnc2NC(=O)Nc2ccc(-c3ncn(-c4ccc(OC(F)(F)F)cc4)n3)cc2)cc1] |
| F31 | 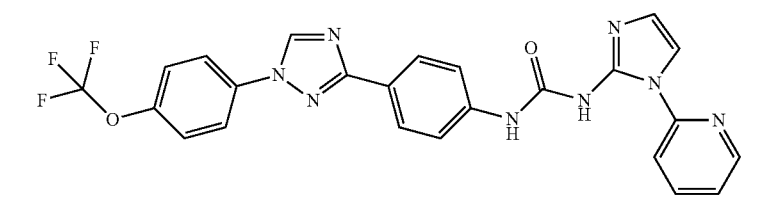 [SMILES: O=C(Nc1ccc(-c2ncn(-c3ccc(OC(F)(F)F)cc3)n2)cc1)Nc1nccn1-c1ccccn1] |
| F32 | 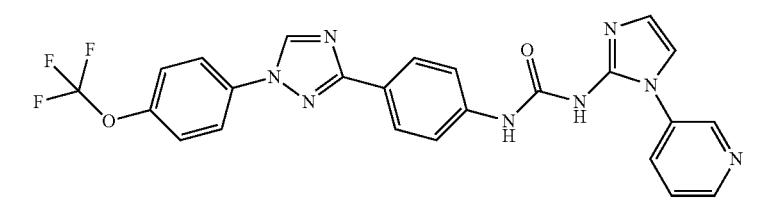 [SMILES: O=C(Nc1ccc(-c2ncn(-c3ccc(OC(F)(F)F)cc3)n2)cc1)Nc1nccn1-c1cccnc1] |
| F33 | 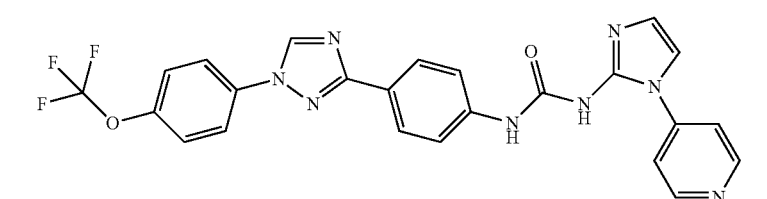 |
| F34 | 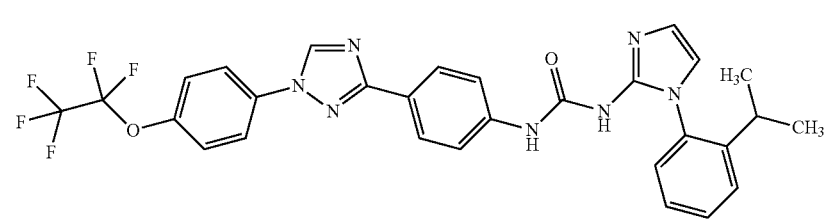 [SMILES: CC(C)c1ccccc1-n1ccnc1NC(=O)Nc1ccc(-c2ncn(-c3ccc(OC(F)(F)C(F)(F)F)cc3)n2)cc1] |

| No. | Structure |
|---|---|
| F35 | 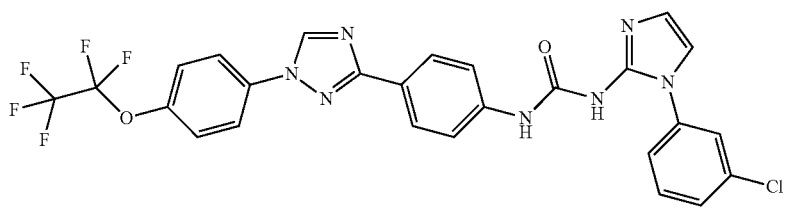 [SMILES: O=C(Nc1ccc(-c2ncn(-c3ccc(OC(F)(F)C(F)(F)F)cc3)n2)cc1)Nc1nccn1-c1cccc(Cl)c1] |
| F36 | 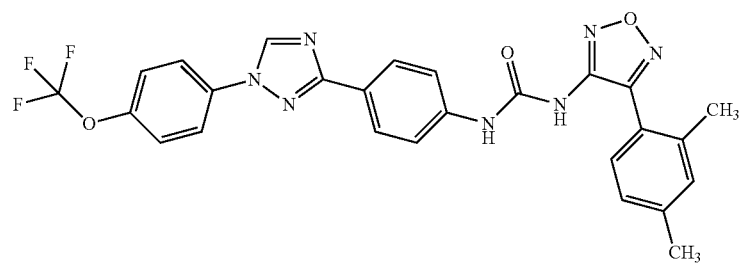 [SMILES: Cc1ccc(-c2nonc2NC(=O)Nc2ccc(-c3ncn(-c4ccc(OC(F)(F)F)cc4)n3)cc2)c(C)c1] |
| F37 | 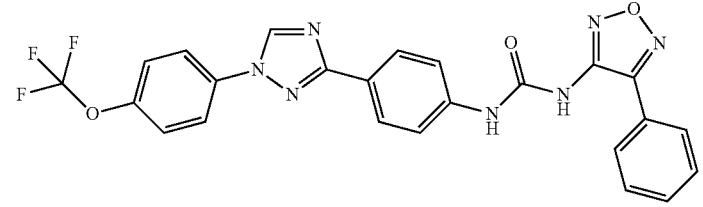 [SMILES: O=C(Nc1ccc(-c2ncn(-c3ccc(OC(F)(F)F)cc3)n2)cc1)Nc1nonc1-c1ccccc1] |
| F38 | 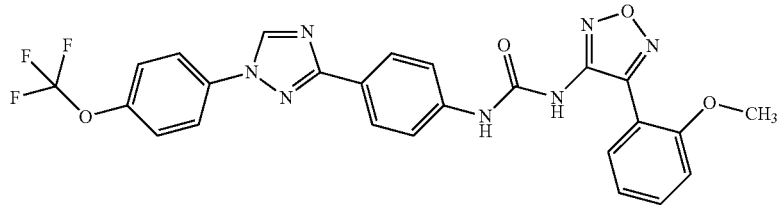 [SMILES: COc1ccccc1-c1nonc1NC(=O)Nc1ccc(-c2ncn(-c3ccc(OC(F)(F)F)cc3)n2)cc1] |
| F39 | 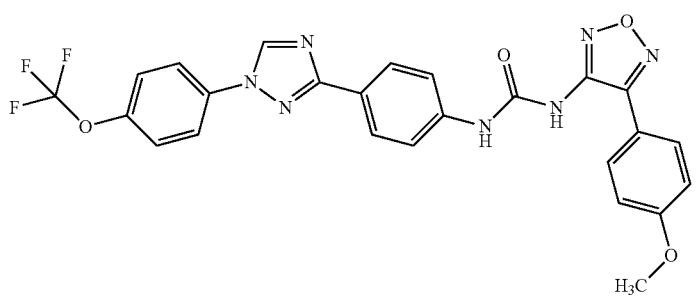 [SMILES: COc1ccc(-c2nonc2NC(=O)Nc2ccc(-c3ncn(-c4ccc(OC(F)(F)F)cc4)n3)cc2)cc1] |
| F40 | 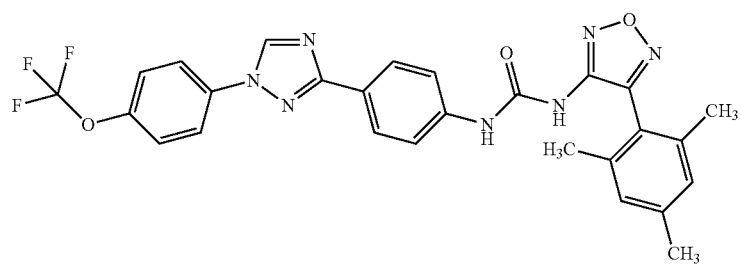 [SMILES: Cc1cc(C)c(-c2nonc2NC(=O)Nc2ccc(-c3ncn(-c4ccc(OC(F)(F)F)cc4)n3)cc2)c(C)c1] |

-continued
| No. | Structure |
|---|---|
| F41 | 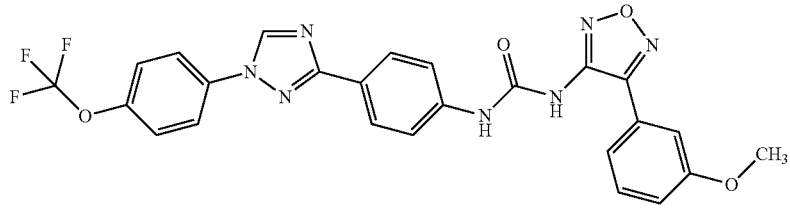 [SMILES: COc1cccc(-c2nonc2NC(=O)Nc2ccc(-c3ncn(-c4ccc(OC(F)(F)F)cc4)n3)cc2)c1] |
| F42 | 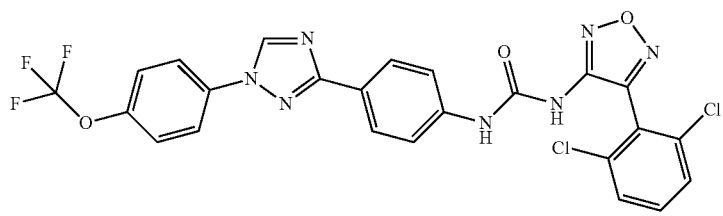 [SMILES: O=C(Nc1ccc(-c2ncn(-c3ccc(OC(F)(F)F)cc3)n2)cc1)Nc1nonc1-c1c(Cl)cccc1Cl] |
| F43 | 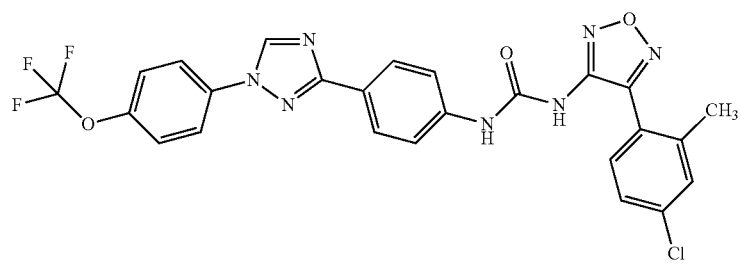 [SMILES: Cc1cc(Cl)ccc1-c1nonc1NC(=O)Nc1ccc(-c2ncn(-c3ccc(OC(F)(F)F)cc3)n2)cc1] |
| F44 | 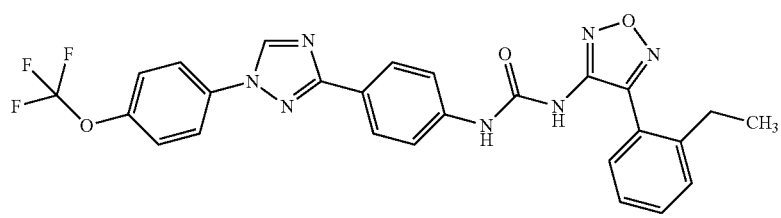 [SMILES: CCc1ccccc1-c1nonc1NC(=O)Nc1ccc(-c2ncn(-c3ccc(OC(F)(F)F)cc3)n2)cc1] |
| F45 | 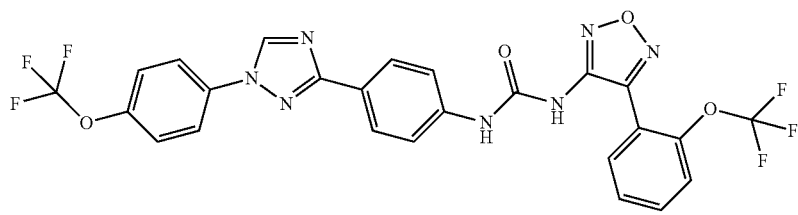 [SMILES: O=C(Nc1ccc(-c2ncn(-c3ccc(OC(F)(F)F)cc3)n2)cc1)Nc1nonc1-c1ccccc1OC(F)(F)F] |
| F46 | 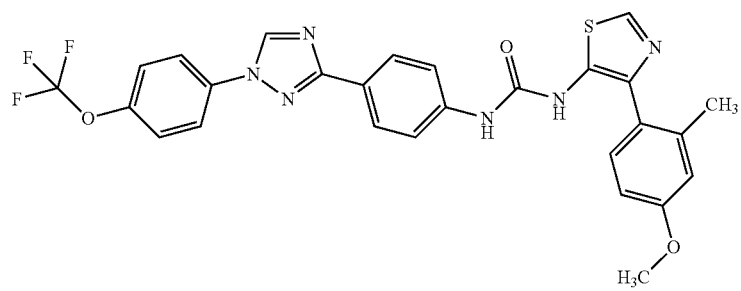 [SMILES: COc1ccc(-c2ncsc2NC(=O)Nc2ccc(-c3ncn(-c4ccc(OC(F)(F)F)cc4)n3)cc2)c(C)c1] |

| No. | Structure |
|---|---|
| F47 | 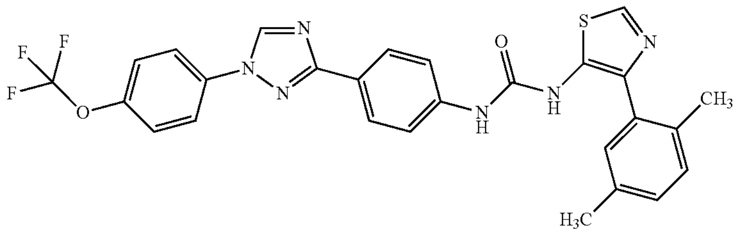 |
| F48 | 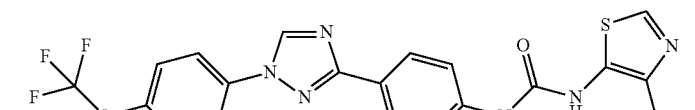 |
| F49 | 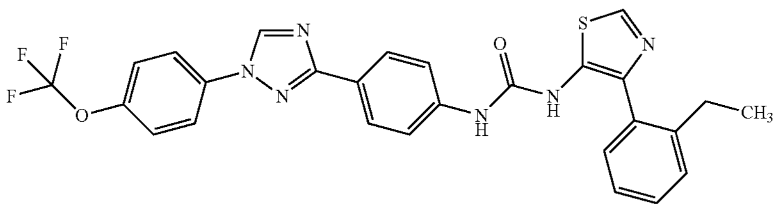 [SMILES: CCc1ccccc1-c1ncsc1NC(=O)Nc1ccc(-c2ncn(-c3ccc(OC(F)(F)F)cc3)n2)cc1] |
| F50 | 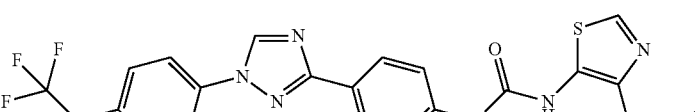 |
| F51 | 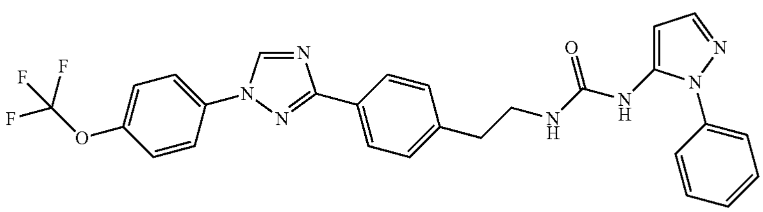 [SMILES: O=C(NCCc1ccc(-c2ncn(-c3ccc(OC(F)(F)F)cc3)n2)cc1)Nc1ccnn1-c1ccccc1] |
| F52 | 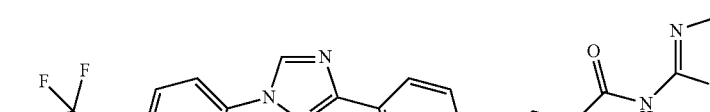 |
| F53 | 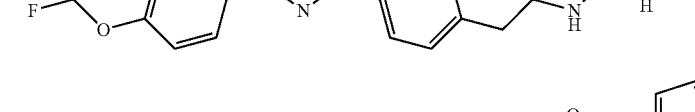 |

| No. | Structure |
|---|---|
| F54 | 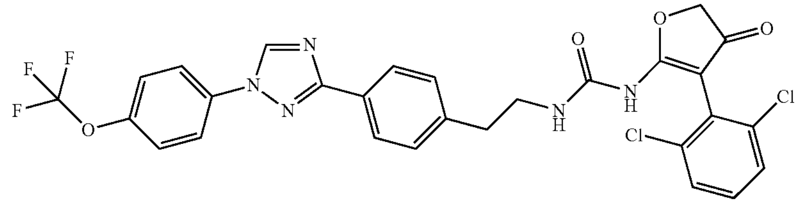 [SMILES: O=C(NCCc1ccc(-c2ncn(-c3ccc(OC(F)(F)F)cc3)n2)cc1)NC1=C(c2c(Cl)cccc2Cl)C(=O)CO1] |
| F55 | 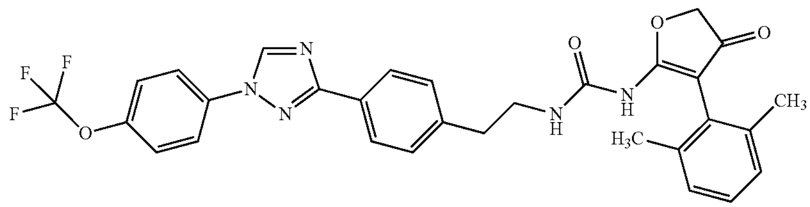 [SMILES: Cc1cccc(C)c1C1=C(NC(=O)NCCc2ccc(-c3ncn(-c4ccc(OC(F)(F)F)cc4)n3)cc2)OCC1=O] |
| F56 | 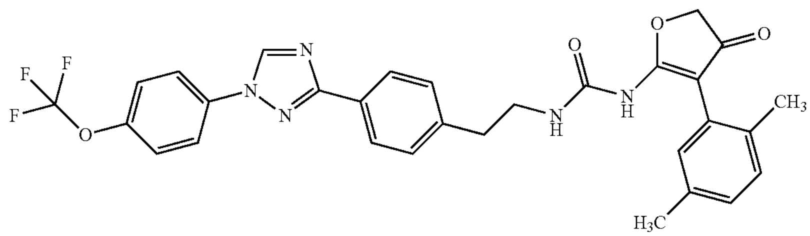 [SMILES: Cc1ccc(C)c(C2=C(NC(=O)NCCc3ccc(-c4ncn(-c5ccc(OC(F)(F)F)cc5)n4)cc3)OCC2=O)c1] |
| F57 | 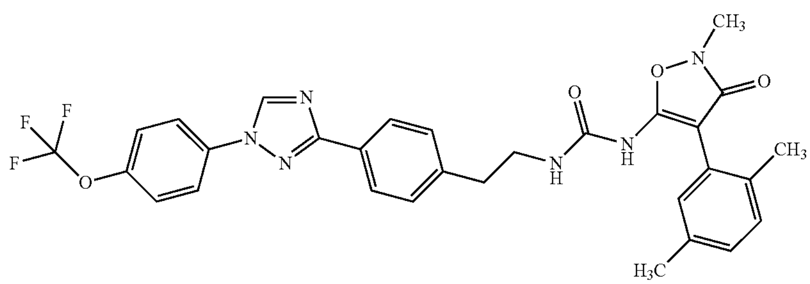 [SMILES: Cc1ccc(C)c(-c2c(NC(=O)NCCc3ccc(-c4ncn(-c5ccc(OC(F)(F)F)cc5)n4)cc3)on(C)c2=O)c1] |
| F58 | 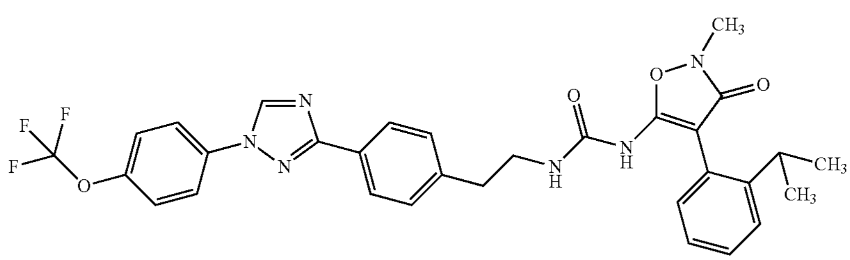 [SMILES: CC(C)c1ccccc1-c1c(NC(=O)NCCc2ccc(-c3ncn(-c4ccc(OC(F)(F)F)cc4)n3)cc2)on(C)c1=O] |
| F59 | 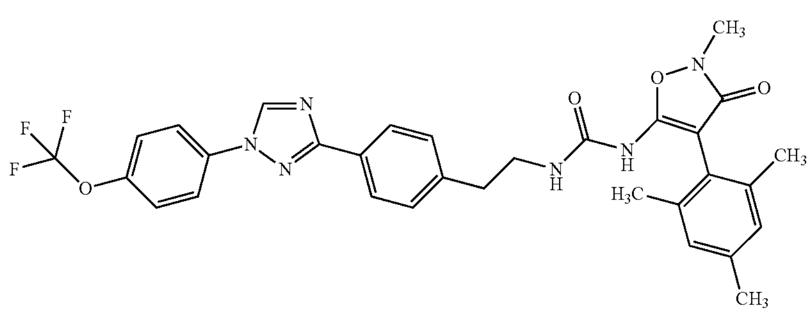 [SMILES: Cc1cc(C)c(-c2c(NC(=O)NCCc3ccc(-c4ncn(-c5ccc(OC(F)(F)F)cc5)n4)cc3)on(C)c2=O)c(C)c1] |

-continued

| No. | Structure |
|---|---|
| F60 | 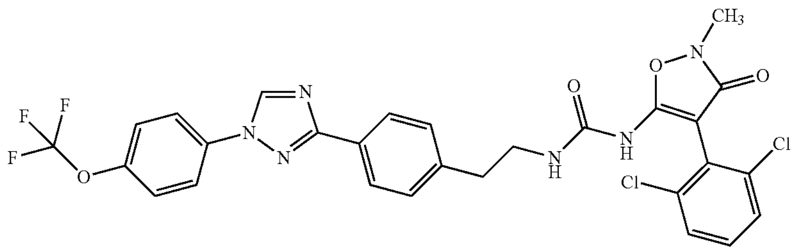 [SMILES: Cn1oc(NC(=O)NCCc2ccc(-c3ncn(-c4ccc(OC(F)(F)F)cc4)n3)cc2)c(-c2c(Cl)cccc2Cl)c1=O] |
| F61 | 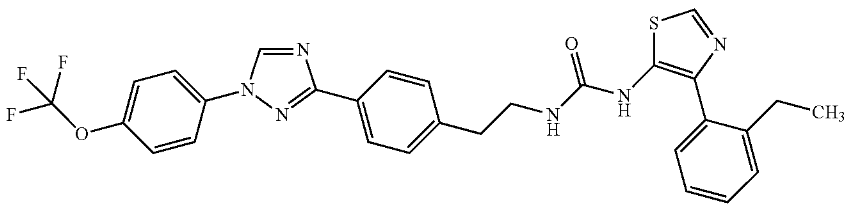 [SMILES: CCc1ccccc1-c1ncsc1NC(=O)NCCc1ccc(-c2ncn(-c3ccc(OC(F)(F)F)cc3)n2)cc1] |
| F62 | 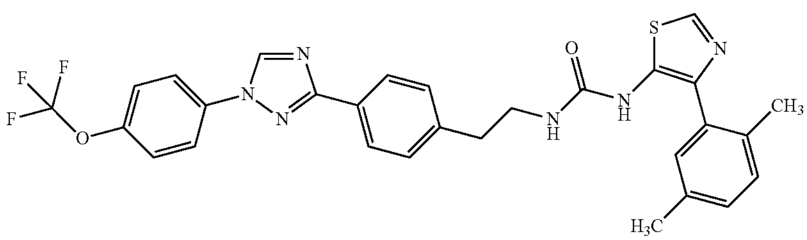 [SMILES: Cc1ccc(C)c(-c2ncsc2NC(=O)NCCc2ccc(-c3ncn(-c4ccc(OC(F)(F)F)cc4)n3)cc2)c1] |
| F63 | 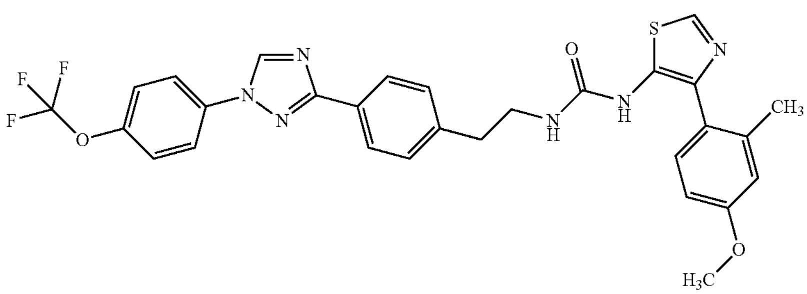 [SMILES: COc1ccc(-c2ncsc2NC(=O)NCCc2ccc(-c3ncn(-c4ccc(OC(F)(F)F)cc4)n3)cc2)c(C)c1] |
| F64 | 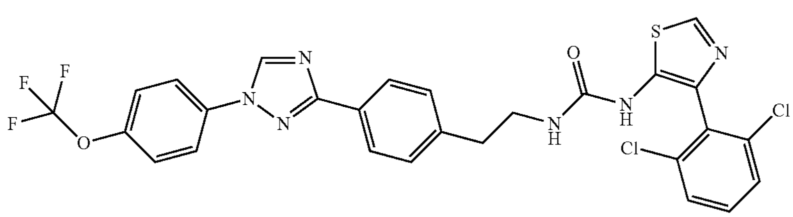 [SMILES: O=C(NCCc1ccc(-c2ncn(-c3ccc(OC(F)(F)F)cc3)n2)cc1)Nc1scnc1-c1c(Cl)cccc1Cl] |
| F65 | 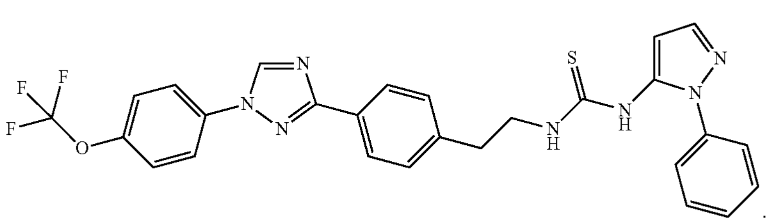 [SMILES: FC(F)(F)Oc1ccc(-n2cnc(-c3ccc(CCNC(=S)Nc4ccnn4-c4ccccc4)cc3)n2)cc1] |

4. A molecule according to 1 wherein said molecule is selected from one of the following molecules

| No. | Structure |
|---|---|
| P1 | 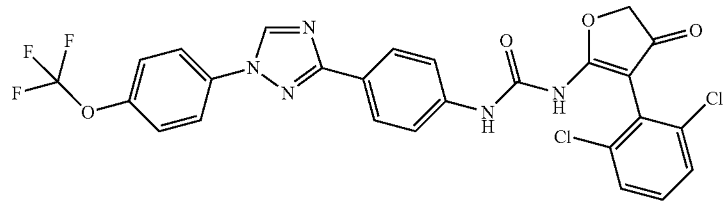 [SMILES: O=C(NC1=C(c2c(Cl)cccc2Cl)C(=O)CO1)Nc1ccc(-c2ncn(-c3ccc(OC(F)(F)F)cc3)n2)cc1] |
| P2 | 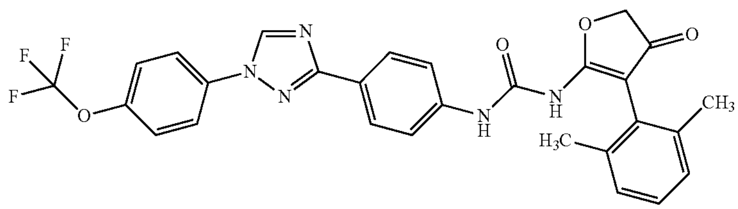 [SMILES: Cc1cccc(C)c1C1=C(NC(=O)Nc2ccc(-c3ncn(-c4ccc(OC(F)(F)F)cc4)n3)cc2)OCC1=O] |
| P3 | 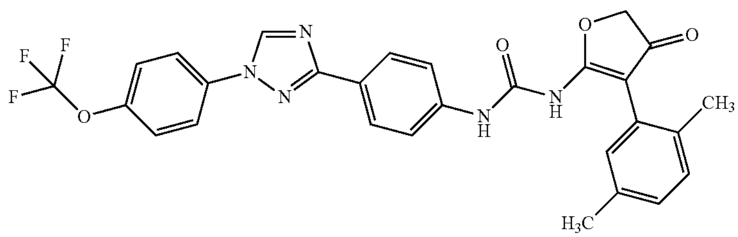 [SMILES: Cc1ccc(C)c(C2=C(NC(=O)Nc3ccc(-c4ncn(-c5ccc(OC(F)(F)F)cc5)n4)cc3)OCC2=O)c1] |
| P4 | 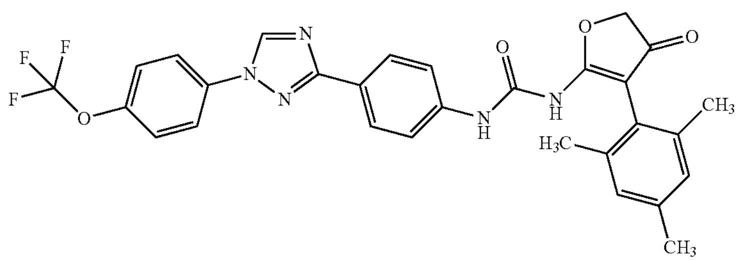 [SMILES: Cc1cc(C)c(C2=C(NC(=O)Nc3ccc(-c4ncn(-c5ccc(OC(F)(F)F)cc5)n4)cc3)OCC2=O)c(C)c1] |
| P5 | 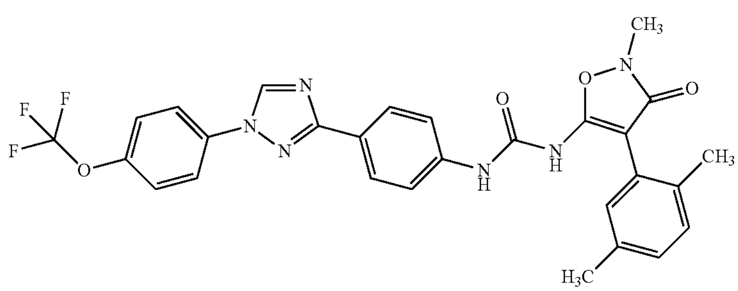 [SMILES: Cc1ccc(C)c(-c2c(NC(=O)Nc3ccc(-c4ncn(-c5ccc(OC(F)(F)F)cc5)n4)cc3)on(C)c2=O)c1] |
| P6 | 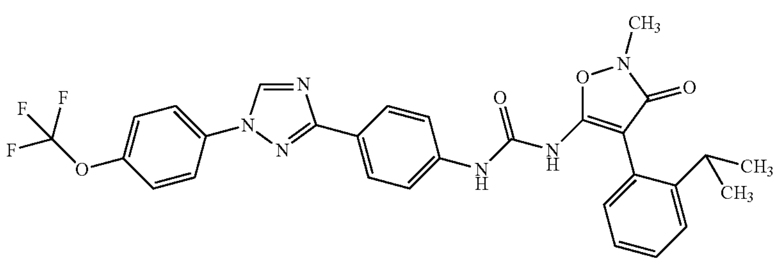 [SMILES: CC(C)c1ccccc1-c1c(NC(=O)Nc2ccc(-c3ncn(-c4ccc(OC(F)(F)F)cc4)n3)cc2)on(C)c1=O] |

| No. | Structure |
|---|---|
| P7 | 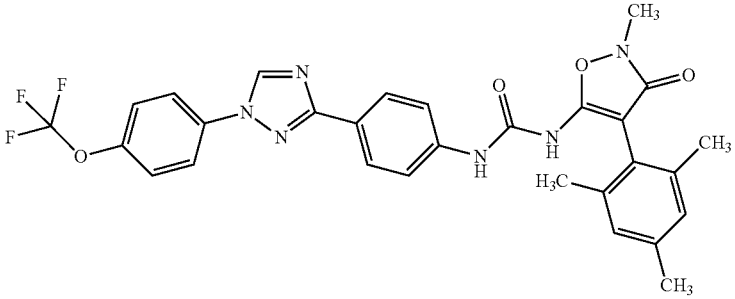 [SMILES: Cc1cc(C)c(-c2c(NC(=O)Nc3ccc(-c4ncn(-c5ccc(OC(F)(F)F)cc5)n4)cc3)on(C)c2=O)c(C)c1] |
| P8 | 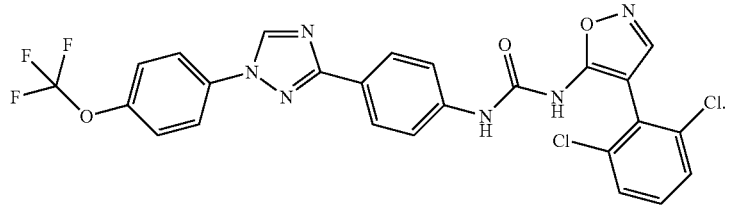 [SMILES: O=C(Nc1ccc(-c2ncn(-c3ccc(OC(F)(F)F)cc3)n2)cc1)Nc1oncc1-c1c(Cl)cccc1Cl] |

5. A pesticidal composition comprising a molecule according to any one of 1, 2, 3, or 4, further comprising one or more active ingredients.

6. A pesticidal composition according to 5 wherein said active ingredient is from AIGA.

7. A pesticidal composition according to 5 wherein said active ingredient is selected from AI-1, 1,3-dichloropropene, chlorpyrifos, chlorpyrifos-methyl, hexaflumuron, methoxyfenozide, noviflumuron, spinetoram, spinosad, sulfoxaflor, and sulfuryl fluoride.

8. A pesticidal composition comprising a molecule according to any one of 1, 2, 3, or 4, further comprising a MoA Material.

9. A pesticidal composition according to 7 wherein said MoA Material is from MoAMGA.

10. A pesticidal composition according to any one of 5, 6, 7, 8, or 9, wherein the weight ratio of the molecule according to Formula One to said active ingredient is
    (a) 100:1 to 1:100;
    (b) 50:1 to 1:50;
    (c) 20:1 to 1 to 20;
    (d) 10:1 to 1:10;
    (e) 5:1 to 1:5;
    (f) 3:1 to 1:3;
    (g) 2:1 to 1:2; or
    (h) 1:1

11. A process to control a pest said process comprising applying to a locus, a pesticidally effective amount of a molecule according to any one of the 1, 2, 3, or 4.

12. A process to control a pest said process comprising applying to a locus, a pesticidally effective amount of a pesticidal composition according to any one of the 5, 6, 7, 8, 9, or 10.

13. A molecule according to any one of 1, 2, 3, or 4, or a pesticidal composition according to any of 5, 6, 7, 8, 9, or 10, wherein said molecule is in the form of agriculturally acceptable acid addition salt.

14. A molecule according to any one of 1, 2, 3, or 4, or a pesticidal composition according to any of 5, 6, 7, 8, 9, or 10, wherein said molecule is in the form of a salt derivative.

15. A molecule according to any one of 1, 2, 3, or 4, or a pesticidal composition according to any of 5, 6, 7, 8, 9, or 10, wherein said molecule is in the form of solvate.

16. A molecule according to any one of 1, 2, 3, or 4, or a pesticidal composition according to any of 5, 6, 7, 8, 9, or 10, wherein said molecule is in the form of an ester derivative.

17. A molecule according to any one of 1, 2, 3, or 4, or a pesticidal composition according to any of 5, 6, 7, 8, 9, or 10, wherein said molecule is in the form of a crystal polymorphs.

18. A molecule according to any one of 1, 2, 3, or 4, or a pesticidal composition according to any of 5, 6, 7, 8, 9, or 10, wherein said molecule has deuterium, tritium, and or $^{14}C$.

19. A molecule according to any one of 1, 2, 3, or 4, or a pesticidal composition according to any of 5, 6, 7, 8, 9, or 10, wherein said molecule is in the form of one or more stereoisomers 20. A molecule according to any one of 1, 2, 3, or 4, or a pesticidal composition according to any of 5, 6, 7, 8, 9, or 10, wherein said molecule is in the form of a resolved stereoisomer.

21. A pesticidal composition according to any of 5, 6, 7, 8, 9, or 10, wherein said pesticidal composition further comprises another active ingredient.

22. A pesticidal composition according to any of 5, 6, 7, 8, 9, or 10, wherein said pesticidal composition further comprises two more active ingredients.

23. A pesticidal composition according to any of 5, 6, 7, 8, 9, or 10, wherein said active ingredient has a MOA different from the MoA of said molecule of Formula One.

24. A pesticidal composition according to any of 5, 6, 7, 8, 9, or 10, wherein said pesticidal composition comprises an active ingredient having acaricidal, algicidal, avicidal, bactericidal, fungicidal, herbicidal, insecticidal, molluscicidal, nematicidal, rodenticidal, and/or virucidal properties.

25. A pesticidal composition according to any of 5, 6, 7, 8, 9, or 10, wherein said pesticidal composition comprises an active ingredient that is an antifeedant, bird repellent, chemosterilant, herbicide safener, insect attractant, insect repellent, mammal repellent, mating disrupter, plant activator, plant growth regulator, and/or synergist.

26. A pesticidal composition according to any of 5, 6, 7, 8, 9, or 10, wherein said pesticidal composition comprises an active ingredient that is a biopesticide.

27. A pesticidal composition according to any of 5, 6, 7, 8, 9, or 10, wherein said the weight ratio of a molecule of Formula One to an active ingredient is 100:1 to 1:100.
28. A pesticidal composition according to any of 5, 6, 7, 8, 9, or 10, wherein said the weight ratio of a molecule of Formula One to an active ingredient is 50:1 to 1:50.
29. A pesticidal composition according to any of 5, 6, 7, 8, 9, or 10, wherein said the weight ratio of a molecule of Formula One to an active ingredient is 20:1 to 1 to 20
30. A pesticidal composition according to any of 5, 6, 7, 8, 9, or 10, wherein said the weight ratio of a molecule of Formula One to an active ingredient is 10:1 to 1:10.
31. A pesticidal composition according to any of 5, 6, 7, 8, 9, or 10, wherein said the weight ratio of a molecule of Formula One to an active ingredient is 5:1 to 1:5.
32. A pesticidal composition according to any of 5, 6, 7, 8, 9, or 10, wherein said the weight ratio of a molecule of Formula One to an active ingredient is 3:1 to 1:3.
33. A pesticidal composition according to any of 5, 6, 7, 8, 9, or 10, wherein said the weight ratio of a molecule of Formula One to an active ingredient is 2:1 to 1:2.
34. A pesticidal composition according to any of 5, 6, 7, 8, 9, or 10, wherein said the weight ratio of a molecule of Formula One to an active ingredient is 1:1
35. A pesticidal composition according to any of 5, 6, 7, 8, 9, or 10, wherein said the weight ratio of a molecule of Formula One to an active ingredient is depicted as X:Y; wherein X is the parts by weight of a molecule of Formula One and Y is the parts by weight of active ingredient; further wherein the numerical range of the parts by weight for X is 0<X≤100 and the parts by weight for Y is 0<Y≤100; and further wherein X and Y are selected from Table C

TABLE C

| active ingredient (Y) Parts by weight | | | | | | | | | |
|---|---|---|---|---|---|---|---|---|---|
| 100 | X, Y | | X, Y | | | X, Y | | | |
| 50 | X, Y | X, Y | X, Y | | | X, Y | X, Y | | |
| 20 | X, Y | | X, Y | X, Y | | X, Y | | X, Y | |
| 15 | X, Y | X, Y | | | | | X, Y | X, Y | X, Y |
| 10 | X, Y | | X, Y | | | | | | |
| 5 | X, Y | X, Y | X, Y | | | X, Y | | | |
| 3 | X, Y | X, Y | | X, Y | X, Y | | X, Y | X, Y | X, Y |
| 2 | X, Y | | X, Y | X, Y | | X, Y | | X, Y | |
| 1 | X, Y | X, Y | X, Y | X, Y | X, Y | X, Y | X, Y | X, Y | X, Y |
| | 1 | 2 | 3 | 5 | 10 | 15 | 20 | 50 | 100 |
| | molecule of Formula One (X) Parts by weight. | | | | | | | | |

36. A pesticidal composition according to 35 wherein a range of weight ratios of a molecule of Formula One to an active ingredient is depicted as $X_1:Y_1$ to $X_2:Y_2$; further wherein $X_1>Y_1$ and $X_2<Y_2$.
37. A pesticidal composition according to 35 wherein a range of weight ratios of a molecule of Formula One to an active ingredient is depicted as $X_1:Y_1$ to $X_2:Y_2$; further wherein $X_1>Y_1$ and $X_2>Y_2$.
38. A pesticidal composition according to 35 wherein a range of weight ratios of a molecule of Formula One to an active ingredient is depicted as $X_1:Y_1$ to $X_2:Y_2$; further wherein $X_1<Y_1$ and $X_2<Y_2$.
39. A pesticidal composition according to 35 wherein is synergistic.
40. A process according to 12 wherein said pest is from Phyla Arthropoda.
41. A process according to 12 wherein said pest is from Phyla Mollusca.
42. A process according to 12 wherein said pest is from Phyla Nematoda.
43. A process according to 12 wherein said pests are are ants, aphids, beetles, bristletails, cockroaches, crickets, earwigs, fleas, flies, grasshoppers, leafhoppers, lice, locusts, mites, moths, nematodes, scales, symphylans, termites, thrips, ticks, wasps, and/or whiteflies.
44. A process according to 12 wherein said locus is where alfalfa, almonds, apples, barley, beans, canola, corn, cotton, crucifers, lettuce, oats, oranges, pears, peppers, potatoes, rice, sorghum, soybeans, strawberries, sugarcane, sugar beets, sunflowers, tobacco, tomatoes, wheat, and other valuable crops are growing or the seeds thereof are planted.
45. A pesticidal composition according to any of 5, 6, 7, 8, 9, or 10, wherein said pesticidal composition further comprises ammonium sulfate.
46. A process according to 12 wherein said locus is where plants genetically modified to express specialized traits are planted.
47. A process according to 12 wherein said applying is done to the foliar and/or fruiting portions of plants.
48. A process according to 12 wherein said applying is done to the soil.
49. A process according to 12 wherein said applying is done by drip irrigation, furrow application, or pre- or post-planting soil drench.
50. A process according to 12 wherein said applying is done to the foliar and/or fruiting portions of plants., or by treating the seeds of a plant before planting.
51. A pesticidal composition comprising a molecule according to any one of 1, 2, 3, or 4, and a seed.
52. A process comprising applying a molecule according to any one of 1, 2, 3, or 4, or a pesticidal composition according to any of 5, 6, 7, 8, 9, or 10, to a seed.
53. A process comprising applying a molecule according to 1, 2, 3, or 4, to a locus that includes a non-human animal to control endoparasites and/or ectoparasites.
54. A process to produce a pestidal composition, said process comprising mixing a molecule according to any one of claim 1, 2, 3, or 4, with one or more active ingredients.

The headings in this document are for convenience only and must not be used to interpret any portion hereof.

Table Section

TABLE 2

Structure and Preparation Method for F Series Molecules

| No. | Structure | Prep.* |
|---|---|---|
| F1 | 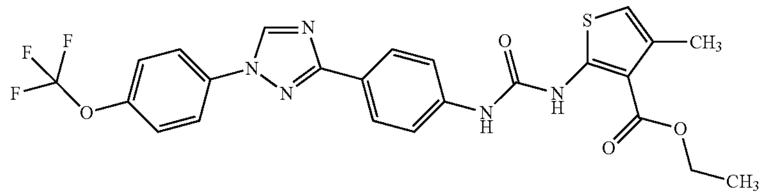 [SMILES: CCOC(=O)c1c(C)csc1NC(=O)Nc1ccc(-c2ncn(-c3ccc(OC(F)(F)F)cc3)n2)cc1] | 1 |
| F2 | 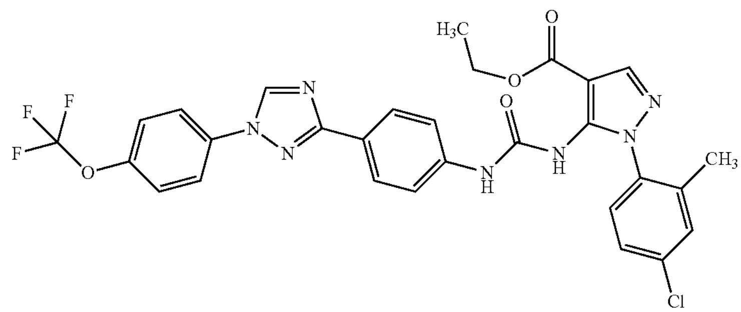 [SMILES: CCOC(=O)c1cnn(-c2ccc(Cl)cc2C)c1NC(=O)Nc1ccc(-c2ncn(-c3ccc(OC(F)(F)F)cc3)n2)cc1] | 1 |
| F3 | 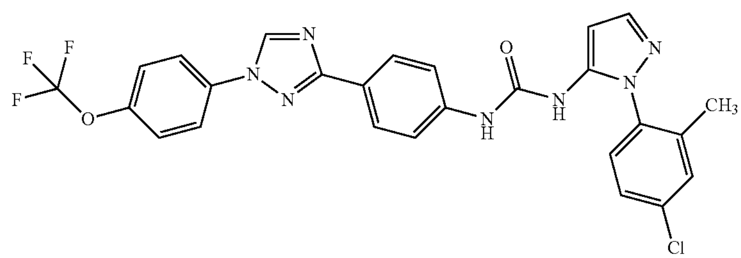 [SMILES: Cc1cc(Cl)ccc1-n1nccc1NC(=O)Nc1ccc(-c2ncn(-c3ccc(OC(F)(F)F)cc3)n2)cc1] | 1 |
| F4 | 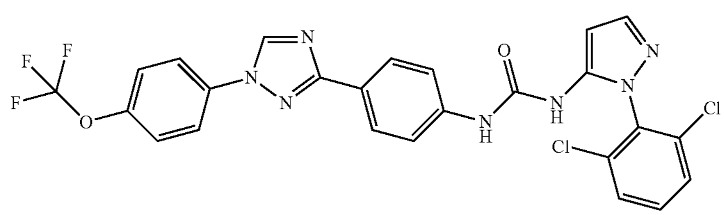 [SMILES: O=C(Nc1ccc(-c2ncn(-c3ccc(OC(F)(F)F)cc3)n2)cc1)Nc1ccnn1-c1c(Cl)cccc1Cl] | 1 |
| F5 | 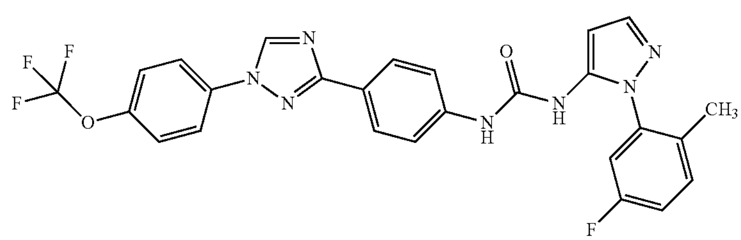 [SMILES: Cc1ccc(F)cc1-n1nccc1NC(=O)Nc1ccc(-c2ncn(-c3ccc(OC(F)(F)F)cc3)n2)cc1] | 1 |
| F6 | 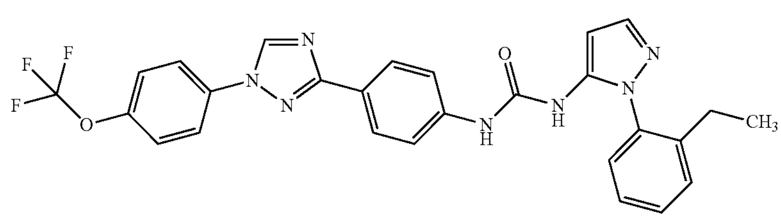 | 1 |

TABLE 2-continued
Structure and Preparation Method for F Series Molecules
| No. | Structure | Prep.* |
|---|---|---|
| F7 | 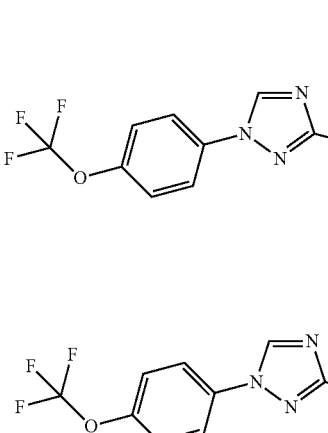 | 1 |
| F8 | 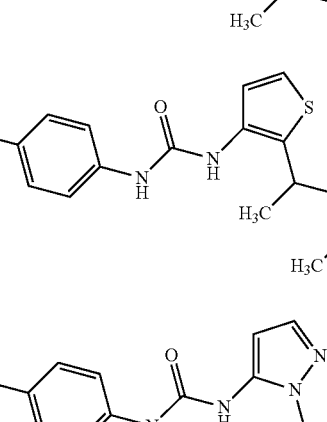 | 1 |
| F9 | 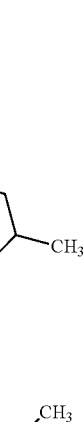 | 1 |
| F10 | 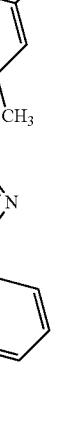 | 1 |
| F11 | 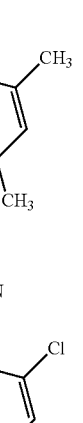 | 1 |
| F12 | 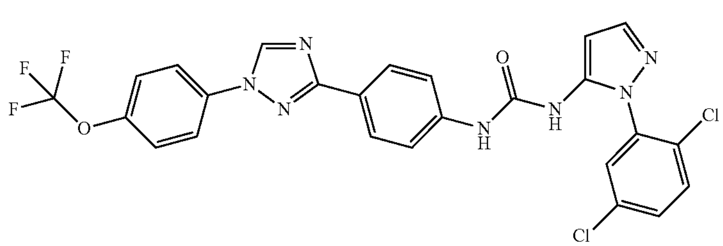 [SMILES: O=C(Nc1ccc(-c2ncn(-c3ccc(OC(F)(F)F)cc3)n2)cc1)Nc1ccnn1-c1cc(Cl)ccc1Cl] | 1 |

TABLE 2-continued

Structure and Preparation Method for F Series Molecules

| No. | Structure | Prep.* |
|---|---|---|
| F13 | 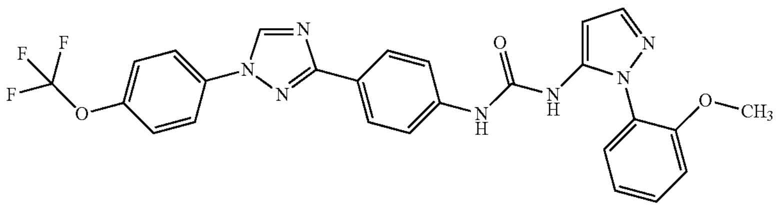 | 1 |
| F14 | 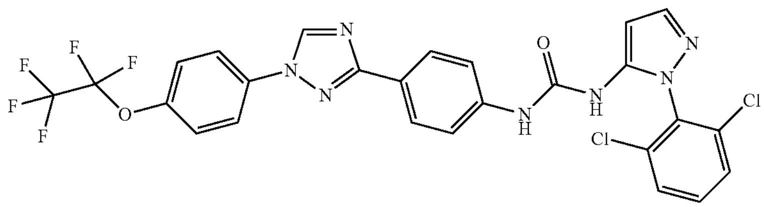 [SMILES: O=C(Nc1ccc(-c2ncn(-c3ccc(OC(F)(F)C(F)(F)F)cc3)n2)cc1)Nc1ccnn1-c1c(Cl)cccc1Cl] | 1 |
| F15 | 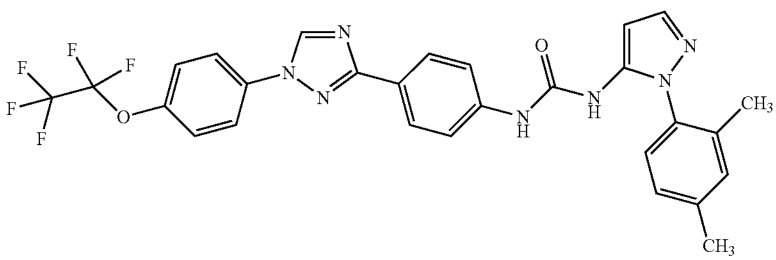 [SMILES: Cc1ccc(-n2nccc2NC(=O)Nc2ccc(-c3ncn(-c4ccc(OC(F)(F)C(F)(F)F)cc4)n3)cc2)c(C)c1] | 1 |
| F16 | 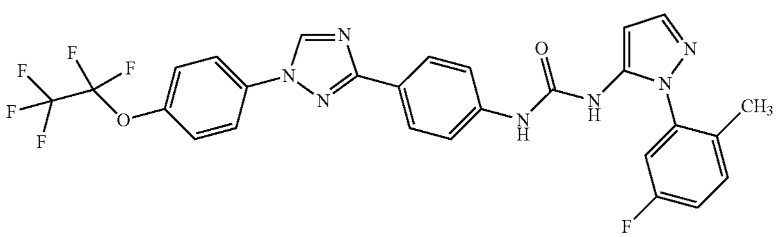 [SMILES: Cc1ccc(F)cc1-n1nccc1NC(=O)Nc1ccc(-c2ncn(-c3ccc(OC(F)(F)C(F)(F)F)cc3)n2)cc1] | 1 |
| F17 | 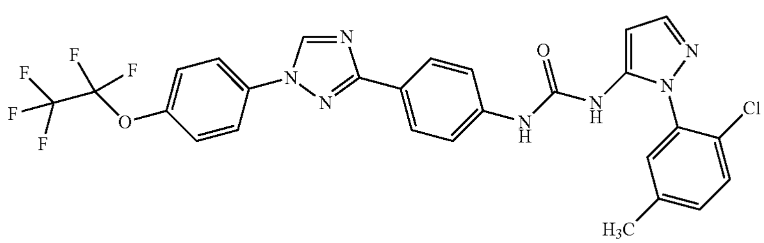 [SMILES: Cc1ccc(Cl)c(-n2nccc2NC(=O)Nc2ccc(-c3ncn(-c4ccc(OC(F)(F)C(F)(F)F)cc4)n3)cc2)c1] | 1 |
| F18 | 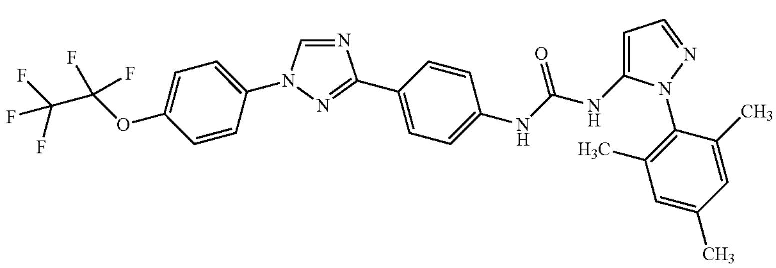 [SMILES: Cc1cc(C)c(-n2nccc2NC(=O)Nc2ccc(-c3ncn(-c4ccc(OC(F)(F)C(F)(F)F)cc4)n3)cc2)c(C)c1] | 1 |

TABLE 2-continued

Structure and Preparation Method for F Series Molecules

| No. | Structure | Prep.* |
|---|---|---|
| F19 | 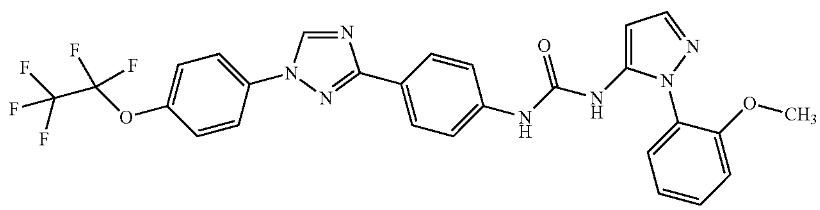 [SMILES: COc1ccccc1-n1nccc1NC(=O)Nc1ccc(-c2ncn(-c3ccc(OC(F)(F)C(F)(F)F)cc3)n2)cc1] | 1 |
| F20 | 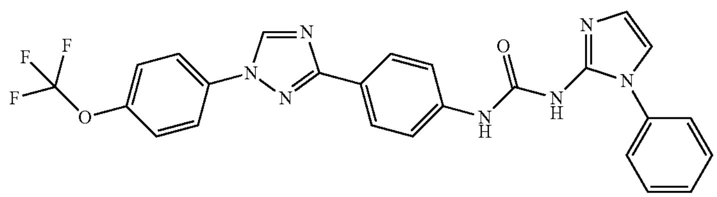 [SMILES: O=C(Nc1ccc(-c2ncn(-c3ccc(OC(F)(F)F)cc3)n2)cc1)Nc1nccn1-c1ccccc1] | 15 |
| F21 | 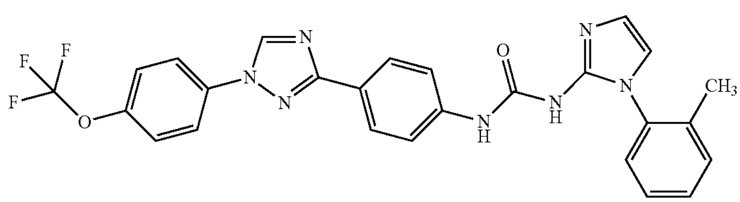 [SMILES: Cc1ccccc1-n1ccnc1NC(=O)Nc1ccc(-c2ncn(-c3ccc(OC(F)(F)F)cc3)n2)cc1] | 15 |
| F22 | 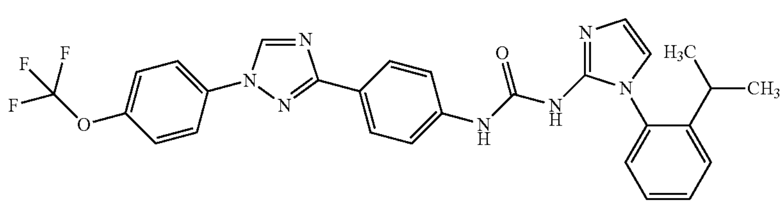 [SMILES: CC(C)c1ccccc1-n1ccnc1NC(=O)Nc1ccc(-c2ncn(-c3ccc(OC(F)(F)F)cc3)n2)cc1] | 15 |
| F23 | 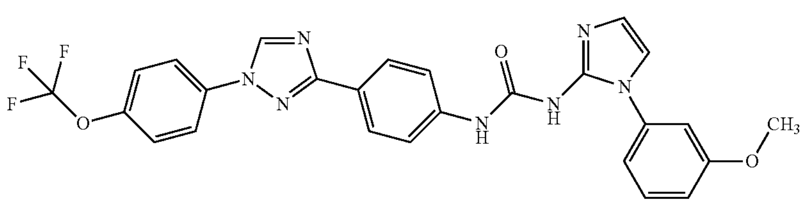 [SMILES: COc1cccc(-n2ccnc2NC(=O)Nc2ccc(-c3ncn(-c4ccc(OC(F)(F)F)cc4)n3)cc2)c1] | 15 |
| F24 | 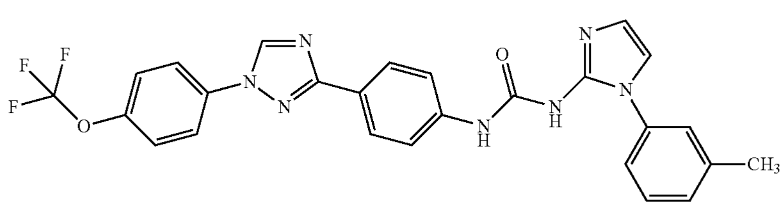 [SMILES: Cc1cccc(-n2ccnc2NC(=O)Nc2ccc(-c3ncn(-c4ccc(OC(F)(F)F)cc4)n3)cc2)c1] | 15 |
| F25 | 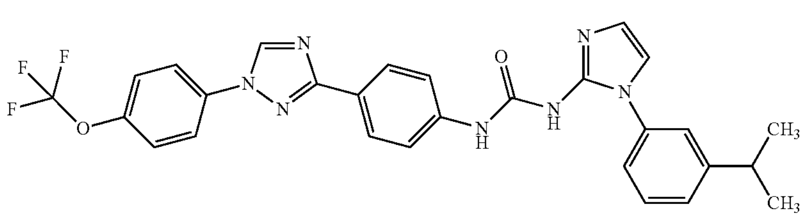 [SMILES: CC(C)c1cccc(-n2ccnc2NC(=O)Nc2ccc(-c3ncn(-c4ccc(OC(F)(F)F)cc4)n3)cc2)c1] | 15 |

TABLE 2-continued

Structure and Preparation Method for F Series Molecules

| No. | Structure | Prep.* |
|---|---|---|
| F26 | 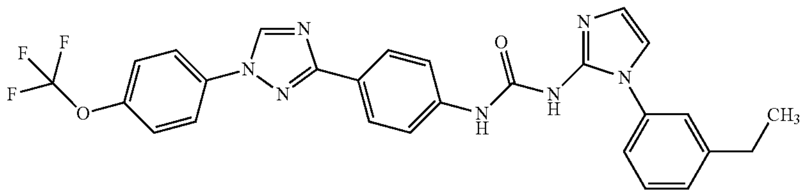 | 15 |
| F27 | 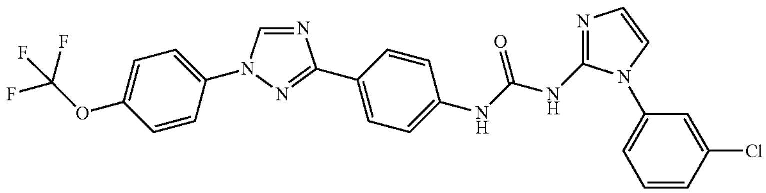 [SMILES: O=C(Nc1ccc(-c2ncn(-c3ccc(OC(F)(F)F)cc3)n2)cc1)Nc1nccn1-c1cccc(Cl)c1] | 15 |
| F28 | 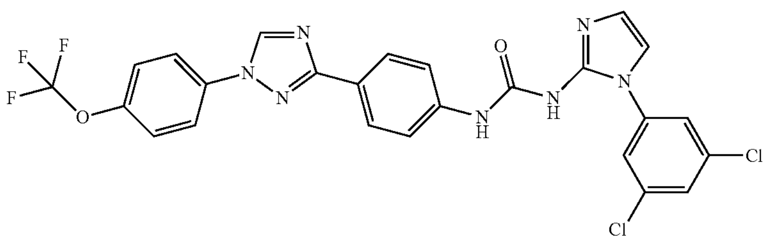 [SMILES: O=C(Nc1ccc(-c2ncn(-c3ccc(OC(F)(F)F)cc3)n2)cc1)Nc1nccn1-c1cc(Cl)cc(Cl)c1] | 15 |
| F29 | 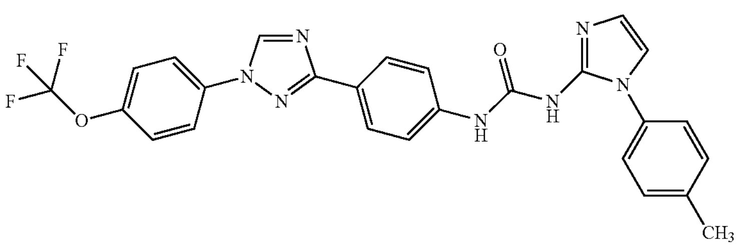 | 15 |
| F30 | 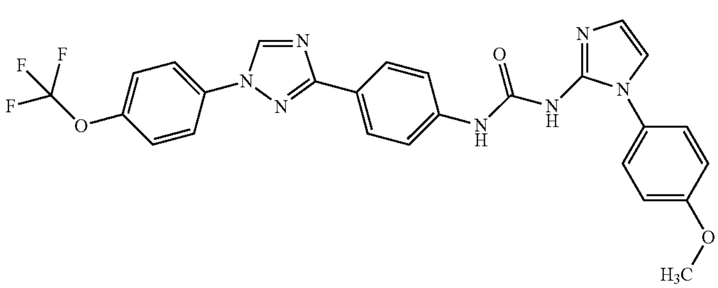 [SMILES: COc1ccc(-n2ccnc2NC(=O)Nc2ccc(-c3ncn(-c4ccc(OC(F)(F)F)cc4)n3)cc2)cc1] | 15 |
| F31 | 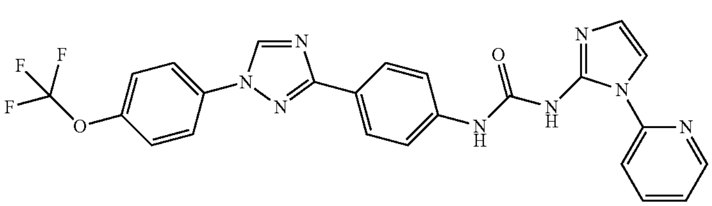 | 15 |

TABLE 2-continued

Structure and Preparation Method for F Series Molecules

| No. | Structure | Prep.* |
|---|---|---|
| F32 | 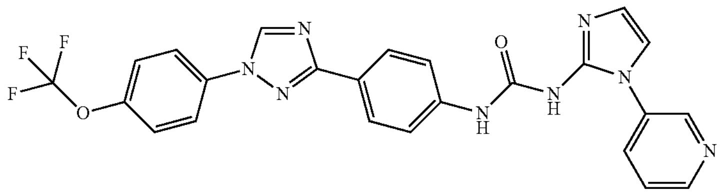 [SMILES: O=C(Nc1ccc(-c2ncn(-c3ccc(OC(F)(F)F)cc3)n2)cc1)Nc1nccn1-c1cccnc1] | 15 |
| F33 | 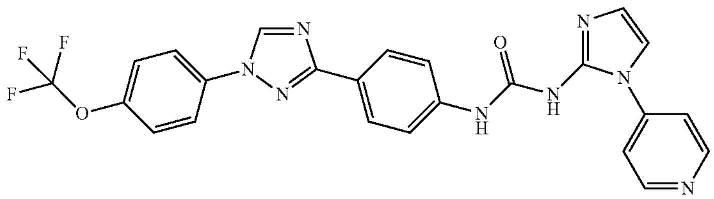 [SMILES: O=C(Nc1ccc(-c2ncn(-c3ccc(OC(F)(F)F)cc3)n2)cc1)Nc1nccn1-c1ccncc1] | 15 |
| F34 | 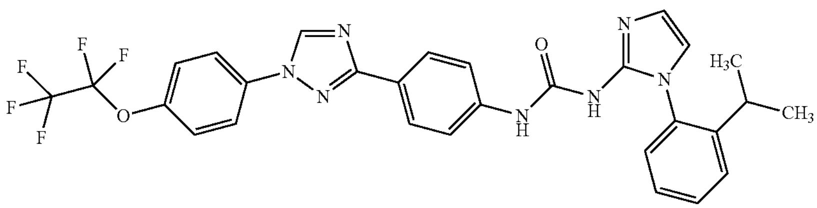 [SMILES: CC(C)c1ccccc1-n1ccnc1NC(=O)Nc1ccc(-c2ncn(-c3ccc(OC(F)(F)C(F)(F)F)cc3)n2)cc1] | 14 |
| F35 | 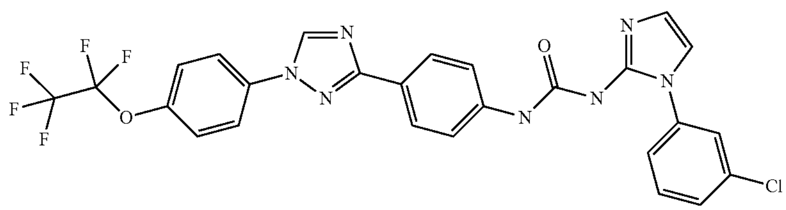 [SMILES: O=C(Nc1ccc(-c2ncn(-c3ccc(OC(F)(F)C(F)(F)F)cc3)n2)cc1)Nc1nccn1-c1cccc(Cl)c1] | 14 |
| F36 | 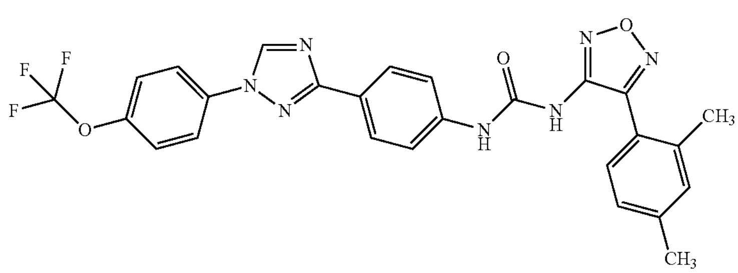 [SMILES: Cc1ccc(-c2nonc2NC(=O)Nc2ccc(-c3ncn(-c4ccc(OC(F)(F)F)cc4)n3)cc2)c(C)c1] | 1 |
| F37 | 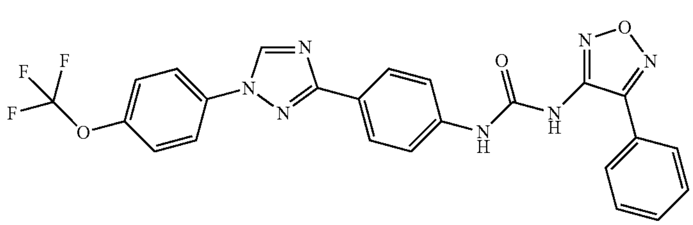 [SMILES: O=C(Nc1ccc(-c2ncn(-c3ccc(OC(F)(F)F)cc3)n2)cc1)Nc1nonc1-c1ccccc1] | 1 |
| F38 | 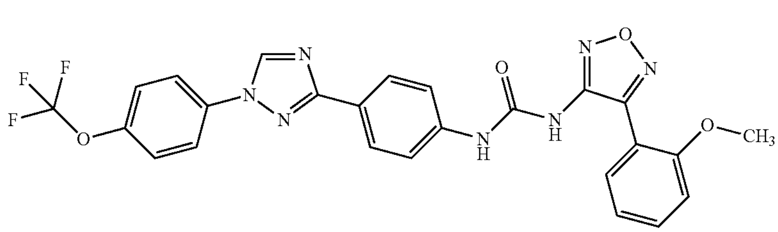 | 1 |

TABLE 2-continued

Structure and Preparation Method for F Series Molecules

| No. | Structure | Prep.* |
|---|---|---|
| F39 | 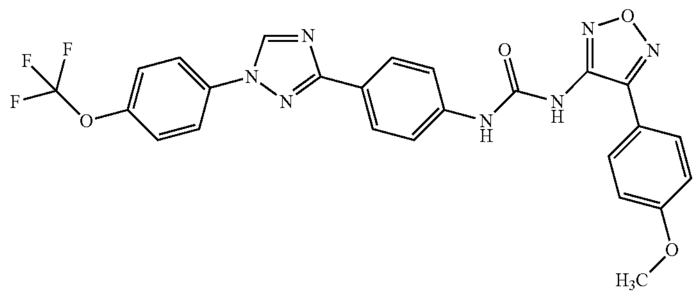 [SMILES: COc1ccc(-c2nonc2NC(=O)Nc2ccc(-c3ncn(-c4ccc(OC(F)(F)F)cc4)n3)cc2)cc1] | 1 |
| F40 | 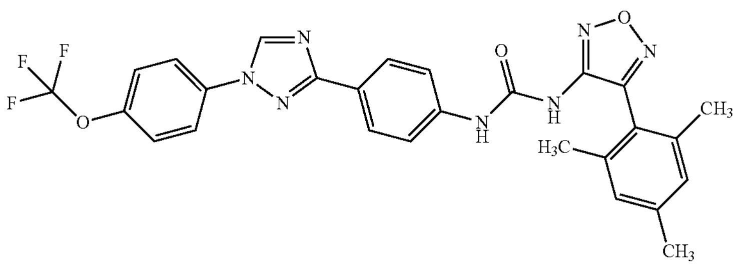 [SMILES: Cc1cc(C)c(-c2nonc2NC(=O)Nc2ccc(-c3ncn(-c4ccc(OC(F)(F)F)cc4)n3)cc2)c(C)c1] | 1 |
| F41 | 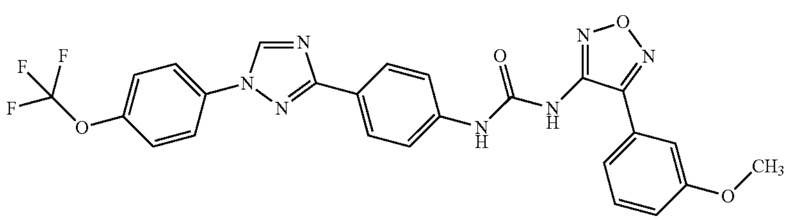 [SMILES: COc1cccc(-c2nonc2NC(=O)Nc2ccc(-c3ncn(-c4ccc(OC(F)(F)F)cc4)n3)cc2)c1] | 1 |
| F42 | 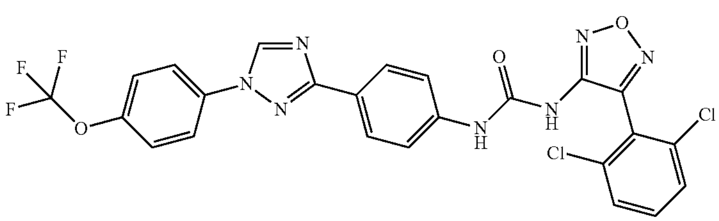 [SMILES: O=C(Nc1ccc(-c2ncn(-c3ccc(OC(F)(F)F)cc3)n2)cc1)Nc1nonc1-c1c(Cl)cccc1Cl] | 1 |
| F43 | 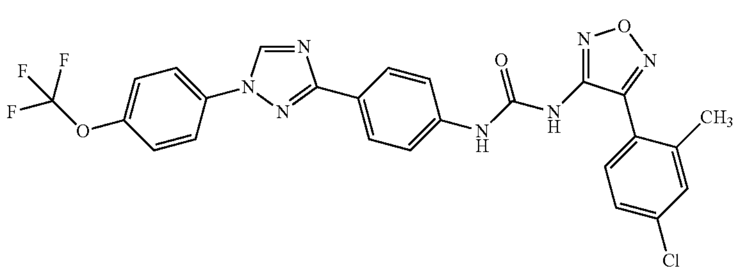 [SMILES: Cc1cc(Cl)ccc1-c1nonc1NC(=O)Nc1ccc(-c2ncn(-c3ccc(OC(F)(F)F)cc3)n2)cc1] | 1 |
| F44 | 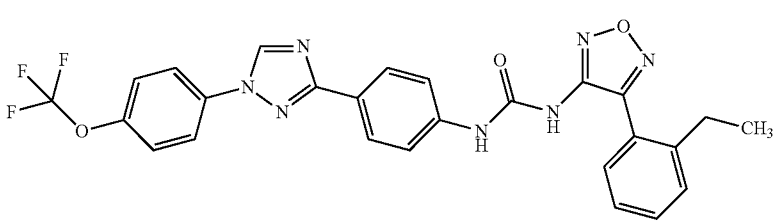 [SMILES: CCc1ccccc1-c1nonc1NC(=O)Nc1ccc(-c2ncn(-c3ccc(OC(F)(F)F)cc3)n2)cc1] | 1 |

TABLE 2-continued

Structure and Preparation Method for F Series Molecules

| No. | Structure | Prep.* |
|---|---|---|
| F45 | 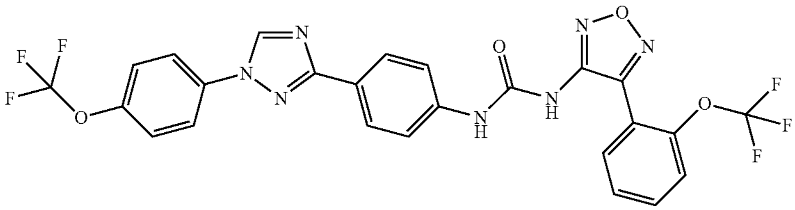 [SMILES: O=C(Nc1ccc(-c2ncn(-c3ccc(OC(F)(F)F)cc3)n2)cc1)Nc1nonc1-c1ccccc1OC(F)(F)F] | 1 |
| F46 | 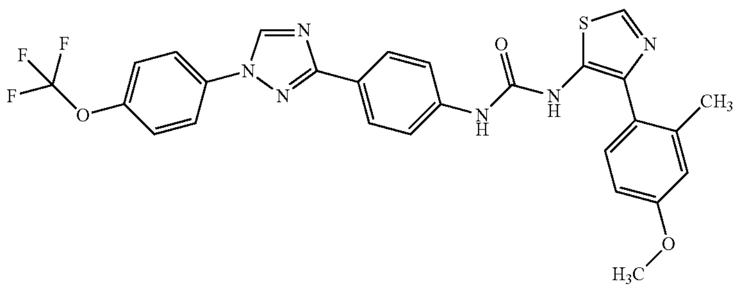 [SMILES: COc1ccc(-c2ncsc2NC(=O)Nc2ccc(-c3ncn(-c4ccc(OC(F)(F)F)cc4)n3)cc2)c(C)c1] | 19 |
| F47 | 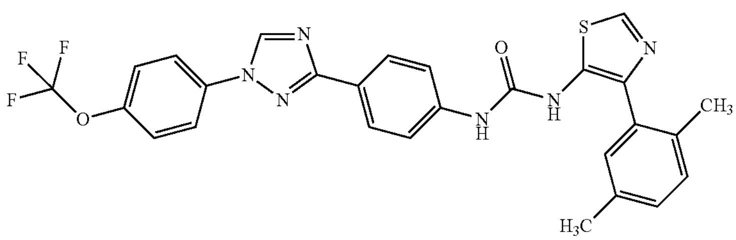 [SMILES: Cc1ccc(C)c(-c2ncsc2NC(=O)Nc2ccc(-c3ncn(-c4ccc(OC(F)(F)F)cc4)n3)cc2)c1] | 19 |
| F48 | 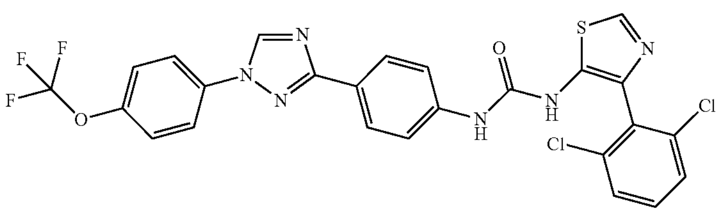 [SMILES: O=C(Nc1ccc(-c2ncn(-c3ccc(OC(F)(F)F)cc3)n2)cc1)Nc1scnc1-c1c(Cl)cccc1Cl] | 9 |
| F49 | 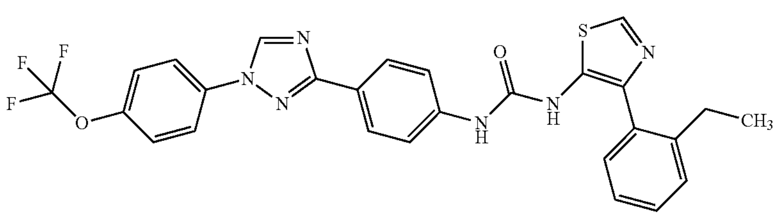 [SMILES: CCc1ccccc1-c1ncsc1NC(=O)Nc1ccc(-c2ncn(-c3ccc(OC(F)(F)F)cc3)n2)cc1] | 19 |
| F50 | 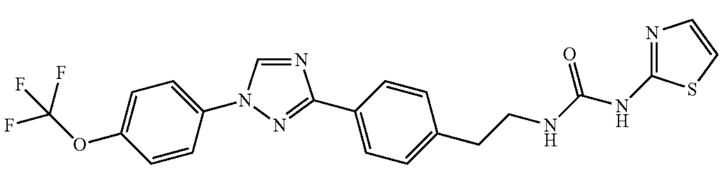 [SMILES: O=C(NCCc1ccc(-c2ncn(-c3ccc(OC(F)(F)F)cc3)n2)cc1)Nc1nccs1] | 7 |
| F51 | 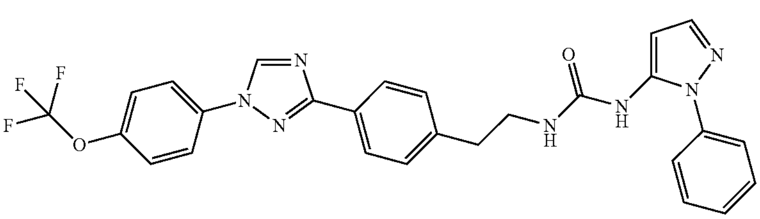 [SMILES: O=C(NCCc1ccc(-c2ncn(-c3ccc(OC(F)(F)F)cc3)n2)cc1)Nc1ccnn1-c1ccccc1] | 8 |

TABLE 2-continued

Structure and Preparation Method for F Series Molecules

| No. | Structure | Prep.* |
|-----|-----------|--------|
| F52 | 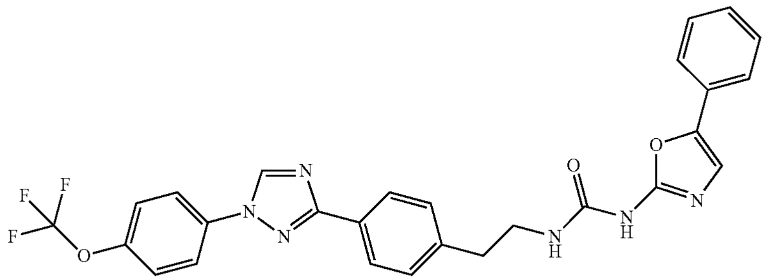 [SMILES: O=C(NCCc1ccc(-c2ncn(-c3ccc(OC(F)(F)F)cc3)n2)cc1)Nc1ncc(-c2ccccc2)o1] | 9 |
| F53 | 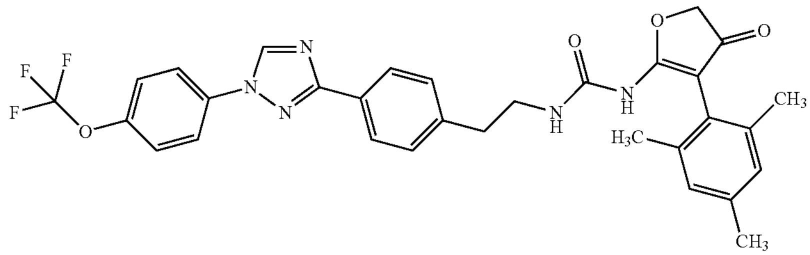 [SMILES: Cc1cc(C)c(C2=C(NC(=O)NCCc3ccc(-c4ncn(-c5ccc(OC(F)(F)F)cc5)n4)cc3)OCC2=O)c(C)c1] | 28 |
| F54 | 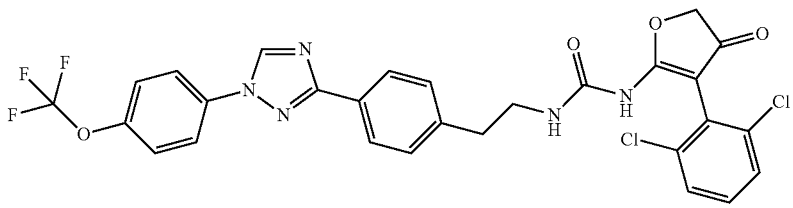 [SMILES: O=C(NCCc1ccc(-c2ncn(-c3ccc(OC(F)(F)F)cc3)n2)cc1)NC1=C(c2c(Cl)cccc2Cl)C(=O)CO1] | 28 |
| F55 | 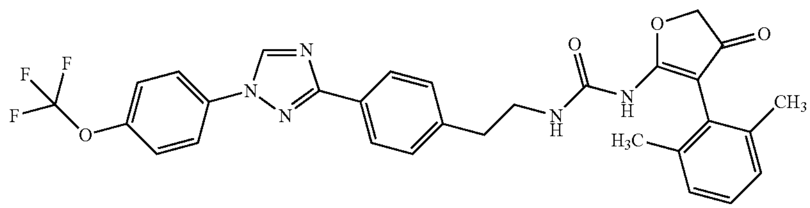 [SMILES: Cc1cccc(C)c1C1=C(NC(=O)NCCc2ccc(-c3ncn(-c4ccc(OC(F)(F)F)cc4)n3)cc2)OCC1=O] | 28 |
| F56 | 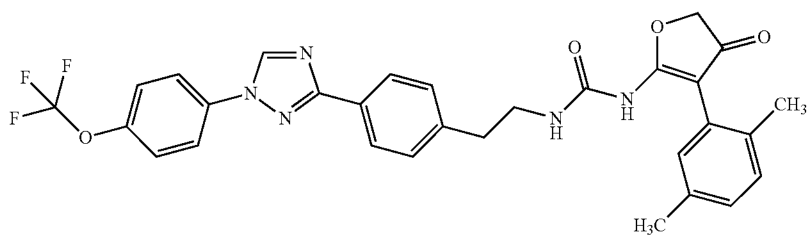 [SMILES: Cc1ccc(C)c(C2=C(NC(=O)NCCc3ccc(-c4ncn(-c5ccc(OC(F)(F)F)cc5)n4)cc3)OCC2=O)c1] | 28 |
| F57 | 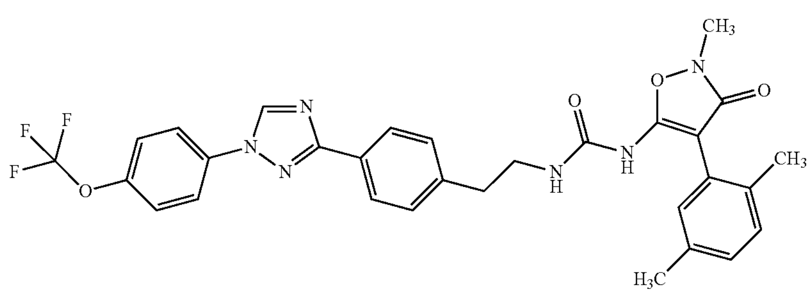 [SMILES: Cc1ccc(C)c(-c2c(NC(=O)NCCc3ccc(-c4ncn(-c5ccc(OC(F)(F)F)cc5)n4)cc3)on(C)c2=O)c1] | 28 |

TABLE 2-continued

Structure and Preparation Method for F Series Molecules

| No. | Structure | Prep.* |
|---|---|---|
| F58 | 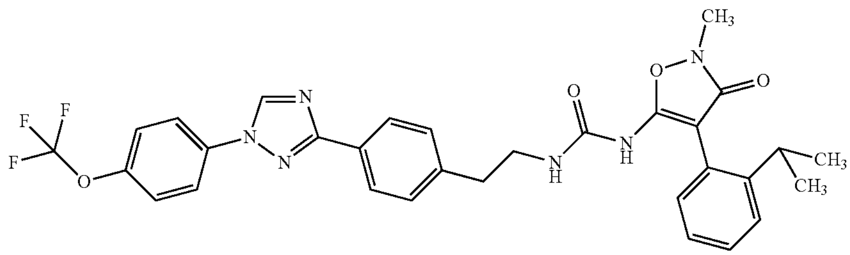 [SMILES: CC(C)c1ccccc1-c1c(NC(=O)NCCc2ccc(-c3ncn(-c4ccc(OC(F)(F)F)cc4)n3)cc2)on(C)c1=O] | 28 |
| F59 | 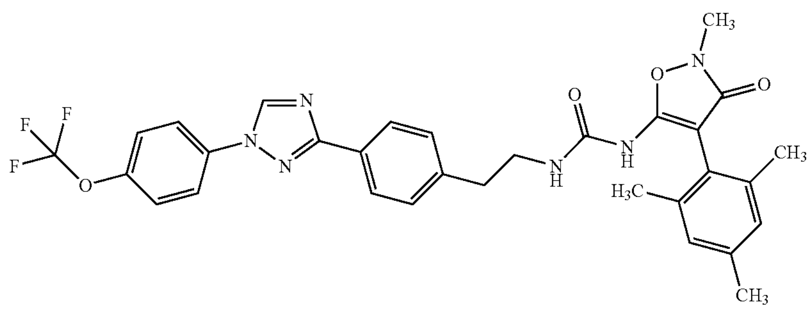 [SMILES: Cc1cc(C)c(-c2c(NC(=O)NCCc3ccc(-c4ncn(-c5ccc(OC(F)(F)F)cc5)n4)cc3)on(C)c2=O)c(C)c1] | 28 |
| F60 | 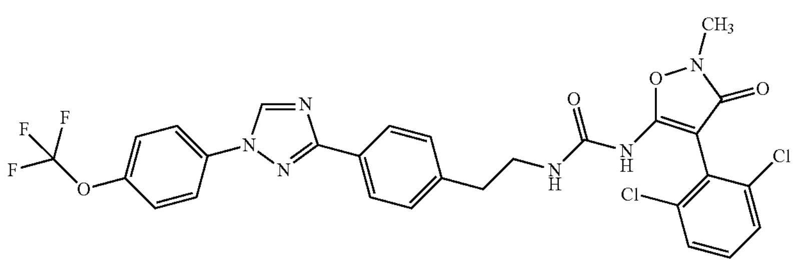 [SMILES: Cn1oc(NC(=O)NCCc2ccc(-c3ncn(-c4ccc(OC(F)(F)F)cc4)n3)cc2)c(-c2c(Cl)cccc2Cl)c1=O] | 28 |
| F61 | 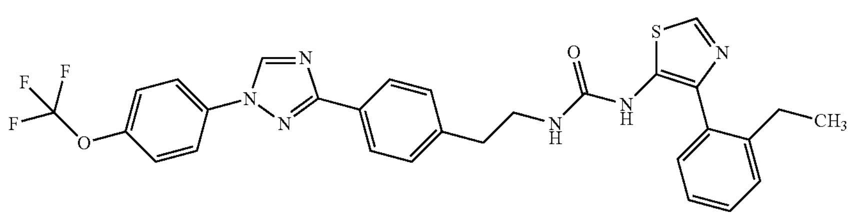 [SMILES: CCc1ccccc1-c1ncsc1NC(=O)NCCc1ccc(-c2ncn(-c3ccc(OC(F)(F)F)cc3)n2)cc1] | 20 |
| F62 | 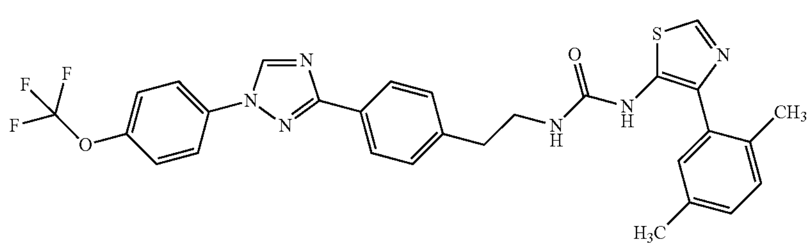 [SMILES: Cc1ccc(C)c(-c2ncsc2NC(=O)NCCc2ccc(-c3ncn(-c4ccc(OC(F)(F)F)cc4)n3)cc2)c1] | 20 |

TABLE 2-continued
Structure and Preparation Method for F Series Molecules
| No. | Structure | Prep.* |
|---|---|---|
| F63 | 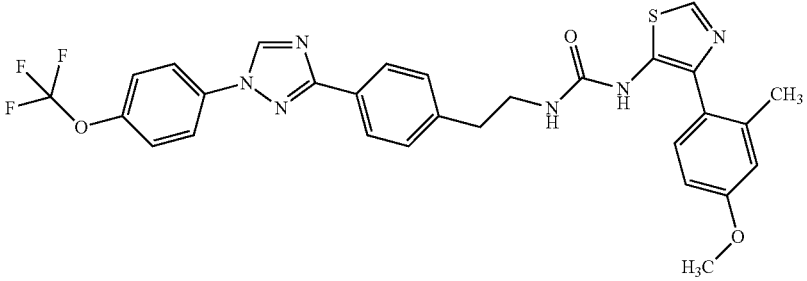 [SMILES: COc1ccc(-c2ncsc2NC(=O)NCCc2ccc(-c3ncn(-c4ccc(OC(F)(F)F)cc4)n3)cc2)c(C)c1] | 20 |
| F64 | 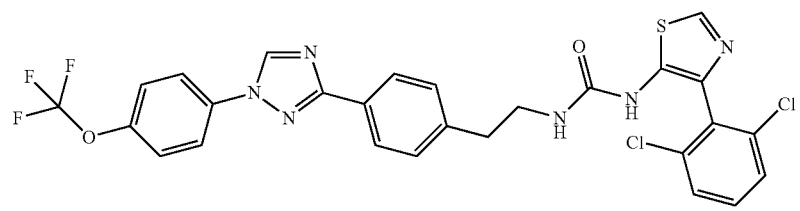 [SMILES: O=C(NCCc1ccc(-c2ncn(-c3ccc(OC(F)(F)F)cc3)n2)cc1)Nc1scnc1-c1c(Cl)cccc1Cl] | 20 |
| F65 | 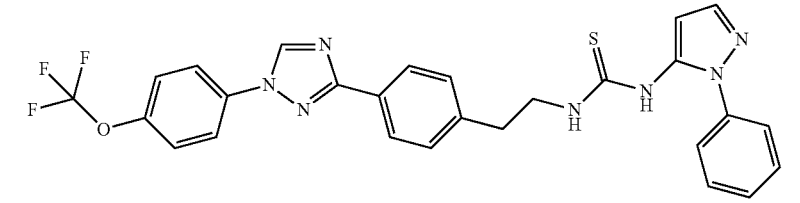 [SMILES: FC(F)(F)Oc1ccc(-n2cnc(-c3ccc(CCNC(=S)Nc4ccnn4-c4ccccc4)cc3)n2)cc1] | 41 |
*prepared according to example number
TABLE 2a
Structure and Preparation Method for Exemplified P Series Molecules
| No. | Structure | Prep.* |
|---|---|---|
| P3 | 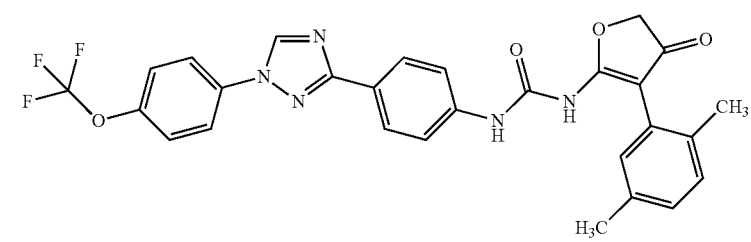 [SMILES: Cc1ccc(C)c(C2=C(NC(=O)Nc3ccc(-c4ncn(-c5ccc(OC(F)(F)F)cc5)n4)cc3)OCC2=O)c1] | 28 |
| P6 | 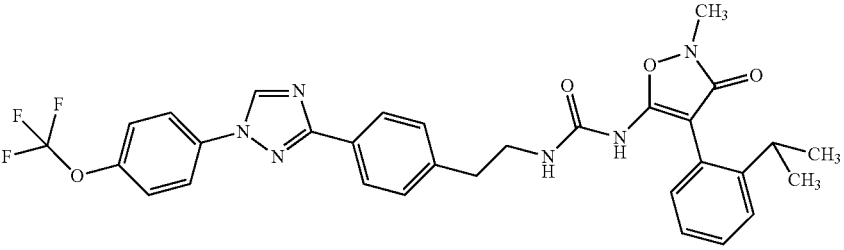 [SMILES: CC(C)c1ccccc1-c1c(NC(=O)NCCc2ccc(-c3ncn(-c4ccc(OC(F)(F)F)cc4)n3)cc2)on(C)c1=O] | 28 |

TABLE 3

Structure and Preparation Method for C Series Molecules

| No. | Structure | Prep.* |
|---|---|---|
| C1 | ethyl 5-amino-1-(4-chloro-2-methylphenyl)-1H-pyrazole-4-carboxylate | 2 |
| C2 | ethyl 5-amino-1-(2,6-dichlorophenyl)-1H-pyrazole-4-carboxylate | 2 |
| C3 | ethyl 5-amino-1-(5-fluoro-2-methylphenyl)-1H-pyrazole-4-carboxylate | 2 |
| C4 | ethyl 5-amino-1-(2-ethylphenyl)-1H-pyrazole-4-carboxylate | 2 |
| C5 | ethyl 5-amino-1-(2,5-dimethylphenyl)-1H-pyrazole-4-carboxylate | 2 |

TABLE 3-continued

Structure and Preparation Method for C Series Molecules

| No. | Structure | Prep.* |
|---|---|---|
| C6 | ethyl 5-amino-1-(2,4-dimethylphenyl)-1H-pyrazole-4-carboxylate | 2 |
| C7 | ethyl 5-amino-1-(2,4,6-trimethylphenyl)-1H-pyrazole-4-carboxylate | 2 |
| C8 | ethyl 5-amino-1-(2,5-dichlorophenyl)-1H-pyrazole-4-carboxylate | 2 |
| C9 | ethyl 5-amino-1-(2-methoxyphenyl)-1H-pyrazole-4-carboxylate | 2 |
| C10 | 5-amino-1-(4-chloro-2-methylphenyl)-1H-pyrazole | 3 |

TABLE 3-continued

Structure and Preparation Method for C Series Molecules

| No. | Structure | Prep.* |
|---|---|---|
| C11 | 5-amino-1-(2,6-dichlorophenyl)pyrazole | 3 |
| C12 | 5-amino-1-(5-fluoro-2-methylphenyl)pyrazole | 3 |
| C13 | 5-amino-1-(2-ethylphenyl)pyrazole | 3 |
| C14 | 5-amino-1-(2,5-dimethylphenyl)pyrazole | 3 |
| C15 | 5-amino-1-(2,4-dimethylphenyl)pyrazole | 3 |
| C16 | 5-amino-1-(2,4,6-trimethylphenyl)pyrazole | 3 |

TABLE 3-continued

Structure and Preparation Method for C Series Molecules

| No. | Structure | Prep.* |
|-----|-----------|--------|
| C17 | 5-amino-1-(2,5-dichlorophenyl)pyrazole | 3 |
| C18 | 5-amino-1-(2-methoxyphenyl)pyrazole | 3 |
| C19 | 4-chloro-2-methylbenzaldehyde oxime | 4 |
| C20 | 2-ethylbenzaldehyde oxime | 4 |
| C21 | 4-chloro-N-hydroxy-2-methylbenzimidoyl chloride | 5 |
| C22 | 2-ethyl-N-hydroxybenzimidoyl chloride | 5 |
| C23 | 4-(4-chloro-2-methylphenyl)-1,2,5-oxadiazol-3-amine | 6 |

TABLE 3-continued

Structure and Preparation Method for C Series Molecules

| No. | Structure | Prep.* |
|---|---|---|
| C24 | 4-amino-3-(2-ethylphenyl)-1,2,5-oxadiazole | 6 |
| C25 | 4-amino-3-(2,4-dimethylphenyl)-1,2,5-oxadiazole | 6 |
| C26 | 4-amino-3-(2,4,6-trimethylphenyl)-1,2,5-oxadiazole | 6 |
| C27 | 4-amino-3-(3-methoxyphenyl)-1,2,5-oxadiazole | 6 |
| C28 | 4-amino-3-(2,6-dichlorophenyl)-1,2,5-oxadiazole | 6 |
| C29 | 4-amino-3-(2-trifluoromethoxyphenyl)-1,2,5-oxadiazole | 6 |

TABLE 3-continued

Structure and Preparation Method for C Series Molecules

| No. | Structure | Prep.* |
|---|---|---|
| C30 | 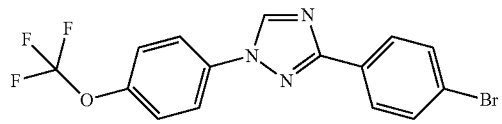 [SMILES: FC(F)(F)Oc1ccc(-n2cnc(-c3ccc(Br)cc3)n2)cc1] | 10 |
| C31 | 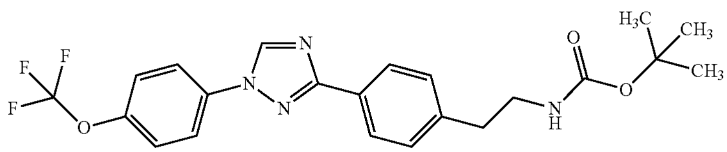 [SMILES: CC(C)(C)OC(=O)NCCc1ccc(-c2ncn(-c3ccc(OC(F)(F)F)cc3)n2)cc1] | 11 |
| C32 | 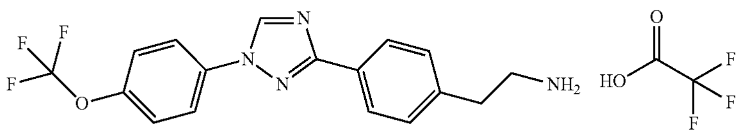 [SMILES: NCCc1ccc(-c2ncn(-c3ccc(OC(F)(F)F)cc3)n2)cc1 ; O=C(O)C(F)(F)F] | 12 |
| C33 | 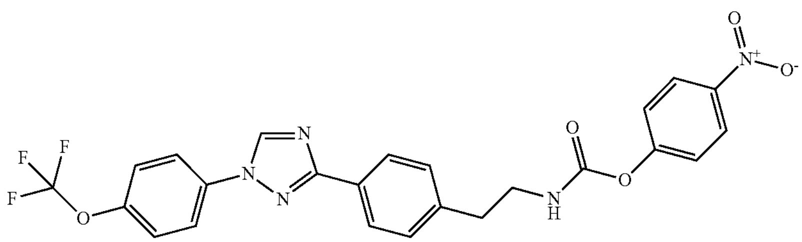 [SMILES: O=C(NCCc1ccc(-c2ncn(-c3ccc(OC(F)(F)F)cc3)n2)cc1)Oc1ccc([N+](=O)[O-])cc1] | 13 |
| C34 | 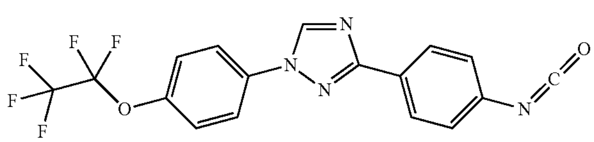 [SMILES: O=C=Nc1ccc(-c2ncn(-c3ccc(OC(F)(F)C(F)(F)F)cc3)n2)cc1] | 16 |
| C35 | 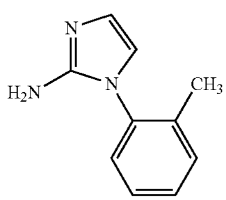 | 17 |
| C36 | 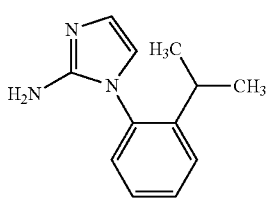 | 17 |
| C37 | 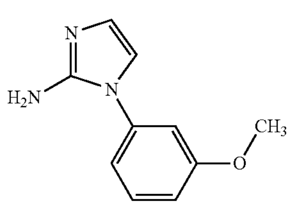 | 17 |

TABLE 3-continued
Structure and Preparation Method for C Series Molecules
| No. | Structure | Prep.* |
|---|---|---|
| C38 | 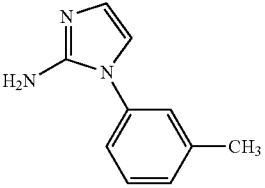 | 17 |
| C39 | 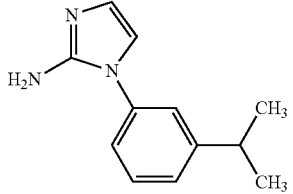 | 17 |
| C40 | 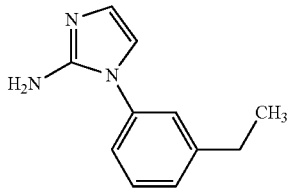 | 17 |
| C41 | 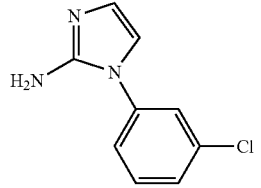 [SMILES: Nc1nccn1-c1cccc(Cl)c1] | 17 |
| C42 | 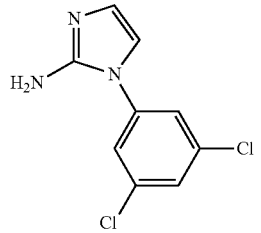 [SMILES: Nc1nccn1-c1cc(Cl)cc(Cl)c1] | 17 |
| C43 | 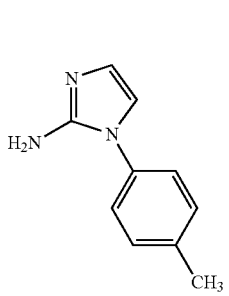 | 17 |

TABLE 3-continued

Structure and Preparation Method for C Series Molecules

| No. | Structure | Prep.* |
|---|---|---|
| C44 | 2-amino-1-(4-methoxyphenyl)imidazole | 17 |
| C45 | 2-amino-1-(pyridin-2-yl)imidazole | 18 |
| C46 | 2-amino-1-(pyridin-3-yl)imidazole | 18 |
| C47 | 2-amino-1-(pyridin-4-yl)imidazole | 18 |
| C48 | ethyl 3-(4-methoxy-2-methylphenyl)-3-oxopropanoate | 21 |
| C49 | ethyl 3-(2,5-dimethylphenyl)-3-oxopropanoate | 21 |
| C50 | ethyl 3-(2,6-dichlorophenyl)-3-oxopropanoate | 21 |

TABLE 3-continued

Structure and Preparation Method for C Series Molecules

| No. | Structure | Prep.* |
|---|---|---|
| C51 | 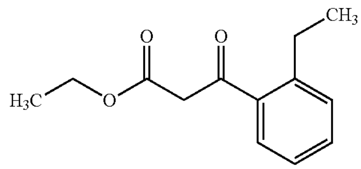 [SMILES: CCOC(=O)CC(=O)c1ccccc1CC] | 21 |
| C52 | 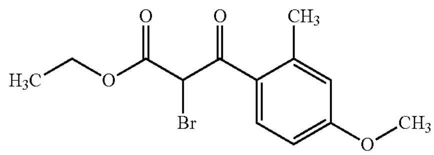 [SMILES: CCOC(=O)C(Br)C(=O)c1ccc(OC)cc1C] | 22 |
| C53 | 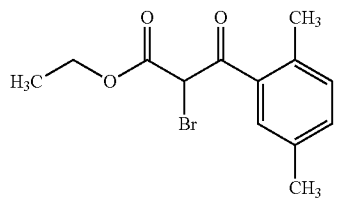 [SMILES: CCOC(=O)C(Br)C(=O)c1cc(C)ccc1C] | 22 |
| C54 | 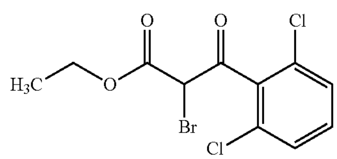 [SMILES: CCOC(=O)C(Br)C(=O)c1c(Cl)cccc1Cl] | 22 |
| C55 | 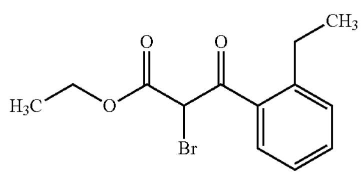 [SMILES: CCOC(=O)C(Br)C(=O)c1ccccc1CC] | 22 |
| C56 | 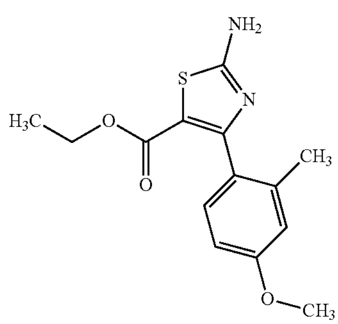 [SMILES: CCOC(=O)c1sc(N)nc1-c1ccc(OC)cc1C] | 23 |
| C57 | 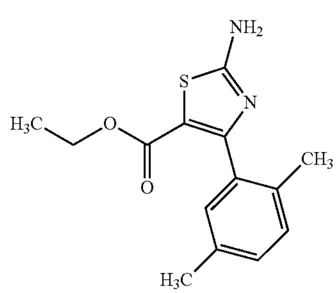 [SMILES: CCOC(=O)c1sc(N)nc1-c1cc(C)ccc1C] | 23 |

тАбTABLE 3-continued

Structure and Preparation Method for C Series Molecules

| No. | Structure | Prep.* |
|---|---|---|
| C58 | 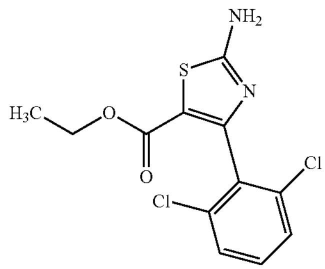 [SMILES: CCOC(=O)c1sc(N)nc1-c1c(Cl)cccc1Cl] | 23 |
| C59 | 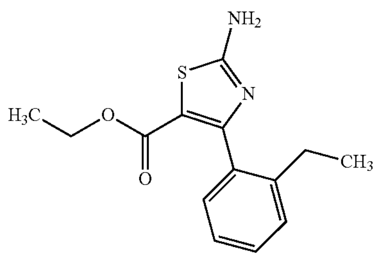 [SMILES: CCOC(=O)c1sc(N)nc1-c1ccccc1CC] | 23 |
| C60 | 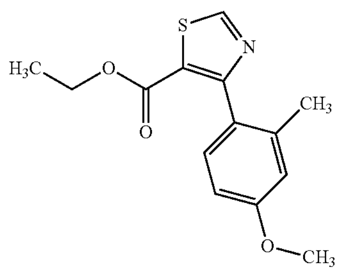 [SMILES: CCOC(=O)c1scnc1-c1ccc(OC)cc1C] | 24 |
| C61 | 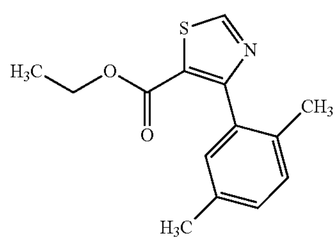 [SMILES: CCOC(=O)c1scnc1-c1cc(C)ccc1C] | 24 |
| C62 | 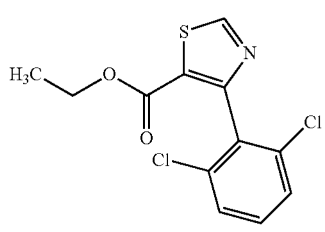 [SMILES: CCOC(=O)c1scnc1-c1c(Cl)cccc1Cl] | 24 |
| C63 | 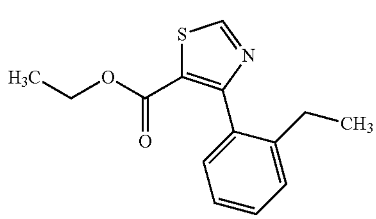 [SMILES: CCOC(=O)c1scnc1-c1ccccc1CC] | 24 |

TABLE 3-continued

Structure and Preparation Method for C Series Molecules

| No. | Structure | Prep. * |
|---|---|---|
| C64 | 4-(4-methoxy-2-methylphenyl)thiazole-5-carboxylic acid | 25 |
| C65 | 4-(2,5-dimethylphenyl)thiazole-5-carboxylic acid | 25 |
| C66 | 4-(2,6-dichlorophenyl)thiazole-5-carboxylic acid | 25 |
| C67 | 4-(2-ethylphenyl)thiazole-5-carboxylic acid | 25 |
| C68 | 4-(2-ethylphenyl)thiazole-5-carbonyl azide | 26 |
| C69 | 4-(2,5-dimethylphenyl)thiazole-5-carbonyl azide | 26 |

TABLE 3-continued

Structure and Preparation Method for C Series Molecules

| No. | Structure | Prep.* |
|---|---|---|
| C70 | 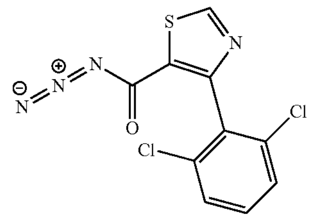 [SMILES: [N-]=[N+]=NC(=O)c1scnc1-c1c(Cl)cccc1Cl] | 26 |
| C71 | 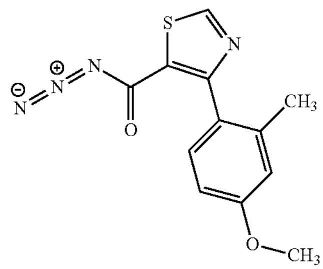 [SMILES: COc1ccc(-c2ncsc2C(=O)N=[N+]=[N-])c(C)c1] | 26 |
| C72 | 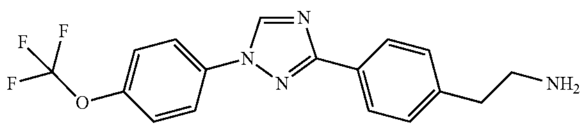 [SMILES: NCCc1ccc(-c2ncn(-c3ccc(OC(F)(F)F)cc3)n2)cc1] | 27 |
| C73 | 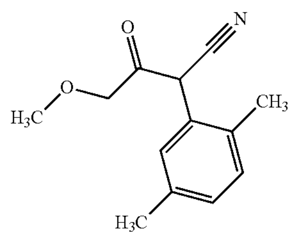 | 29 |
| C74 | 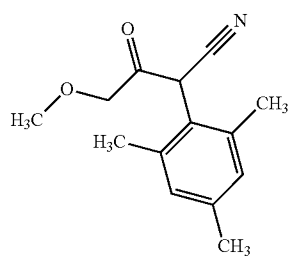 | 29 |
| C75 | 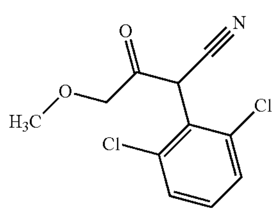 [SMILES: COCC(=O)C(C#N)c1c(Cl)cccc1Cl] | 29 |
| C76 | 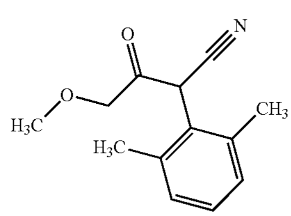 | 29 |

TABLE 3-continued

Structure and Preparation Method for C Series Molecules

| No. | Structure | Prep. * |
|---|---|---|
| C77 | (2,6-dimethylphenyl)acetonitrile structure | 30 |
| C78 | 2-amino-3-(2,5-dimethylphenyl)furan-4(5H)-one | 31 |
| C79 | 2-amino-3-(2,4,6-trimethylphenyl)furan-4(5H)-one | 31 |
| C80 | 2-amino-3-(2,6-dichlorophenyl)furan-4(5H)-one | 31 |
| C81 | 2-amino-3-(2,6-dimethylphenyl)furan-4(5H)-one | 31 |
| C82 | ethyl 2-cyano-2-(2-isopropylphenyl)acetate | 32 |

TABLE 3-continued

Structure and Preparation Method for C Series Molecules

| No. | Structure | Prep.* |
|---|---|---|
| C83 | 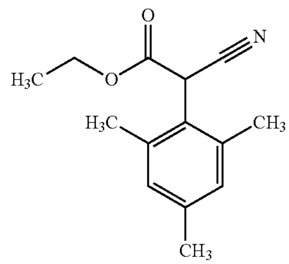 [SMILES: CCOC(=O)C(C#N)c1c(C)cc(C)cc1C] | 32 |
| C84 | 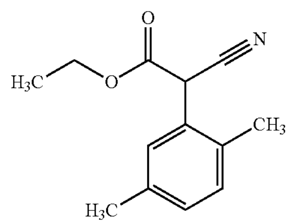 [SMILES: CCOC(=O)C(C#N)c1cc(C)ccc1C] | 32 |
| C85 | 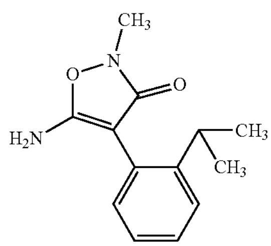 [SMILES: CC(C)c1ccccc1-c1c(N)on(C)c1=O] | 33 |
| C86 | 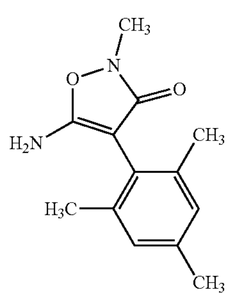 [SMILES: Cc1cc(C)c(-c2c(N)on(C)c2=O)c(C)c1] | 33 |
| C87 | 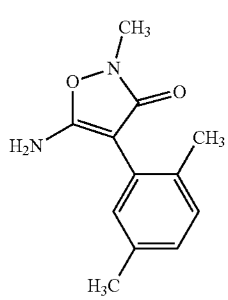 [SMILES: Cc1ccc(C)c(-c2c(N)on(C)c2=O)c1] | 33 |

TABLE 3-continued

Structure and Preparation Method for C Series Molecules

| No. | Structure | Prep.* |
|---|---|---|
| C88 | [structure: 2-(2,6-dichlorophenyl)-3-(dimethylamino)acrylonitrile] | 34 |
| C89 | [structure: 5-amino-4-(2,6-dichlorophenyl)isoxazole] | 35 |
| C90 | [structure: 1-(4-trifluoromethoxyphenyl)-3-[4-(2-isocyanatoethyl)phenyl]-1,2,4-triazole] | 36 |
| C91 | [structure: 3-{4-[1-(4-trifluoromethoxyphenyl)-1,2,4-triazol-3-yl]phenyl}propanoic acid] | 37 |
| C92 | [structure: ethyl 3-{4-[1-(4-trifluoromethoxyphenyl)-1,2,4-triazol-3-yl]phenyl}propanoate] | 38 |
| C93 | [structure: ethyl (E)-3-{4-[1-(4-trifluoromethoxyphenyl)-1,2,4-triazol-3-yl]phenyl}acrylate] | 39 |
| C94 | [structure: 1-(4-trifluoromethoxyphenyl)-3-[4-(2-isothiocyanatoethyl)phenyl]-1,2,4-triazole] | 40 |

*prepared according to example number

| BAW, CEW, & CL Rating Table | | GPA & YFM Rating Table | |
|---|---|---|---|
| % Control (or Mortality) | Rating | % Control (or Mortality) | Rating |
| 50-100 | A | 80-100 | A |
| More than 0-Less than 50 | B | More than 0-Less than 80 | B |
| Not Tested | C | Not Tested | C |
| No activity noticed in this bioassay | D | No activity noticed in this bioassay | D |

TABLE ABC

Biological Results

| No. | Insect species | | | | |
|-----|-----|-----|-----|-----|-----|
|     | BAW | CL  | CEW | GPA | YFM |
| F1  | D | D | C | C | D |
| F2  | D | D | C | C | D |
| F3  | A | A | C | D | A |
| F4  | A | A | C | B | A |
| F5  | A | A | C | D | A |
| F6  | A | A | C | D | A |
| F7  | A | A | C | B | A |
| F8  | D | A | C | C | D |
| F9  | A | A | C | B | A |
| F10 | A | A | C | C | D |
| F11 | A | A | C | D | A |
| F12 | A | A | C | B | A |
| F13 | A | A | C | D | A |
| F14 | A | A | C | B | A |
| F15 | A | A | C | B | A |
| F16 | A | A | C | D | A |
| F17 | A | A | C | B | A |
| F18 | A | A | C | B | A |
| F19 | A | A | C | B | A |
| F20 | A | A | A | C | C |
| F21 | A | A | A | C | C |
| F22 | A | A | A | C | C |
| F23 | A | A | A | C | C |
| F24 | A | A | A | C | C |
| F25 | A | A | A | C | C |
| F26 | A | A | A | C | C |
| F27 | A | A | A | C | C |
| F28 | A | D | C | C | C |
| F29 | A | A | A | C | C |
| F30 | A | A | A | C | C |
| F31 | A | A | A | C | C |
| F32 | A | B | C | C | C |
| F33 | A | A | A | C | C |
| F34 | A | A | A | C | D |
| F35 | A | A | A | C | D |
| F36 | A | A | A | C | A |
| F37 | A | A | A | C | A |
| F38 | A | A | A | C | A |
| F39 | B | A | A | C | D |
| F40 | A | A | A | C | B |
| F41 | A | A | A | C | B |
| F42 | A | A | A | C | D |
| F43 | A | A | A | C | A |
| F44 | A | A | A | C | D |
| F45 | A | A | A | C | A |
| F46 | A | A | C | C | A |
| F47 | A | A | C | C | A |
| F48 | C | C | C | C | A |
| F49 | A | A | C | C | C |
| F50 | D | D | C | C | D |
| F51 | D | D | C | C | C |
| F52 | A | A | D | C | C |
| F53 | B | A | C | C | A |
| F54 | D | D | C | C | A |
| F55 | A | D | C | C | A |
| F56 | A | A | C | C | A |
| F57 | A | A | C | C | A |
| F58 | A | A | C | C | A |
| F59 | A | A | C | C | A |
| F60 | A | A | C | C | A |
| F61 | D | A | C | C | A |
| F62 | D | A | C | C | A |
| F63 | D | A | C | C | A |
| F64 | D | A | C | C | A |
| F65 | A | A | A | C | A |
| P3  | A | A | C | C | C |
| P6  | A | A | C | C | C |

The invention claimed is:

1. A molecule having the following formula

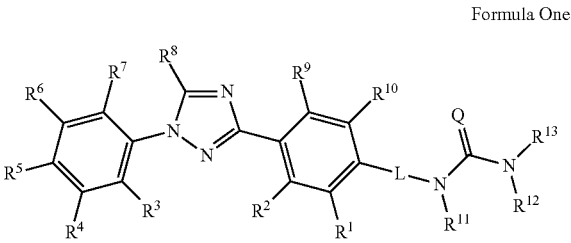

Formula One wherein:
(A) $R^1$, $R^2$, $R^3$, $R^4$, $R^5$, $R^6$, $R^7$, $R^9$, and $R^{10}$ are each independently selected from the group consisting of H, F, Cl, Br, I, CN, $NO_2$, OH, $(C_1-C_4)$alkyl, $(C_2-C_4)$alkenyl, $(C_1-C_4)$haloalkyl, $(C_1-C_4)$alkoxy, $(C_1-C_4)$haloalkoxy, and $(C_3-C_6)$cycloalkyl,
wherein each alkyl, alkenyl, haloalkyl, alkoxy, haloalkoxy, and cycloalkyl, are optionally substituted with one or more substituents independently selected from the group consisting of F, Cl, Br, I, CN, $NO_2$, OH, $(C_1-C_4)$alkyl, $(C_2-C_4)$alkenyl, $(C_1-C_4)$haloalkyl, $(C_1-C_4)$alkoxy, $(C_1-C_4)$haloalkoxy, and $(C_3-C_6)$cycloalkyl
(B) $R^8$ is H;
(C) L is selected from the group consisting of
(1) a bond connecting nitrogen to carbon in the ring, and
(2) a $(C_1-C_4)$alkyl wherein said alkyl is optionally substituted with one or more substituents independently selected from the group consisting of F, Cl, CN, OH, and oxo;
(D) $R^{11}$ and $R^{12}$ are each independently selected from the group consisting of H, $(C_1-C_4)$alkyl, $(C_2-C_4)$alkenyl, $(C_2-C_4)$alkenyloxy, $(C_2-C_4)$alkynyl, $(C_2-C_4)$alkynyloxy, $(C_1-C_4)$haloalkyl, $(C_1-C_4)$alkoxy, $(C_1-C_4)$haloalkoxy, $(C_3-C_6)$cycloalkyl, $(C_3-C_6)$cycloalkoxy, $(C_3-C_6)$cycloalkenyl, $(C_3-C_6)$cycloalkenyloxy, $((C_1-C_4)$alkyl$)((C_3-C_6)$cycloalkyl$)$, $C(O)((C_1-C_4)$alkyl$)$, $((C_1-C_4)$alkyl$)C(O)((C_1-C_4)$alkyl$)$, and $((C_1-C_4)$alkyl$)C(O)O((C_1-C_4)$alkyl$)$,
wherein each alkyl, alkenyl, alkenyloxy, alkynyl, alkynyloxy, haloalkyl, alkoxy, haloalkoxy, cycloalkyl, cycloalkoxy, cycloalkenyl, and cycloalkenyloxy, are optionally substituted with one or more substituents independently selected from the group consisting of F, Cl, Br, I, CN, $NO_2$, OH, and oxo;
(E) $R^{13}$ is heterocyclyl, wherein said heterocyclyl is selected from the group consisting of dihydrofuranyl, furanyl, indazolyl, indolyl, imidazolyl, isoindolyl, isothiazolyl, isoxazolyl, oxadiazolyl, oxazolyl, pyrazolinyl, pyrazolyl, pyrrolyl, tetrazolyl, thiazolyl, thienyl, triazinyl, and triazolyl,
wherein each heterocyclyl is optionally substituted with one or more substituents independently selected from the group consisting of oxo, $(C_1-C_8)$alkyl, $C(O)O(C_1-C_4)$alkyl, phenyl, and pyridyl,
wherein each phenyl is optionally substituted with one or more substituents R, independently selected from the group consisting of F, Cl, Br, I, $(C_1-C_4)$alkyl, $(C_1-C_4)$alkoxy, and $(C_1-C_4)$haloalkoxy; and
(F) Q is selected from the group consisting of O and S; and
agriculturally acceptable acid addition salts, salt derivatives, solvates, ester derivatives, crystal polymorphs, isotopes, resolved stereoisomers, and tautomers, of the molecules of Formula One.

2. A molecule according to claim 1 wherein
(A) $R^1$, $R^2$, $R^3$, $R^4$, $R^5$, $R^6$, $R^7$, $R^9$, and $R^{10}$ are H;
(B) $R^8$ is H;
(C) L is selected from the group consisting of
 (1) a bond connecting nitrogen to carbon in the ring, and
 (2) a $(C_1-C_4)$alkyl;
(D) $R^{11}$ and $R^{12}$ are H;
(E) $R^{13}$ is heterocyclyl, wherein said heterocyclyl is selected from the group consisting of dihydrofuranyl, imidazolyl, isoxazolyl, oxadiazolyl, oxazolyl, pyrazolyl, thiazolyl, and thienyl, wherein each heterocyclyl is optionally substituted with one or more substituents independently selected from the group consisting of oxo, $(C_1-C_8)$alkyl, $C(O)O(C_1-C_4)$alkyl, phenyl, and pyridyl, wherein each phenyl is optionally substituted with one or more substituents R, independently selected from the group consisting of F, Cl, $(C_1-C_4)$alkyl, $(C_1-C_4)$alkoxy, and $(C_1-C_4)$haloalkoxy; and (F) Q is selected from O and S.

3. A molecule according to claim 1 wherein said molecule is selected from the group consisting of

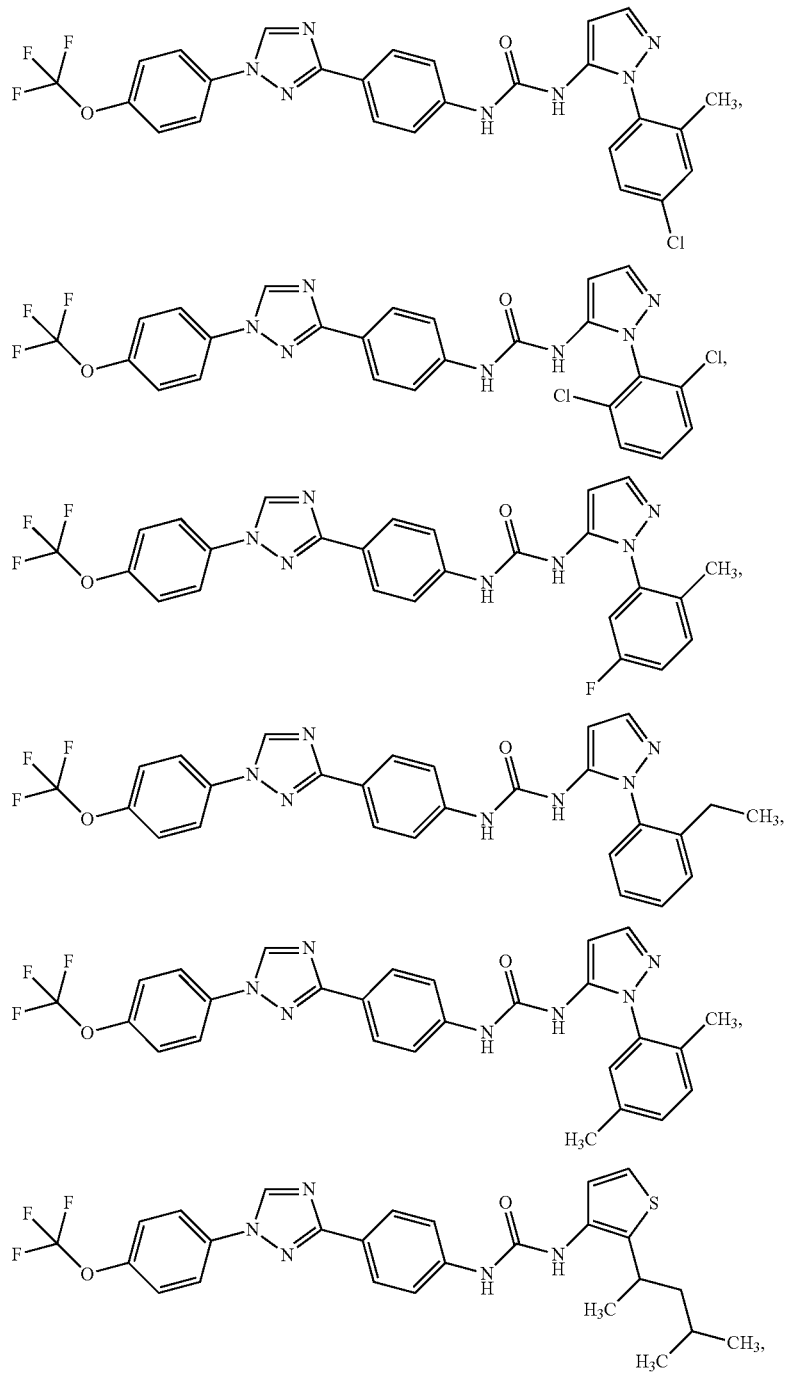

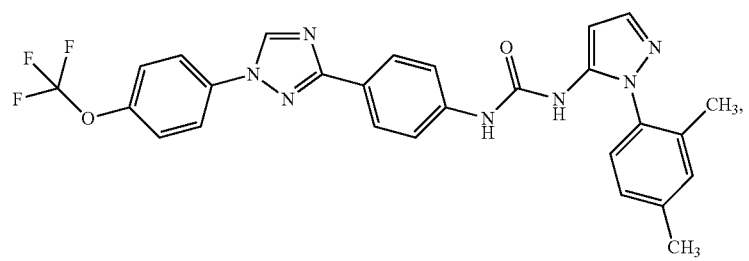
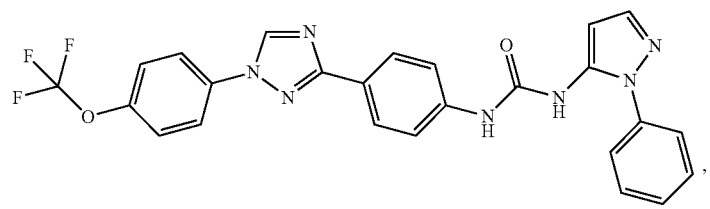
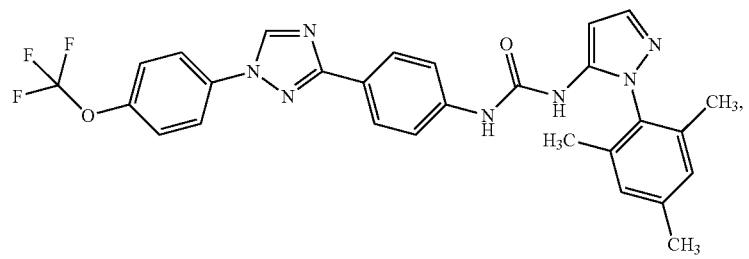
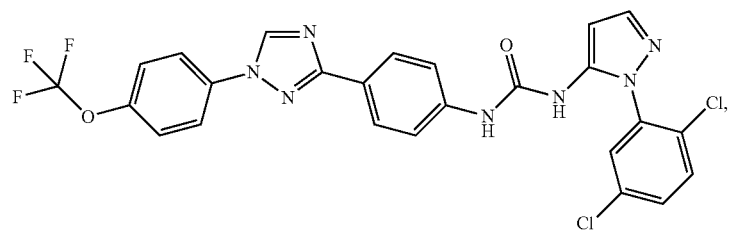
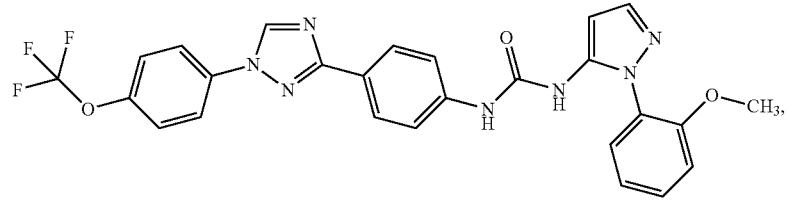
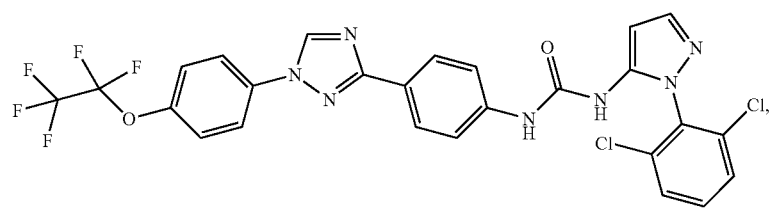
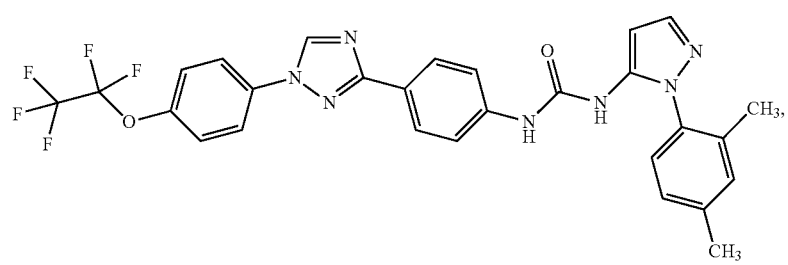

-continued
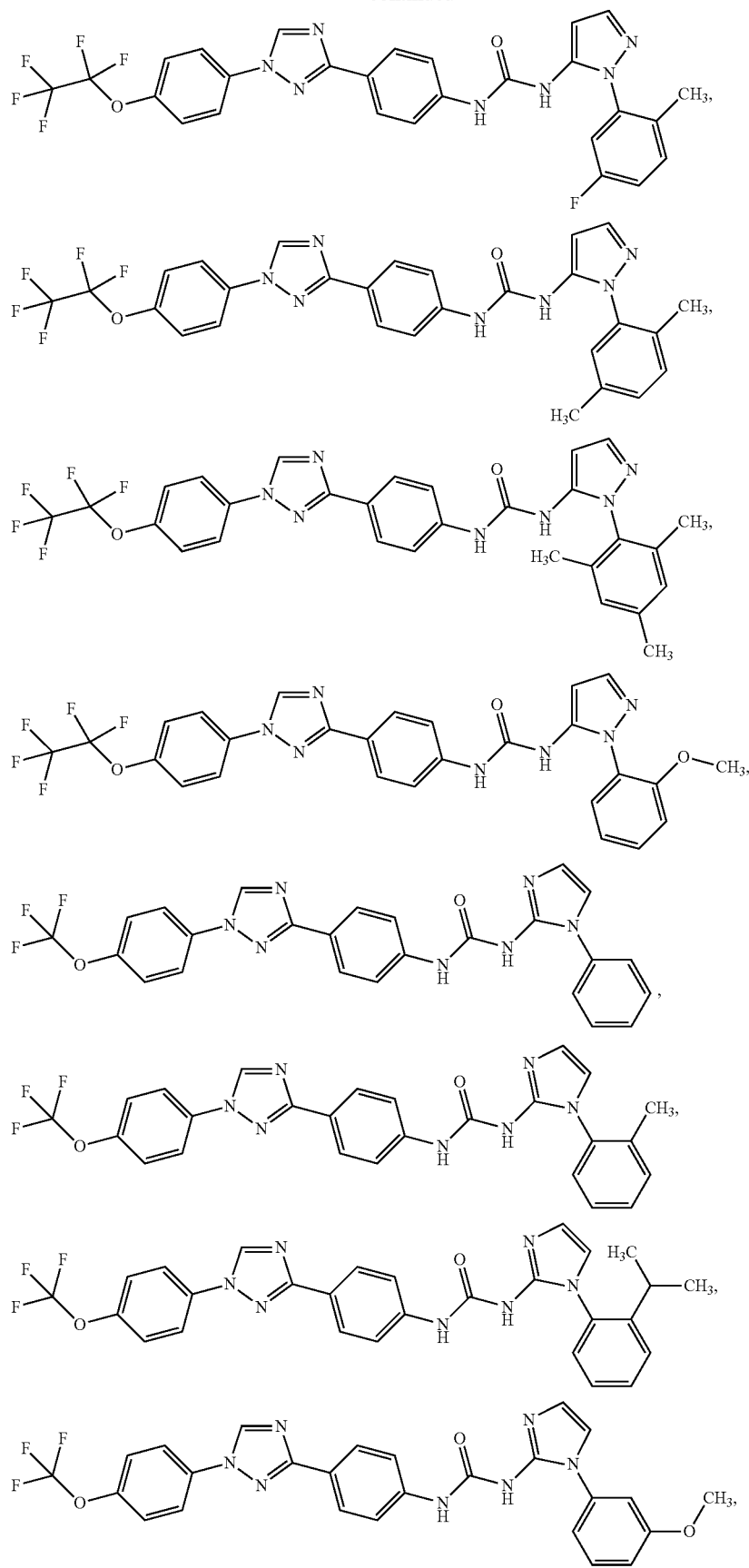

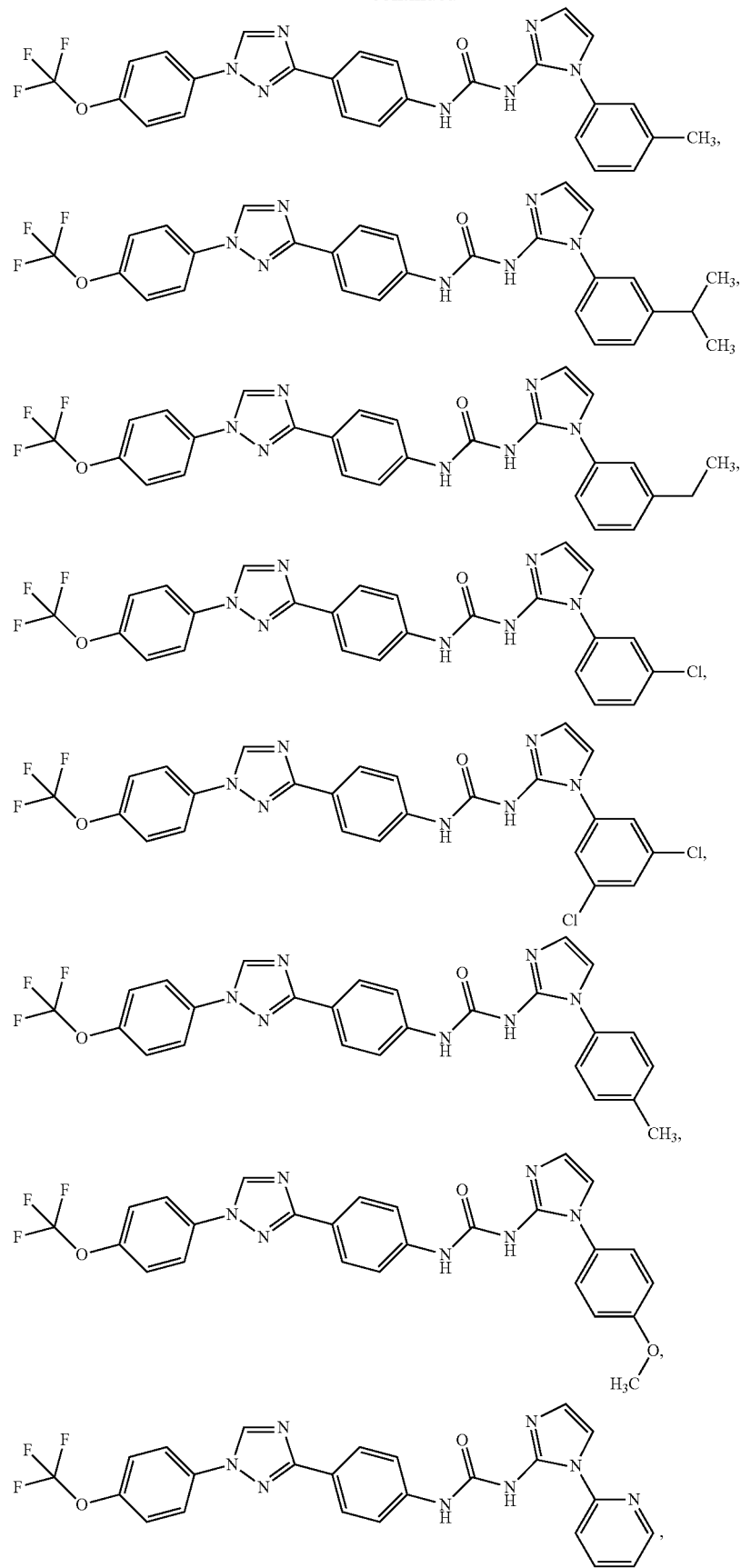

-continued
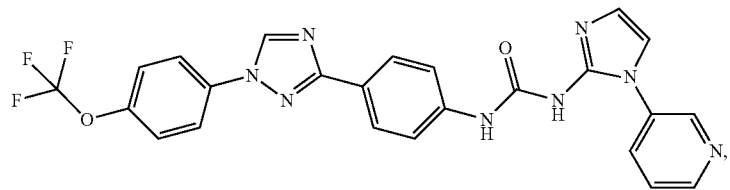
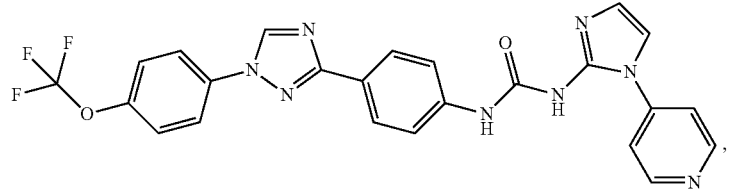
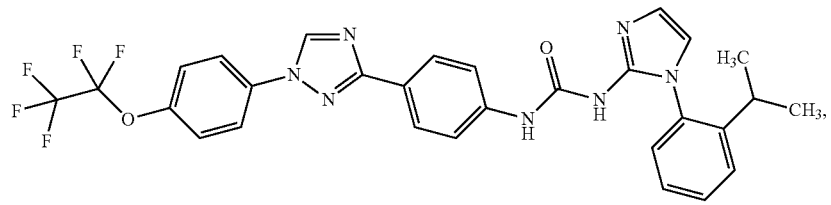
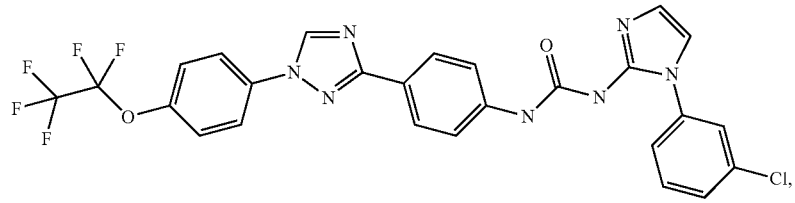
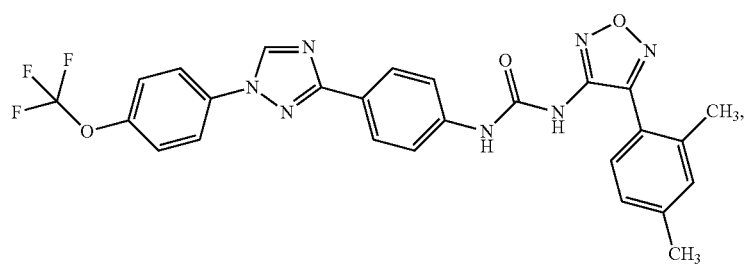
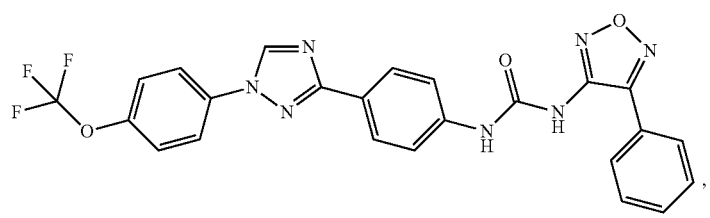
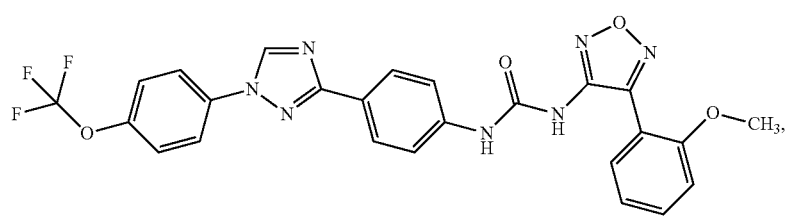

-continued
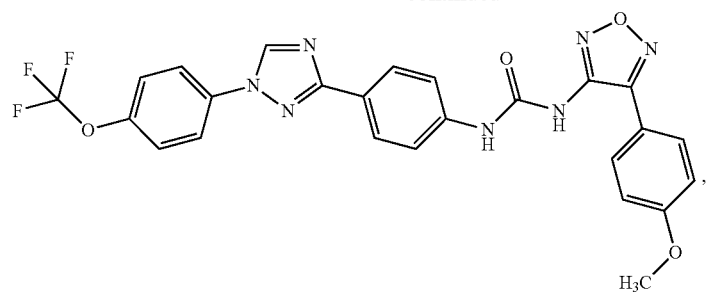
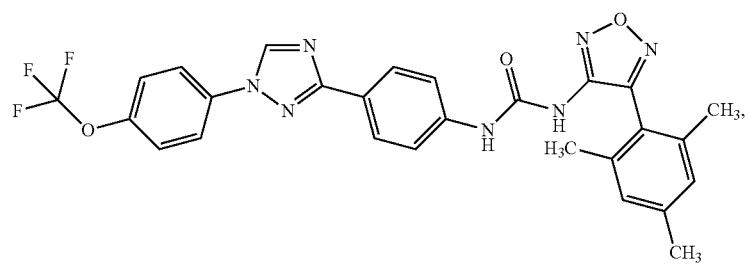
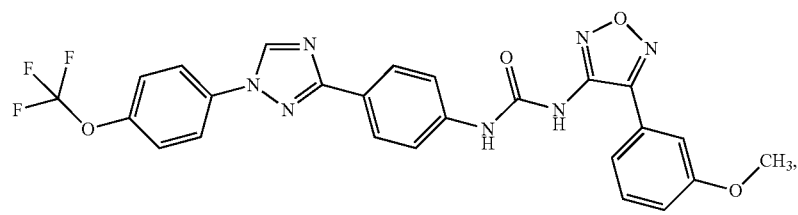
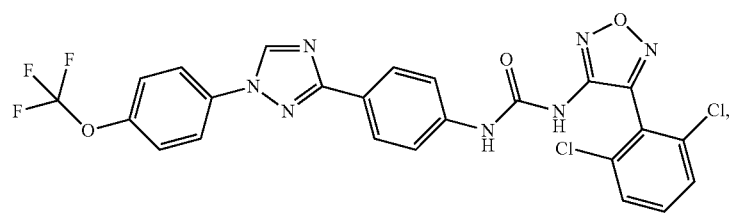
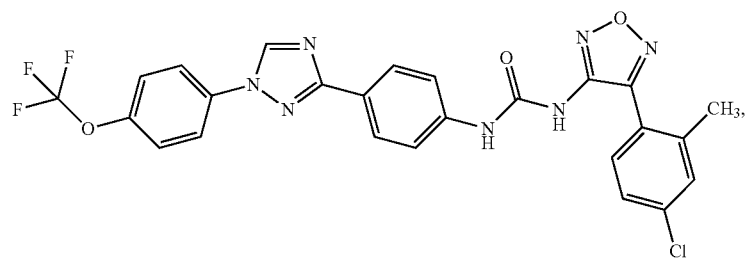
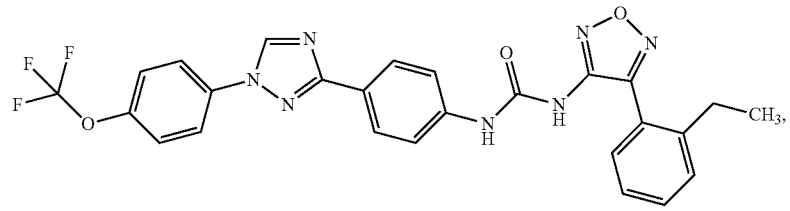
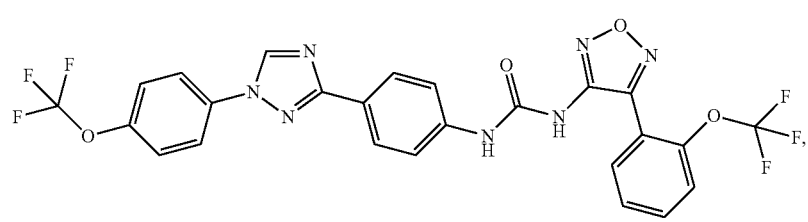

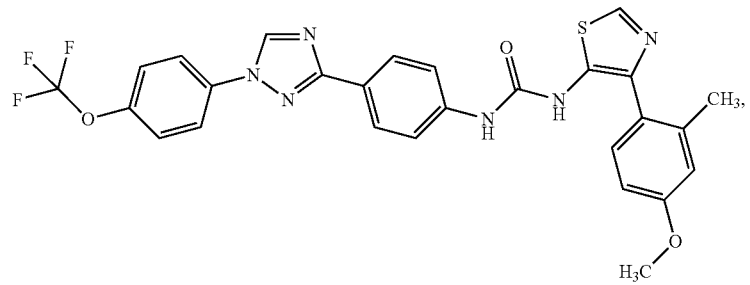
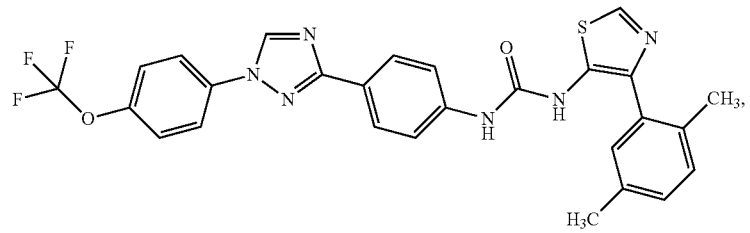
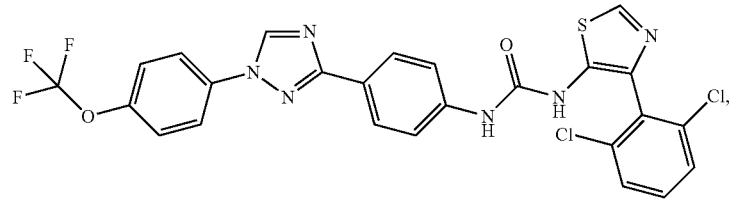
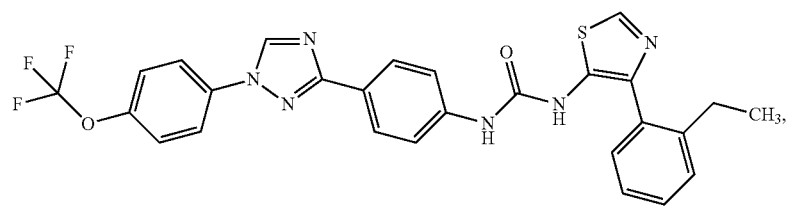
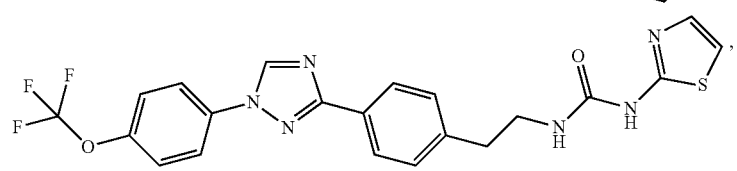
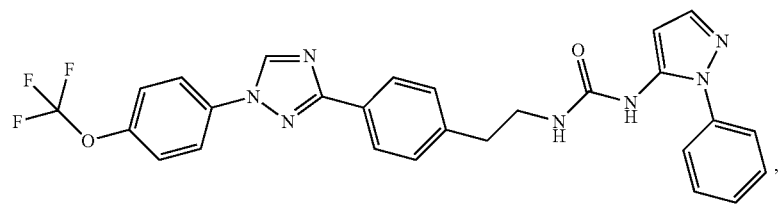
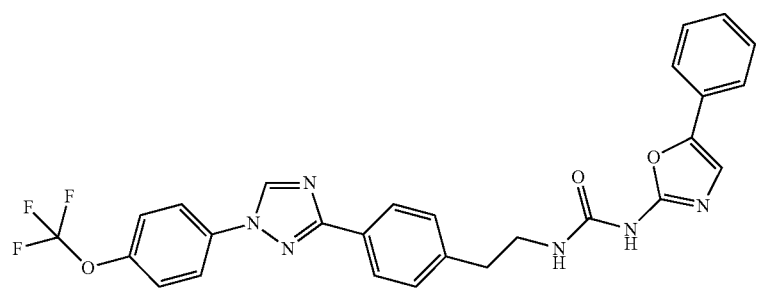

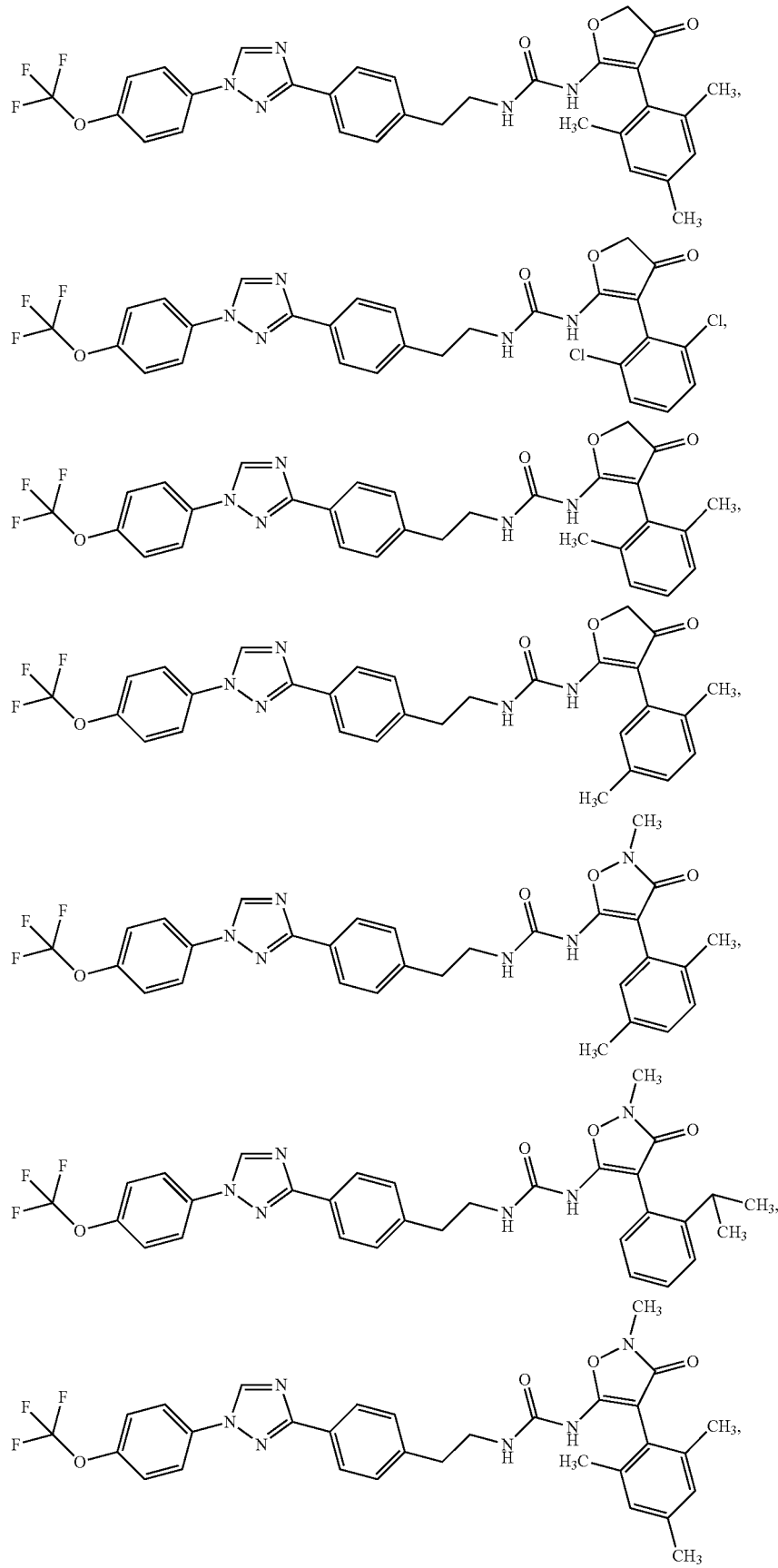

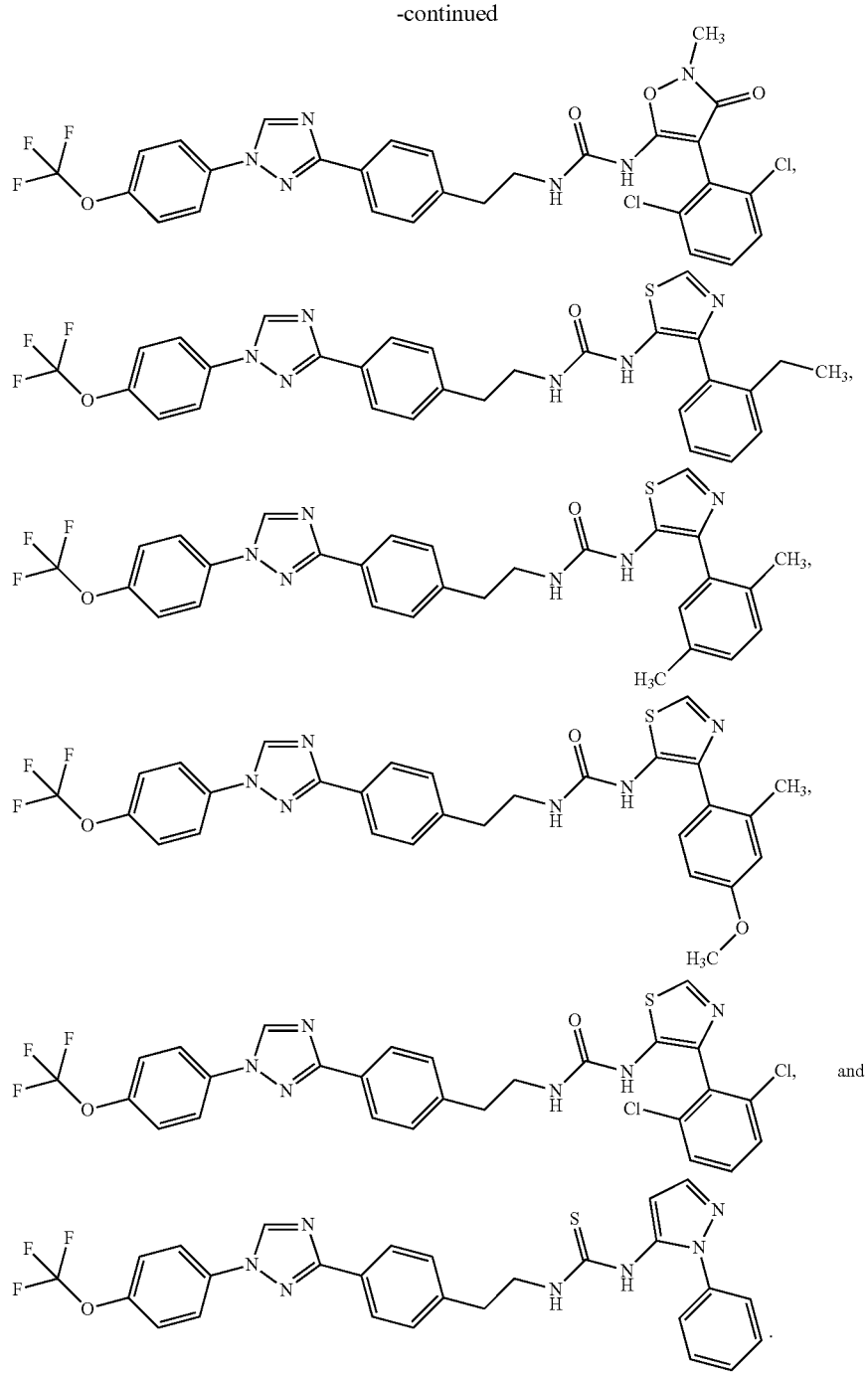
4. A molecule according to claim 1 wherein said molecule is selected from the group consisting of
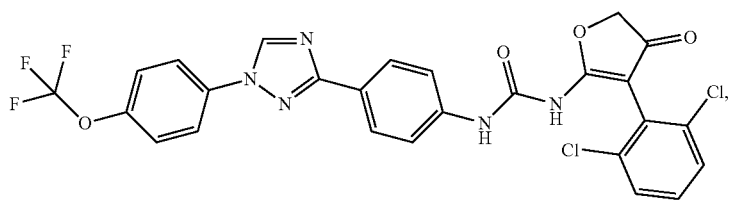

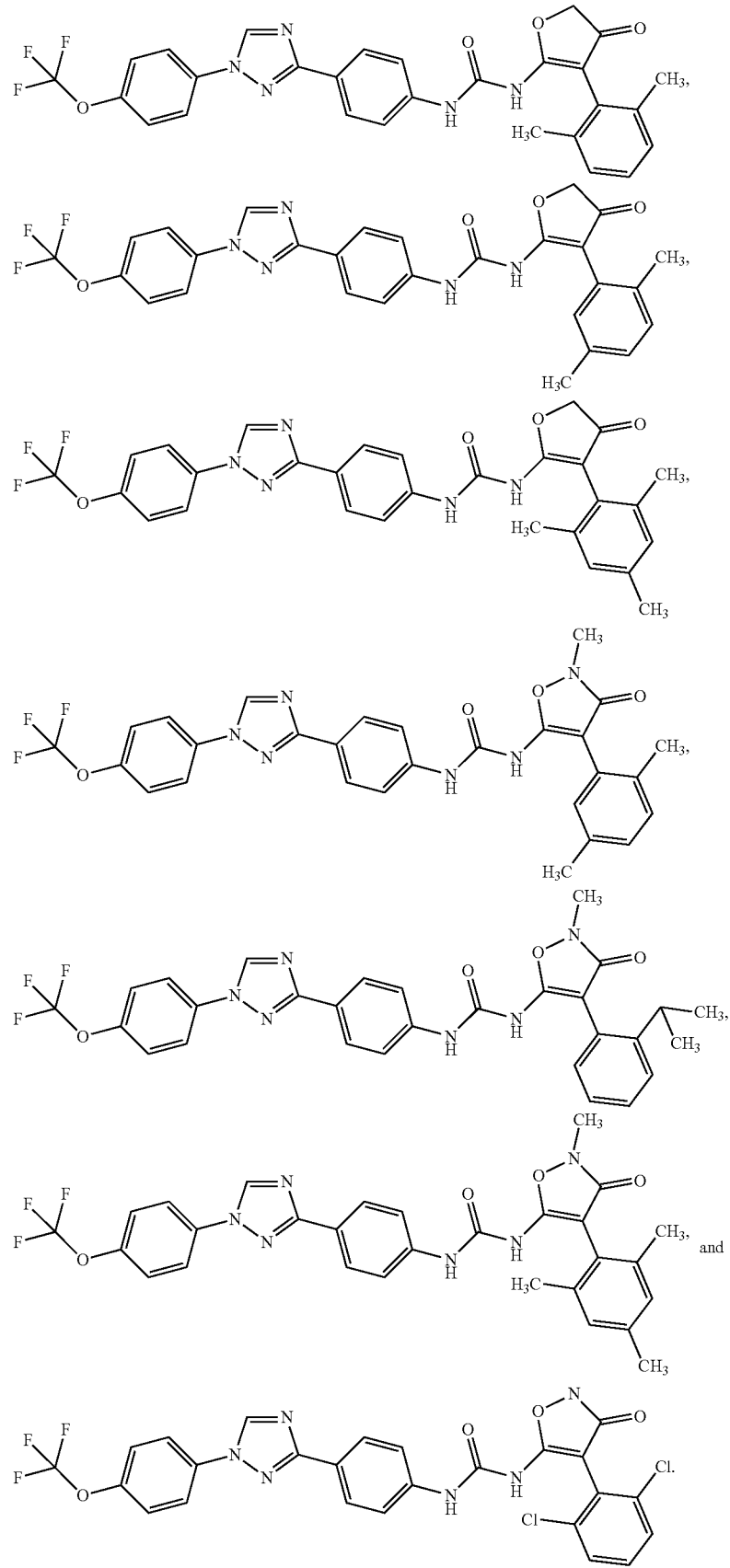

5. A pesticidal composition comprising a molecule according to claim 1, further comprising one or more active ingredients.

6. A pesticidal composition according to claim 5 wherein said active ingredient is selected from AIGA.

7. A pesticidal composition according to claim 5 wherein said active ingredient is selected from AI-1, 1,3-dichloropropene, chlorpyrifos, chlorpyrifos-methyl, hexaflumuron, methoxyfenozide, noviflumuron, spinetoram, spinosad, sulfoxaflor, and sulfuryl fluoride.

8. A pesticidal composition comprising a molecule according to claim 1, further comprising a MoA Material.

9. A pesticidal composition according to claim 8 wherein said MoA Material is selected from MoAMGA.

10. A pesticidal composition according to claim 5 wherein the weight ratio of the molecule according to Formula One to said active ingredient is
   (a) 100:1 to 1:100;
   (b) 50:1 to 1:50;
   (c) 20:1 to 1 to 20;
   (d) 10:1 to 1:10;
   (e) 5:1 to 1:5;
   (f) 3:1 to 1:3;
   (g) 2:1 to 1:2; or
   (h) 1:1.

11. A process to control a pest said process comprising applying to a locus, a pesticidally effective amount of a molecule according to claim 1.

12. A process to control a pest said process comprising applying to a locus, a pesticidally effective amount of a pesticidal composition according to claim 5.

13. A molecule according to claim 1 wherein $R^1$, $R^2$, $R^3$, $R^4$, $R^6$, $R^7$, $R^8$, $R^9$, $R^{10}$, $R^{11}$, and $R^{12}$ are H, and $R^5$ is $(C_1-C_4)$haloalkoxy.

14. A molecule according to claim 13 wherein $R^5$ is $OCF_3$ or $OCF_2CF_3$.

15. A molecule according to claim 1 wherein L is a bond or L is $—CH_2CH_2—$.

16. A molecule according to claim 1 wherein $R^{13}$ is dihydrofuranyl, imidazolyl, isoxazolyl, oxadiazolyl, oxazolyl, pyrazolyl, thienyl, or thiazolyl that is substituted with one or more substituents selected from the group consisting of oxo, $CH_3$, $CH(CH_3)CH_2CH(CH_3)_2$, $C(O)OCH_2CH_3$, phenyl, and pyridyl that is further substituted with one or more substituents R, selected from F, Cl, $CH_3$, $CH_2CH_3$, $CH(CH_3)_2$, $OCH_3$, and $OCF_3$.

\* \* \* \* \*